US007901693B2

(12) United States Patent
Gaiger et al.

(10) Patent No.: US 7,901,693 B2

(45) Date of Patent: *Mar. 8, 2011

(54) COMPOSITIONS AND METHODS FOR WT1 SPECIFIC IMMUNOTHERAPY

(75) Inventors: Alexander Gaiger, Vienna (AT); Martin A Cheever, Mercer Island, WA (US)

(73) Assignee: Corixa Corporation, Wilmington, DE (US)

(*) Notice: Subject to any disclaimer, the term of this patent is extended or adjusted under 35 U.S.C. 154(b) by 1493 days.

This patent is subject to a terminal disclaimer.

(21) Appl. No.: 10/002,603

(22) Filed: Oct. 30, 2001

(65) Prior Publication Data

US 2003/0095971 A1 May 22, 2003

Related U.S. Application Data

(63) Continuation-in-part of application No. 09/938,864, filed on Aug. 24, 2001, now abandoned.

(51) Int. Cl.

| | |
|---|---|
| ***C07K 14/435*** | (2006.01) |
| ***C07K 14/47*** | (2006.01) |
| ***A61K 39/00*** | (2006.01) |
| ***A61K 38/17*** | (2006.01) |

(52) U.S. Cl. ................ 424/277.1; 424/185.1; 424/192.1; 514/19.3; 514/19.6; 514/21.2; 530/350; 530/828

(58) Field of Classification Search ........................ None
See application file for complete search history.

(56) References Cited

U.S. PATENT DOCUMENTS

| | | | | |
|---|---|---|---|---|
| 5,350,840 | A | 9/1994 | Call et al. | 536/23.1 |
| 5,622,835 | A | 4/1997 | Herlyn et al. | 435/328 |
| 5,633,142 | A | 5/1997 | Herlyn et al. | 435/7.23 |
| 5,670,317 | A | 9/1997 | Ladanyi et al. | 435/6 |
| 5,679,356 | A | 10/1997 | Bonnem et al. | 424/278.1 |
| 5,693,522 | A | 12/1997 | Chada et al. | 435/2.402 |
| 5,726,288 | A | 3/1998 | Call et al. | 530/350 |
| 6,034,235 | A | 3/2000 | Sugiyama et al. | 536/24.5 |
| 6,096,313 | A | 8/2000 | Jäger et al. | 424/184.1 |
| 6,277,832 | B1 | 8/2001 | Sugiyama et al. | 514/44 |
| 6,316,599 | B1 | 11/2001 | Call et al. | 530/387.7 |
| 6,818,751 | B1 | 11/2004 | Xu et al. | 536/23.1 |
| 7,063,854 | B1 | 6/2006 | Gaiger et al. | 424/277.1 |
| 7,115,272 | B1 | 10/2006 | Gaiger et al. | 424/277.1 |
| 7,144,581 | B2 * | 12/2006 | Gaiger et al. | 424/277.1 |
| 7,316,924 | B2 | 1/2008 | Bron et al. | 435/320.1 |
| 7,329,410 | B1 | 2/2008 | Gaiger et al. | 424/277.1 |
| 7,553,494 | B2 | 6/2009 | Gaiger et al. | |
| 2003/0039635 | A1 | 2/2003 | Gaiger et al. | 424/93.2 |
| 2003/0072767 | A1 | 4/2003 | Gaiger et al. | 424/185.1 |
| 2004/0018204 | A1 | 1/2004 | Gaiger et al. | |

FOREIGN PATENT DOCUMENTS

| | | |
|---|---|---|
| EP | 1004319 A1 | 5/2000 |
| EP | 1103564 A1 | 5/2001 |
| JP | 06-128299 | 5/1994 |
| WO | WO 91/07509 | 5/1991 |
| WO | WO 94/21287 | 9/1994 |
| WO | WO95/06725 | 3/1995 |
| WO | WO95/29995 | 11/1995 |
| WO | WO 96/38176 | 12/1996 |
| WO | WO 99/03506 | 1/1999 |
| WO | 99/51753 A1 | 10/1999 |
| WO | WO99/58135 | 11/1999 |
| WO | WO 00/06602 | 2/2000 |
| WO | WO 00/18795 | 4/2000 |
| WO | WO 00/26249 | 5/2000 |
| WO | WO 01/25273 | 4/2001 |
| WO | WO 01/60970 | 8/2001 |
| WO | WO 01/62920 | 8/2001 |
| WO | WO 01/72786 | 10/2001 |
| WO | WO 01/94629 | 12/2001 |
| WO | WO 02/00677 | 1/2002 |
| WO | WO 02/28414 | 4/2002 |
| WO | WO 03/037060 | 5/2003 |

OTHER PUBLICATIONS

Grosenbach, D.W. et al., "Synergy of Vaccines Strategies to Amplify Antigen-specific Immune Responses and Antitumor Effects," *Cancer Research 61*: 4497-4505, Jun. 1, 2001.

Hale, R.S. et al., "Codon Optimization of the Gene Encoding a Domain from Human Type 1 Neurofibromin Protein Results in a Threefold Improvement in Expression Level in *Escherichia coli,*" *Protein Expression and Purification 12*: 185-188, 1998.

Oka, Y. et al., "Cancer Immunotherapy Targeting Wilms' Tumor Gene WT1 Product," *The Journal of Immunology 164*: 1873-1880, 2000.

Oka, Y. et al., "Human cytotoxic T-lymphocyte responses specific for peptides of the wild-type Wilms' tumor gene (*WT1*) product," *Immunogenetics 51*: 99-107, 2000.

Tsuboi, A. et al., "Cytotoxic T-Lymphocyte Responses Elicited to Wilms' Tumor Gene WT1 Product by DNA Vaccination," *Journal of Clinical Immunology 20*(3): 195-202, 2000.

TrEMBL Database Accession No. Q93046, Feb. 2, 1997.

Gaiger, A. and Cheever, M.A., "Compositions and Methods for WT1 Specific Immunotherapy," U.S. Appl. No. 09/164,223, filed Sep. 30, 1998. Gaiger, A. and Cheever, M.A., "Compositions and Methods for WT1 Specific Immunotherapy," U.S. Appl. No. 09/276,484, filed Mar. 25, 1999.

Gaiger, A. and Cheever, M.A., "Compositions and Methods for WT1 Specific Immunotherapy," U.S. Appl. No. 09/684,361, filed Oct. 6, 2000.

Gaiger, A. and Cheever, M.A., "Compositions and Methods for WT1 Specific Immunotherapy," U.S. Appl. No. 09/685,830, filed Oct. 9, 2000.

Gaiger, A. et al., "Compositions and Methods for WT1 Specific Immunotherapy," U.S. Appl. No. 09/785,019, filed Feb. 15, 2001.

Boon, T., "Tumor Antigens Recognized by Cytolytic T Lymphocytes: Present Perspectives for Specific Immunotherapy," *Int. J. Cancer 54*: 177-180, 1993.

(Continued)

*Primary Examiner* — Ron Schwadron

(74) *Attorney, Agent, or Firm* — Seed IP Law Group PLLC

(57) ABSTRACT

Compositions and methods for the therapy of malignant diseases, such as leukemia and cancer, are disclosed. The compositions comprise one or more of a WT1 polynucleotide, a WT1 polypeptide, an antigen-presenting cell presenting a WT1 polypeptide, an antibody that specifically binds to a WT1 polypeptide; or a T cell that specifically reacts with a WT1 polypeptide. Such compositions may be used, for example, for the prevention and treatment of metastatic diseases.

9 Claims, 42 Drawing Sheets

OTHER PUBLICATIONS

Wu, L.F. et al., "Bacterial Twin-Arginine Signal Peptide-Dependent Protein Translocation Pathway: Evolution and Mechanism," *J. Mol. Microbiol. Biotechnol.* *2*(2): 179-189, Apr. 2000.
Oka, Y. et al., "Wilms Tumor Gene Peptide-Based Immunotherapy for Patients with Overt Leukemia from Myelodysplastic Syndrome (MDS) or MDS with Myelofibrosis," *International Journal of Hematology 78*: 56-61, 2003.
GenBank Database, Accession No. A39692, Feb. 16, 1997.
GenBank Database, Accession No. AAA36810, Jun. 15, 1990.
GenBank Database, Accession No. AAA62825, Oct. 27, 1994.
GenBank Database, Accession No. AAB33427, May 12, 1995.
GenBank Database, Accession No. AAB33443, Jul. 11, 1995.
GenBank Database, Accession No. AAC60039, Nov. 8, 1996.
GenBank Database, Accession No. BAA94794, Apr. 21, 2000.
GenBank Database, Accession No. CAA35956, May 29, 1991.
GenBank Database, Accession No. CAA43819, Dec. 3, 1993.
GenBank Database, Accession No. CAA59736, Feb. 13, 1996.
GenBank Database, Accession No. I51960, Nov. 5, 1999.
GenBank Database, Accession No. M30393, Jun. 15, 1990.
GenBank Database, Accession No. NM_000378, Nov. 5, 2000.
GenBank Database, Accession No. NM_024424, Mar. 20, 2001.
GenBank Database, Accession No. NM_ 024426, Mar. 20, 2001.
GenBank Database, Accession No. NP_000369, Nov. 5, 2000.
GenBank Database, Accession No. NP_077742, Mar. 20, 2001.
GenBank Database, Accession No. NP_077743, Mar. 20, 2001.
GenBank Database, Accession No. NP_077744, Mar. 20, 2001.
GenBank Database, Accession No. NP_113722, Apr. 6, 2003.
GenBank Database, Accession No. O62651, Nov. 1, 1998.
GenBank Database, Accession No. P50902, Oct. 1, 1996.
GenBank Database, Accession No. S75264, Jul. 11, 1995.
GenBank Database, Accession No. X51630, May 29, 1991.
Derwent Geneseq Database, Accession No. AAT45130, Aug. 19, 1997.
Derwent Geneseq Database, Accession No. AAT45131, Aug. 20, 1997.
Derwent Geneseq Database, Accession No. AAT45132, Aug. 20, 1997.
Derwent Geneseq Database, Accession No. AAT45133, Aug. 20, 1997.
Derwent Geneseq Database, Accession No. AAT45134, Aug. 20, 1997.
Derwent Geneseq Database, Accession No. AAT45135, Aug. 20, 1997.
Derwent Geneseq Database, Accession No. AAT45136, Aug. 20, 1997.
Derwent Geneseq Database, Accession No. AAT45137, Aug. 20, 1997.
Derwent Geneseq Database, Accession No. AAT45138, Aug. 20, 1997.
Derwent Geneseq Database, Accession No. AAT45139, Aug. 20, 1997.
Derwent Geneseq Database, Accession No. AAT45140, Aug. 20, 1997.
Derwent Geneseq Database, Accession No. AAT45141, Aug. 20, 1997.
Derwent Geneseq Database, Accession No. AAT45142, Aug. 20, 1997.
Derwent Geneseq Database, Accession No. AAT97855, Mar. 9, 1998.
Derwent Geneseq Database, Accession No. AAT97856, Mar. 9, 1998.
Derwent Geneseq Database, Accession No. AAT97857, Mar. 9, 1998.
Derwent Geneseq Database, Accession No. AAT97858, Mar. 9, 1998.
Derwent Geneseq Database, Accession No. AAT97859, Mar. 9, 1998.
Derwent Geneseq Database, Accession No. AAT97860, Mar. 9, 1998.
Derwent Geneseq Database, Accession No. AAT97861, Mar. 9, 1998.
Derwent Geneseq Database, Accession No. AAT97862, Mar. 9, 1998.
Derwent Geneseq Database, Accession No. AAT97863, Mar. 9, 1998.
Derwent Geneseq Database, Accession No. AAT97864, Mar. 9, 1998.
Derwent Geneseq Database, Accession No. AAT97865, Mar. 9, 1998.
Derwent Geneseq Database, Accession No. AAT97866, Mar. 9, 1998.
Derwent Geneseq Database, Accession No. AAT97867, Mar. 9, 1998.
Derwent Geneseq Database, Accession No. AAT97868, Mar. 9, 1998.
Derwent Geneseq Database, Accession No. AAX15839, May 11, 1999.
Derwent Geneseq Database, Accession No. AAX15840, May 11, 1999.
Derwent Geneseq Database, Accession No. AAX15841, May 11, 1999.
Derwent Geneseq Database, Accession No. AAX15842, May 11, 1999.
Derwent Geneseq Database, Accession No. AAX15843, May 11, 1999.
Derwent Geneseq Database, Accession No. AAX15844, May 11, 1999.
Derwent Geneseq Database, Accession No. AAX15845, May 11, 1999.
Derwent Geneseq Database, Accession No. AAX15846, May 11, 1999.
Derwent Geneseq Database, Accession No. AAX15847, May 11, 1999.
Derwent Geneseq Database, Accession No. AAX15848, May 11, 1999.
Derwent Geneseq Database, Accession No. AAX15849, May 11, 1999.
Derwent Geneseq Database, Accession No. AAX15850, May 11, 1999.
Derwent Geneseq Database, Accession No. AAX15851, May 11, 1999.
Derwent Geneseq Database, Accession No. AAX15852, May 11, 1999.
Derwent Geneseq Database, Accession No. AAX15853, May 11, 1999.
Derwent Geneseq Database, Accession No. AAX15854, May 11, 1999.
Derwent Geneseq Database, Accession No. AAX15855, May 11, 1999.
Derwent Geneseq Database, Accession No. AAX23927, Jun. 25, 1999.
Derwent Geneseq Database, Accession No. AAX23928, Jun. 25, 1999.
Derwent Geneseq Database, Accession No. AAX23929, Jun. 25, 1999.
Derwent Geneseq Database, Accession No. AAX23930, Jun. 25, 1999.
Derwent Geneseq Database, Accession No. AAX23931, Jun. 25, 1999.
Derwent Geneseq Database, Accession No. AAX34315, Jul. 6, 1999.
Derwent Geneseq Database, Accession No. AAX34316, Jul. 6, 1999.
Derwent Geneseq Database, Accession No. AAX34317, Jul. 6, 1999.
Derwent Geneseq Database, Accession No. AAX34318, Jul. 6, 1999.
Derwent Geneseq Database, Accession No. AAX34319, Jul. 6, 1999.
Derwent Geneseq Database, Accession No. AAX34320, Jul. 6, 1999.
Derwent Geneseq Database, Accession No. AAX34321, Jul. 6, 1999.
Derwent Geneseq Database, Accession No. AAY80196, May 24, 2000.
Derwent Geneseq Database, Accession No. AAY80197, May 24, 2000.
Derwent Geneseq Database, Accession No. AAY80198, May 24, 2000.
Derwent Geneseq Database, Accession No. AAY80199, May 24, 2000.

Derwent Geneseq Database, Accession No. AAY80200, May 24, 2000.
Derwent Geneseq Database, Accession No. AAY80201, May 24, 2000.
Derwent Geneseq Database, Accession No. AAY80202, May 24, 2000.
Derwent Geneseq Database, Accession No. AAY80203, May 24, 2000.
Derwent Geneseq Database, Accession No. ABP42234, Aug. 22, 2002.
Altman et al., "Phenotypic analysis of antigen-specific T lymphocytes," *Science 274*:94-96, Oct. 4, 1996.
Appel, R.D. et al., "A new generation of information retrieval tools for biologists: the example of the ExPASy WWW server," *Trends in Biochemical Sciences 19*(6): 258-260, Jun. 1994.
Blaudeck, N. et al., "Specificity of Signal Peptide Recognition in Tat-Dependent Bacterial Protein Translocation," *Journal of Bacteriology 183*(2): 604-610, Jan. 2001.
Corixa Corporation, Ribi Adjuvant System (RAS), "Research Adjuvant Fact Sheet," 2005, pp. 1-2.
Crawford et al., "Detection of antigen-specific T cells with multivalent soluble class II MHC covalent peptide complexes," *Immunity 8*:675-682, Jun. 1998.
Genbank Database, Accession No. NM_024425, Sep. 14, 2008.
Genbank Database, Accession No. P19544, Jul. 1, 2008.
Genbank Database, Accession No. P22561, Jun. 10, 2008.
Genbank Database, Accession No. P49952, Jun. 10, 2008.
Genbank Database, Accession No. S74529, May 16, 1995.
Derwent Geneseq Database, Accession No. AAG78443, Apr. 12, 2002.
Derwent Geneseq Database, Accession No. AAG78444, Apr. 12, 2002.
Derwent Geneseq Database, Accession No. AAG78446, Apr. 12, 2002.
Derwent Geneseq Database, Accession No. AAH99946, Apr. 12, 2002.
Derwent Geneseq Database, Accession No. AAQ12020, Mar. 25, 2003.
Derwent Geneseq Database, Accession No. AAR12240, Mar. 25, 2003.
Derwent Geneseq Database, Accession No. AAR85065, Feb. 2, 1996.
Derwent Geneseq Database, Accession No. AAR85066, Feb. 2, 1996.
Derwent Geneseq Database, Accession No. AAS13085, Dec. 17, 2001.
Derwent Geneseq Database, Accession No. AAT02461, Feb. 2, 1996.
Derwent Geneseq Database, Accession No. AAT02462, Feb. 2, 1996.
Derwent Geneseq Database, Accession No. AAT97869, Mar. 9, 1998.
Derwent Geneseq Database, Accession No. AAT97870, Mar. 9, 1998.
Derwent Geneseq Database, Accession No. AAU08555, Dec. 17, 2001.
Derwent Geneseq Database, Accession No. AAV17060, Jun. 1, 1998.
Derwent Geneseq Database, Accession No. AAW34972, Mar. 9, 1998.
Derwent Geneseq Database, Accession No. AAW47173, Jun. 1, 1998.
Derwent Geneseq Database, Accession No. AAW47175, Jun. 1, 1998.
Derwent Geneseq Database, Accession No. AAW47176, Jun. 1, 1998.
Derwent Geneseq Database, Accession No. ABL65410, May 15, 2002.
Pardoll, D.M., "New strategies for enhancing the immunogenicity of tumors," *Current Opinion in Immunology 5*:719-725, 1993.
Peitsch, M.C., "ProMod and Swiss-Model: Internet-based tools for automated comparative protein modelling," *Biochemical Society Transactions 24*(1): 274-279, Feb. 1996.
Rammensee, H.-G. et al., "MHC ligands and peptide motifs: first listing," *Immunogenetics 41*:178-228, 1995.
Rammensee, H. et al., "SYFPEITHI: database for MHC ligands and peptide motifs," *Immunogenetics 50*(3-4): 213-219, Nov. 1999.
Santini, Claire-Lise et al., "Translocation of Jellyfish Green Fluorescent Protein via the Tat System of *Escherichia coli* and Change of Its Periplasmic Localization in Response to Osmotic Up-shock," *Journal of Biological Chemistry 276*(11): 8159-8164, Mar. 16, 2001.
Shu, Q. et al., "Effects of various adjuvants on efficacy of a vaccine against *Streptococcus bovis* and *Lactobacillus* spp in cattle," *American Journal of Veterinary Research 61*(7):839-843, Jul. 2000.
Van Brunt, J. (ed.), Pharmalicensing.com, "Biotech's old soldiers—Signals," Nov. 15, 2005, pp. 1-12, accessed Jan. 18, 2007.
Yewdell, J.W. et al., "Immunodominance in major histocompatibility complex class I-restricted T lymphocyte responses," *Annu. Rev. Immunol. 17*:51-88, 1999.
Rivera, M.N. et al., "Wilm's Tumour: Connecting Tumorigenesis and Organ Development in the Kidney," *Nature Reveiws Cancer 5*: 699-712, Sep. 2005.
Wagner, K.-D. et al., "The complex life of WT1," *Journal of Cell Science 116*(9): 1653-1658, 2003.
Aaronson and Todaro, "Development of 3t3-like lines from Balb/c mouse embryo cultures: transformation susceptibility to SV40," *J. Cell. Physiol. 72*(2):141-148, Oct. 1968.
Adachi et al., "Midkine as a novel target gene for the Wilms' tumor suppressor gene (WT1)," *Oncogene 13*: 2197-2203, 1996.
Algar et al., "A WT1 antisense oligonucleotide inhibits proliferation and induces apoptosis in myeloid leukaemia cell lines," *Oncogene 12*: 1005-1014, 1996.
Armstrong et al., "The expression of the Wilms' tumour gene, WT1, in the developing mammalian embryo," *Mechanisms of Development 40*: 85-97, 1992.
Bellantuono et al., "Selective elimination of leukemic progenitors by allorestricted CTL specific for WILMS Tumor Antigen-1 (WT-1)," *Blood*, 94(10):532A-533A, Nov. 15, 1999.
Bergmann et al., "High Levels of Wilms' Tumor Gene (wt1) mRNA in Acute Myeloid Leukemias Are Associated With a Worse Long-Term Outcome," *Blood 90*(3): 1217-1225, 1997.
Bergmann et al., "Wilms Tumor Gene Expression in Acute Myeloid Leukemias," *Leukemia and Lymphoma 25*: 435-443, 1997.
Brenner et al., "RNA polymerase chain reaction detects different levels of four alternatively spliced *WT1* transcripts in Wilms' tumors," *Oncogene 7*: 1431-1433, 1992.
Brieger et al., "The Expression of the Wilms' Tumor Gene in Acute Myelocytic Leukemias as Possible Marker for Leukemic Blast Cells," *Leukemia 8*(12): 2138-2143, 1994.
Brieger et al., "The Wilms' tumor gene is frequently expressed in acute myeloblastic leukemias and may provide a marker for residual blast cells detectable by PCR," *Annals of Oncology 6*: 811-816, 1995.
Buckler et al., "Isolation, Characterization, and Expression of the Murine Wilms' Tumor Gene (WT1) During Kidney Development," *Molecular and Cellular Biology 11*: 1707-1712, 1991.
Call et al., "Isolation and Characterization of a Zinc Finger Polypeptide Gene at the Human Chromosome 11 Wilms' Tumor Locus," *Cell 60*: 509-520, 1990.
Carapeti et al., "Dominant-negative mutations of the Wilms' tumour predisposing gene (WT1) are infrequent in CML blast crisis and de novo acute leukaemia," *Eur. J. Haematol. 58*: 346-349, 1997.
Charles et al., "Expression of the Wilms' tumour gene WT1 in the developing human and in paediatric renal tumours: an immunohistochemical study," *J. Clin. Pathol.: Mol. Pathol. 50*: 138-144, 1997.
Charles et al., "Immunohistochemical detection of the Wilms' tumour gene WT1 in desmoplastic small round cell tumour," *Histopathology 30*: 312-314, 1997.
Chen et al., "T-cells for tumor therapy can be obtained from antigen-loaded sponge implants," *Cancer Research 54*(4):1065-1070, Feb. 15, 1994.
Chesebro et al., "Characterization of Ia8 antigen, THY-1.2 antigen, complemnt receptors, and virus production in a group of murine virus-induced leukemia cell lines," *The Journal of Immunology 117*(4):1267-1274, Oct. 1976.

De Bruijn et al., "Peptide loading of empty major histocompatibility complex molecules on RMA-S cells allows the induction of primary cytotoxic T lymphocyte responses," *Eur J Immunol 21*(12):2963-2970, Dec. 1991.
Deavin et al., "Statistical comparison of established T-cell eptiope predictors against a large database of human and murine antigens," *Molecular Immunology*, 33(2):145-155, 1996.
Drummond et al., "Repression of the Insulin-Like Growth Factor Gene by the Wilms Tumor Suppressor WT1," *Science 257*: 674-677, 1992.
Feller and de la Cruz, "Tsites (Version 1.1) A computer program to determine T cell epitopes using four predictive algorithms," *Nature 349*: 720-721, 1991.
Foster et al., "Characterization of prostatic epithelial cell lines derived from transgenic adenocarcinoma of the mouse prostate (TRAMP) model," *Cancer Research 57*(16):3325-3330, Aug. 15, 1997.
Frazier et al., "Expression of the Tumor Suppressor Gene WT1 in Both Human and Mouse Bone Marrow," *Blood 86*: 4704-4706, 1995 (letter).
Gaiger et al., "WT1: A new leukemia and cancer antigen A," *Proceedings of the Annual Meeting of the American Association for Cancer Research*, 40:424, 1999.
Gaiger et al., "Immunity to WT1 in animal models and leukemia pateints," *Blood*, 94(10):78, Nov. 15, 1999.
Gaiger et al., "Immunity to WT1 in the animal model and in patients with acute myeloid leukemia," *Blood 96*(4):1480-1489, Aug. 15, 2000.
Gillis and Smith, "Long term culture of tumour-specific cytotoxic T cells," *Nature 268*:154-156, Jul. 14, 1977.
Glynn et al., "Cross-resistance to the transplantation of syngeneic friend, moloney, and rauscher virus-induced tumors," *Cancer Research 28*(3):434-439, Mar. 1968.
Goodyer et al., "Repression of the retinoic acid receptor-α gene by the Wilms' tumor suppressor gene product, wtl," *Oncogene 10*: 1125-1129, 1995.
Haber et al., "A dominant mutation in the Wilms tumor gene *WT1* cooperates with the viral oncogene *E1A* in transformation of primary kidney cells," *Proc. Natl. Acad. Sci. USA 89*: 6010-6014, 1992.
Haber et al., "Alternative splicing and genomic structure of the Wilms tumor gene *WT1," Proc. Natl. Acad. Sci. USA 88*: 9618-9622, 1991.
Haber et al., "An Internal Deletion within an 11p13 Zinc Finger Gene Contributes to the Development of Wilms' Tumor," *Cell 61*: 1257-1269, 1990.
Hamilton et al., "High affinity binding sites for the Wilms' tumour suppressor protein WT1," *Nucleic Acids Research 23*(2): 277-284, 1995.
Harrington et al., "Inhibition of Colony-stimulating Factor-1 Promoter Activity by the Product of the Wilms' Tumor Locus," *The Journal of Biological Chemistry 268*(28): 21271-21275, 1993.
Harrington et al., "Inhibition of Colony-stimulating Factor-1 Promoter Activity by the Product of the Wilms' Tumor Locus," *The Journal of Biological Chemistry 268*(28): 21271-21275, 1993.
Horibata and Harris, "Mouse myelomas and lyphomas in culture," *Experimental Cell Research 60*:61-77, 1970.
Huang et al., "Tissue, Developmental, and Tumor-Specific Expression of Divergent Transcripts in Wilms Tumor," *Science 250*: 991-994, 1990.
Inoue et al., "Aberrant Overexpression of the Wilms Tumor Gene (WT1) in Human Leukemia," *Blood 89*(4): 1405-1412, 1997.
Inoue et al., "Long-Term Follow-Up of Minimal Residual Disease in Leukemia Patients by Monitoring WT1 (Wilms Tumor Gene) Expression Levels," *Blood 88*: 2267-2278, 1996.
Inoue et al., "Wilms' Tumor Gene (WT1) Competes With Differentiation-Inducing Signal in Hematopoetic Progenitor Cells," *Blood 91*(8): 2969-2976, 1998.
Inoue et al., "*WT1* as a New Prognostic Factor and a New Marker for the Detection of Minimal Residual Disease in Acute Leukemia," *Blood 84*: 3071-3079, 1994.
King-Underwood and Pritchard-Jones, "Wilms' Tumor (*WT1*) Gene Mutations Occur Mainly in Acute Myeloid Leukemia and May Confer Drug Resistance," *Blood 91*(8): 2961-2968, 1998.
King-Underwood et al., "Mutations in the Wilms' Tumor Gene WT1 in Leukemias," *Blood 91*: 2961-2968, 1998.
Kreidberg et al., "WT-1 Is Required for Early Kidney Development," *Cell 74*: 679-691, 1993.
Kudoh et al., "Constitutive expression of the Wilms tumor suppressor gene WT1 in F9 embryonal carcinoma cells induces apoptotic cell death in response to retinoic acid," *Oncogene 13*: 1431-1439, 1996.
Kudoh et al., "$G_1$ phase arrest induced by Wilms tumor protein WT1 is abrogated by cyclin/CDK complexes," *Proc. Natl. Acad. Sci. USA 92*: 4517-4521, 1995.
Kwok and Higuchi, "Avoiding false positives with PCR," *Nature 339*:237-238, May 18, 1989.
Larsson et al., "Subnuclear Localization of WT1 in Splicing or Transcription Factor Domains Is Regulated by Alternative Splicing," *Cell 81*: 391-401, 1995.
Ljunggren et al., "Empty MHC class I molecules come out in the cold," *Nature 346*:476-480, Aug. 2, 1990.
Lozzio and Lozzio, "Human chronic myelogenous leukemia cell-line with positive Philadelphia chromosome," *Blood 45*(3):321-334, Mar. 1975.
Luo et al., "The tumor suppressor gene WT1 inhibits *ras*-mediated transformation," *Oncogene 11*: 743-750, 1995.
Madden et al., "Transcriptional Repression Mediated by the WT1 Wilms Tumor Gene Product," *Science 253*: 1550-1552, 1991.
Maurer et al., "The Wilms' tumor gene is expressed in a subset of CD34 progenitors and downregulated early in the course of differentiation in vitro," *Experimental Hematology 25*: 945-950, 1997.
Menke et al., "Wilms' Tumor 1 splice variants have opposite effects on the tumorigenicity of adenovirus-transformed baby-rat kidney cells," *Oncogene 12*: 537-546, 1996.
Menssen et al., "Detection by Monoclonal Antibodies of the Wilms' Tumor (WT1) Nuclear Protein in Patients With Acute Leukemia," *Int. J. Cancer 70*: 518-523, 1997.
Menssen et al., "Presence of Wilms' tumor gene (*wt1*) transcripts and the WT1 nuclear protein in the majority of human acute leukemias," *Leukemia 9*: 1060-1067, 1995.
Menssen et al., "Wilms' Tumor Gene Expression in Human CD34 Hematopoietic Progenitors During Fetal Development and Early Clonogenic Growth," *Blood 89*(9): 3486-3487, 1997 (letter).
Miwa et al., "Expression of the Wilms' Tumor Gene (WT1) in Human Leukemias," *Leukemia 6*(5): 405-409, 1992.
Miyagi et al., "Expression of the Candidate Wilms' Tumor Gene, *WT1*, in Human Leukemia Cells," *Leukemia 7*(7): 970-977, 1993.
Morris et al., "Characterization of the zinc finger protein encoded by the WT1 Wilms' tumor locus," *Oncogene 6*: 2339-2348, 1991.
Mundlos et al., "Nuclear localization of the protein encoded by the Wilms' tumor gene *WT1* in embryonic and adult tissues," *Development 119*: 1329-1341, 1993.
Murata et al., "The Wilms tumor suppressor gene WT1 induces G1 arrest and apoptosis in myeloblastic leukemia M1 cells," *FEBS Letters 409*: 41-45, 1997.
Nakagama et al., "Sequence and Structural Requirements for High-Affinity DNA Binding by the WT1 Gene Product," *Molecular and Cellular Biology 15*(3): 1489-1498, 1995.
Nichols et al., "WT1 Induces Expression of Insulin-like Growth Factor 2 in Wilms' Tumor Cells," *Cancer Research 55*: 4540-4543, 1995.
Ogawa et al., "Successful donor leukocyte transfusion at molecular relapse for a patient with acute myeloid leukemia who was treated with allogeneic bone marrow transplantation: importance of the monitoring of minimal residual disease by WT1 assay," *Bone Marrow Transplantation 21*: 525-527, 1998.
Old et al., "Antigenic properties of chemically induced tumors," *Annals of the New York Academy of Sciences 101*:80-107, Nov. 20, 1962.
Osaka et al., "WT1 Contributes to Leukemogenesis: Expression Patterns in 7,12-Dimethylbenz[a]Anthracene (DMBA)-Induced Leukemia," *International Journal of Cancer 72*: 696-699, 1997.
Parker et al., "Scheme for Ranking Potential HLA-A2 Binding Peptides Based on Independent Binding of Individual Peptide Side-Chains," *Journal of Immunology 152*: 163-175, 1994.

Patek et al., "Transformed cell lines susceptible or resistant to in vivo surveillance against tumorigenesis," *Nature 276*:510-511, Nov. 30, 1978.
Patmasiriwat et al., "Expression pattern of WT1 and GATA-1 in AML with chromosome 16q22 abnormalities," *Leukemia 10*: 1127-1133, 1996.
Pelletier et al., "Expression of the Wilms' tumor gene WT1 in the murine urogenital system," *Genes & Development 5*: 1345-1356, 1991.
Pelletier et al., "Germline Mutations in the Wilms' Tumor Suppressor Gene Are Associated with Abnormal Urogenital Development in Denys-Drash Syndrome," *Cell 67*: 437-447, 1991.
Phelan et al., "Wilms' Tumor Gene, *WT1*, mRNA Is Down-regulated during Induction of Erythroid and Megakaryocytic Differentiation of K562 Cells," *Cell Growth & Differentiation 5*: 677-686, 1994.
Pogue et al., "Amino-terminal alteration of the HLA-A*0201-restricted human immunodeficiency virus pol peptide increases complex stability and in vitro immunogenicity," *Proc. Natl. Acad. Sci. USA 92*: 8166-8170, 1995.
Pritchard-Jones et al., "The candidate Wilms' tumour gene is involved in genitourinary development," *Nature 346*: 194-197, 1990.
Pritchard-Jones et al., "The Wilms tumour (WT1) gene is mutated in a secondary leukaemia in a WAGR patient," *Human Molecular Genetics 3*(9): 1633-1637, 1994.
Rackley et al., "Expression of the Wilms' Tumor Suppressor Gene *WT1* during Mouse Embryogenesis," *Cell Growth & Differentiation 4*: 1023-1031, 1993.
Ramani and Cowell, "The Expression Pattern of Wilms' Tumour Gene (*WT1*) Product in Normal Tissues and Paediatric Renal Tumours," *Journal of Pathology 179*: 162-168, 1996.
Rauscher et al., "Binding of the Wilms' Tumor Locus Zinc Finger Protein to the EGR-1 Consensus Sequence," *Science 250*: 1259-1262, 1990.
Rauscher, "The WT1 Wilms tumor gene product: a developmentally regulated transcription factor in the kidney that functions as a tumor suppressor," *FASEB J. 7*: 896-903, 1993.
Rauscher et al., "Characterization of monoclonal antibodies directed to the amino-terminus of the WT1, Wilms' tumor suppressor," *Hybridoma*, 17(2):191-198, Apr. 1998.
Reddy et al., "WT1-mediated Transcriptional Activation Is Inhibited by Dominant Negative Mutant Proteins," *The Journal of Biological Chemistry 270*(18): 10878-10884, 1995.
Rothbard and Taylor, "A sequence pattern common to T cell epitopes," *EMBO Journal*, 7(1):93-100, 1988.
Rupprecht et al., "The Wilms' Tumor Suppressor Gene WT1 Is Negatively Autoregulated," *The Journal of Biological Chemistry 269*(8): 6198-6206, 1994.
Sadovnikova et al., "Generation of human tumor-reactive cytotoxic T-cells against peptides presented by non-self HLA class I molecules," *Eur.J. Immunol.*, 28:193-200, 1998.
Schmid et al., "Prognostic significance of WT1 gene expression at diagnosis in adult de novo acute myeloid leukemia," *Leukemia 11*: 639-643, 1997.
Sekiya et al., "Downregulation of Wilms' Tumor Gene (wtl) During Myelomonocytic Differentiation in HL60 Cells," *Blood 83*(7): 1876-1882, 1994.
Sharma et al., "Molecular Cloning of Rat Wilms' Tumor Complementary DNA and a Study of Messenger RNA Expression in the Urogenital System and the Brain," *Cancer Research 52*: 6407-6412, 1992.
Silberstein et al., "Altered expression of the WT1 Wilms tumor suppressor gene in human breast cancer," *Proc. Natl. Acad. Sci. USA 94*: 8132-8137, 1997.
Skeiky et al., "Cloning, expression, and immunological evaluation of two putative secreted serine protease antigens of *Mycobacterium tuberculosis," Infection and Immunity 67*(8):3998-4007, Aug. 1999.
Slavin and Strober, "Spontaneous murine B-cell leukaemia," *Nature 272*:624-626, Apr. 13, 1978.
Svedberg et al., "Constitutive expression of the Wilms' tumor gene (WT1) in the leukemic cell line U937 blocks parts of the differentiation program," *Oncogene 15*: 1-8, 1997.
Tadokoro et al., "Genomic Organization of the Human WT1 Gene," *Jpn. J. Cancer Res. 83*: 1198-1203, 1992.
Tadokoro et al., "Intragenic homozygous deletion of the *WT1* gene in Wilms' tumor," *Oncogene 7*: 1215-1221, 1992.
Tadokoro et al., "PCR Detection of 9 Polymorphisms in the WT1 Gene," *Human Molecular Genetics 2*(12): 2205-2206, 1993.
Tadokoro et al., "Taql RFLPs at the Wilms' tumor gene (WT1)," *Nucleic Acids Research 19*(9): 2514, 1991.
Telerman et al., "Identification of the cellular protein encoded by the human Wilms' tumor (*WT1*) gene," *Oncogene 7*: 2545-2548, 1992.
Toes et al., "Efficient tumor eradication by adoptively transferred cytotoxic T-cell clones in allogeneic hosts," *Int. J. Cancer*, 66:686-691, 1996.
Tsurutani et al., "cDNA cloning and developmental expression of the porcine homologue of *WT1," Gene 211* (2): 215-220, 1998.
Wang et al., "A second transcriptionally active DNA-binding site for the Wilms tumor gene product, WT1," *Proc. Natl. Acad. Sci. USA 90*: 8896-8900, 1993.
Wang et al., "The Wilms' Tumor Gene Product WT1 Activates or Suppresses Transcription through Separate Functional Domains," *The Journal of Biological Chemistry 268* (13): 9172-9175, 1993.
Wang et al., "The Wilms' Tumor Gene Product, WT1, Represses Transcription of the Platelet-derived Growth Factor A-chain Gene," *The Journal of Biological Chemistry 267*(31): 21999-22002, 1992.
Wang et al., "WT1, the Wilms' tumor suppressor gene product, represses transcription through an interactive nuclear protein," *Oncogene 10*(6): 1243-1247, 1995.
Watson et al., "Leukemia viruses associated with mouse myeloma cells," *Proceeding of the National Academy of Sciences 66*(2):344-351, Jun. 1970.
Werner et al., "Inhibition of Cellular Proliferation by the Wilms' Tumor Suppressor WT1 Is Associated with Suppression of Insulin-Like Growth Factor I Receptor Gene Expression," *Molecular and Cellular Biology* 15: 3516-3522, 1995.
Wu et al., "GATA-1 Transactivates the WT1 Hematopoietic Specific Enhancer," *The Journal of Biological Chemistry 270*(11): 5944-5949, 1995.
Yamagami et al., "Growth Inhibition of Human Leukemic Cells by WT1 (Wilms Tumor Gene) Antisene Oligodeoxynucleotides: Implications for the Involvement of WT1 in Leukemogenesis," *Blood 87*(7): 2878-2884, 1996.
Ye et al., "Regulation of WT1 by phosphorylation: inhibition of DNA binding, alteration of transcriptional activity and cellular translocation," *The EMBO Journal 15*(20): 5606-5615, 1996.
Altman et al., "Phenotypic analysis of antigen-specific T lymphocytes," *Science 274*:94-96, Oct. 4, 1996.
Crawford et al., "Detection of antigen-specific T cells with multivalent soluble class II MHC covalent peptide complexes," *Immunity 8*:675-682, Jun. 1998.
Berks, "A common export pathway for proteins binding complex redox cofactors," *Molecular Microbiology 22*(3):393-404, 1996.
Robinson, "The Twin-Arginine Translocation System: A Novel Means of Transporting Folded Proteins in Chloroplasts and Bacteria," *Biol. Chem. 381*:89-93, Feb. 2000.

* cited by examiner

HU: MGSDVRDLNALLPAVPSLGGGGGCALPVSGAAQWAPVLDFAPPGASAYGSL
MO: MGSDVRDLNALLPAVSSLGGGGGCGLPVSGAAQWAPVLDFAPPGASAYGSL

HU: GGPAPPPAPPPPPPPPPPHSFIKQEPSWGGAEPHEEQCLSAFTVHFSGQFTGTAG
MO: GGPAPPPAPPPPPPPPPPHSFIKQEPSWGGAEPHEEQCLSAFTLHFSGQFTGTAG

HU: ACRYGPFGPPPPSQASSGQARMFPNAPYLPSCLESQPAIRNQGYSTVTFDGTPS
MO: ACRYGPFGPPPPSQASSGQARMFPNAPYLPSCLESQPTIRNQGYSTVTFDGAPS

HU: YGHTPSHHAAQFPNHSFKHEDPMGQQGSLGEQQYSVPPPVYGCHTPTDSCTG
MO: YGHTPSHHAAQFPNHSFKHEDPMGQQGSLGEQQYSVPPPVYGCHTPTDSCTG

HU: SQALLLRTPYSSDNLYQMTSQLECMTWNQMNLGATLKGVAAGSSSSVKWTE
MO: SQALLLRTPYSSDNLYQMTSQLECMTWNQMNLGATLKGMAAGSSSSVKWTE

HU: GQSNHSTGYESDNHTTPILCGAQYRIHTHGVFRGIQDVRRVPGVAPTLVRSAS
MO: GQSNHGIGYESDNHTAPILCGAQYRIHTHGVFRGIQDVRRVSGVAPTLVRSAS

HU: ETSEKRPFMCAYPGCNKRYFKLSHLQMHSRKHTGEKPYQCDFKDCERRFSR
MO: ETSEKRPFMCAYPGCNKRYFKLSHLQMHSRKHTGEKPYQCDFKDCERRFSR

HU: SDQLKRHQRRHTGVKPFQCKTCQRKFSRSDHLKTHTRTHTGKTSEKPFSCR
MO: SDQLKRHQRRHTGVKPFQCKTCQRKFSRSDHLKTHTRTHTGKTSEKPFSCR

HU: WPSCQKKFARSDELVRHHNMHQRNMTKLQLAL
MO: WHSCQKKFARSDELVRHHNMHQRNMTKLHVAL

*Fig. 1* p117-139 stimulated line p117-139 stimulated clone p6-22 stimulated line p6-22 stimulated clone

```
    5   10   15   20   25   30   35   40   45   50   55   60   65   70   75
MGSDVRDLNALLPAVPSLGGGGCALPVSGAAQWAPVLDFAPPGASAYGSLGGPAPPPAPPPPPPPPPHSFIKQE
.....AAAAAAAAAAAAAAAAA.......AAAAAA.........AAAAAAAAAAAA...................
.............................RRRR..........................................
...........................................................................
...........................................................................

   80   85   90   95  100  105  110  115  120  125  130  135  140  145  150
PSWGGAEPHEEQCLSAFTVHFSGQFTGTAGACRYGPFGPPPPSQASSGQARMFPNAPYLPSCLESQPAIRNQGYS
...............AAA......AAAA.....................AAA......AAAAAA...........
..........................RRRR....................RRRRR....................
.........................................DDDDDDDD..........................
...........................................................................

  155  160  165  170  175  180  185  190  195  200  205  210  215  220  225
TVTFDGTPSYGHTPSHHAAQFPNHSFKHEDPMGQQGSLGEQQYSVPPPVYGCHTPTDSCTGSQALLLRTPYSSDN
................AAAAA..............................AAAAAA................AA
................RRRR.......................................................
..........................................................DDDDDDDDDDDDDD...
...........................................................................

  230  235  240  245  250  255  260  265  270  275  280  285  290  295  300
LYQMTSQLECMTWNQMNLGATLKGVAAGSSSSVKWTEGQSNHSTGYESDNHTTPILCGAQYRIHTHGVFRGIQDV
AAAAAAAA............AAA.AAA.....................................AAAAAAAAAAA
..................RRRRRRRRRR.....RRRR.............................RRRR.....
DDDDDD...............DDDDDDDDDDD...........................................
.............................................................ddddd.........

  305  310  315  320  325  330  335  340  345  350  355  360  365  370  375
RRVPGVAPTLVRSASETSEKRPFMCAYPGCNKRYFKLSHLQMHSRKHTGEKPYQCDFKDCERRFSRSDQLKRHQR
AAAAA..AAAAAAAAAAA..........................................AAAA.AAAAAAAAA.
....RRRRR.......................RRRR.......................................
.......DDDDDD..............................................................
...........................................................................

  380  385  390  395  400  405  410  415  420  425  430  435  440  445  450
RHTGVKPFQCKTCQRKFSRSDHLKTHTRTHTGKTSEKPFSCRWPSCQKKFARSDELVRHHNMHQRNMTKLQLAL
.............AAAA.AAAA..AA.....AAAA..........AAA....AAAAAAAA...AAA........
................................................RRRR..RRRR................
..........................................................................
..................dddddddddddd............................................
```

*Fig. 8A*

```
    5    10   15   20   25   30   35   40   45   50   55   60   65   70   75
MGSDVRDLNALLPAVSSLGGGGGCGLPVSGAAQWAPVLDFAPPGASAYGSLGGPAPPPAPPPPPPPPPHSFIKQE
.....AAAAAAAAAAAAAAAA.......AAAAAA.........AAAAAAAAAAAA...................
...........................RRRR...........................................
..........................................................................
..........................................................................

   80   85   90   95  100  105  110  115  120  125  130  135  140  145  150
PSWGGAEPHEEQCLSAFTLHFSGQFTGTAGACRYGPFGPPPPSQASSGQARMFPNAPYLPSCLESQPTIRNQGYS
.......................AAAA.....................AAA......AAAAAA...........
.........................RRRR....................RRRRR.....................
...................................DDDDDDDDD..............................
..........................................................................

  155  160  165  170  175  180  185  190  195  200  205  210  215  220  225
TVTFDGAPSYGHTPSHHAAQFPNHSFKHEDPMGQQGSLGEQQYSVPPPVYGCHTPTDSCTGSQALLLRTPYSSDN
...............AAAAA..............................AAAAAA................AA
...............RRRR.......................................................
..................................................DDDDDDDDDDDDDD...
..........................................................................

  230  235  240  245  250  255  260  265  270  275  280  285  290  295  300
LYQMTSQLECMTWNQMNLGATLKGMAAGSSSSVKWTEGQSNHGIGYESDNHTAPILCGAQYRIHTHGVFRGIQDV
AAAAAAA............AAA.AAA.....................................AAAAAAAAAAA
..................RRRRRRRRRR.....RRRR.............................RRRR.....
DDDDDD..............DDDDDDDDDD............................................
.......................................................ddddd.........

  305  310  315  320  325  330  335  340  345  350  355  360  365  370  375
RRVSGVAPTLVRSASETSEKRPFMCAYPGCNKRYFKLSHLQMHSRKHTGEKPYQCDFKDCERRFSRSDQLKRHQR
AAAAA..AAAAAAAAAAA.........................................AAAA.AAAAAAAAA.
....RRRRR.......................RRRR......................................
..DDDDDDDDDDD.............................................................
..........................................................................

  380  385  390  395  400  405  410  415  420  425  430  435  440  445  450
RHTGVKPFQCKTCQRKFSRSDHLKTHTRTHTGKTSEKPFSCRWHSCQKKFARSDELVRHHNMHQRNMTKLHVAL
.............AAAA.AAAA..AA.....AAAA...........AA....AAAAAAAA...AAAA.......
...............................................RRRR..RRRR................
..........................................................................
................ddddddddddd...............................................
```

*Fig. 8B*

TABLE 1: Characteristics of Recombinant WT1 Proteins Used for Serological Analysis

| NAME | Recombinant Protein | WT1 Amino Acid Position | Molecular Weight |
|---|---|---|---|
| WT1/full-length | Ral2-WT1 full length fusion protein | aa 1-449 | 85kDa |
| WT1/N-terminus | TRX-WT1 N-terminus fusion protein | aa 1-249 | 60kDa |
| WT1/C-terminus | WT1 C-terminus protein | aa 267-449 | 50kDa |

*Fig. 18*

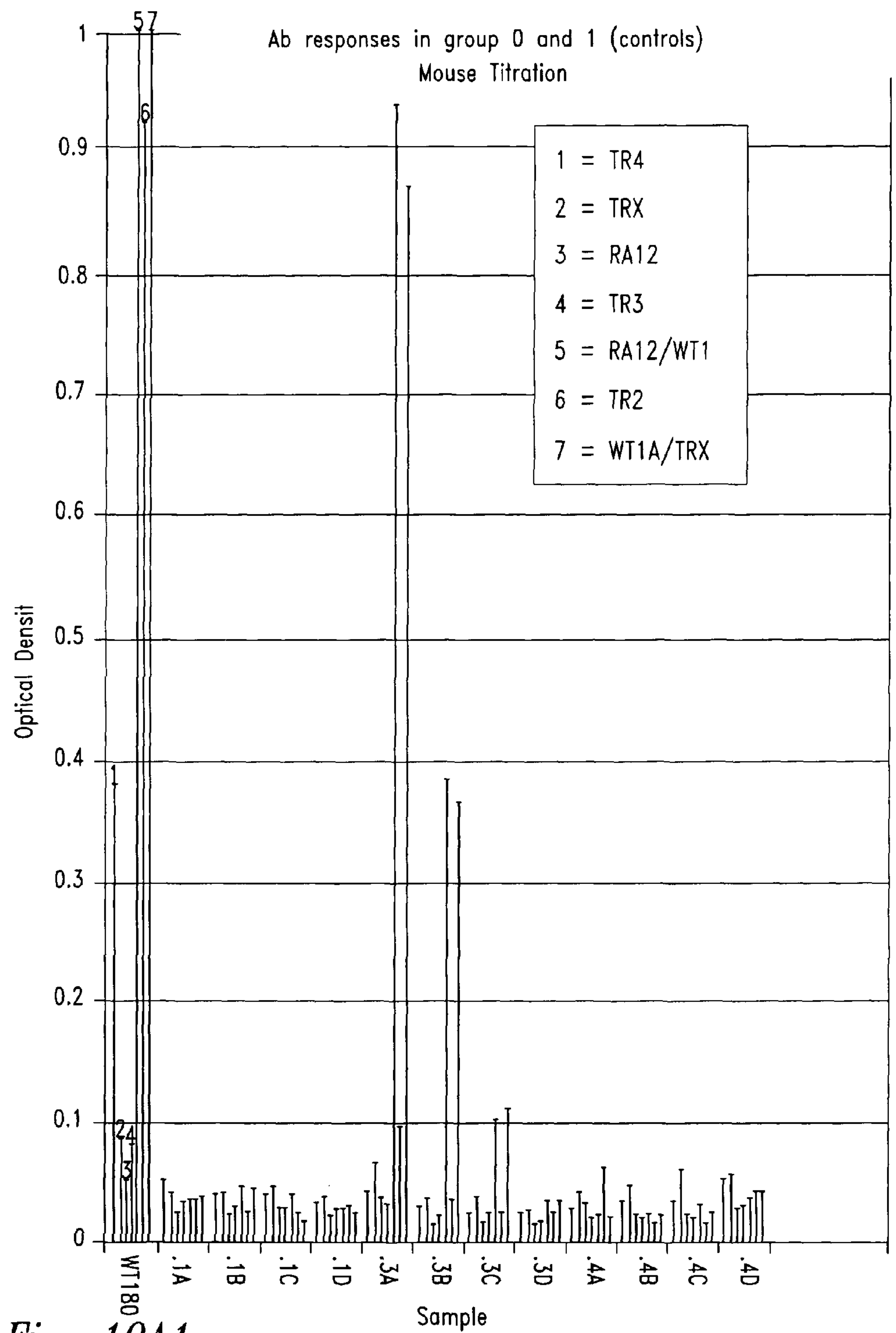
*Fig. 19A1* Control groups. A: 1:500 Dilution, B: 1:2000, C: 1:8000, D: 1:16000

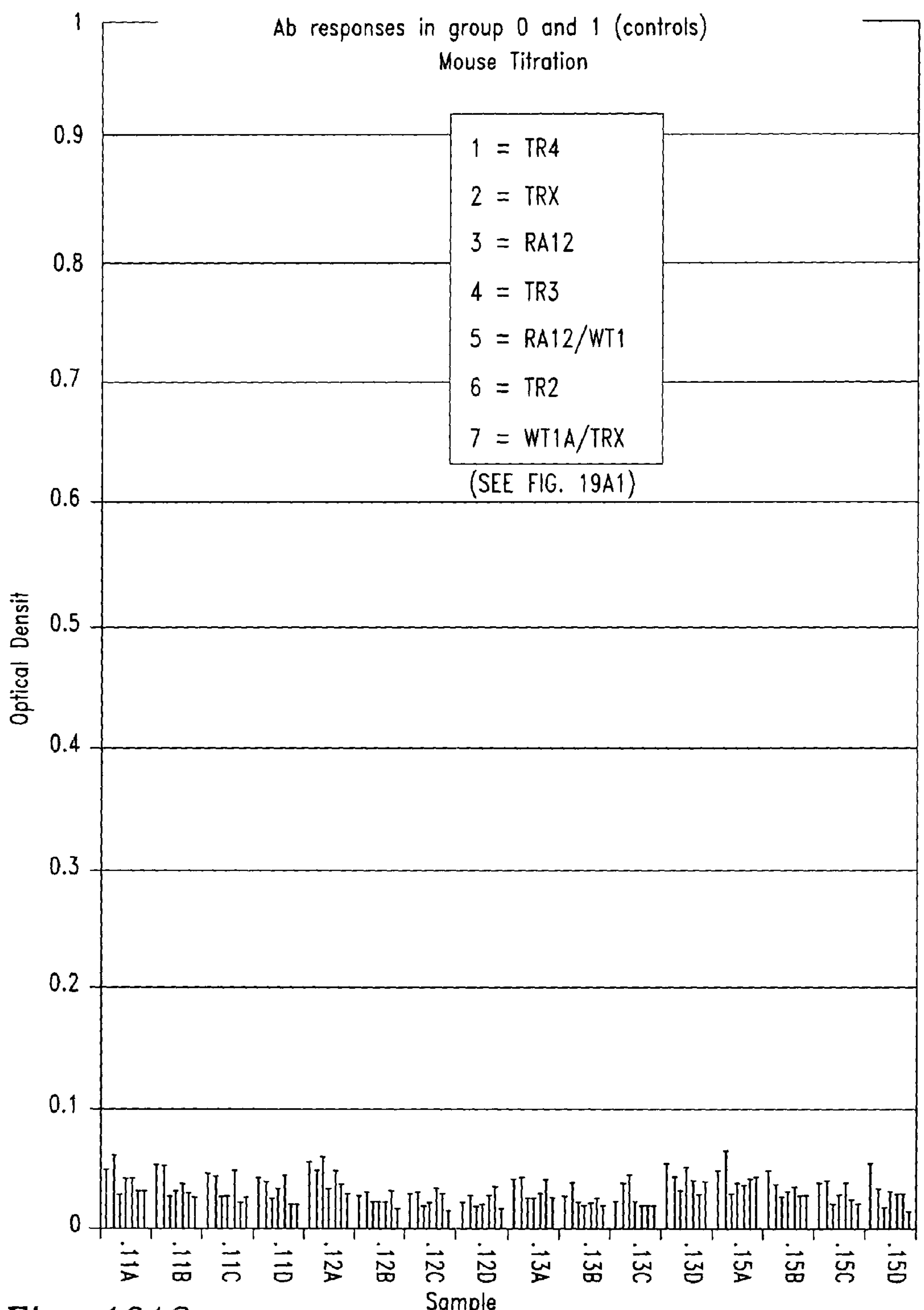
*Fig. 19A2* Control groups. A: 1:500 Dilution, B: 1:2000, C: 1:8000, D: 1:16000

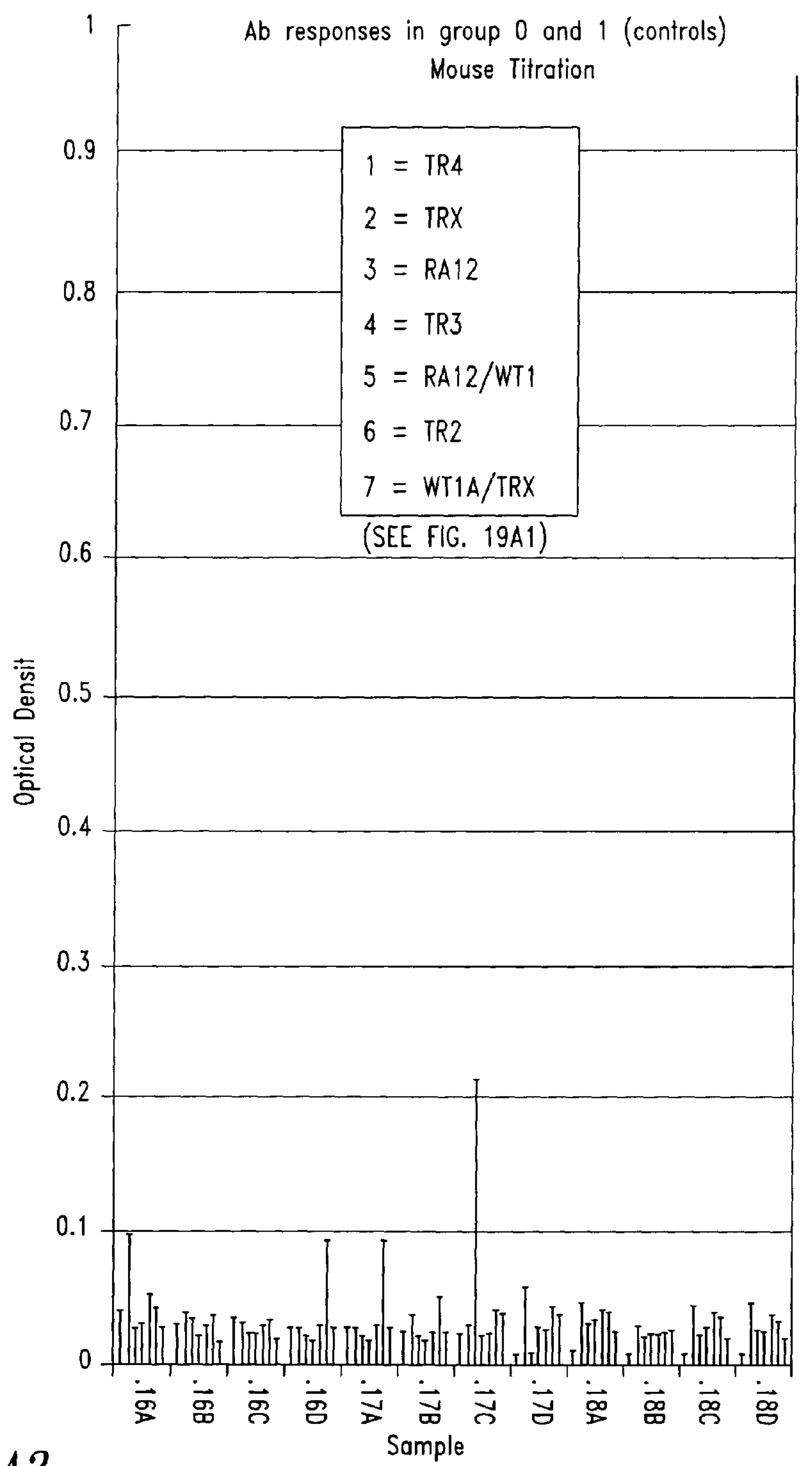
*Fig. 19A3* Control groups. A: 1:500 Dilution, B: 1:2000, C: 1:8000, D: 1:16000

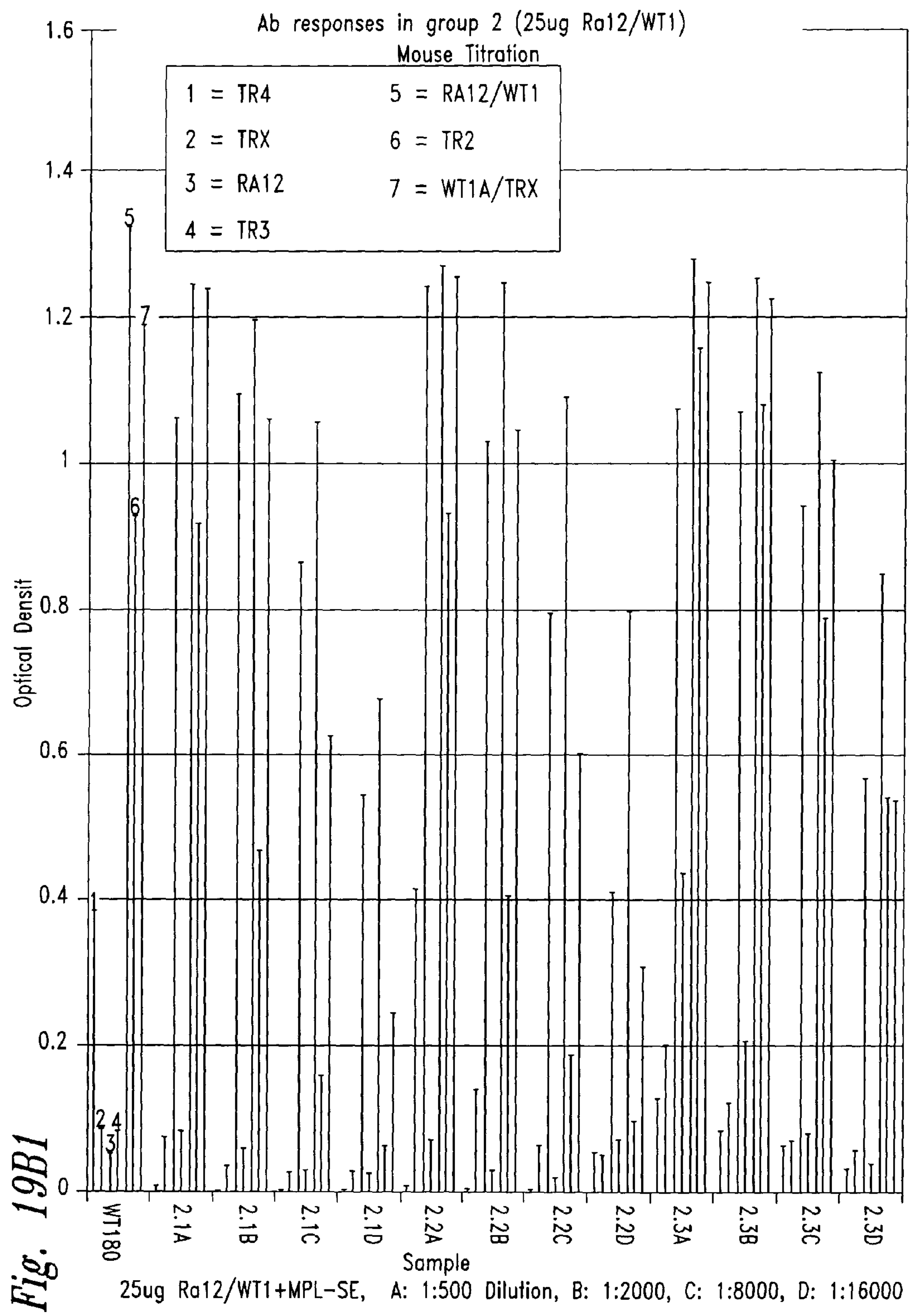
*Fig. 19B1*

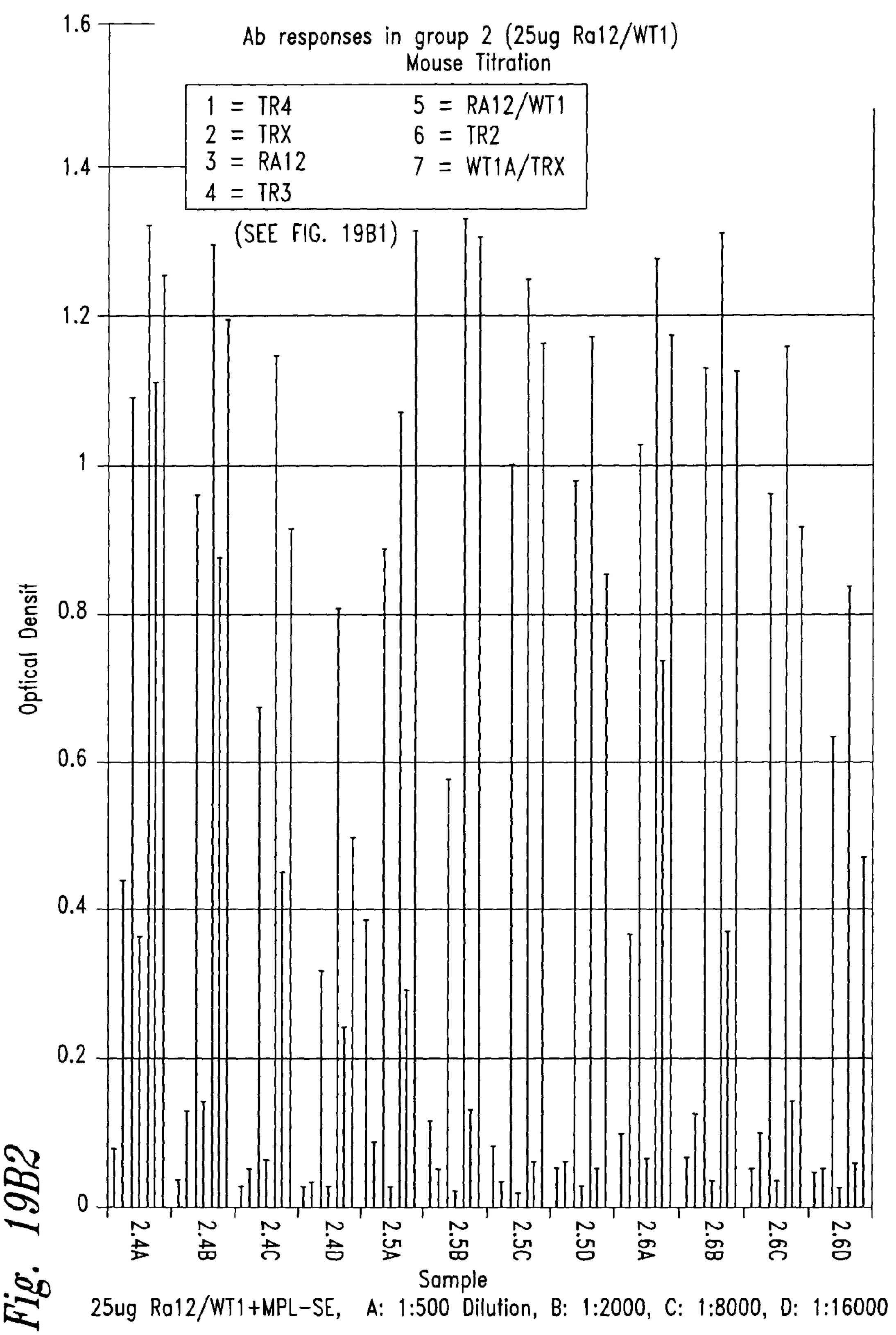
*Fig. 19B2*

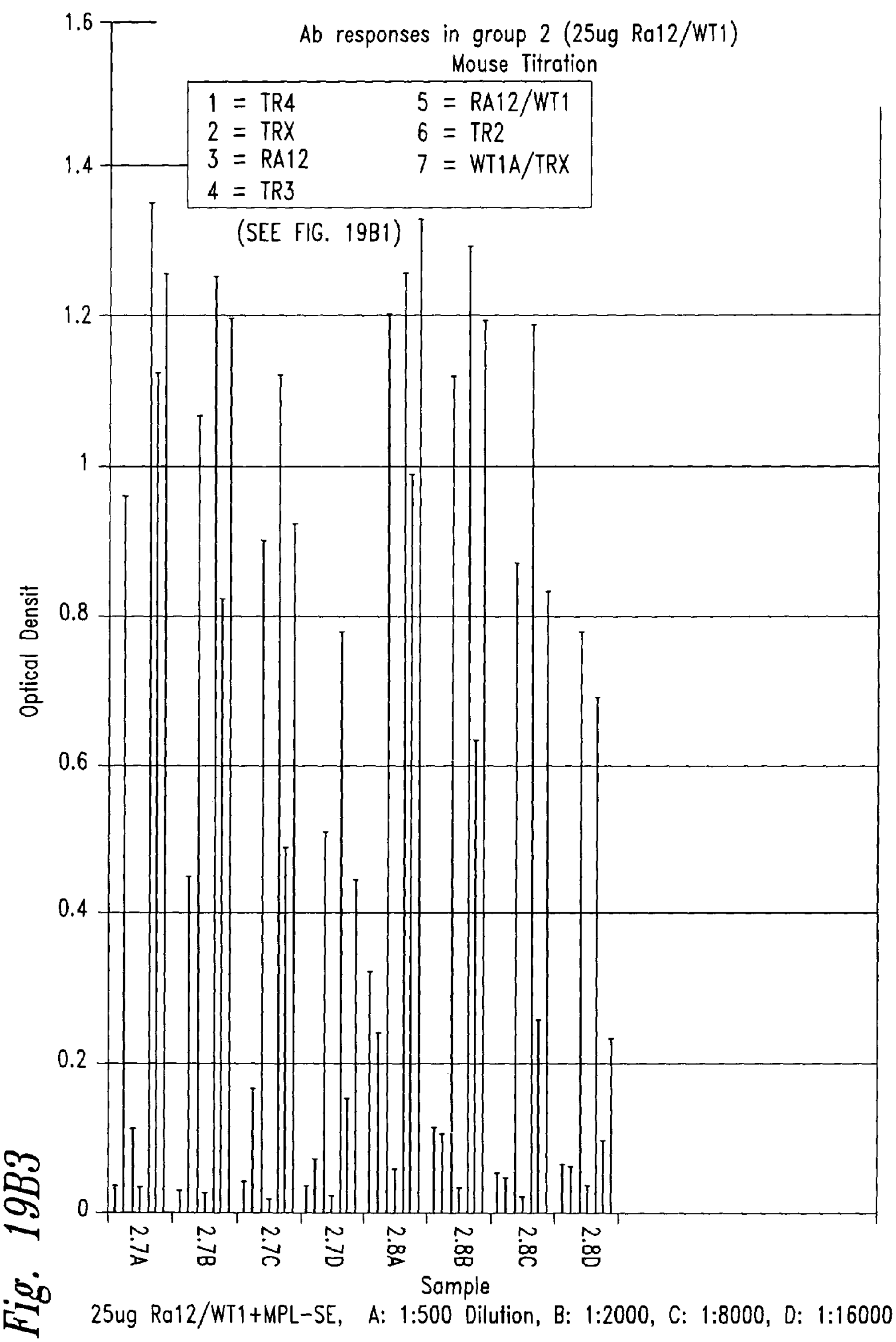
*Fig. 19B3*

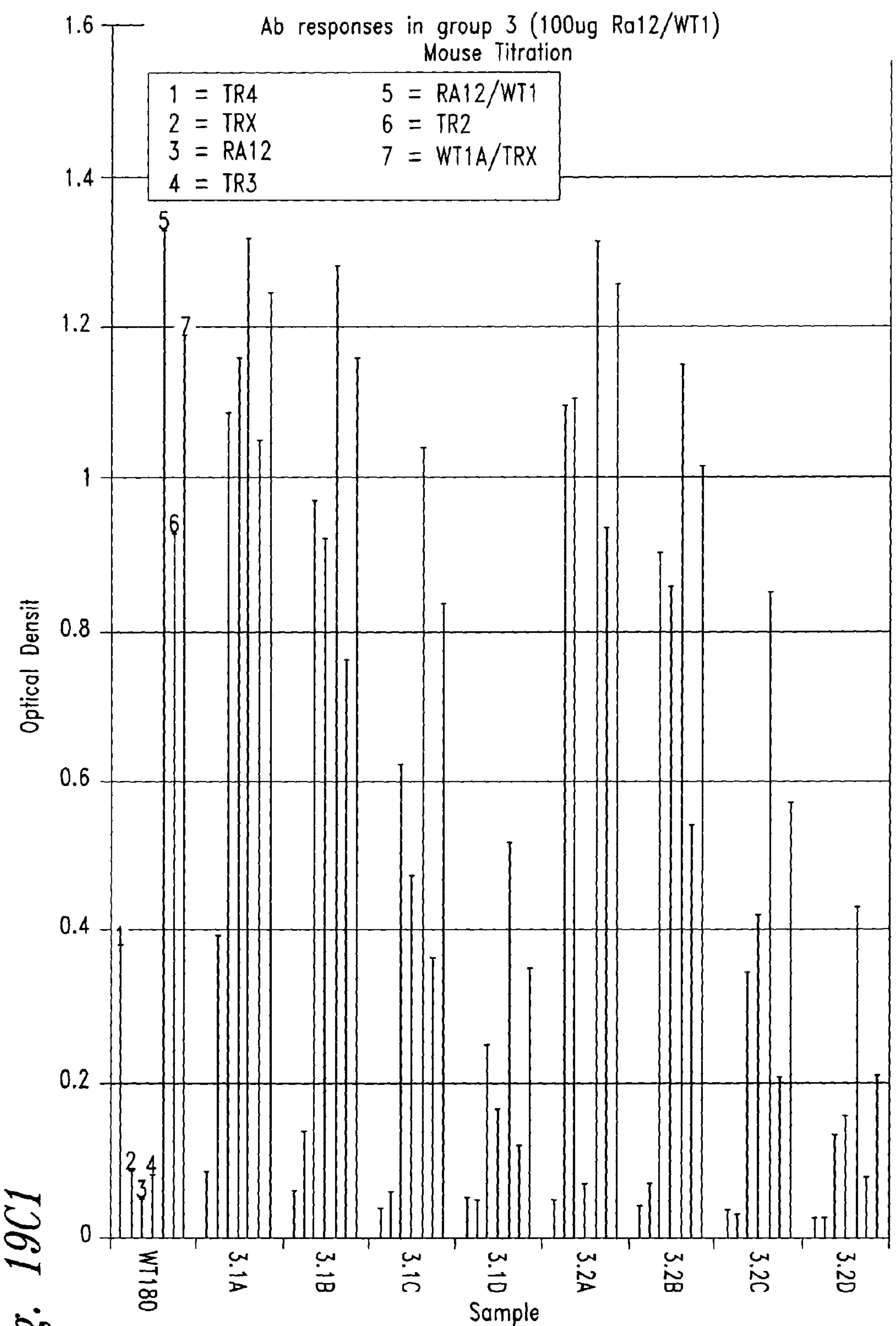
*Fig. 19C1*

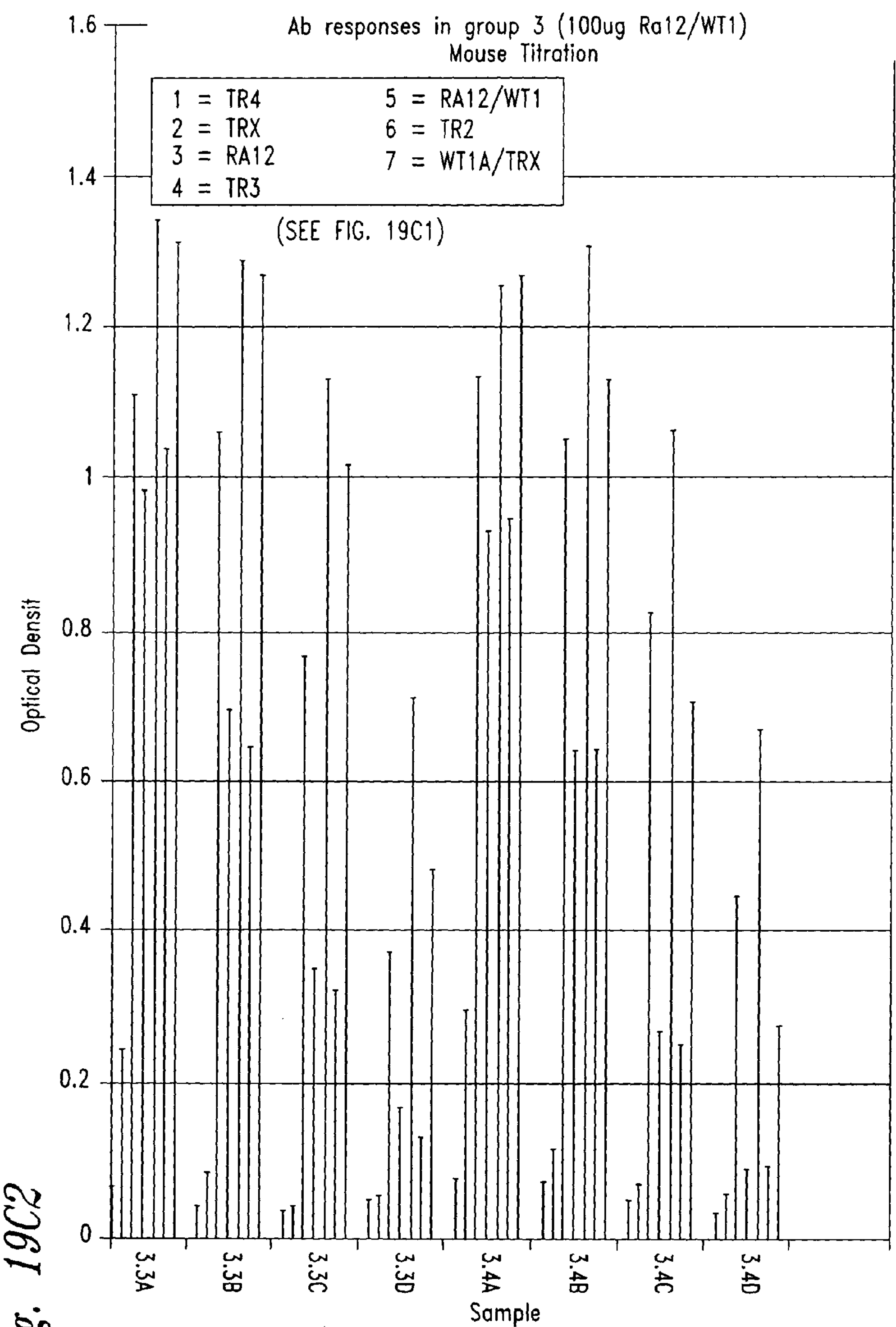
WT1. Dose Titration. Ab responses to WT1. 100ug Ra12-WT1+MPL-SE.
A: 1:500 Dilution, B: 1:2000, C: 1:8000, D: 1:16000
*Fig. 19C2*

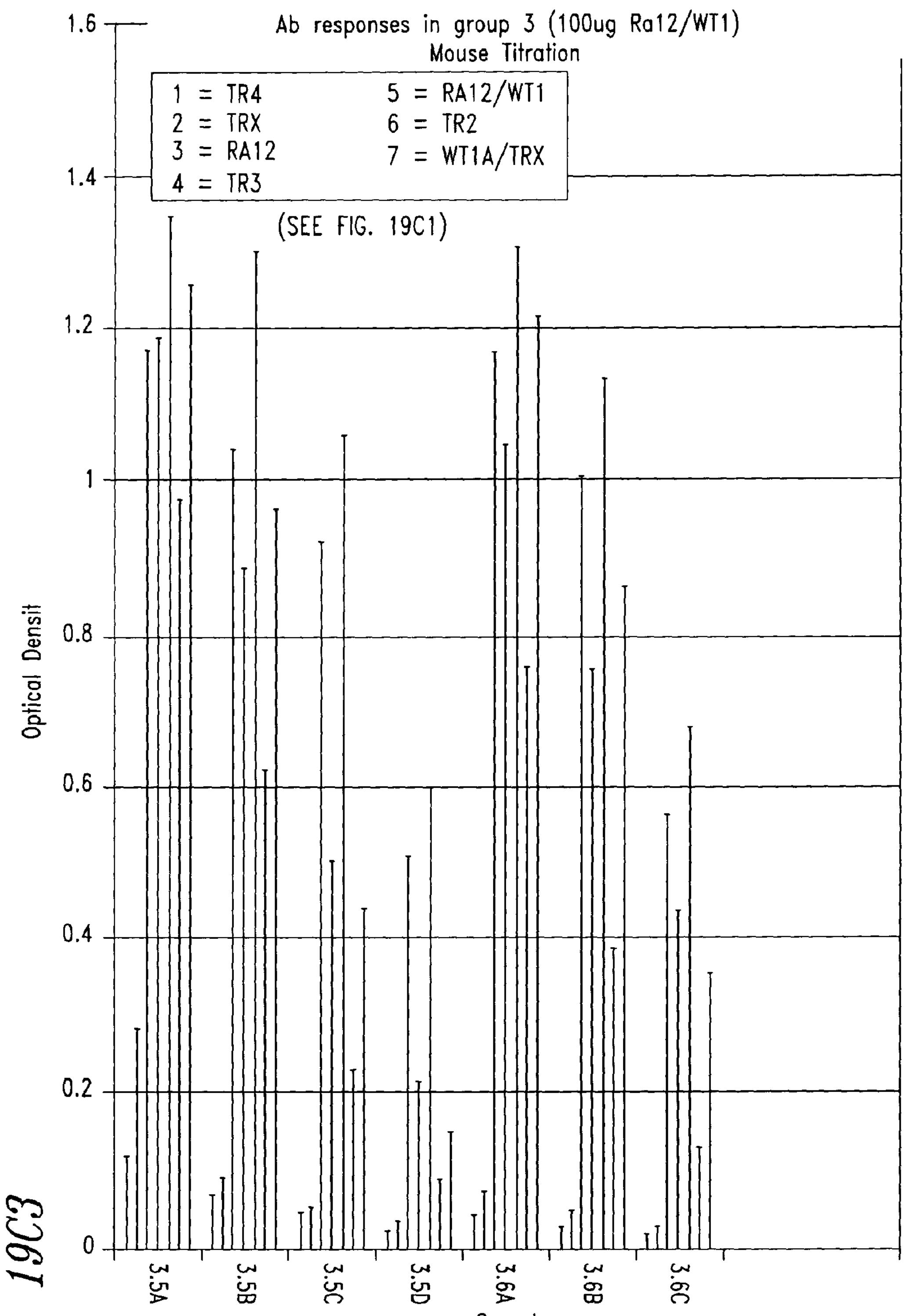
WT1. Dose Titration. Ab responses to WT1. 100ug Ra12-WT1+MPL-SE.
A: 1:500 Dilution, B: 1:2000, C: 1:8000, D: 1:16000
*Fig. 19C3*

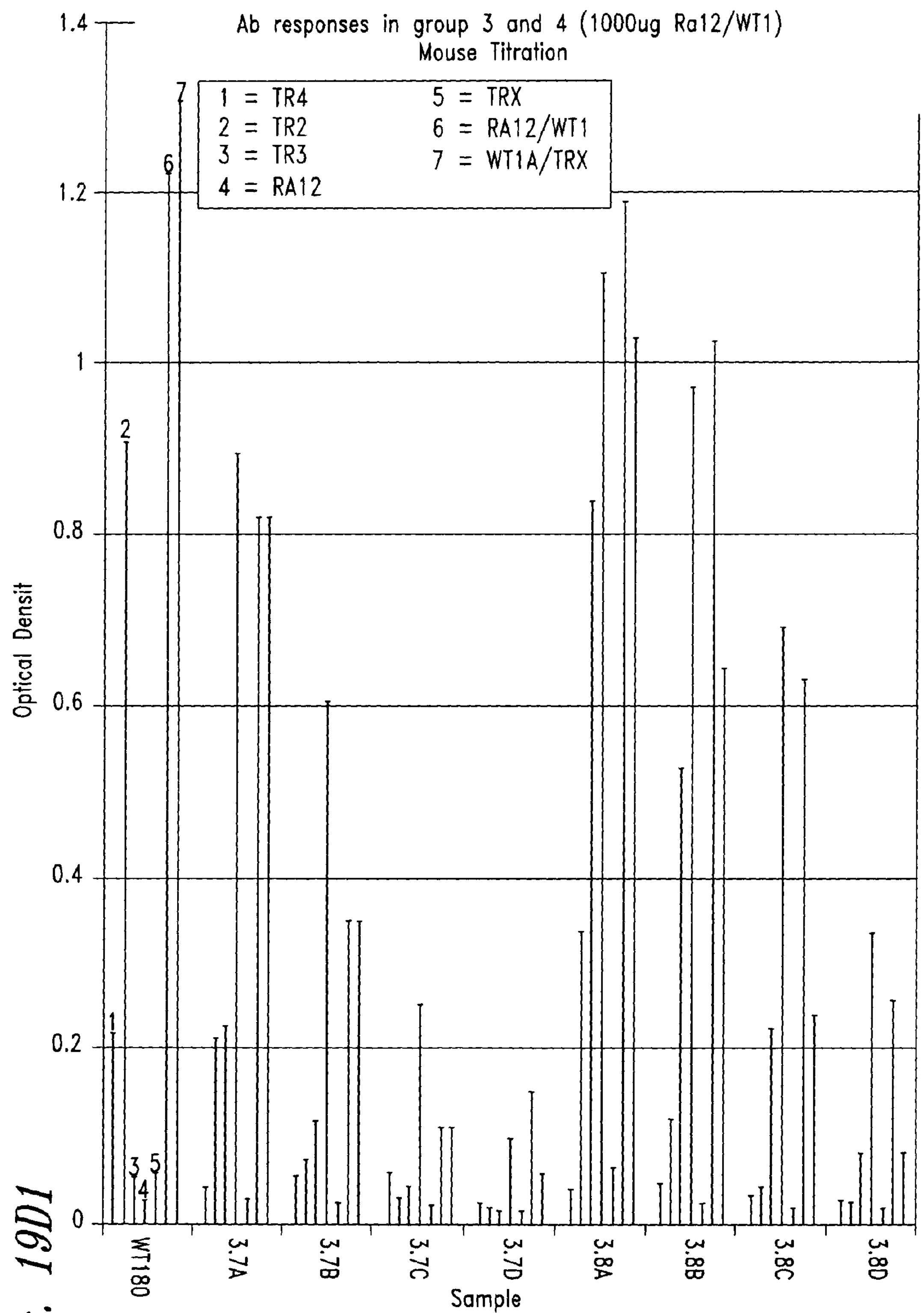
WT1. Dose Titration. Ab responses to WT1. 1000ug Ra12-WT1+MPL-SE.
A: 1:500 Dilution, B: 1:2000, C: 1:8000, D: 1:16000
*Fig. 19D1*

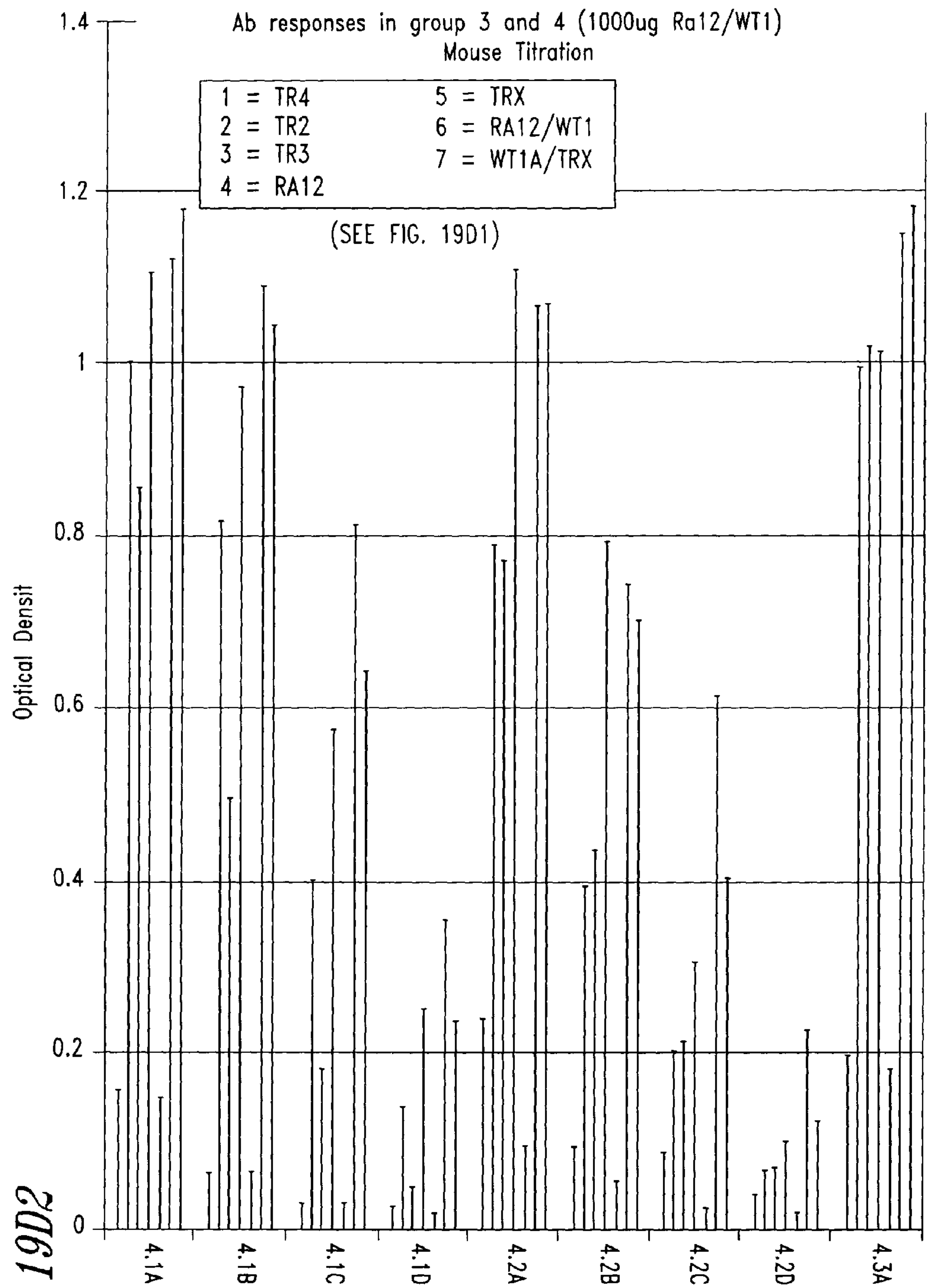
WT1. Dose Titration. Ab responses to WT1. 1000ug Ra12-WT1+MPL-SE.
A: 1:500 Dilution, B: 1:2000, C: 1:8000, D: 1:16000
*Fig. 19D2*

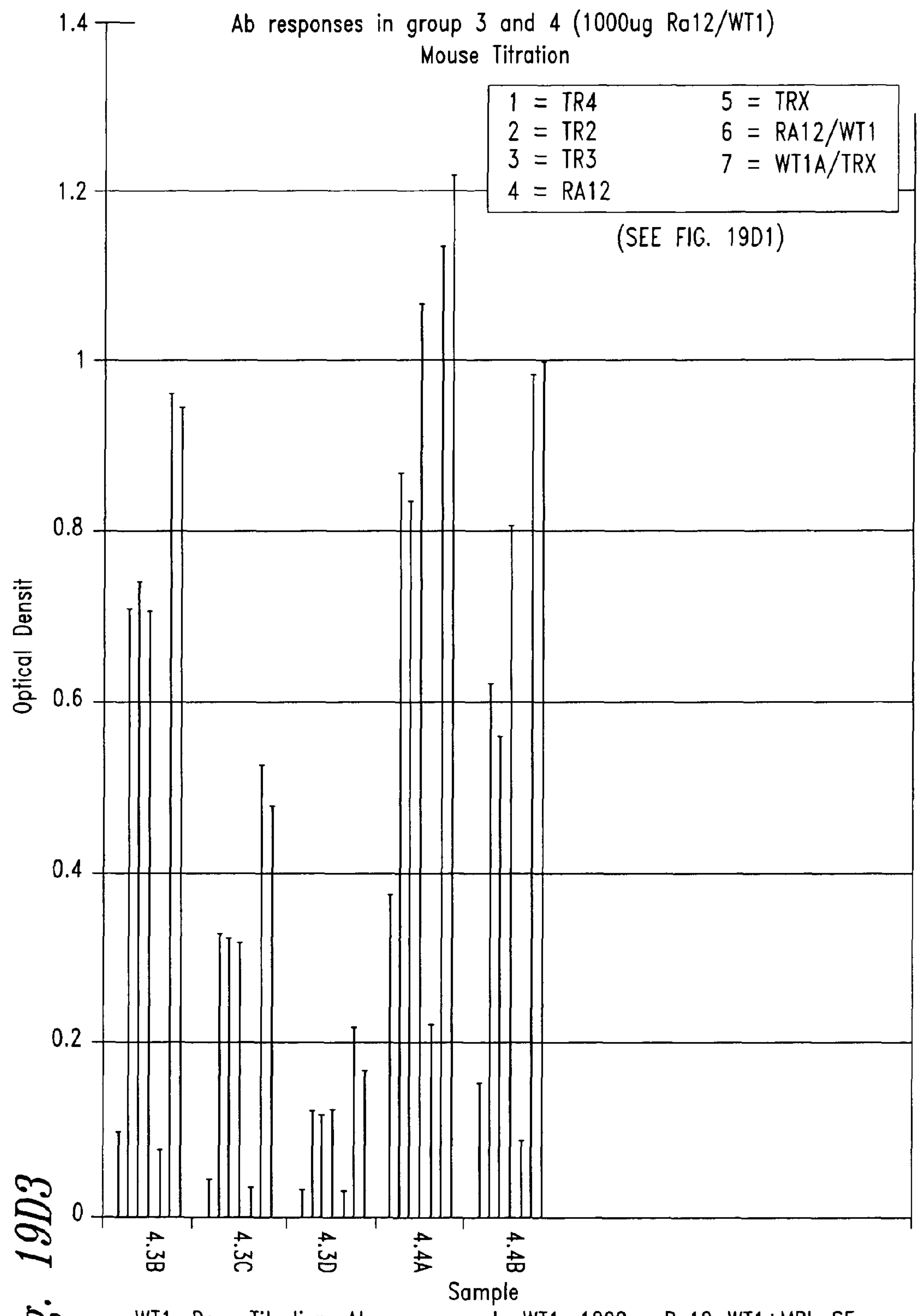
WT1. Dose Titration. Ab responses to WT1. 1000ug Ra12-WT1+MPL-SE.
A: 1:500 Dilution, B: 1:2000, C: 1:8000, D: 1:16000
*Fig. 19D3*

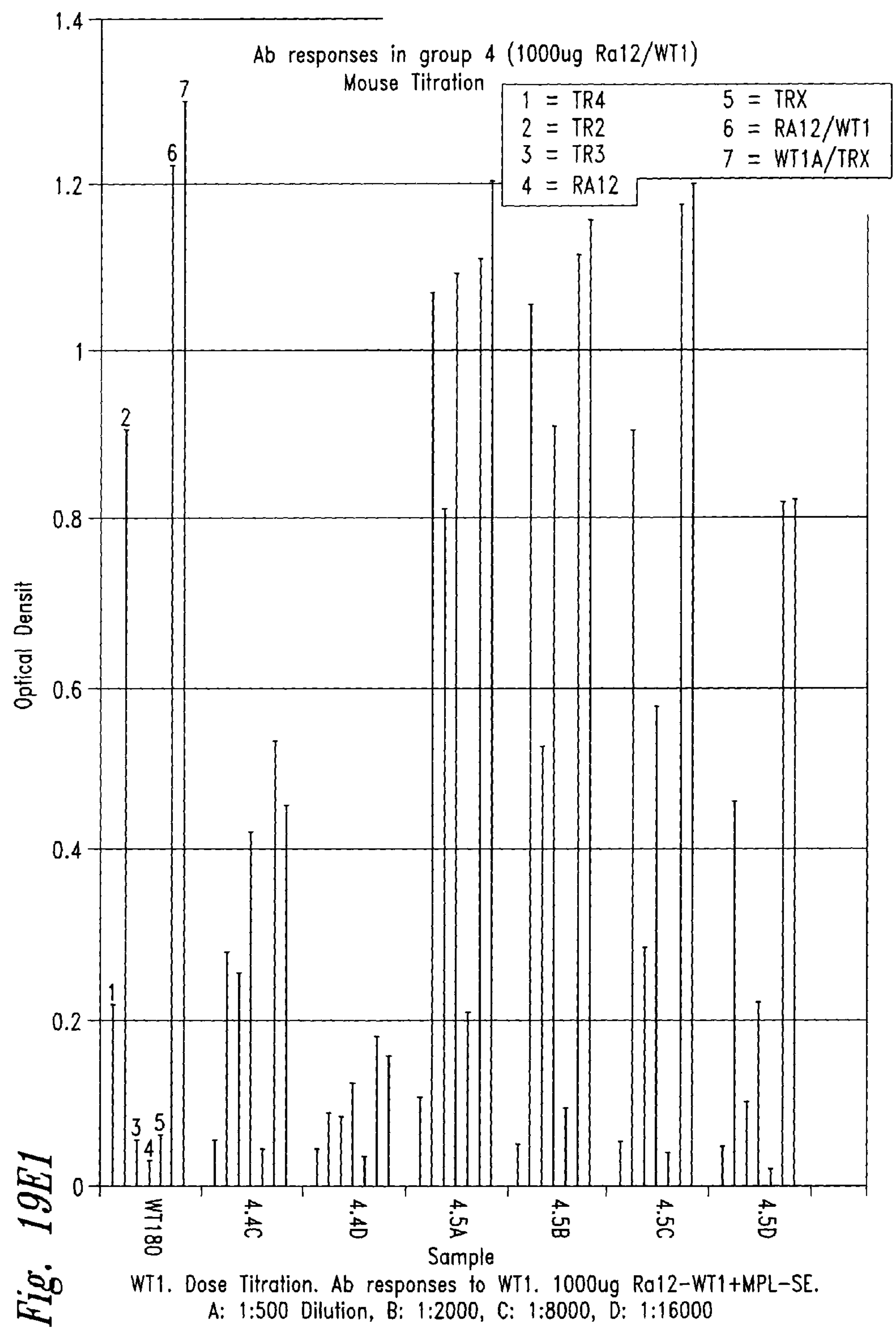
WT1. Dose Titration. Ab responses to WT1. 1000ug Ra12-WT1+MPL-SE.
A: 1:500 Dilution, B: 1:2000, C: 1:8000, D: 1:16000
*Fig. 19E1*

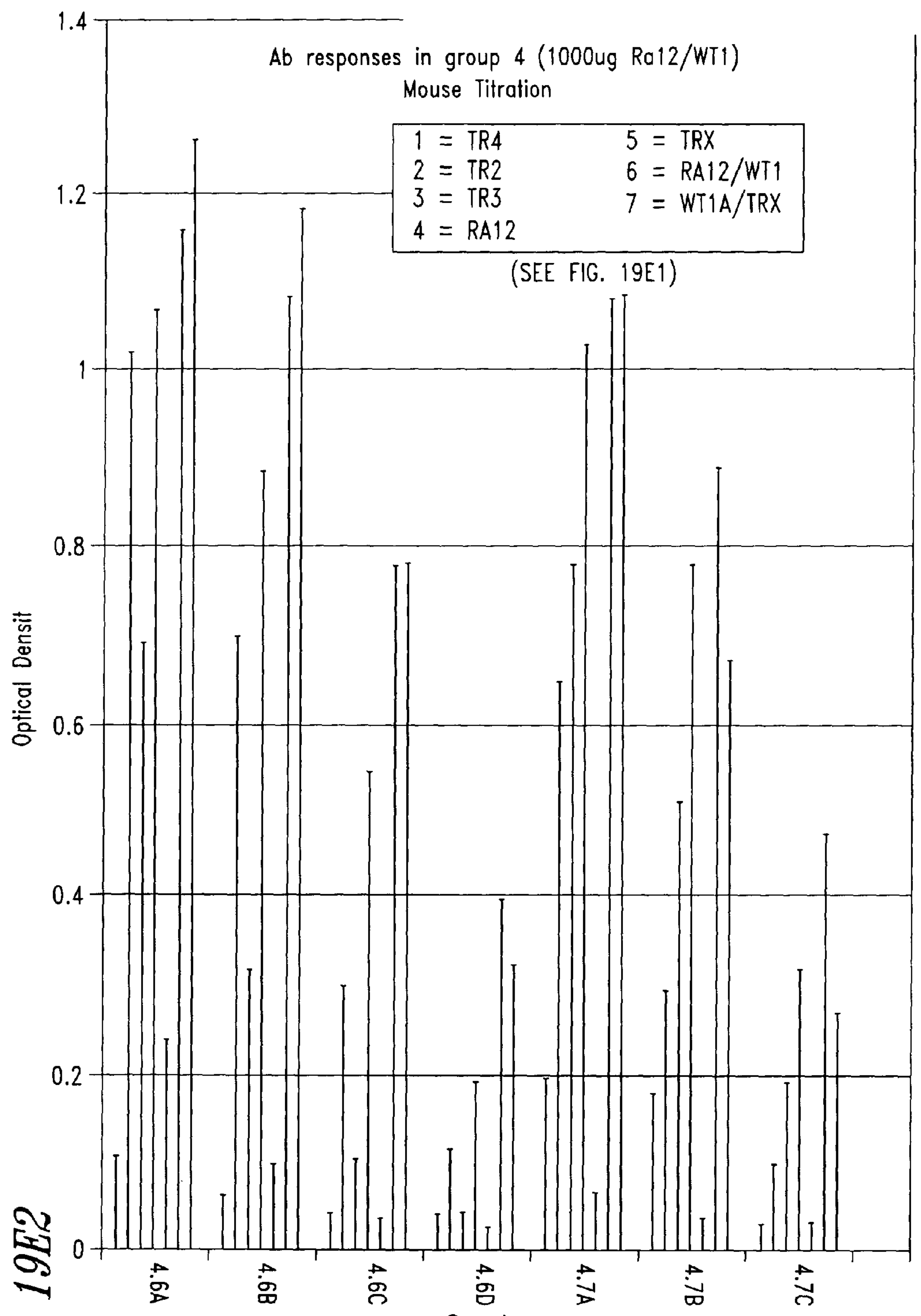
WT1. Dose Titration. Ab responses to WT1. 1000ug Ra12-WT1+MPL-SE.
A: 1:500 Dilution, B: 1:2000, C: 1:8000, D: 1:16000
*Fig. 19E2*

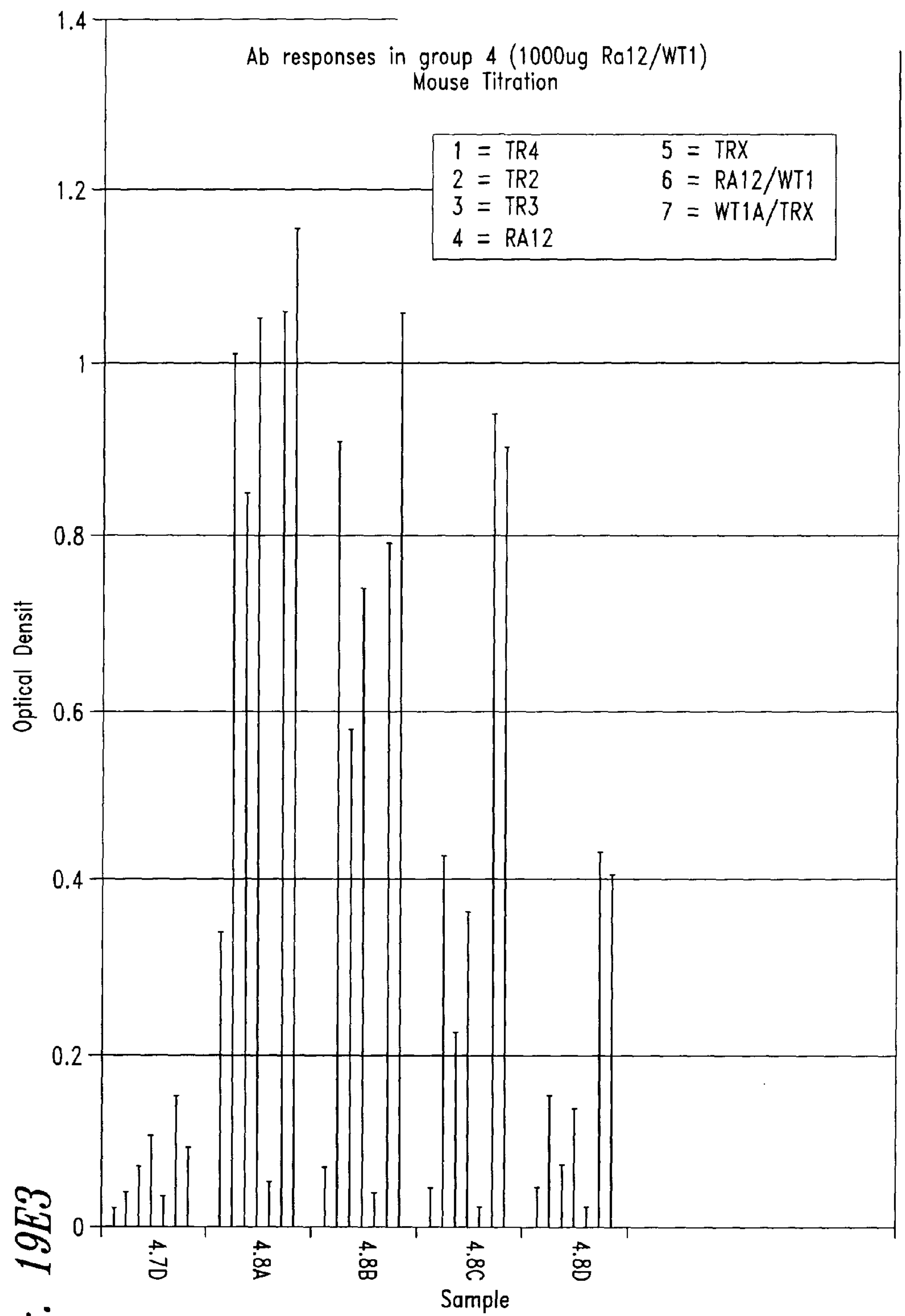
WT1. Dose Titration. Ab responses to WT1. 1000ug Ra12-WT1+MPL-SE.
A: 1:500 Dilution, B: 1:2000, C: 1:8000, D: 1:16000
*Fig. 19E3*

WT1 expression in human DC following adeno WT1 and Vaccinia WT1 infection
Control
(uninfected human DC)
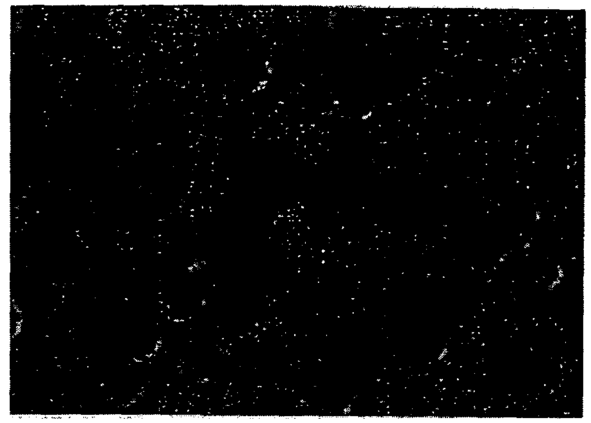
Adeno WT1
(infected human DC)
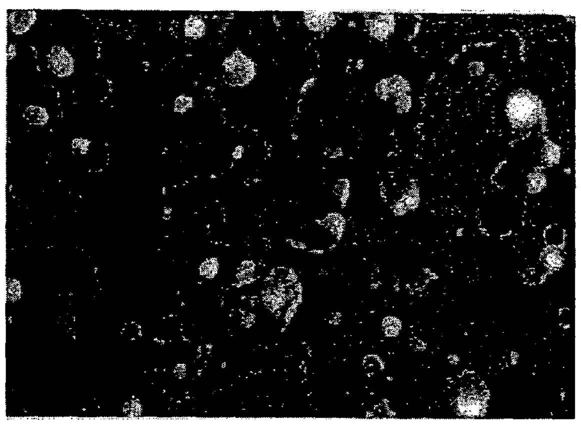
Vaccinia WT1
(infected human DC)
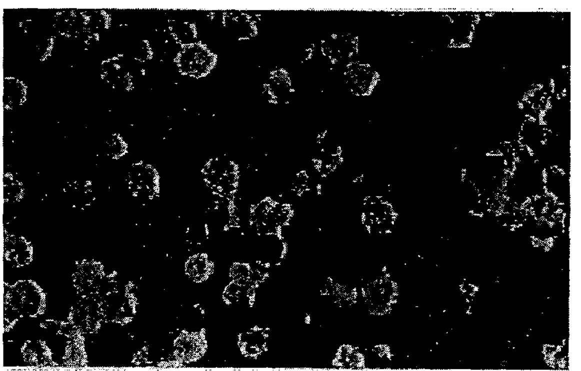
*Fig. 21*

WT1 can be expressed reproducible in human DC following adeno WT1 infection and is not induced by a control Adeno infection
Control (Adeno EGFP infected human DC)
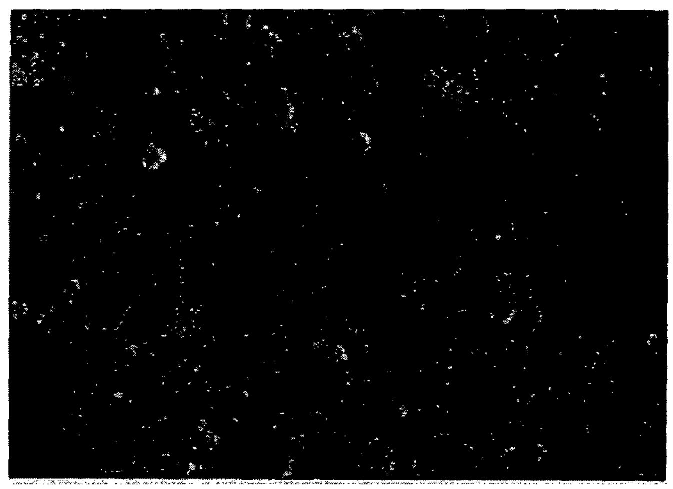
Vaccinia WT1 (infected human DC)
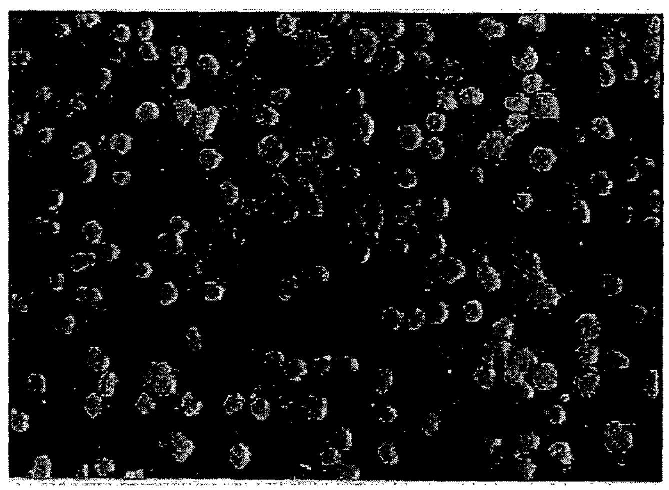
*Fig. 22*

COMPOSITIONS AND METHODS FOR WT1 SPECIFIC IMMUNOTHERAPY

STATEMENT REGARDING FEDERALLY SPONSORED RESEARCH OR DEVELOPMENT

This invention was made in part with government support under Grant Nos. IR43 CA81752-01A1and R37CA30558 awarded by the National Institutes of Health. The U.S. Government has certain rights in this invention.

STATEMENT REGARDING SEQUENCE LISTING

The Sequence Listing associated with this application is provided in text format in Lieu of a paper copy, and is hereby incorporated by reference into the specification. The name of the text file containing the Sequence Listing is 21021_465C6_SEQUENCE_LISTING.txt. The text file is 165 KB, was created on Apr. 15, 2010, and is being submitted electronically via EFS-Web.

BACKGROUND OF THE INVENTION

1. Field of the Invention

The present invention relates generally to the immunotherapy of malignant diseases such as leukemia and cancers. The invention is more specifically related to compositions for generating or enhancing an immune response to WT1, and to the use of such compositions for preventing and/or treating malignant diseases.

2. Description of the Related Art

Cancer and leukemia are significant health problems in the United States and throughout the world. Although advances have been made in detection and treatment of such diseases, no vaccine or other universally successful method for prevention or treatment of cancer and leukemia is currently available. Management of the diseases currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and the high mortality continues to be observed in many cancer patients.

Immunotherapies have the potential to substantially improve cancer and leukemia treatment and survival. Recent data demonstrate that leukemia can be cured by immunotherapy in the context of bone marrow transplantation (e.g., donor lymphocyte infusions). Such therapies may involve the generation or enhancement of an immune response to a tumor-associated antigen (TAA). However, to date relatively few TAAs are known and the generation of an immune response against such antigens has, with rare exception, not been shown to be therapeutically beneficial.

Accordingly, there is a need in the art for improved methods for leukemia and cancer prevention and therapy. The present invention fulfills these needs and further provides other related advantages.

BRIEF SUMMARY OF THE INVENTION

Briefly stated, this invention provides compositions and methods for the diagnosis and therapy of diseases such as leukemia and cancer. In one aspect, the present invention provides polypeptides comprising an immunogenic portion of a native WT1, or a variant thereof that differs in one or more substitutions, deletions, additions and/or insertions such that the ability of the variant to react with antigen-specific antisera and/or T-cell lines or clones is not substantially diminished. Within certain embodiments, the polypeptide comprises no more than 16 consecutive amino acid residues of a native WT1 polypeptide. Within other embodiments, the polypeptide comprises an immunogenic portion of amino acid residues 1-174 of a native WT1 polypeptide or a variant thereof, wherein the polypeptide comprises no more than 16 consecutive amino acid residues present within amino acids 175 to 449 of the native WT1 polypeptide. The immunogenic portion preferably binds to an MHC class I and/or class II molecule. Within certain embodiments, the polypeptide comprises a sequence selected from the group consisting of (a) sequences recited in any one or more of Tables II-XLVI, (b) variants of the foregoing sequences that differ in one or more substitutions, deletions, additions and/or insertions such that the ability of the variant to react with antigen-specific antisera and/or T-cell lines or clones is not substantially diminished and (c) mimetics of the polypeptides recited above, such that the ability of the mimetic to react with antigen-specific antisera and/or T cell lines or clones is not substantially diminished.

Within other embodiments, the polypeptide comprises a sequence selected from the group consisting of (a) ALLPAVPSL (SEQ ID NO:34), GATLKGVAA (SEQ ID NO:88), CMTWNQMNL (SEQ ID NOs: 49 and 258), SCLESQPTI (SEQ ID NOs: 199 and 296), SCLESQPAI (SEQ ID NO: 198), NLYQMTSQL (SEQ ID NOs: 147 and 284), ALLPAVSSL (SEQ ID NOs: 35 and 255), RMFPNAPYL (SEQ ID NOs: 185 and 293), VLDFAPPGA (SEQ ID NO:241), VLDFAPPGAS (SEQ ID NO:411), (b) variants of the foregoing sequences that differ in one or more substitutions, deletions, additions and/or insertions such that the ability of the variant to react with antigen-specific antisera and/or T-cell lines or clones is not substantially diminished and (c) mimetics of the polypeptides recited above, such that the ability of the mimetic to react with antigen-specific antisera and/or T cell lines or clones is not substantially diminished. Mimetics may comprises amino acids in combination with one or more amino acid mimetics or may be entirely nonpeptide mimetics.

Within further aspects, the present invention provides polypeptides comprising a variant of an immunogenic portion of a WT1 protein, wherein the variant differs from the immunogenic portion due to substitutions at between 1 and 3 amino acid positions within the immunogenic portion such that the ability of the variant to react with antigen-specific antisera and/or T-cell lines or clones is enhanced relative to a native WT1 protein.

The present invention further provides WT1 polynucleotides that encode a WT1 polypeptide as described above.

Within other aspects, the present invention provides pharmaceutical compositions and vaccines. Pharmaceutical compositions may comprise a polypeptide or mimetic as described above and/or one or more of (i) a WT1 polynucleotide; (ii) an antibody or antigen-binding fragment thereof that specifically binds to a WT1 polypeptide; (iii) a T cell that specifically reacts with a WT1 polypeptide or (iv) an antigen-presenting cell that expresses a WT1 polypeptide, in combination with a pharmaceutically acceptable carrier or excipient. Vaccines comprise a polypeptide as described above and/or one or more of (i) a WT1 polynucleotide, (ii) an antigen-presenting cell that expresses a WT1 polypeptide or (iii) an anti-idiotypic antibody, and a non-specific immune response enhancer. Within certain embodiments, less than 23 consecutive amino acid residues, preferably less than 17 amino acid residues, of a native WT1 polypeptide are present within a WT1 polypeptide employed within such pharmaceutical compositions and vaccines. The immune response enhancer may be an adjuvant. Preferably, an immune response enhancer enhances a T cell response.

The present invention further provides methods for enhancing or inducing an immune response in a patient, comprising administering to a patient a pharmaceutical composition or vaccine as described above. In certain embodiments, the patient is a human.

The present invention further provides methods for inhibiting the development of a malignant disease in a patient, comprising administering to a patient a pharmaceutical composition or vaccine as described above. Malignant diseases include, but are not limited to leukemias (e.g., acute myeloid, acute lymphocytic and chronic myeloid) and cancers (e.g., breast, lung, thyroid or gastrointestinal cancer or a melanoma). The patient may, but need not, be afflicted with the malignant disease, and the administration of the pharmaceutical composition or vaccine may inhibit the onset of such a disease, or may inhibit progression and/or metastasis of an existing disease.

The present invention further provides, within other aspects, methods for removing cells expressing WT1 from bone marrow and/or peripheral blood or fractions thereof, comprising contacting bone marrow, peripheral blood or a fraction of bone marrow or peripheral blood with T cells that specifically react with a WT1 polypeptide, wherein the step of contacting is performed under conditions and for a time sufficient to permit the removal of WT1 positive cells to less than 10%, preferably less than 5% and more preferably less than 1%, of the number of myeloid or lymphatic cells in the bone marrow, peripheral blood or fraction. Bone marrow, peripheral blood and fractions may be obtained from a patient afflicted with a disease associated with WT1 expression, or may be obtained from a human or non-human mammal not afflicted with such a disease.

Within related aspects, the present invention provides methods for inhibiting the development of a malignant disease in a patient, comprising administering to a patient bone marrow, peripheral blood or a fraction of bone marrow or peripheral blood prepared as described above. Such bone marrow, peripheral blood or fractions may be autologous, or may be derived from a related or unrelated human or non-human animal (e.g., syngeneic or allogeneic).

In other aspects, the present invention provides methods for stimulating (or priming) and/or expanding T cells, comprising contacting T cells with a WT1 polypeptide under conditions and for a time sufficient to permit the stimulation and/or expansion of T cells. Such T cells may be autologous, allogeneic, syngeneic or unrelated WT1-specific T cells, and may be stimulated in vitro or in vivo. Expanded T cells may, within certain embodiments, be present within bone marrow, peripheral blood or a fraction of bone marrow or peripheral blood, and may (but need not) be clonal. Within certain embodiments, T cells may be present in a mammal during stimulation and/or expansion. WT1-specific T cells may be used, for example, within donor lymphocyte infusions.

Within related aspects, methods are provided for inhibiting the development of a malignant disease in a patient, comprising administering to a patient T cells prepared as described above. Such T cells may, within certain embodiments, be autologous, syngeneic or allogeneic.

The present invention further provides, within other aspects, methods for monitoring the effectiveness of an immunization or therapy for a malignant disease associated with WT1 expression in a patient. Such methods are based on monitoring antibody, CD4+ T cell and/or CD8+ T cell responses in the patient. Within certain such aspects, a method may comprise the steps of: (a) incubating a first biological sample with one or more of: (i) a WT1 polypeptide; (ii) a polynucleotide encoding a WT1 polypeptide; or (iii) an antigen presenting cell that expresses a WT1 polypeptide, wherein the first biological sample is obtained from a patient prior to a therapy or immunization, and wherein the incubation is performed under conditions and for a time sufficient to allow immunocomplexes to form; (b) detecting immunocomplexes formed between the WT1 polypeptide and antibodies in the biological sample that specifically bind to the WT1 polypeptide; (c) repeating steps (a) and (b) using a second biological sample obtained from the same patient following therapy or immunization; and (d) comparing the number of immunocomplexes detected in the first and second biological samples, and therefrom monitoring the effectiveness of the therapy or immunization in the patient.

Within certain embodiments of the above methods, the step of detecting comprises (a) incubating the immunocomplexes with a detection reagent that is capable of binding to the immunocomplexes, wherein the detection reagent comprises a reporter group, (b) removing unbound detection reagent, and (c) detecting the presence or absence of the reporter group. The detection reagent may comprise, for example, a second antibody, or antigen-binding fragment thereof, capable of binding to the antibodies that specifically bind to the WT1 polypeptide or a molecule such as Protein A. Within other embodiments, a reporter group is bound to the WT1 polypeptide, and the step of detecting comprises removing unbound WT1 polypeptide and subsequently detecting the presence or absence of the reporter group.

Within further aspects, methods for monitoring the effectiveness of an immunization or therapy for a malignant disease associated with WT1 expression in a patient may comprise the steps of: (a) incubating a first biological sample with one or more of: (i) a WT1 polypeptide; (ii) a polynucleotide encoding a WT1 polypeptide; or (iii) an antigen presenting cell that expresses a WT1 polypeptide, wherein the biological sample comprises CD4+ and/or CD8+ T cells and is obtained from a patient prior to a therapy or immunization, and wherein the incubation is performed under conditions and for a time sufficient to allow specific activation, proliferation and/or lysis of T cells; (b) detecting an amount of activation, proliferation and/or lysis of the T cells; (c) repeating steps (a) and (b) using a second biological sample comprising CD4+ and/or CD8+ T cells, wherein the second biological sample is obtained from the same patient following therapy or immunization; and (d) comparing the amount of activation, proliferation and/or lysis of T cells in the first and second biological samples, and therefrom monitoring the effectiveness of the therapy or immunization in the patient.

The present invention further provides methods for inhibiting the development of a malignant disease associated with WT1 expression in a patient, comprising the steps of: (a) incubating $CD4^+$ and/or CD8+ T cells isolated from a patient with one or more of: (i) a WT1 polypeptide; (ii) a polynucleotide encoding a WT1 polypeptide; or (iii) an antigen presenting cell that expresses a WT1 polypeptide, such that the T cells proliferate; and (b) administering to the patient an effective amount of the proliferated T cells, and therefrom inhibiting the development of a malignant disease in the patient. Within certain embodiments, the step of incubating the T cells may be repeated one or more times.

Within other aspects, the present invention provides methods for inhibiting the development of a malignant disease associated with WT1 expression in a patient, comprising the steps of: (a) incubating $CD4^+$ and/or CD8+ T cells isolated from a patient with one or more of: (i) a WT1 polypeptide; (ii) a polynucleotide encoding a WT1 polypeptide; or (iii) an antigen presenting cell that expresses a WT1 polypeptide, such that the T cells proliferate; (b) cloning one or more cells that proliferated; and (c) administering to the patient an effective amount of the cloned T cells.

Within other aspects, methods are provided for determining the presence or absence of a malignant disease associated with WT1 expression in a patient, comprising the steps of: (a) incubating $CD4^+$ and/or CD8+ T cells isolated from a patient with one or more of: (i) a WT1 polypeptide; (ii) a polynucleotide encoding a WT1 polypeptide; or (iii) an antigen presenting cell that expresses a WT1 polypeptide; and (b) detecting the presence or absence of specific activation of the T cells, therefrom determining the presence or absence of a malignant disease associated with WT1 expression. Within certain embodiments, the step of detecting comprises detecting the presence or absence of proliferation of the T cells.

Within further aspects, the present invention provides methods for determining the presence or absence of a malignant disease associated with WT1expression in a patient, comprising the steps of: (a) incubating a biological sample obtained from a patient with one or more of: (i) a WT1 polypeptide; (ii) a polynucleotide encoding a WT1 polypeptide; or (iii) an antigen presenting cell that expresses a WT1 polypeptide, wherein the incubation is performed under conditions and for a time sufficient to allow immunocomplexes to form; and (b) detecting immunocomplexes formed between the WT1 polypeptide and antibodies in the biological sample that specifically bind to the WT1 polypeptide; and therefrom determining the presence or absence of a malignant disease associated with WT1 expression.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1 depicts a comparison of the mouse (MO) and human (HU) WT1 protein sequences (SEQ ID NOS: 320 and 319 respectively).

FIG. 6A) or p287-301 (p287), p299-313 (p299), p421-435 (p421) (Vaccine B; FIG. 6B) and spleen cells pulsed with an irrelevant control peptide (irrelevant peptide) at 25 ug/ml and were assayed after 96 hr for proliferation by ($^3$H) thymidine incorporation. Bars represent the stimulation index (SI), which is calculated as the mean of the experimental wells divided by the mean of the control (B6 spleen cells with no antigen).

FIGS. 8A and 8B present the results of TSITES Analysis of human WT1 (SEQ ID NO:319) and mouse WT1 (SEQ ID NO: 320), respectively, for peptides that have the potential to elicit Th responses. Regions indicated by "A" are AMPHI midpoints of blocks, "R" indicates residues matching the Rothbard/'Taylor motif, "D" indicates residues matching the IAd motif, and 'd' indicates residues matching the IEd motif.

FIG. 9A illustrates the lysis of target cells by allogeneic cell lines and FIG. 9B shows the lysis of peptide coated cell lines. In each case, the % lysis (as determined by standard chromium release assays) is shown at three indicated effector: target ratios. Results are provided for lymphoma cells (LSTRA and E10), as well as E10+p235-243 (E10+P235). E10 cells are also referred to herein as EL-4 cells.

FIG. 10A illustrates that T-cells of non-immunized B6 mice do not kill WT1 positive tumor cell lines. FIG. 10B illustrates the lysis of the target cells by allogeneic cell lines. FIGS. 10C and 10D demonstrate the lysis of WT1 positive tumor cell lines, as compared to WT1 negative cell lines in two different experiments. In addition, FIGS. 10C and 10D show the lysis of peptide-coated cell lines (WT1 negative cell line E10 coated with the relevant WT1 peptide P117) In each case, the % lysis (as determined by standard chromium release assays) is shown at three indicated effector:target ratios. Results are provided for lymphoma cells (E10), prostate cancer cells (TRAMP-C), a transformed fibroblast cell line (BLK-SV40), as well as E10+p117.

FIG. 11A shows the cytotoxic activity of the p235-243 specific T cell line against the WT1 negative cell line EL-4 (EL-4, WT1 negative); EL-4 pulsed with the relevant (used for immunization as well as for restimulation) peptide p235-243 (EL-4+p235); EL-4 pulsed with the irrelevant peptides p117-139 (EL-4+p117), p126-134 (EL-4+p126) or p130-138 (EL-4+p130) and the WT1 positive tumor cells BLK-SV40 (BLK-SV40, WT1 positive) and TRAMP-C (TRAMP-C, WT1 positive), as indicated. FIG. 11B shows cytotoxic activity of the p117-139 specific T cell line against EL-4; EL-4 pulsed with the relevant peptide P117-139 (EL-4+p117) and EL-4 pulsed with the irrelevant peptides p123-131 (EL-4+p123), or p128-136 (EL-4+p128); BLK-SV40 and TRAMP-C, as indicated.

FIG. 12A shows the cytotoxic activity of the p117-139 specific T cell line against the WT1 negative cell line EL-4 (EL-4, WT1 negative); the WT1 positive tumor cell line TRAMP-C (TRAMP-C, WT1 positive); TRAMP-C cells incubated with a ten-fold excess (compared to the hot target) of EL-4 cells pulsed with the relevant peptide p117-139 (TRAMP-C+p117 cold target) without $^{51}$Cr labeling and TRAMP-C cells incubated with EL-4 pulsed with an irrelevant peptide without $^{51}$Cr labeling (TRAMP-C+irrelevant cold target), as indicated. FIG. 12B shows the cytotoxic activity of the p117-139 specific T cell line against the WT1 negative cell line EL-4 (EL-4, WT1 negative); the WT1 positive tumor cell line BLK-SV40 (BLK-SV40, WT1 positive); BLK-SV40 cells incubated with the relevant cold target (BLK-SV40+p117 cold target) and BLK-SV40 cells incubated with the irrelevant cold target (BLK-SV40+irrelevant cold target), as indicated.

FIG. 13A shows the cytotoxic activity of the p117-139 specific T cell line against the WT1 negative cell line EL-4 (EL-4, WT1 negative) and EL-4 cells pulsed with the peptides p117-139 (EL-4+p117), p119-127 (EL-4+p119), p120-128 (EL-4+p120), p123-131 (EL-4+p123), p126-134 (EL-4+p126), p128-136 (EL-4+p128), and p130-138 (EL-4+p130). FIG. 13B shows the cytotoxic activity of the CTL line after restimulation with p126-134 against the WT1 negative cell line EL-4, EL-4 cells pulsed with p117-139 (EL-4+p117), p126-134 (EL-4+p126) and the WT1 positive tumor cell line TRAMP-C. FIG. 13C shows the cytotoxic activity of the CTL line after restimulation with p130-138 against EL-4, EL-4 cells pulsed with p117-139 (EL-4+p117), p130-138 (EL-4+p130) and the WT1 positive tumor cell line TRAMP-C.

FIG. 18 provides the characteristics of the recombinant WT1 proteins used for serological analysis.

FIG. 19A-19E is a bar graph depicting the antibody responses in mice elicited by vaccination with different doses of WT1 protein.

FIG. 21 is a photograph of human DC, examined by fluorescent microscopy, expressing WT1 following adeno WT1 and Vaccinia WT1 infection.

FIG. 22 is a photograph that demonstrates that WT1 expression in human DC is reproducible following adeno WT1 infection and is not induced by a control Adeno infection.

DETAILED DESCRIPTION OF THE INVENTION

Figure 2:
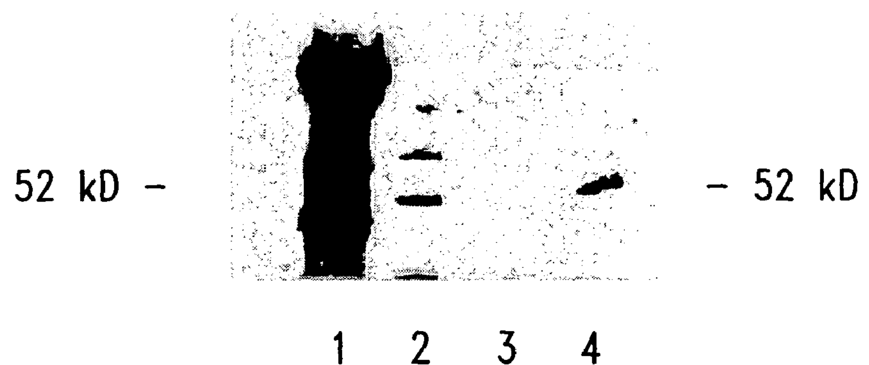
FIG. 2 is a Western blot illustrating the detection of WT1 specific antibodies in patients with hematological malignancy (AML). Lane 1 shows molecular weight markers; lane 2 shows a positive control (WT1 positive human leukemia cell line immunoprecipitated with a WT1 specific antibody); lane 3 shows a negative control (WT1 positive cell line immunoprecipitated with mouse sera); and lane 4 shows a WT1 positive cell line immunoprecipitated with sera of a patient with AML. For lanes 2-4, the immunoprecipitate was separated by gel electrophoresis and probed with a WT1 specific antibody.

As noted above, the present invention is generally directed to compositions and methods for the immunotherapy and diagnosis of malignant diseases. The compositions described herein may include WT1 polypeptides, WT1 polynucleotides, antigen-presenting cells (APC, e.g., dendritic cells) that express a WT1 polypeptide, agents such as antibodies that bind to a WT1 polypeptide and/or immune system cells (e.g., T cells) specific for WT1. WT1 Polypeptides of the present invention generally comprise at least a portion of a Wilms Tumor gene product (WT1) or a variant thereof. Nucleic acid sequences of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a portion of a WT1 polypeptide. T cells that may be employed within such compositions are generally T cells (e.g., $CD4^+$ and/or $CD8^+$) that are specific for a WT1 polypeptide. Certain methods described herein further employ antigen-presenting cells that express a WT1 polypeptide as provided herein.

The present invention is based on the discovery that an immune response raised against a Wilms Tumor (WT) gene product (e.g., WT1) can provide prophylactic and/or therapeutic benefit for patients afflicted with malignant diseases characterized by increased WT1 gene expression. Such diseases include, but are not limited to, leukemias (e.g., acute myeloid leukemia (AML), chronic myeloid leukemia (CML), acute lymphocytic leukemia (ALL) and childhood ALL), as well as many cancers such as lung, breast, thyroid and gastrointestinal cancers and melanomas. The WT1 gene was originally identified and isolated on the basis of a cytogenetic deletion at chromosome 11p13 in patients with Wilms' tumor (see Call et al., U.S. Pat. No. 5,350,840). The gene consists of 10 exons and encodes a zinc finger transcription factor, and sequences of mouse and human WT1 proteins are provided in FIG. 1 and SEQ ID NOs: 319 and 320.

WT1 Polypeptides

Within the context of the present invention, a WT1 polypeptide is a polypeptide that comprises at least an immunogenic portion of a native WT1 (i.e., a WT1 protein expressed by an organism that is not genetically modified), or a variant thereof, as described herein. A WT1 polypeptide may be of any length, provided that it comprises at least an immunogenic portion of a native protein or a variant thereof. In other words, a WT1 polypeptide may be an oligopeptide (i.e., consisting of a relatively small number of amino acid residues, such as 8-10 residues, joined by peptide bonds), a full length WT1 protein (e.g., present within a human or non-human animal, such as a mouse) or a polypeptide of intermediate size. Within certain embodiments, the use of WT1 polypeptides that contain a small number of consecutive amino acid residues of a native WT1 polypeptide is preferred. Such polypeptides are preferred for certain uses in which the generation of a T cell response is desired. For example, such a WT1 polypeptide may contain less than 23, preferably no more than 18, and more preferably no more than 15 consecutive amino acid residues, of a native WT1 polypeptide. Polypeptides comprising nine consecutive amino acid residues of a native WT1 polypeptide are generally suitable for such purposes. Additional sequences derived from the native protein and/or heterologous sequences may be present within any WT1 polypeptide, and such sequences may (but need not) possess further immunogenic or antigenic properties. Polypeptides as provided herein may further be associated (covalently or noncovalently) with other polypeptide or non-polypeptide compounds.

An "immunogenic portion," as used herein is a portion of a polypeptide that is recognized (i.e., specifically bound) by a B-cell and/or T-cell surface antigen receptor. Certain preferred immunogenic portions bind to an MHC class I or class II molecule. As used herein, an immunogenic portion is said to "bind to" an MHC class I or class II molecule if such binding is detectable using any assay known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., *J. Immunol.* 152:163, 1994). Alternatively, functional peptide competition assays that are known in the art may be employed. Certain immunogenic portions have one or more of the sequences recited within one or more of Tables II-XIV. Representative immunogenic portions include, but are not limited to, RDLNALLPAVPSLGGGG (human WT1 residues 6-22; SEQ ID NO: 1), PSQASSGQARMFPNAPYLPSCLE (human and mouse WT1 residues 117-139; SEQ ID NOs: 2 and 3 respectively), GATLKGVAAGSSSSVKWTE (human WT1 residues 244-262; SEQ ID NO: 4), GATLKGVAA (human WT1 residues 244-252; SEQ ID NO: 88), CMTWNQMNL (human and mouse WT1 residues 235-243; SEQ ID NOs: 49 and 258 respectively), SCLESQPTI (mouse WT1 residues 136-144; SEQ ID NO: 296), SCLESQPAI (human WT1 residues 136-144; SEQ ID NO: 198), NLYQMTSQL (human and mouse WT1 residues 225-233; SEQ ID NOs: 147 and 284 respectively); ALLPAVSSL (mouse WT1 residues 10-18; SEQ ID NO: 255); RMFPNAPYL (human and mouse WT1 residues 126-134; SEQ ID NOs: 185 and 293 respectively), VLDFAPPGA (human WT1 residues 37-45; SEQ ID NO: 241), or VLDFAPPGAS (human WT1 residues 37-46; SEQ ID NO: 411). Further immunogenic portions are provided herein, and others may generally be identified using well known techniques, such as those summarized in Paul, *Fundamental Immunology,* 3rd ed., 243-247 (Raven Press, 1993) and references cited therein. Representative techniques for identifying immunogenic portions include screening polypeptides for the ability to react with antigen-specific antisera and/or T-cell lines or clones. An immunogenic portion of a native WT1 polypeptide is a portion that reacts with such antisera and/or T-cells at a level that is not substantially less than the reactivity of the full length WT1 (e.g., in an ELISA and/or T-cell reactivity assay). In other words, an immunogenic portion may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988.

Alternatively, immunogenic portions may be identified using computer analysis, such as the Tsites program (see Rothbard and Taylor, *EMBO J.* 7:93-100, 1988; Deavin et al., *Mol. Immunol.* 33:145-155, 1996), which searches for peptide motifs that have the potential to elicit Th responses. CTL peptides with motifs appropriate for binding to murine and human class I or class II MHC may be identified according to BIMAS (Parker et al., *J. Immunol.* 152:163, 1994) and other HLA peptide binding prediction analyses. To confirm immunogenicity, a peptide may be tested using an HLA A2 transgenic mouse model and/or an in vitro stimulation assay using dendritic cells, fibroblasts or peripheral blood cells.

As noted above, a composition may comprise a variant of a native WT1 protein. A polypeptide "variant," as used herein, is a polypeptide that differs from a native polypeptide in one or more substitutions, deletions, additions and/or insertions, such that the immunogenicity of the polypeptide is retained (i.e., the ability of the variant to react with antigen-specific antisera and/or T-cell lines or clones is not substantially diminished relative to the native polypeptide). In other words, the ability of a variant to react with antigen-specific antisera and/or T-cell lines or clones may be enhanced or unchanged, relative to the native polypeptide, or may be diminished by less than 50%, and preferably less than 20%, relative to the native polypeptide. Such variants may generally be identified by modifying one of the above polypeptide sequences and evaluating the reactivity of the modified polypeptide with antisera and/or T-cells as described herein. It has been found, within the context of the present invention, that a relatively small number of substitutions (e.g., 1 to 3) within an immunogenic portion of a WT1 polypeptide may serve to enhance the ability of the polypeptide to elicit an immune response. Suitable substitutions may generally be identified by using computer programs, as described above, and the effect confirmed based on the reactivity of the modified polypeptide with antisera and/or T-cells as described herein. Accordingly, within certain preferred embodiments, a WT1 polypeptide comprises a variant in which 1 to 3 amino acid resides within an immunogenic portion are substituted such that the ability to react with antigen-specific antisera and/or T-cell lines or clones is statistically greater than that for the unmodified polypeptide. Such substitutions are preferably located within an MHC binding site of the polypeptide, which may be identified as described above. Preferred substitutions allow increased binding to MHC class I or class II molecules.

Certain variants contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants may also (or alternatively) be modified by, for example, the deletion or addition of amino acids that have minimal influence on the immunogenicity, secondary structure and hydropathic nature of the polypeptide.

In a preferred embodiment, a variant polypeptide of the WT1 N-terminus (amino acids 1-249) is constructed, wherein the variant polypeptide is capable of binding to an antibody that recognizes full-length WT1 and/or WT1 N-terminus polypeptide. A non-limiting example of an antibody is anti WT1 antibody WT180 (Santa Cruz Biotechnology, Inc., Santa Cruz, Calif.).

As noted above, WT1 polypeptides may be conjugated to a signal (or leader) sequence at the N-terminal end of the protein which co-translationally or post-translationally directs transfer of the protein. A polypeptide may also, or alternatively, be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

WT1 polypeptides may be prepared using any of a variety of well known techniques. Recombinant polypeptides encoded by a WT1 polynucleotide as described herein may be readily prepared from the polynucleotide. In general, any of a variety of expression vectors known to those of ordinary skill in the art may be employed to express recombinant WT1 polypeptides. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. The concentrate may then be applied to a suitable purification matrix such as an affinity matrix or an ion exchange resin. Finally, one or more reverse phase HPLC steps can be employed to further purify a recombinant polypeptide. Such techniques may be used to prepare native polypeptides or variants thereof. For example, polynucleotides that encode a variant of a native polypeptide may generally be prepared using standard mutagenesis techniques, such as oligonucleotide-directed site-specific mutagenesis, and sections of the DNA sequence may be removed to permit preparation of truncated polypeptides.

Certain portions and other variants may also be generated by synthetic means, using techniques well known to those of ordinary skill in the art. For example, polypeptides having fewer than about 500 amino acids, preferably fewer than about 100 amino acids, and more preferably fewer than about 50 amino acids, may be synthesized. Polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146, 1963. Equipment for automated synthesis of polypeptides is commercially available from suppliers such as Applied BioSystems, Inc. (Foster City, Calif.), and may be operated according to the manufacturer's instructions.

In general, polypeptides and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Within further aspects, the present invention provides mimetics of WT1 polypeptides. Such mimetics may comprise amino acids linked to one or more amino acid mimetics (i.e., one or more amino acids within the WT1 protein may be replaced by an amino acid mimetic) or may be entirely non-peptide mimetics. An amino acid mimetic is a compound that is conformationally similar to an amino acid such that it can be substituted for an amino acid within a WT1 polypeptide without substantially diminishing the ability to react with antigen-specific antisera and/or T cell lines or clones. A non-peptide mimetic is a compound that does not contain amino acids, and that has an overall conformation that is similar to a WT1 polypeptide such that the ability of the mimetic to react with WT1-specific antisera and/or T cell lines or clones is not substantially diminished relative to the ability of a WT1 polypeptide. Such mimetics may be designed based on standard techniques (e.g., nuclear magnetic resonance and computational techniques) that evaluate the three dimensional structure of a peptide sequence. Mimetics may be designed where one or more of the side chain functionalities of the WT1 polypeptide are replaced by groups that do not necessarily have the same size or volume, but have similar chemical and/or physical properties which produce similar biological responses. It should be understood that, within embodiments described herein, a mimetic may be substituted for a WT1 polypeptide.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.,* 336:86-91, 1997).

In one preferred embodiment, the immunological fusion partner is derived from a Mycobacterium sp., such as a *Mycobacterium tuberculosis*-derived Ra12 fragment. Ra12 compositions and methods for their use in enhancing the expression and/or immunogenicity of heterologous polynucleotide/polypeptide sequences is described in U.S. patent application 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. patent application 60/158,585; see also, Skeiky et al., *Infection and Immun*. (1999) 67:3998-4007, incorporated herein by reference). C-terminal fragments of the MTB32A coding sequence express at high levels and remain as soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LYTA gene; *Gene* 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798, 1992). Within a preferred embodiment, a repeat portion of LYTA may be incorporated into a fusion polypeptide. A repeat portion is found in the C-terminal region starting at residue 178. A particularly preferred repeat portion incorporates residues 188-305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of $CD4^+$ T-cells specific for the polypeptide.

The invention provides truncated forms of WT1 polypeptides that can be recombinantly expressed in *E. coli* without the addition of a fusion partner. Examples of these truncated forms are shown in SEQ ID NOs:342-346, and are encoded by polynucleotides shown in SEQ ID NOs:337-341. In variations of these truncations, the first 76 amino acids of WT1 can be fused to the C-terminus of the protein, creating a recombinant protein that is easier to express in *E. coli*. Other hosts in addition to *E. coli* can also be used, such as, for example, *B. megaterium*. The protein can further be prepared without a histidine tag.

In other embodiments, different subunits can be made and fused together in an order which differs from that of native WT1. In addition, fusions can be made with, for example, Ra12. Exemplary fusion proteins are shown in SEQ ID NOs: 332-336 and can be encoded by polynucleotides shown in SEQ ID NOs: 327-331.

WT1 Polynucleotides

Any polynucleotide that encodes a WT1 polypeptide as described herein is a WT1 polynucleotide encompassed by the present invention. Such polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

WT1 polynucleotides may encode a native WT1 protein, or may encode a variant of WT1 as described herein. Polynucleotide variants may contain one or more substitutions, additions, deletions and/or insertions such that the immunogenicity of the encoded polypeptide is not diminished, relative to a native WT1 protein. The effect on the immunogenicity of the encoded polypeptide may generally be assessed as described herein. Preferred variants contain nucleotide substitutions, deletions, insertions and/or additions at no more than 20%, preferably at no more than 10%, of the nucleotide positions that encode an immunogenic portion of a native WT1 sequence. Certain variants are substantially homologous to a native gene, or a portion thereof. Such polynucleotide variants are capable of hybridizing under moderately stringent conditions to a naturally occurring DNA sequence encoding a WT1 polypeptide (or a complementary sequence). Suitable moderately stringent conditions include prewashing in a solution of 5×SSC, 0.5% SDS, 1.0 mM EDTA (pH 8.0); hybridizing at 50° C.-65° C., 5×SSC, overnight; followed by washing twice at 65° C.for 20 minutes with each of 2×, 0.5× and 0.2×SSC containing 0.1% SDS). Such hybridizing DNA sequences are also within the scope of this invention.

It will be appreciated by those of ordinary skill in the art that, as a result of the degeneracy of the genetic code, there are many nucleotide sequences that encode a WT1 polypeptide. Some of these polynucleotides bear minimal homology to the nucleotide sequence of any native gene. Nonetheless, polynucleotides that vary due to differences in codon usage are specifically contemplated by the present invention.

Once an immunogenic portion of WT1 is identified, as described above, a WT1 polynucleotide may be prepared using any of a variety of techniques. For example, a WT1 polynucleotide may be amplified from cDNA prepared from cells that express WT1. Such polynucleotides may be amplified via polymerase chain reaction (PCR). For this approach, sequence-specific primers may be designed based on the sequence of the immunogenic portion and may be purchased or synthesized. For example, suitable primers for PCR amplification of a human WT1 gene include: first step—P118: 1434-1414: 5' GAG AGT CAG ACT TGA AAG CAGT 3' (SEQ ID NO:5) and P135: 5' CTG AGC CTC AGC AAA TGG GC 3' (SEQ ID NO:6); second step—P136: 5' GAG CAT GCA TGG GCT CCG ACG TGC GGG 3' (SEQ ID NO:7) and P137: 5' GGG GTA CCC ACT GAA CGG TCC CCG A 3' (SEQ ID NO:8). Primers for PCR amplification of a mouse WT1 gene include: first step—P138: 5' TCC GAG CCG CAC CTC ATG 3' (SEQ ID NO:9) and P139: 5' GCC TGG GAT GCT GGA CTG 3' (SEQ ID NO:10), second step—P140: 5' GAG CAT GCG ATG GGT TCC GAC GTG CGG 3' (SEQ ID NO:11) and P141: 5' GGG GTA CCT CAA AGC GCC ACG TGG AGT TT 3' (SEQ ID NO:12).

An amplified portion may then be used to isolate a full length gene from a human genomic DNA library or from a suitable cDNA library, using well known techniques. Alternatively, a full length gene can be constructed from multiple PCR fragments. WT1 polynucleotides may also be prepared by synthesizing oligonucleotide components, and ligating components together to generate the complete polynucleotide.

WT1 polynucleotides may also be synthesized by any method known in the art, including chemical synthesis (e.g., solid phase phosphoramidite chemical synthesis). Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding a WT1 polypeptide, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells such as dendritic cells with a cDNA construct encoding a WT1 polypeptide, and administering the transfected cells to the patient).

Polynucleotides that encode a WT1 polypeptide may generally be used for production of the polypeptide, in vitro or in vivo. WT1 polynucleotides that are complementary to a coding sequence (i.e., antisense polynucleotides) may also be used as a probe or to inhibit WT1 expression. cDNA constructs that can be transcribed into antisense RNA may also be introduced into cells of tissues to facilitate the production of antisense RNA.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art. cDNA constructs within such a vector may be used, for example, to transfect human or animal cell lines for use in establishing WT1 positive tumor models which may be used to perform tumor protection and adoptive immunotherapy experiments to demonstrate tumor or leukemia-growth inhibition or lysis of such cells.

Other therapeutic formulations for polynucleotides include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Antibodies and Fragments Thereof

The present invention further provides binding agents, such as antibodies and antigen-binding fragments thereof, that specifically bind to a WT1 polypeptide. As used herein, an agent is said to "specifically bind" to a WT1 polypeptide if it reacts at a detectable level (within, for example, an ELISA) with a WT1 polypeptide, and does not react detectably with unrelated proteins under similar conditions. As used herein, "binding" refers to a noncovalent association between two separate molecules such that a "complex" is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant maybe determined using methods well known in the art.

Any agent that satisfies the above requirements may be a binding agent. In a preferred embodiment, a binding agent is an antibody or an antigen-binding fragment thereof. Certain antibodies are commercially available from, for example, Santa Cruz Biotechnology (Santa Cruz, Calif.). Alternatively, antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies and fragments thereof may be coupled to one or more therapeutic agents. Suitable agents in this regard include radioactive tracers and chemotherapeutic agents, which may be used, for example, to purge autologous bone marrow in vitro). Representative therapeutic agents include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein. For diagnostic purposes, coupling of radioactive agents may be used to facilitate tracing of metastases or to determine the location of WT 1-positive tumors.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used. A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Also provided herein are anti-idiotypic antibodies that mimic an immunogenic portion of WT1. Such antibodies may be raised against an antibody, or antigen-binding fragment thereof, that specifically binds to an immunogenic portion of WT1,using well known techniques. Anti-idiotypic antibodies that mimic an immunogenic portion of WT1 are those antibodies that bind to an antibody, or antigen-binding fragment thereof, that specifically binds to an immunogenic portion of WT1, as described herein.

T Cells

Immunotherapeutic compositions may also, or alternatively, comprise T cells specific for WT1. Such cells may generally be prepared in vitro or ex vivo, using standard procedures. For example, T cells may be present within (or isolated from) bone marrow, peripheral blood or a fraction of bone marrow or peripheral blood of a mammal, such as a patient, using a commercially available cell separation system, such as the CEPRATE™ system, available from CellPro Inc., Bothell Wash. (see also U.S. Pat. No. 5,240,856; U.S. Pat. No. 5,215,926; WO 89/06280; WO 91/16116 and WO 92/07243). Alternatively, T cells may be derived from related or unrelated humans, non-human animals, cell lines or cultures.

T cells may be stimulated with WT1 polypeptide, polynucleotide encoding a WT1 polypeptide and/or an antigen presenting cell (APC) that expresses a WT1 polypeptide. Such stimulation is performed under conditions and for a time sufficient to permit the generation of T cells that are specific for the WT1 polypeptide. Preferably, a WT1 polypeptide or polynucleotide is present within a delivery vehicle, such as a microsphere, to facilitate the generation of antigen-specific T cells. Briefly, T cells, which may be isolated from a patient or a related or unrelated donor by routine techniques (such as by FICOLL®/HYPAQUE® density gradient centrifugation of peripheral blood lymphocytes), are incubated with WT1 polypeptide. For example, T cells may be incubated in vitro for 2-9 days (typically 4 days) at 37° C. with WT1 polypeptide (e.g., 5 to 25 μg/ml) or cells synthesizing a comparable amount of WT1 polypeptide. It may be desirable to incubate a separate aliquot of a T cell sample in the absence of WT1 polypeptide to serve as a control.

T cells are considered to be specific for a WT1 polypeptide if the T cells kill target cells coated with a WT1 polypeptide or expressing a gene encoding such a polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of T cells that can respond to a WT1 polypeptide may be quantified. Contact with a WT1 polypeptide (200 ng/ml-100 μg/ml, preferably 100 ng/ml-25 μg/ml) for 3-7 days should result in at least a two fold increase in proliferation of the T cells and/or contact as described above for 2-3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998). WT1 specific T cells may be expanded using standard techniques. Within preferred embodiments, the T cells are derived from a patient or a related or unrelated donor and are administered to the patient following stimulation and expansion.

T cells that have been activated in response to a WT1 polypeptide, polynucleotide or WT1-expressing APC may be $CD4^+$ and/or $CD8^+$. Specific activation of $CD4^+$ or $CD8^+$ T cells may be detected in a variety of ways. Methods for detecting specific T cell activation include detecting the proliferation of T cells, the production of cytokines (e.g., lymphokines), or the generation of cytolytic activity (i.e., generation of cytotoxic T cells specific for WT1). For $CD4^+$ T cells, a preferred method for detecting specific T cell activation is the detection of the proliferation of T cells. For $CD8^+$ T cells, a preferred method for detecting specific T cell activation is the detection of the generation of cytolytic activity.

For therapeutic purposes, $CD4^+$ or $CD8^+$ T cells that proliferate in response to the WT1 polypeptide, polynucleotide or APC can be expanded in number either in vitro or in vivo. Proliferation of such T cells in vitro may be accomplished in a variety of ways. For example, the T cells can be re-exposed to WT1 polypeptide, with or without the addition of T cell growth factors, such as interleukin-2, and/or stimulator cells that synthesize a WT1 polypeptide. The addition of stimulator cells is preferred where generating $CD8^+$ T cell responses. T cells can be grown to large numbers in vitro with retention of specificity in response to intermittent restimulation with WT1 polypeptide. Briefly, for the primary in vitro stimulation (IVS), large numbers of lymphocytes (e.g., greater than $4\times10^7$) may be placed in flasks with media containing human serum. WT1 polypeptide (e.g., peptide at 10 μg/ml) may be added directly, along with tetanus toxoid (e.g., 5 μg/ml). The flasks may then be incubated (e.g., 37° C. for 7 days). For a second IVS, T cells are then harvested and placed in new flasks with $2\text{-}3\times10^7$ irradiated peripheral blood mononuclear cells. WT1 polypeptide (e.g., 10 μg/ml) is added directly. The flasks are incubated at 37° C. for 7 days. On day 2 and day 4 after the second IVS, 2-5 units of interleukin-2 (IL-2) may be added. For a third IVS, the T cells may be placed in wells and stimulated with the individual's own EBV transformed B cells coated with the peptide. IL-2 may be added on days 2 and 4 of each cycle. As soon as the cells are shown to be specific cytotoxic T cells, they may be expanded using a 10 day stimulation cycle with higher IL-2 (20 units) on days 2, 4 and 6.

Alternatively, one or more T cells that proliferate in the presence of WT1 polypeptide can be expanded in number by cloning. Methods for cloning cells are well known in the art, and include limiting dilution. Responder T cells may be purified from the peripheral blood of sensitized patients by density gradient centrifugation and sheep red cell resetting and established in culture by stimulating with the nominal antigen in the presence of irradiated autologous filler cells. In order to generate $CD4^+$ T cell lines, WT1 polypeptide is used as the antigenic stimulus and autologous peripheral blood lymphocytes (PBL) or lymphoblastoid cell lines (LCL) immortalized by infection with Epstein Barr virus are used as antigen presenting cells. In order to generate $CD8^+$ T cell lines, autologous antigen-presenting cells transfected with an expression vector which produces WT1 polypeptide may be used as stimulator cells. Established T cell lines may be cloned 2-4 days following antigen stimulation by plating stimulated T cells at a frequency of 0.5 cells per well in 96-well flat-bottom plates with $1\times10^6$ irradiated PBL or LCL cells and recombinant interleukin-2 (rIL2) (50 U/ml). Wells with established clonal growth may be identified at approximately 2-3 weeks after initial plating and restimulated with appropriate antigen in the presence of autologous antigen-presenting cells, then subsequently expanded by the addition of low doses of rIL2 (10 U/ml) 2-3 days following antigen stimulation. T cell clones may be maintained in 24-well plates by periodic restimulation with antigen and rIL2 approximately every two weeks.

Within certain embodiments, allogeneic T-cells may be primed (i.e., sensitized to WT1) in vivo and/or in vitro. Such priming may be achieved by contacting T cells with a WT1 polypeptide, a polynucleotide encoding such a polypeptide or a cell producing such a polypeptide under conditions and for a time sufficient to permit the priming of T cells. In general, T cells are considered to be primed if, for example, contact with a WT1 polypeptide results in proliferation and/or activation of the T cells, as measured by standard proliferation, chromium release and/or cytokine release assays as described herein. A stimulation index of more than two fold increase in proliferation or lysis, and more than three fold increase in the level of cytokine, compared to negative controls, indicates T-cell specificity. Cells primed in vitro may be employed, for example, within a bone marrow transplantation or as donor lymphocyte infusion.

T cells specific for WT1 can kill cells that express WT1 protein. Introduction of genes encoding T-cell receptor (TCR) chains for WT1 are used as a means to quantitatively and qualitatively improve responses to WT1 bearing leukemia and cancer cells. Vaccines to increase the number of T cells that can react to WT1 positive cells are one method of targeting WT1 bearing cells. T cell therapy with T cells specific for WT1 is another method. An alternative method is to introduce the TCR chains specific for WT1 into T cells or other cells with lytic potential. In a suitable embodiment, the TCR alpha and beta chains are cloned out from a WT1 specific T cell line and used for adoptive T cell therapy, such as described in WO96/30516, incorporated herein by reference.

T Cell Receptor Compositions

The T cell receptor (TCR) consists of 2 different, highly variable polypeptide chains, termed the T-cell receptor α and β chains, that are linked by a disulfide bond (Janeway, Travers, Walport. Immunobiology. Fourth Ed., 148-159. Elsevier Science Ltd/Garland Publishing. 1999). The α/β heterodimer complexes with the invariant CD3 chains at the cell membrane. This complex recognizes specific antigenic peptides bound to MHC molecules. The enormous diversity of TCR specificities is generated much like immunoglobulin diversity, through somatic gene rearrangement. The β chain genes contain over 50 variable (V), 2 diversity (D), over 10 joining (J) segments, and 2 constant region segments (C). The α chain genes contain over 70 V segments, and over 60 J segments but no D segments, as well as one C segment. During T cell development in the thymus, the D to J gene rearrangement of the β chain occurs, followed by the V gene segment rearrangement to the DJ. This functional VDJβ exon is transcribed and spliced to join to a Cβ. For the a chain, a Vα gene segment rearranges to a Jα gene segment to create the functional exon that is then transcribed and spliced to the Cα. Diversity is further increased during the recombination process by the random addition of P and N-nucleotides between the V, D, and J segments of the β chain and between the V and J segments in the □ chain (Janeway, Travers, Walport. Immunobiology. Fourth Ed., 98 and 150. Elsevier Science Ltd/ Garland Publishing. 1999).

The present invention, in another aspect, provides TCRs specific for a polypeptide disclosed herein, or for a variant or derivative thereof. In accordance with the present invention, polynucleotide and amino acid sequences are provided for the V-J or V-D-J junctional regions or parts thereof for the alpha and beta chains of the T-cell receptor which recognize tumor polypeptides described herein. In general, this aspect of the invention relates to T-cell receptors which recognize or bind tumor polypeptides presented in the context of MHC. In a preferred embodiment the tumor antigens recognized by the T-cell receptors comprise a polypeptide of the present invention. For example, cDNA encoding a TCR specific for a WT1 peptide can be isolated from T cells specific for a tumor polypeptide using standard molecular biological and recombinant DNA techniques.

This invention further includes the T-cell receptors or analogs thereof having substantially the same function or activity as the T-cell receptors of this invention which recognize or bind tumor polypeptides. Such receptors include, but are not limited to, a fragment of the receptor, or a substitution, addition or deletion mutant of a T-cell receptor provided herein. This invention also encompasses polypeptides or peptides that are substantially homologous to the T-cell receptors provided herein or that retain substantially the same activity. The term “analog” includes any protein or polypeptide having an amino acid residue sequence substantially identical to the T-cell receptors provided herein in which one or more residues, preferably no more than 5 residues, more preferably no more than 25 residues have been conservatively substituted with a functionally similar residue and which displays the functional aspects of the T-cell receptor as described herein.

The present invention further provides for suitable mammalian host cells, for example, non-specific T cells, that are transfected with a polynucleotide encoding TCRs specific for a polypeptide described herein, thereby rendering the host cell specific for the polypeptide. The α and β chains of the TCR may be contained on separate expression vectors or alternatively, on a single expression vector that also contains an internal ribosome entry site (IRES) for cap-independent translation of the gene downstream of the IRES. Said host cells expressing TCRs specific for the polypeptide may be used, for example, for adoptive immunotherapy of WT1-associated cancer as discussed farther below.

In further aspects of the present invention, cloned TCRs specific for a polypeptide recited herein may be used in a kit for the diagnosis of WT1-associated cancer. For example, the nucleic acid sequence or portions thereof, of tumor-specific TCRs can be used as probes or primers for the detection of expression of the rearranged genes encoding the specific TCR in a biological sample. Therefore, the present invention further provides for an assay for detecting messenger RNA or DNA encoding the TCR specific for a polypeptide.

Peptide-MHC Tetrameric Complexes

The present invention, in another aspect, provides peptide-MHC tetrameric complexes (tetramers) specific for T cells that recognize a polypeptide disclosed herein, or for a variant or derivative thereof. In one embodiment, tetramers may be used in the detection of WT1 specific T-cells. Tetramers may be used in monitoring WT1 specific immune responses, early detection of WT1 associated malignancies and for monitoring minimal residual disease. Tetramer staining is typically carried out with flow cytometric analysis and can be used to identify groups within a patient population suffering from a WT1 associated disease at a higher risk for relapse or disease progression.

Pharmaceutical Compositions and Vaccines

Within certain aspects, polypeptides, polynucleotides, antibodies and/or T cells may be incorporated into pharmaceutical compositions or vaccines. Alternatively, a pharmaceutical composition may comprise an antigen-presenting cell (e.g., a dendritic cell) transfected with a WT1 polynucleotide such that the antigen presenting cell expresses a WT1 polypeptide. Pharmaceutical compositions comprise one or more such compounds or cells and a physiologically acceptable carrier or excipient. Certain vaccines may comprise one or more such compounds or cells and a non-specific immune response enhancer, such as an adjuvant or a liposome (into which the compound is incorporated). Pharmaceutical compositions and vaccines may additionally contain a delivery system, such as biodegradable microspheres which are disclosed, for example, in U.S. Pat. Nos. 4,897,268 and 5,075,109. Pharmaceutical compositions and vaccines within the scope of the present invention may also contain other compounds, which may be biologically active or inactive.

Within certain embodiments, pharmaceutical compositions and vaccines are designed to elicit T cell responses specific for a WT1 polypeptide in a patient, such as a human. In general, T cell responses may be favored through the use of relatively short polypeptides (e.g., comprising less than 23 consecutive amino acid residues of a native WT1 polypeptide, preferably 4-16 consecutive residues, more preferably 8-16 consecutive residues and still more preferably 8-10 consecutive residues. Alternatively, or in addition, a vaccine may comprise a non-specific immune response enhancer that preferentially enhances a T cell response. In other words, the immune response enhancer may enhance the level of a T cell response to a WT1 polypeptide by an amount that is proportionally greater than the amount by which an antibody response is enhanced. For example, when compared to a standard oil based adjuvant, such as CFA, an immune response enhancer that preferentially enhances a T cell response may enhance a proliferative T cell response by at least two fold, a lytic response by at least 10%, and/or T cell activation by at least two fold compared to WT1-megative control cell lines, while not detectably enhancing an antibody response. The amount by which a T cell or antibody response to a WT1 polypeptide is enhanced may generally be determined using any representative technique known in the art, such as the techniques provided herein.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacterial and viral expression systems and mammalian expression systems. Appropriate nucleic acid expression systems contain the necessary DNA, cDNA or RNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745-1749, 1993 and reviewed by Cohen, *Science* 259:1691-1692, 1993. The uptake of naked DNA may be increased by coating the DNA onto biodegradable beads, which are efficiently transported into the cells.

As noted above, a pharmaceutical composition or vaccine may comprise an antigen-presenting cell that expresses a WT1 polypeptide. For therapeutic purposes, as described herein, the antigen presenting cell is preferably an autologous dendritic cell. Such cells may be prepared and transfected using standard techniques, such as those described by Reeves et al., *Cancer Res.* 56:5672-5677, 1996; Tuting et al., *J. Immunol.* 160:1139-1147, 1998; and Nair et al., *Nature Biotechnol.* 16:364-369, 1998). Expression of a WT1 polypeptide on the surface of an antigen-presenting cell may be confirmed by in vitro stimulation and standard proliferation as well as chromium release assays, as described herein.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. For certain topical applications, formulation as a cream or lotion, using well known components, is preferred.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology. In one embodiment of the present invention, compositions comprise a buffer comprising one or more sugars including, but not limited to, trehalose, maltose, sucrose, fructose, and glucose, each at a concentration generally between about 1 and 25%, typically between about 7 and 13%. In a further embodiment, the concentration is between about 8 and about 12%. In yet a further embodiment the concentration is about 10%. In an additional aspect of the present invention, the compositions may comprise ethanolamine; cysteine; or Polysorbate-80, generally at concentrations effective for enhancing the efficacy, stability and/or solubility of the formulation.

Any of a variety of non-specific immune response enhancers, such as adjuvants, may be employed in the vaccines of this invention. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable non-specific immune response enhancers include alum-based adjuvants (e.g., ALHYDROGEL®, REHYDRAGEL®, aluminum phosphate, Algammulin, aluminum hydroxide); oil based adjuvants (Freund's adjuvant (FA), Specol, RIBI, TITERMAX®, MONTANIDE® ISA50 or MONTANIDE® ISA 720 (Seppic, France); cytokines (e.g., GM-CSF or FLT3-ligand); microspheres; nonionic block copolymer-based adjuvants; dimethyl dioctadecyl ammoniumbromide (DDA) based adjuvants AS-1, AS-2 (Smith Kline Beecham); Ribi Adjuvant system based adjuvants; QS21 (Aquila); saponin based adjuvants (crude saponin, the saponin Quil A); muramyl dipeptide (MDP) based adjuvants such as SAF (Syntex adjuvant in its microfluidized form (SAF-m)); dimethyl-dioctadecyl ammonium bromide (DDA); human complement based adjuvants *m. vaccae* and derivatives; immune stimulating complex (iscom) based adjuvants; inactivated toxins; and attenuated infectious agents (such as *M. tuberculosis*).

Additional illustrative adjuvants for use in the pharmaceutical compositions of the invention include MONTANIDE® ISA 720 (Seppic, France), SAF™ (Chiron, Calif., United States), ISCOM®s (CSL), MF-59™ (Chiron), the SBAS™, series of adjuvants (e.g., SBAS™-2 or SBAS™-4, available from SmithKline Beecham, Rixensart, Belgium), Detox (ENHANZYN®) (Corixa, Hamilton, Mont.), RC-529™ (Corixa, Hamilton, Mont.) and other aminoalkyl glucosaminide 4-phosphates (AGPs), such as those described in pending U.S. patent application Ser. No. 08/853,826 (U.S. Pat. No. 6,113,918) and Ser. No. 09/074,720 (U.S. Pat. No. 6,355, 257), the disclosures of which are incorporated herein by reference in their entireties, and polyoxyethylene ether adjuvants such as those described in WO 99/52549A1.

Other preferred adjuvants include adjuvant molecules of the general formula $$HO(CH_2CH_2O)_n—A—R, \quad (I)$$

wherein, n is 1-50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4-24, most preferably 9; the R component is $C_{1-50}$, preferably $C_4$-$C_{20}$ alkyl and most preferably $C_{12}$ alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

As noted above, within certain embodiments, immune response enhancers are chosen for their ability to preferentially elicit or enhance a T cell response (e.g., $CD4^+$ and/or $CD8^+$) to a WT1 polypeptide. Such immune response enhancers are well known in the art, and include (but are not limited to) MONTANIDE® ISA50, Seppic MONTANIDE® ISA 720, cytokines (e.g., GM-CSF, Flat3-ligand), microspheres, dimethyl dioctadecyl ammoniumbromide (DDA) based adjuvants, AS-1 (Smith Kline Beecham), AS-2 (Smith Kline Beecham), Ribi Adjuvant system based adjuvants, QS21 (Aquila), saponin based adjuvants (crude saponin, the saponin Quil A), Syntex adjuvant in its microfluidized form (SAF-m), MV, ddMV (Genesis), immune stimulating complex (iscom) based adjuvants and inactivated toxins.

In another aspect of the present invention, compositions may comprise adjuvants for eliciting a predominantly Th1-type response. Certain preferred adjuvants for eliciting a predominantly Th1-type response include, for example, a combination of monophosphoryl lipid A (MPL®), preferably 3-de-O-acylated monophosphoryl lipid A (3D-MPL™), together with an aluminum salt. MPL® adjuvants, such as MPL-SE, are available from Corixa Corporation (Seattle, Wash.; see, for example, U.S. Pat. Nos. 4,436,727; 4,877,611; 4,866,034 and 4,912,094, incorporated herein in their entirety). CpG-containing oligonucleotides (in which the CpG dinucleotide is umnethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other preferred formulations include more than one saponin in the adjuvant combinations of the present invention, for example combinations of at least two of the following group comprising QS21, QS7, Quil A, β-escin, or digitonin.

The compositions and vaccines described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide, antibody or cell dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Therapy of Malignant Diseases

In further aspects of the present invention, the compositions and vaccines described herein may be used to inhibit the development of malignant diseases (e.g., progressive or metastatic diseases or diseases characterized by small tumor burden such as minimal residual disease). In general, such methods may be used to prevent, delay or treat a disease associated with WT1 expression. In other words, therapeutic methods provided herein may be used to treat an existing WT1-associated disease, or may be used to prevent or delay the onset of such a disease in a patient who is free of disease or who is afflicted with a disease that is not yet associated with WT1 expression.

As used herein, a disease is "associated with WT1 expression" if diseased cells (e.g., tumor cells) at some time during the course of the disease generate detectably higher levels of a WT1 polypeptide than normal cells of the same tissue. Association of WT1 expression with a malignant disease does not require that WT1 be present on a tumor. For example, overexpression of WT1 may be involved with initiation of a tumor, but the protein expression may subsequently be lost. Alternatively, a malignant disease that is not characterized by an increase in WT1 expression may, at a later time, progress to a disease that is characterized by increased WT1 expression. Accordingly, any malignant disease in which diseased cells formerly expressed, currently express or are expected to subsequently express increased levels of WT1 is considered to be "associated with WT1 expression."

Immunotherapy may be performed using any of a variety of techniques, in which compounds or cells provided herein function to remove WT1-expressing cells from a patient. Such removal may take place as a result of enhancing or inducing an immune response in a patient specific for WT1 or a cell expressing WT1. Alternatively, WT1-expressing cells may be removed ex vivo (e.g., by treatment of autologous bone marrow, peripheral blood or a fraction of bone marrow or peripheral blood). Fractions of bone marrow or peripheral blood may be obtained using any standard technique in the art.

Within such methods, pharmaceutical compositions and vaccines may be administered to a patient. As used herein, a "patient" refers to any warm-blooded animal, preferably a human. A patient may or may not be afflicted with a malignant disease. Accordingly, the above pharmaceutical compositions and vaccines may be used to prevent the onset of a disease (i.e., prophylactically) or to treat a patient afflicted with a disease (e.g., to prevent or delay progression and/or metastasis of an existing disease). A patient afflicted with a disease may have a minimal residual disease (e.g., a low tumor burden in a leukemia patient in complete or partial remission or a cancer patient following reduction of the tumor burden after surgery radiotherapy and/or chemotherapy). Such a patient may be immunized to inhibit a relapse (i.e., prevent or delay the relapse, or decrease the severity of a relapse). Within certain preferred embodiments, the patient is afflicted with a leukemia (e.g., AML, CML, ALL or childhood ALL), a myelodysplastic syndrome (MDS) or a cancer (e.g., gastrointestinal, lung, thyroid or breast cancer or a melanoma), where the cancer or leukemia is WT1 positive (i.e., reacts detectably with an anti-WT1 antibody, as provided herein or expresses WT1 mRNA at a level detectable by RT-PCR, as described herein) or suffers from an autoimmune disease directed against WT1-expressing cells.

Other diseases associated with WT1 overexpression include kidney cancer (such as renal cell carcinoma, or Wilms tumor), as described in Satoh F., et al., *Pathol. Int.* 50(6):458-71(2000), and Campbell C. E. et al., *Int. J. Cancer* 78(2): 182-8 (1998); and mesothelioma, as described in Amin, K. M. et al., *Am. J. Pathol.* 146(2):344-56 (1995). Harada et al. (*Mol. Urol.* 3(4):357-364 (1999) describe WT1 gene expression in human testicular germ-cell tumors. Nonomura et al. *Hinyokika Kiyo* 45(8):593-7 (1999) describe molecular staging of testicular cancer using polymerase chain reaction of the testicular cancer-specific genes. Shimizu et al., *Int. J. Gynecol. Pathol.* 19(2):158-63 (2000) describe the immunohistochemical detection of the Wilms' tumor gene (WT1) in epithelial ovarian tumors.

WT1 overexpression was also described in desmoplastic small round cell tumors, by Bamoud, R. et al., *Am. J. Surg. Pathol.* 24(6):830-6 (2000); and *Pathol. Res. Pract.* 194(10): 693-700 (1998). WT1 overexpression in glioblastoma and other cancer was described by Menssen, H. D. et al., *J. Cancer Res. Clin. Oncol.* 126(4):226-32 (2000), "Wilms' tumor gene (WT1) expression in lung cancer, colon cancer and glioblastoma cell lines compared to freshly isolated tumor specimens." Other diseases showing WT1 overexpression include EBV associated diseases, such as Burkitt's lymphoma and nasopharyngeal cancer (Spinsanti P. et al., *Leuk. Lymphoma* 38(5-6):611-9 (2000), "Wilms' tumor gene expression by normal and malignant human B lymphocytes."

In *Leukemia* 14(9):1634-4 (2000), Pan et al., describe in vitro IL-12 treatment of peripheral blood mononuclear cells from patients with leukemia or myelodysplastic syndromes, and reported an increase in cytotoxicity and reduction in WT1 gene expression. In *Leukemia* 13(6):891-900 (1999), Patmasiriwat et al. reported WT1 and GATA1 expression in myelodysplastic syndrome and acute leukemia. In *Leukemia* 13(3): 393-9 (1999), Tamaki et al. reported that the Wilms' tumor gene WT1 is a good marker for diagnosis of disease progression of myelodysplastic syndromes. Expression of the Wilms' tumor gene WT1 in solid tumors, and its involvement in tumor cell growth, was discussed in relation to gastric cancer, colon cancer, lung cancer, breast cancer cell lines, germ cell tumor cell line, ovarian cancer, the uterine cancer, thyroid cancer cell line, hepatocellular carcinoma, in Oji et al., *Jpn. J. Cancer Res.* 90(2):194-204 (1999).

The compositions provided herein may be used alone or in combination with conventional therapeutic regimens such as surgery, irradiation, chemotherapy and/or bone marrow transplantation (autologous, syngeneic, allogeneic or unrelated). As discussed in greater detail below, binding agents and T cells as provided herein may be used for purging of autologous stem cells. Such purging may be beneficial prior to, for example, bone marrow transplantation or transfusion of blood or components thereof. Binding agents, T cells, antigen presenting cells (APC) and compositions provided herein may further be used for expanding and stimulating (or priming) autologous, allogeneic, syngeneic or unrelated WT1-specific T-cells in vitro and/or in vivo. Such WT1-specific T cells may be used, for example, within donor lymphocyte infusions.

Routes and frequency of administration, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. In some tumors, pharmaceutical compositions or vaccines may be administered locally (by, for example, rectocoloscopy, gastroscopy, videoendoscopy, angiography or other methods known in the art). Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response that is at least 10-50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent complete or partial remissions, or longer disease-free and/or overall survival) in vaccinated patients as compared to non-vaccinated patients. In general, for pharmaceutical compositions and vaccines comprising one or more polypeptides, the amount of each polypeptide present in a dose ranges from about 100 μg to 5 mg. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent complete or partial remissions, or longer disease-free and/or overall survival) in treated patients as compared to non-treated patients. Increases in preexisting immune responses to WT1 generally correlate with an improved clinical outcome. Such immune responses may generally be evaluated using standard proliferation, cytotoxicity or cytokine assays, which may be performed using samples obtained from a patient before and after treatment.

Within further aspects, methods for inhibiting the development of a malignant disease associated with WT1 expression involve the administration of autologous T cells that have been activated in response to a WT1 polypeptide or WT1-expressing APC, as described above. Such T cells may be $CD4^+$ and/or $CD8^+$, and may be proliferated as described above. The T cells may be administered to the individual in an amount effective to inhibit the development of a malignant disease. Typically, about $1\times10^9$ to $1\times10^{11}$ T cells/$M^2$ are administered intravenously, intracavitary or in the bed of a resected tumor. It will be evident to those skilled in the art that the number of cells and the frequency of administration will be dependent upon the response of the patient.

Within certain embodiments, T cells may be stimulated prior to an autologous bone marrow transplantation. Such stimulation may take place in vivo or in vitro. For in vitro stimulation, bone marrow and/or peripheral blood (or a fraction of bone marrow or peripheral blood) obtained from a patient may be contacted with a WT1 polypeptide, a polynucleotide encoding a WT1 polypeptide and/or an APC that expresses a WT1 polypeptide under conditions and for a time sufficient to permit the stimulation of T cells as described above. Bone marrow, peripheral blood stem cells and/or WT1-specific T cells may then be administered to a patient using standard techniques.

Within related embodiments, T cells of a related or unrelated donor may be stimulated prior to a syngeneic or allogeneic (related or unrelated) bone marrow transplantation. Such stimulation may take place in vivo or in vitro. For in vitro stimulation, bone marrow and/or peripheral blood (or a fraction of bone marrow or peripheral blood) obtained from a related or unrelated donor may be contacted with a WT1 polypeptide, WT1 polynucleotide and/or APC that expresses a WT1 polypeptide under conditions and for a time sufficient to permit the stimulation of T cells as described above. Bone marrow, peripheral blood stem cells and/or WT1-specific T cells may then be administered to a patient using standard techniques.

Within other embodiments, WT1-specific T cells as described herein may be used to remove cells expressing WT1 from autologous bone marrow, peripheral blood or a fraction of bone marrow or peripheral blood (e.g., $CD34^+$ enriched peripheral blood (PB) prior to administration to a patient). Such methods may be performed by contacting bone marrow or PB with such T cells under conditions and for a time sufficient to permit the reduction of WT1 expressing cells to less than 10%, preferably less than 5% and more preferably less than 1%, of the total number of myeloid or lymphatic cells in the bone marrow or peripheral blood. The extent to which such cells have been removed may be readily determined by standard methods such as, for example, qualitative and quantitative PCR analysis, morphology, immunohistochemistry and FACS analysis. Bone marrow or PB (or a fraction thereof) may then be administered to a patient using standard techniques.

Diagnostic Methods

The present invention further provides methods for detecting a malignant disease associated with WT1 expression, and for monitoring the effectiveness of an immunization or therapy for such a disease. Such methods are based on the discovery, within the present invention, that an immune response specific for WT1 protein can be detected in patients afflicted with such diseases, and that methods which enhance such immune responses may provide a preventive or therapeutic benefit.

To determine the presence or absence of a malignant disease associated with WT1 expression, a patient may be tested for the level of T cells specific for WT1. Within certain methods, a biological sample comprising $CD4^+$ and/or $CD8^+$ T cells isolated from a patient is incubated with a WT1 polypeptide, a polynucleotide encoding a WT1 polypeptide and/or an APC that expresses a WT1 polypeptide, and the presence or absence of specific activation of the T cells is detected, as described herein. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2-9 days (typically 4 days) at 37° C. with WT1 polypeptide (e.g., 5-25 μg/ml). It may be desirable to incubate another aliquot of a T cell sample in the absence of WT1 polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a malignant disease associated with WT1 expression. Further correlation may be made, using methods well known in the art, between the level of proliferation and/or cytolytic activity and the predicted response to therapy. In particular, patients that display a higher antibody, proliferative and/or lytic response may be expected to show a greater response to therapy.

Within other methods, a biological sample obtained from a patient is tested for the level of antibody specific for WT1. The biological sample is incubated with a WT1 polypeptide, a polynucleotide encoding a WT1 polypeptide and/or an APC that expresses a WT1 polypeptide under conditions and for a time sufficient to allow immunocomplexes to form. Immunocomplexes formed between the WT1 polypeptide and antibodies in the biological sample that specifically bind to the WT1 polypeptide are then detected. A biological sample for use within such methods may be any sample obtained from a patient that would be expected to contain antibodies. Suitable biological samples include blood, sera, ascites, bone marrow, pleural effusion, and cerebrospinal fluid.

The biological sample is incubated with the WT1 polypeptide in a reaction mixture under conditions and for a time sufficient to permit immunocomplexes to form between the polypeptide and antibodies specific for WT1. For example, a biological sample and WT1 polypeptide may be incubated at 4° C. for 24-48 hours.

Following the incubation, the reaction mixture is tested for the presence of immunocomplexes. Detection of inununocomplexes formed between the WT1 polypeptide and antibodies present in the biological sample may be accomplished by a variety of known techniques, such as radioimmuno assays (RIA) and enzyme linked immuno sorb ent assays (ELISA). Suitable assays are well known in the art and are amply described in the scientific and patent literature (e.g., Harlow and Lane, *Antibodies: A Laboratory Manual*, Cold Spring Harbor Laboratory, 1988). Assays that may be used include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh, 1970); the "western blot" method of Gordon et al. (U.S. Pat. No. 4,452,901); immunoprecipitation of labeled ligand (Brown et al., *J. Biol. Chem.* 255:4980-4983, 1980); enzyme-linked immunosorbent assays as described by, for example, Raines and Ross (*J. Biol. Chem.* 257:5154-5160, 1982); immunocytochemical techniques, including the use of fluorochromes (Brooks et al., *Clin. Exp. Immunol.* 39: 477, 1980);

and neutralization of activity (Bowen-Pope et al., *Proc. Natl. Acad. Sci. USA* 81:2396-2400, 1984). Other immunoassays include, but are not limited to, those described in U.S. Pat. Nos. 3,817,827; 3,850,752; 3,901,654; 3,935,074; 3,984,533; 3,996,345; 4,034,074; and 4,098,876.

For detection purposes, WT1 polypeptide may either be labeled or unlabeled. Unlabeled WT1 polypeptide may be used in agglutination assays or in combination with labeled detection reagents that bind to the immunocomplexes (e.g., anti-immunoglobulin, protein G, protein A or a lectin and secondary antibodies, or antigen-binding fragments thereof, capable of binding to the antibodies that specifically bind to the WT1 polypeptide). If the WT1 polypeptide is labeled, the reporter group may be any suitable reporter group known in the art, including radioisotopes, fluorescent groups, luminescent groups, enzymes, biotin and dye particles.

Within certain assays, unlabeled WT1 polypeptide is immobilized on a solid support. The solid support may be any material known to those of ordinary skill in the art to which the polypeptide may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The polypeptide may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the WT1 polypeptide, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of polypeptide ranging from about 10 ng to about 10 μg, and preferably about 100 ng to about 1 μg, is sufficient to immobilize an adequate amount of polypeptide.

Following immobilization, the remaining protein binding sites on the support are typically blocked. Any suitable blocking agent known to those of ordinary skill in the art, such as bovine serum albumin, TWEEN® 20™ (Sigma Chemical Co., St. Louis, Mo.), heat-inactivated normal goat serum (NGS), or BLOTTO (buffered solution of nonfat dry milk which also contains a preservative, salts, and an antifoaming agent). The support is then incubated with a biological sample suspected of containing specific antibody. The sample can be applied neat, or, more often, it can be diluted, usually in a buffered solution which contains a small amount (0.1%-5.0% by weight) of protein, such as BSA, NGS, or BLOTTO. In general, an appropriate contact time (i.e., incubation time) is a period of time that is sufficient to detect the presence of antibody that specifically binds WT1 within a sample containing such an antibody. Preferably, the contact time is sufficient to achieve a level of binding that is at least about 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% TWEEN® 20™. A detection reagent that binds to the immunocomplexes and that comprises a reporter group may then be added. The detection reagent is incubated with the immunocomplex for an amount of time sufficient to detect the bound antibody. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups (e.g., horseradish peroxidase, beta-galactosidase, alkaline phosphatase and glucose oxidase) may generally be detected by the addition of substrate (generally for a specific period of time), followed by spectroscopic or other analysis of the reaction products. Regardless of the specific method employed, a level of bound detection reagent that is at least two fold greater than background (i.e., the level observed for a biological sample obtained from a disease-free individual) indicates the presence of a malignant disease associated with WT1 expression.

In general, methods for monitoring the effectiveness of an immunization or therapy involve monitoring changes in the level of antibodies or T cells specific for WT1 in the patient. Methods in which antibody levels are monitored may comprise the steps of: (a) incubating a first biological sample, obtained from a patient prior to a therapy or immunization, with a WT1 polypeptide, wherein the incubation is performed under conditions and for a time sufficient to allow immunocomplexes to form; (b) detecting immunocomplexes formed between the WT1 polypeptide and antibodies in the biological sample that specifically bind to the WT1 polypeptide; (c) repeating steps (a) and (b) using a second biological sample taken from the patient following therapy or immunization; and (d) comparing the number of immunocomplexes detected in the first and second biological samples. Alternatively, a polynucleotide encoding a WT1 polypeptide, or an APC expressing a WT1 polypeptide may be employed in place of the WT1 polypeptide. Within such methods, immunocomplexes between the WT1 polypeptide encoded by the polynucleotide, or expressed by the APC, and antibodies in the biological sample are detected.

Methods in which T cell activation and/or the number of WT1 specific precursors are monitored may comprise the steps of: (a) incubating a first biological sample comprising CD4+ and/or CD8+ cells (e.g., bone marrow, peripheral blood or a fraction thereof), obtained from a patient prior to a therapy or immunization, with a WT1 polypeptide, wherein the incubation is performed under conditions and for a time sufficient to allow specific activation, proliferation and/or lysis of T cells; (b) detecting an amount of activation, proliferation and/or lysis of the T cells; (c) repeating steps (a) and (b) using a second biological sample comprising CD4+ and/or CD8+ T cells, and taken from the same patient following therapy or immunization; and (d) comparing the amount of activation, proliferation and/or lysis of T cells in the first and second biological samples. Alternatively, a polynucleotide encoding a WT1 polypeptide, or an APC expressing a WT1 polypeptide may be employed in place of the WT1 polypeptide.

A biological sample for use within such methods may be any sample obtained from a patient that would be expected to contain antibodies, CD4+ T cells and/or CD8+ T cells. Suitable biological samples include blood, sera, ascites, bone marrow, pleural effusion and cerebrospinal fluid. A first biological sample may be obtained prior to initiation of therapy or immunization or part way through a therapy or vaccination regime. The second biological sample should be obtained in a similar manner, but at a time following additional therapy or immunization. The second biological sample may be obtained at the completion of, or part way through, therapy or immunization, provided that at least a portion of therapy or immunization takes place between the isolation of the first and second biological samples.

Incubation and detection steps for both samples may generally be performed as described above. A statistically significant increase in the number of immunocomplexes in the second sample relative to the first sample reflects successful therapy or immunization.

The following Examples are offered by way of illustration and not by way of limitation.

EXAMPLES

Example 1

Identification of an Immune Response to WT1 in Patients with Hematological Malignancies This Example illustrates the identification of an existent immune response in patients with a hematological malignancy.

To evaluate the presence of preexisting WT1 specific antibody responses in patients, sera of patients with acute myelogenous leukemia (AML), acute lymphocytic leukemia (ALL), chronic myelogenous leukemia (CML) and severe aplastic anemia were analyzed using Western blot analysis. Sera were tested for the ability to immunoprecipitate WT1 from the human leukemic cell line K562 (American Type Culture Collection, Manassas, Va.). In each case, immunoprecipitates were separated by gel electrophoresis, transferred to membrane and probed with the anti WT1 antibody WT180 (Santa Cruz Biotechnology, Inc., Santa Cruz, Calif.). This Western blot analysis identified potential WT1 specific antibodies in patients with hematological malignancy. A representative Western blot showing the results for a patient with AML is shown in FIG. 2. A 52 kD protein in the immunoprecipitate generated using the patient sera was recognized by the WT1 specific antibody. The 52 kD protein migrated at the same size as the positive control.

Additional studies analyzed the sera of patients with AML and CML for the presence of antibodies to full-length and truncated WT1 proteins. cDNA constructs representing the human WT1/full-length (aa 1-449), the N-terminus (aa 1-249) (WT1/N-terminus) and C-terminus (aa 267-449) (WT1/C-terminus) region were subcloned into modified pET28 vectors. The WT1/full-length and WT1/N-terminus proteins were expressed as Ra12 fusion proteins. Ra12 is the C-terminal fragment of a secreted *Mycobacterium tuberculosis* protein, denoted as MTB32B. (Skeiky et al., *Infect Immun.* 67;3998, 1999). The Ra12-WT1/full-length fusion region was cloned 3' to a histidine-tag in a histidine-tag modified pET28 vector. The WT1/N-terminus region was subcloned into a modified pET28 vector that has a 5' histidine-tag followed by the thioredoxin (TRX)-WT1/N-terminus fusion region followed by a 3' histidine-tag. The WT1/C-terminus coding region was subcloned into a modified pET28 vector without a fusion partner containing only the 5' and 3' histidine-tag, followed by a Thrombin and EK site.

BL21 pLysS *E. coli* (Stratagene, La Jolla, Calif.) were transformed with the three WT1 expression constructs, grown overnight and induced with isopropyl-β-D-thiogalactoside (IPTG). WT1 proteins were purified as follows: Cells were harvested and lysed by incubation in 10 mM Tris, pH 8.0 with Complete Protease Inhibitor Tablets (Boehringer Mannheim Biochemicals, Indianapolis, Ind.) at 37° C. followed by repeated rounds of sonication. Inclusion bodies were washed twice with 10 mM Tris, pH 8.0. Proteins were then purified by metal chelate affinity chromatography over nickel-nitrilotriacetic acid resin (QIAGEN Inc., Valencia, Calif.; Hochuli et al., *Biologically Active Molecules* :217, 1989) followed by chromatography on a Source Q anion exchange resin (Amersham Pharmacia Biotech, Upsala, Sweden). The identity of the WT1 proteins was confirmed by N-terminal sequencing.

Sera from adult patients with de nova AML or CML were studied for the presence of WT1 specific Ab. Recombinant proteins were adsorbed to TC microwell plates (Nunc, Roskilde, Denmark). Plates were washed with PBS/0.5% TWEEN™ 20 and blocked with 1% BSA/PBS/0.1% TWEEN™ 20. After washing, serum dilutions were added and incubated overnight at 4° C. Plates were washed and Donkey anti-human IgG-HRP secondary antibody was added (Jackson-Immunochem, West Grove, Pa.) and incubated for 2 h at room temperature. Plates were washed, incubated with TMB Peroxidase substrate solution (Kirkegaard and Perry Laboratories, Mass.), quenched with 1N $H_2SO_4$, and immediately read (Cyto-Fluor 2350; Millipore, Bedford, Mass.).

For the serological survey, human sera were tested by ELISA over a range of serial dilutions from 1:50 to 1:20,000. A positive reaction was defined as an OD value of a 1:500 diluted serum that exceeded the mean OD value of sera from normal donors (n=96) by three (WT1/full-length, WT1C-terminus) standard deviations. Due to a higher background in normal donors to the WT1/N-terminus protein a positive reaction to WT1/N-terminus was defined as an OD value of 1:500 diluted serum that exceeded the mean OD value of sera from normal donors by four standard deviations. To verify that the patient Ab response was directed against WT1 and not to the Ra12 or TRX fusion part of the protein or possible *E. coli* contaminant proteins, controls included the Ra12 and TRX protein alone purified in a similar manner. Samples that showed reactivity against the Ra12 and/or TRX proteins were excluded from the analysis.

To evaluate for the presence of immunity to WT1, Ab to recombinant full-length and truncated WT1 proteins in the sera of normal individuals and patients with leukemia were determined. Antibody reactivity was analyzed by ELISA reactivity to WT1/full-length protein, WT1/N-terminus protein and WT1/C-terminus protein.

Figure 16:
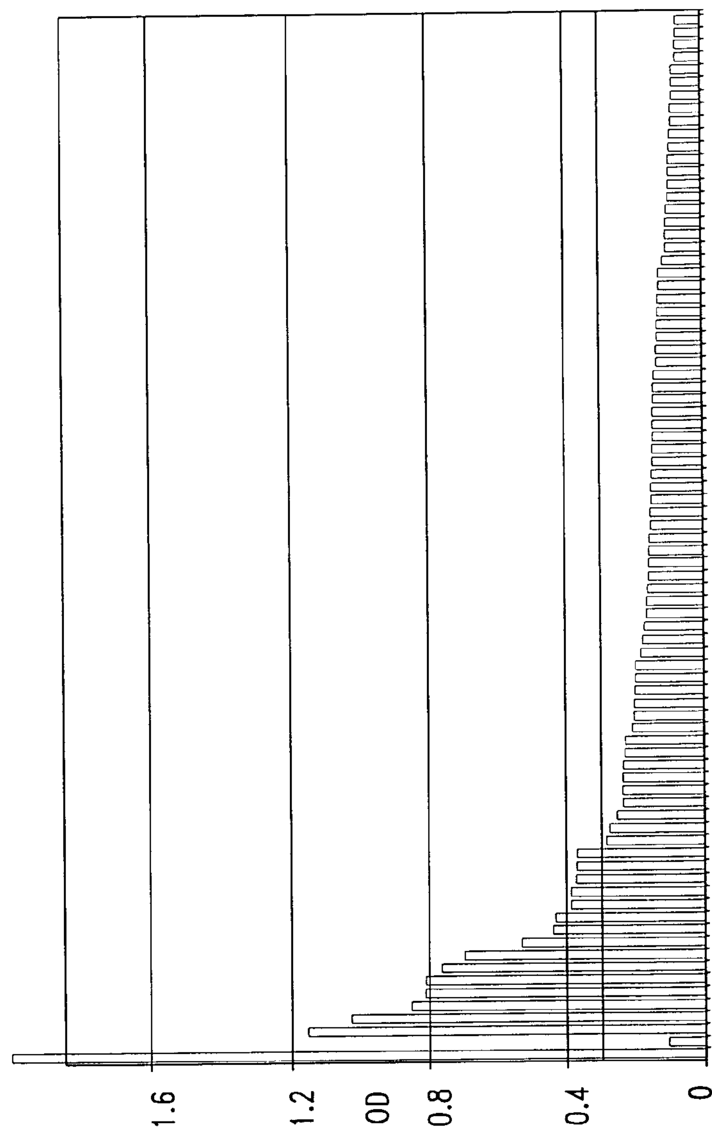
FIG. 16 depicts serum antibody reactivity to WT1 in 81 patients with CML. Reactivity of serum antibody to WT1/full-length protein was evaluated by ELISA in patients with AML. The first and second lanes represent the positive and negative controls, respectively. Commercially obtained WT1 specific antibody WT180 was used for the positive control. The next 81 lanes represent results using sera from each individual patient. The OD values depicted were from ELISA using a 1:500 serum dilution. The figure includes cumulative data from 3 separate experiments.
Figure 17:
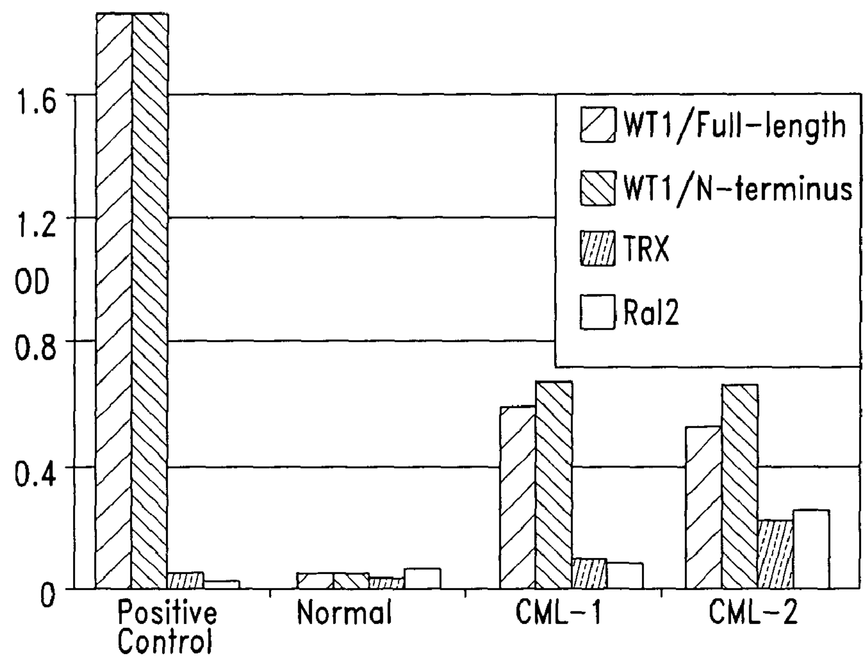
FIG. 17 depicts serum antibody reactivity to WT1 proteins and control proteins in 2 patients with CML. Reactivity of serum antibody to WT1/full-length, WT1/N-terminus, TRX and Ra12 proteins was evaluated by ELISA in 2 patients with CML. The OD values depicted were from ELISA using a 1:500 serum dilution. CML-1 and CML-2 denote serum from 2 of the individual patients in FIG. 3 with demonstrated antibody reactivity to WT1/full-length. The WT1/full-length protein was expressed as a fusion protein with Ra12. The WT1/N-terminus protein was expressed as a fusion protein with TRX. The control Ra12 and TRX proteins were purified in a similar manner. The results confirm that the serum antibody reactivity against the WT1 fusion proteins is directed against the WT1 portions of the protein.

Only 2 of 96 normal donors had serum antibodies reactive with WT1/full-length protein (FIG. 18). One of those individuals had antibody to WT1/N-terminus protein and one had antibody to WT1/C-terminus protein. In contrast, 16 of 63 patients (25%) with AML had serum antibodies reactive with WT1/full-length protein. By marked contrast, only 2 of 63 patients (3%) had reactivity to WT1/C-terminus protein. Fifteen of 81 patients (19%) with CML had serum antibodies reactive with WT1/full-length protein and 12 of 81 patients (15%) had serum antibodies reactive with WT1/N-terminus. Only 3 of 81 patients (3%) had reactivity to WT1/C-terminus protein. (FIGS. 16 and 17.)

These data demonstrate that Ab responses to WT1 are detectable in some patients with AML and CML. The greater incidence of antibody in leukemia patients provides strong evidence that immunization to the WT1 protein occurred as a result of patients bearing malignancy that expresses or at some time expressed WT1. Without being limited to a specific theory, it is believed that the observed antibody responses to WT1 most probably result from patients becoming immune to WT1 on their own leukemia cells and provide direct evidence that WT1 can be immunogenic despite being a "self" protein.

The presence of antibody to WT1 strongly implies that concurrent helper T cell responses are also present in the same patients. WT1 is an internal protein. Thus, CTL responses are likely to be the most effective in terms of leukemia therapy and the most toxic arm of immunity. Thus, these data provide evidence that therapeutic vaccines directed against WT1 will be able to elicit an immune response to WT1.

The majority of the antibodies detected were reactive with epitopes within the N-terminus while only a small subgroup of patients showed a weak antibody response to the C-terminus. This is consistent with observations in the animal model, where immunization with peptides derived from the N-terminus elicited antibody, helper T cell and CTL responses, whereas none of the peptides tested from the C-terminus elicited antibody or T cell responses (Gaiger et al., *Blood* 96:1334, 2000).

Example 2

Induction of Antibodies to WT1 in Mice Immunized with Cell Lines Expressing WT1

This Example illustrates the use of cells expressing WT1 to induce a WT1 specific antibody response in vivo.

Detection of existent antibodies to WT1 in patients with leukemia strongly implied that it is possible to immunize to WT1 protein to elicit immunity to WT1. To test whether immunity to WT1 can be generated by vaccination, mice were injected with TRAMP-C, a WT1 positive tumor cell line of B6 origin. Briefly, male B6 mice were immunized with $5\times10^6$ TRAMP-C cells subcutaneously and boosted twice with $5\times10^6$ cells at three week intervals. Three weeks after the final immunization, sera were obtained and single cell suspensions of spleens were prepared in RPMI 1640 medium (GIBCO®) with 25 μM β-2-mercaptoethanol, 200 units of penicillin per ml, 10 mM L-glutamine, and 10% fetal bovine serum.

Figure 3:
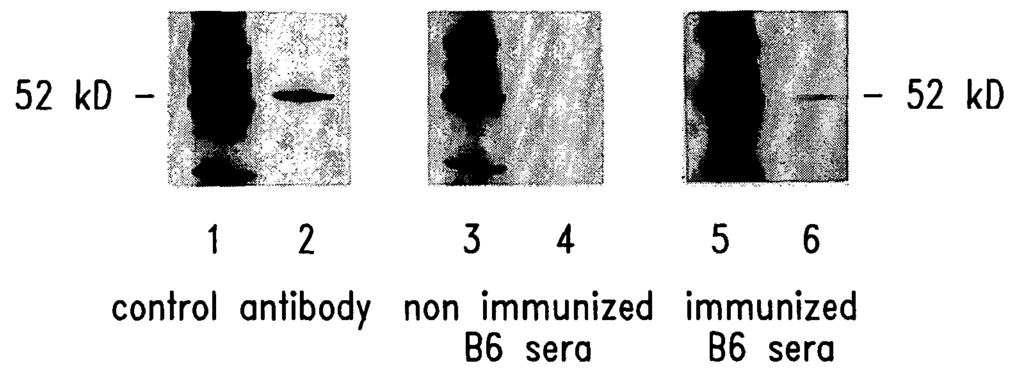
FIG. 3 is a Western blot illustrating the detection of a WT1 specific antibody response in B6 mice immunized with TRAMP-C, a WT1 positive tumor cell line. Lanes 1, 3 and 5 show molecular weight markers, and lanes 2, 4 and 6 show a WT1 specific positive control (N180, Santa Cruz Biotechnology, polypeptide spanning 180 amino acids of the N-terminal region of the WT1 protein, migrating on the Western blot at 52 kD). The primary antibody used was WT180 in lane 2, sera of non-immunized B6 mice in lane 4 and sera of the immunized B6 mice in lane 6.

Following immunization to TRAMP-C, a WT1 specific antibody response in the immunized animals was detectable. A representative Western blot is shown in FIG. 3. These results show that immunization to WT1 protein can elicit an immune response to WT1 protein.

Example 3

Induction of TH and Antibody Responses in Mice Immunized with WT1 Peptides

This Example illustrates the ability of immunization with WT1 peptides to elicit an immune response specific for WT1.

Peptides suitable for eliciting Ab and proliferative T cell responses were identified according to the Tsites program (Rothbard and Taylor, *EMBO J.* 7:93-100, 1988; Deavin et al., *Mol. Immunol.* 33:145-155, 1996), which searches for peptide motifs that have the potential to elicit Th responses. Peptides shown in Table I were synthesized and sequenced.

TABLE I

WT1 Peptides

| Peptide | Sequence | Comments |
|---|---|---|
| Mouse: p6-22 | RDLNALLPAVSSLGGGG (SEQ ID NO:13) | 1 mismatch relative to human WT1 sequence |
| Human: p6-22 | RDLNALLPAVPSLGGGG (SEQ ID NO:1) | |
| Human/mouse: p117-139 | PSQASSGQARMFPNAPYLPSCLE (SEQ ID NOs:2 and 3) | |
| Mouse: p244-262 | GATLKGMAAGSSSSVKWTE (SEQ ID NO:14) | 1 mismatch relative to human WT1 sequence |
| Human: p244-262 | GATLKGVAAGSSSSVKWTE (SEQ ID NO:4) | |
| Human/mouse: p287-301 | RIHTHGVFRGIQDVR (SEQ ID NOs:15 and 16) | |
| Mouse: p299-313 | VRRVSGVAPTLVRS (SEQ ID NO:17) | 1 mismatch relative to human WT1 sequence |
| Human/mouse: p421-435 | CQKKFARSDELVRHH (SEQ ID NOs:19 and 20) | |

For immunization, peptides were grouped as follows:

| | |
|---|---|
| Group A: | p6–22 human: 10.9 mg in 1 ml (10 μl = 100 μg) |
| | p117–139 human/mouse: 7.6 mg in 1 ml (14 μl = 100 μg) |
| | p244–262 human: 4.6. mg in 1 ml (22 μl = 100 μg) |
| Group B: | p287–301 human/mouse: 7.2 mg in 1 ml (14 μl = 100 μg) |
| | mouse p299–313: 6.6. mg in 1 ml (15 μl = 100 μg) |
| | p421–435 human/mouse: 3.3 mg in 1 ml (30 μl = 100 μg) |
| Control: | (FBL peptide 100 μg) + CFA/IFA |
| Control: | (CD45 peptide 100 μg) + CFA/IFA |

Group A contained peptides present within the amino terminus portion of WT1 (exon 1) and Group B contained peptides present within the carboxy terminus, which contains a four zinc finger region with sequence homology to other DNA-binding proteins. Within group B, p287-301 and p299-313 were derived from exon 7, zinc finger 1, and p421-435 was derived from exon 10, zinc finger IV.

B6 mice were immunized with a group of WT1 peptides or with a control peptide. Peptides were dissolved in 1 ml sterile water for injection, and B6 mice were immunized 3 times at time intervals of three weeks. Adjuvants used were CFA/IFA, GM-CSF, and MONTANIDE®. The presence of antibodies specific for WT1 was then determined as described in Examples 1 and 2, and proliferative T cell responses were evaluated using a standard thymidine incorporation assay, in which cells were cultured in the presence of antigen and proliferation was evaluated by measuring incorporated radioactivity (Chen et al., *Cancer Res.* 54:1065-1070, 1994). In particular, lymphocytes were cultured in 96-well plates at $2\times10^5$ cells per well with $4\times10^5$ irradiated (3000 rads) syngeneic spleen cells and the designated peptide.

Figure 4:
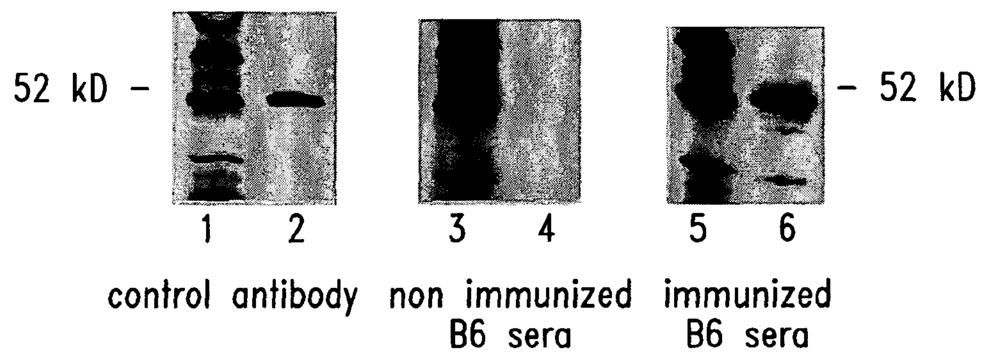
FIG. 4 is a Western blot illustrating the detection of WT1 specific antibodies in mice immunized with representative WT1 peptides. Lanes 1, 3 and 5 show molecular weight markers and lanes 2, 4 and 6 show a WT1 specific positive control (N180, Santa Cruz Biotechnology, polypeptide spanning 180 amino acids of the N-terminal region of the WT1 protein, migrating on the Western blot at 52 kD). The primary antibody used was WT180 in lane 2, sera of non-immunized B6 mice in lane 4 and sera of the immunized B6 mice in lane 6.
Figure 5A:
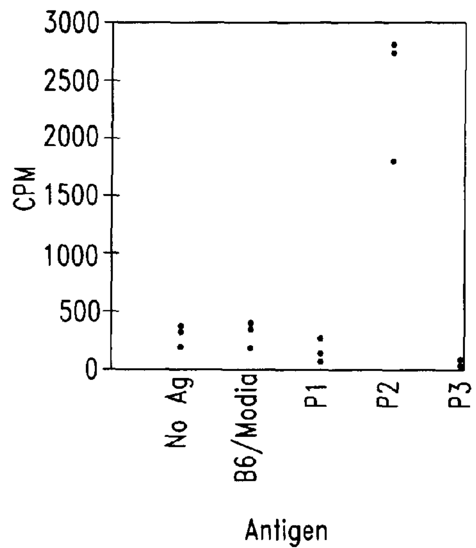
FIGS. 5A to 5C are graphs illustrating the stimulation of proliferative T cell responses in mice immunized with representative WT1 peptides. Thymidine incorporation assays were performed using one T cell line and two different clones, as indicated, and results were expressed as cpm. Controls indicated on the x axis were no antigen (No Ag) and B6/media; antigens used were p6-22 human (p1), p117-139 (p2) or p244-262 human (p3).
Figure 5B:
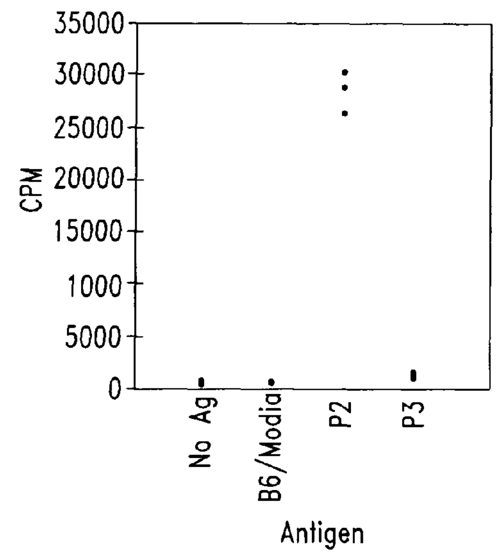
Figure 5C:
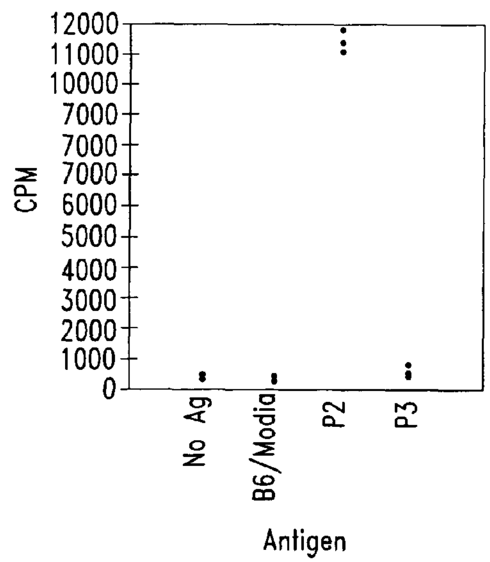

Immunization of mice with the group of peptides designated as Group A elicited an antibody response to WT1 (FIG. 4). No antibodies were detected following immunization to Vaccine B, which is consistent with a lack of helper T cell response from immunization with Vaccine B. P117-139 elicited proliferative T cell responses (FIGS. 5A-5C). The stimulation indices (SI) varied between 8 and 72. Other peptides (P6-22 and P299-313) also were shown to elicit proliferative T cell responses. Immunization with P6-22 resulted in a stimulation index (SI) of 2.3 and immunization with P299-313 resulted in a SI of 3.3. Positive controls included ConA stimulated T cells, as well as T cells stimulated with known antigens, such as CD45 and FBL, and allogeneic T cell lines (DeBruijn et al., *Eur. J. Immunol.* 21:2963-2970, 1991).

Figures 6A, 6B:
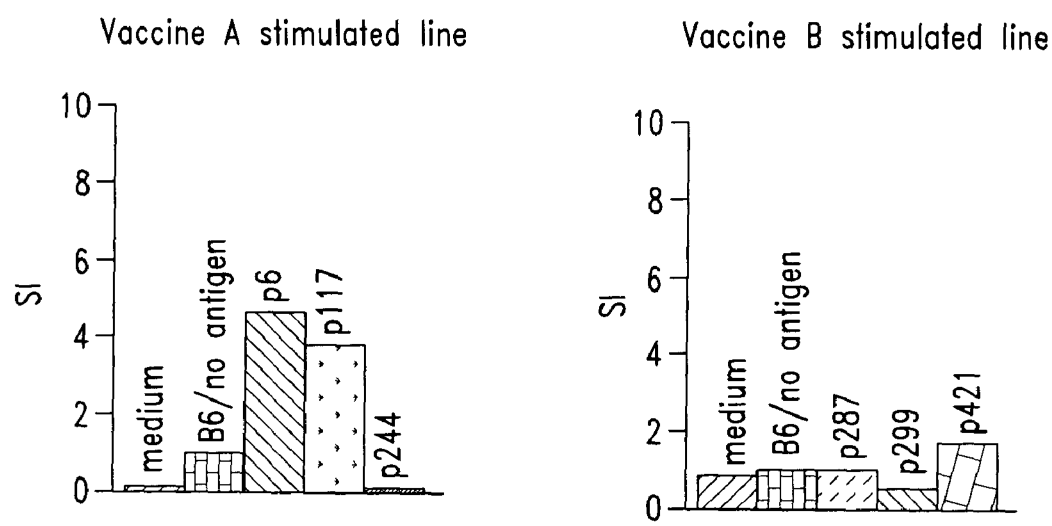
FIG. 6A and 6B are histograms illustrating the stimulation of proliferative T cell responses in mice immunized with representative WT1 peptides. Three weeks after the third immunization, spleen cells of mice that had been inoculated with Vaccine A or Vaccine B were cultured with medium alone (medium) or spleen cells and medium (B6/no antigen), B6 spleen cells pulsed with the peptides p6-22 (p6), p117-139 (p117), p244-262 (p244) (Vaccine A.

FIGS. 6A and 6B show the proliferative response observed for each of the three peptides within vaccine A (FIG. 6A) and vaccine B (FIG. 6B). Vaccine A elicited proliferative T cell responses to the immunizing peptides p6-22 and p117-139, with stimulation indices (SI) varying between 3 and 8 (bulk lines). No proliferative response to p244-262 was detected (FIG. 6A).

Figure 7A:
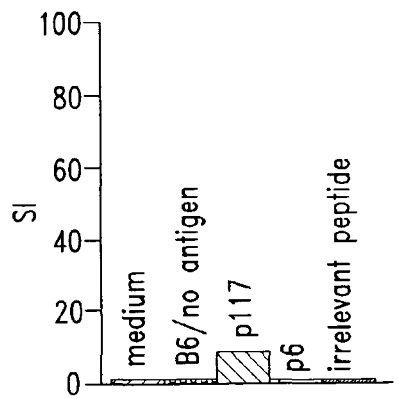
FIGS. 7A-7D are histograms illustrating the generation of proliferative T-cell lines and clones specific for p117-139 and p6-22. Following in vivo immunization, the initial three in vitro stimulations (IVS) were carried out using all three peptides of Vaccine A or B, respectively. Subsequent IVS were carried out as single peptide stimulations using only the two relevant peptides p117-139 and p6-22. Clones were derived from both the p6-22 and p117-139 specific T cell lines, as indicated. T cells were cultured with medium alone (medium) or spleen cells and medium (B6/no antigen), B6 spleen cells pulsed with the peptides p6-22 (p6), p117-139 (p117) or an irrelevant control peptide (irrelevant peptide) at 25 ug/ml and were assayed after 96 hr for proliferation by ($^3$H) thymidine incorporation. Bars represent the stimulation index (SI), which is calculated as the mean of the experimental wells divided by the mean of the control (B6 spleen cells with no antigen).
Figure 7B:
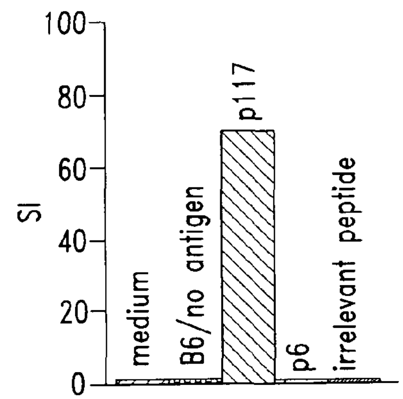
Figure 7C:
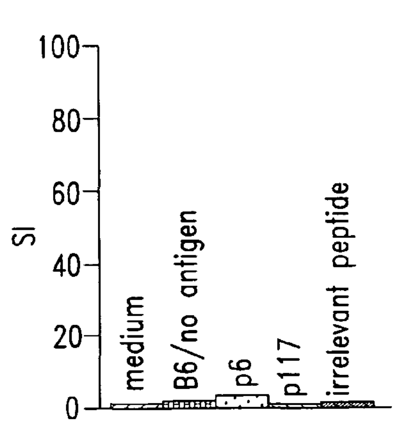
Figure 7D:
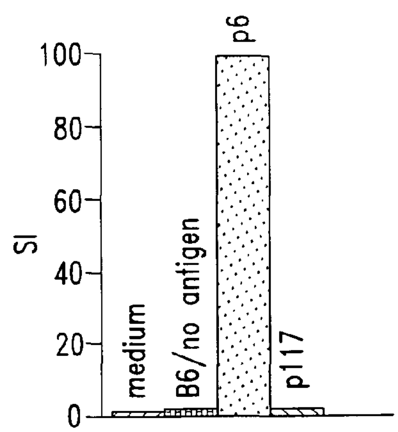

Subsequent in vitro stimulations were carried out as single peptide stimulations using only p6-22 and p117-139. Stimulation of the Vaccine A specific T cell line with p117-139 resulted in proliferation to p117-139 with no response to p6-22 (FIG. 7A). Clones derived from the line were specific for p117-139 (FIG. 7B). By contrast, stimulation of the Vaccine A specific T cell line with p6-22 resulted in proliferation to p6-22 with no response to p117-139 (FIG. 7C). Clones derived from the line were specific for p6-22 (FIG. 7D).

These results show that vaccination with WT1 peptides can elicit antibody responses to WT1 protein and proliferative T cell responses to the immunizing peptides.

Example 4

Induction of CTL Responses in Mice Immunized with WT1 Peptides

This Example illustrates the ability of WT1 peptides to elicit CTL immunity.

Peptides (9-mers) with motifs appropriate for binding to class I MHC were identified using a BIMAS HLA peptide binding prediction analysis (Parker et al., *J. Immunol.* 152: 163, 1994). Peptides identified within such analyses are shown in Tables II-XLIV. In each of these tables, the score reflects the theoretical binding affinity (half-time of disociation) of the peptide to the MHC molecule indicated.

Peptides identified using the Tsites program (Rothbard and Taylor, *EMBO J.* 7:93-100, 1988; Deavin et al., *Mol. Immunol.* 33:145-155, 1996), which searches for peptide motifs that have the potential to elicit Th responses are further shown in FIGS. 8A and 8B, and Table XLV.

TABLE II

Results of BIMAS HLA Peptide Binding Prediction Analysis for Binding of Human WT1 Peptides to Human HLA A1

| Rank | Start Position | Subsequence Residue Listing | Score (Estimate of Half Time of Disassociation of a Molecule Containing This Subsequence) |
|---|---|---|---|
| 1 | 137 | (SEQ ID NO:47) CLESQPAIR | 18.000 |
| 2 | 80 | (SEQ ID NO:87) GAEPHEEQC | 9.000 |

TABLE II-continued

Results of BIMAS HLA Peptide Binding Prediction Analysis for Binding of Human WT1 Peptides to Human HLA A1

| Rank | Start Position | Subsequence Residue Listing | Score (Estimate of Half Time of Disassociation of a Molecule Containing This Subsequence) |
|---|---|---|---|
| 3 | 40 | (SEQ ID NO:74) FAPPGASAY | 5.000 |
| 4 | 354 | (SEQ ID NO:162) QCDFKDCER | 5.000 |
| 5 | 2 | (SEQ ID NO:101) GSDVRDLNA | 3.750 |
| 6 | 152 | (SEQ ID NO:244) VTFDGTPSY | 2.500 |
| 7 | 260 | (SEQ ID NO:247) WTEGQSNHS | 2.250 |
| 8 | 409 | (SEQ ID NO:232) TSEKPFSCR | 1.350 |
| 9 | 73 | (SEQ ID NO:125) KQEPSWGGA | 1.350 |
| 10 | 386 | (SEQ ID NO:128) KTCQRKFSR | 1.250 |
| 11 | 37 | (SEQ ID NO:241) VLDFAPPGA | 1.000 |
| 12 | 325 | (SEQ ID NO:44) CAYPGCNKR | 1.000 |
| 13 | 232 | (SEQ ID NO:167) QLECMTWNQ | 0.900 |
| 14 | 272 | (SEQ ID NO:71) ESDNHTTPI | 0.750 |
| 15 | 366 | (SEQ ID NO:193) RSDQLKRHQ | 0.750 |
| 16 | 222 | (SEQ ID NO:217) SSDNLYQMT | 0.750 |
| 17 | 427 | (SEQ ID NO:191) RSDELVRHH | 0.750 |
| 18 | 394 | (SEQ ID NO:192) RSDHLKTHT | 0.750 |
| 19 | 317 | (SEQ ID NO:233) TSEKRPFMC | 0.675 |
| 20 | 213 | (SEQ ID NO:160) QALLLRTPY | 0.500 |

TABLE III

Results of BIMAS HLA Peptide Binding Prediction Analysis for Binding of Human WT1 Peptides to Human HLA A 0201

| Rank | Start Position | Subsequence Residue Listing | Score (Estimate of Half Time of Disassociation of a Molecule Containing This Subsequence) |
|---|---|---|---|
| 1 | 126 | RMFPNAPYL (SEQ ID NO:185) | 313.968 |
| 2 | 187 | (SEQ ID NO:214) SLGEQQYSV | 285.163 |
| 3 | 10 | (SEQ ID NO:34) ALLPAVPSL | 181.794 |
| 4 | 242 | (SEQ ID NO:146) NLGATLKGV | 159.970 |
| 5 | 225 | (SEQ ID NO:147) NLYQMTSQL | 68.360 |
| 6 | 292 | (SEQ ID NO:103) GVFRGJQDV | 51.790 |
| 7 | 191 | (SEQ ID NO:171) QQYSVPPPV | 22.566 |
| 8 | 280 | (SEQ ID NO:116) ILCGAQYRI | 17.736 |
| 9 | 235 | (SEQ ID NO:49) CMTWNQMNL | 15.428 |
| 10 | 441 | (SEQ ID NO:149) NMTKLQLAL | 15.428 |
| 11 | 7 | (SEQ ID NO:58) DLNALLPAV | 11.998 |
| 12 | 227 | (SEQ ID NO:251) YQMTSQLEC | 8.573 |
| 13 | 239 | (SEQ ID NO:151) NQMNLGATL | 8.014 |
| 14 | 309 | (SEQ ID NO:226) TLVRSASET | 7.452 |
| 15 | 408 | (SEQ ID NO:129) KTSEKPFSC | 5.743 |
| 16 | 340 | (SEQ ID NO:139) LQMHSRKHT | 4.752 |
| 17 | 228 | (SEQ ID NO:169) QMTSQLECM | 4.044 |
| 18 | 93 | (SEQ ID NO:235) TVHFSGQFT | 3.586 |
| 19 | 37 | (SEQ ID NO:241) VLDFAPPGA | 3.378 |
| 20 | 86 | (SEQ ID NO:69) EQCLSAFTV | 3.068 |

TABLE IV

Results of BIMAS HLA Peptide Binding Prediction Analysis for Binding of Human WT1 Peptides to Human HLA A 0205

| Rank | Start Position | Subsequence Residue Listing | Score (Estimate of Half Time of Disassociation of a Molecule Containing This Subsequence) |
|---|---|---|---|
| 1 | 10 | ALLPAVPSL (SEQ ID NO:34) | 42.000 |
| 2 | 292 | (SEQ ID NO:103) GVFRGIQDV | 24.000 |
| 3 | 126 | (SEQ ID NO:185) RMFPNAPYL | 21.000 |
| 4 | 225 | (SEQ ID NO:147) NLYQMTSQL | 21.000 |
| 5 | 239 | (SEQ ID NO:151) NQMNLGATL | 16.800 |
| 6 | 302 | (SEQ ID NO:195) RVPGVAPTL | 14.000 |
| 7 | 441 | (SEQ ID NO:149) NMTKLQLAL | 7.000 |
| 8 | 235 | (SEQ ID NO:49) CMTWNQMNL | 7.000 |
| 9 | 187 | (SEQ ID NO:214) SLGEQQYSV | 6.000 |
| 10 | 191 | (SEQ ID NO:171) QQYSVPPPV | 4.800 |
| 11 | 340 | (SEQ ID NO:139) LQMHSRKHT | 4.080 |
| 12 | 242 | (SEQ ID NO:146) NLGATLKGV | 4.000 |
| 13 | 227 | (SEQ ID NO:251) YQMTSQLEC | 3.600 |
| 14 | 194 | (SEQ ID NO:218) SVPPPVYGC | 2.000 |
| 15 | 93 | (SEQ ID NO:235) TVHFSGQFT | 2.000 |
| 16 | 280 | (SEQ ID NO:116) ILCGAQYRI | 1.700 |
| 17 | 98 | (SEQ ID NO:99) GQFTGTAGA | 1.200 |
| 18 | 309 | (SEQ ID NO:226) TLVRSASET | 1.000 |
| 19 | 81 | (SEQ ID NO:30) AEPHEEQCL | 0.980 |
| 20 | 73 | (SEQ ID NO:125) KQEPSWGGA | 0.960 |

TABLE V

Results of BIMAS HLA Peptide Binding Prediction Analysis for Binding of Human WT1 Peptides to Human HLA A24

| Rank | Start Position | Subsequence Residue Listing | Score (Estimate of Half Time of Disassociation of a Molecule Containing This Subsequence) |
|---|---|---|---|
| 1 | 302 | (SEQ ID NO:195) RVPGVAPTL | 16.800 |
| 2 | 218 | (SEQ ID NO:194) RTPYSSDNL | 12.000 |
| 3 | 356 | (SEQ ID NO:55) DFRDCERRF | 12.000 |
| 4 | 126 | (SEQ ID NO:185) RMFPNAPYL | 9.600 |
| 5 | 326 | (SEQ ID NO:42) AYPGCNKRY | 7.500 |
| 6 | 270 | (SEQ ID NO:106)T GYESDNHT | 7.500 |
| 7 | 239 | (SEQ ID NO:151) NQMNLGATL | 7.200 |
| 8 | 10 | (SEQ ID NO:34) ALLPAVPSL | 7.200 |
| 9 | 130 | (SEQ ID NO:144) NAPYLPSCL | 7.200 |
| 10 | 329 | (SEQ ID NO:90) GCNKRYFKL | 6.600 |
| 11 | 417 | (SEQ ID NO:196) RWPSCQKKF | 6.600 |
| 12 | 47 | (SEQ ID NO:41) AYGSLGGPA | 6.000 |
| 13 | 180 | (SEQ ID NO:59) DPMGQQGSL | 6.000 |
| 14 | 4 | (SEQ ID NO:62) DVRDLNALL | 5.760 |
| 15 | 285 | (SEQ ID NO:175) QYRIHTHGV | 5.000 |
| 16 | 192 | (SEQ ID NO:176) QYSVPPPVY | 5.000 |
| 17 | 207 | (SEQ ID NO:61) DSCTGSQAL | 4.800 |
| 18 | 441 | (SEQ ID NO:149) NMTKLQLAL | 4.800 |
| 19 | 225 | (SEQ ID NO:147) NLYQMTSQL | 4.000 |
| 20 | 235 | (SEQ ID NO:49) CMTWNQMNL | 4.000 |

TABLE VI

Results of BIMAS HLA Peptide Binding Prediction Analysis for Binding of Human WT1 Peptides to Human HLA A3

| Rank | Start Position | Subsequence Residue Listing | Score (Estimate of Half Time of Disassociation of a Molecule Containing This Subsequence) |
|---|---|---|---|
| 1 | 436 | (SEQ ID NO:148) NMHQRNMTK | 40.000 |
| 2 | 240 | (SEQ ID NO:168) QMNLGATLK | 20.000 |
| 3 | 88 | (SEQ ID NO:48) CLSAFTVHF | 6.000 |
| 4 | 126 | (SEQ ID NO:185) RMFPNAPYL | 4.500 |
| 5 | 169 | (SEQ ID NO:36) AQFPNHSFK | 4.500 |
| 6 | 10 | (SEQ ID NO:34) ALLPAVPSL | 4.050 |
| 7 | 137 | (SEQ ID NO:47) CLESQPAIR | 4.000 |
| 8 | 225 | (SEQ ID NO:147) NLYQMTSQL | 3.000 |
| 9 | 32 | (SEQ ID NO:37) AQWAPVLDF | 2.700 |
| 10 | 280 | (SEQ ID NO:116) ILCGAQYRI | 2.700 |
| 11 | 386 | (SEQ ID NO:128) KTCQRKFSR | 1.800 |
| 12 | 235 | (SEQ ID NO:49) CMTWNQMNL | 1.200 |
| 13 | 441 | (SEQ ID NO:149) NMTKLQLAL | 1.200 |
| 14 | 152 | (SEQ ID NO:244) VTFDGTPSY | 1.000 |
| 15 | 187 | (SEQ ID NO:214) SLGEQQYSV | 0.900 |
| 16 | 383 | (SEQ ID NO:80) FQCKTCQRK | 0.600 |
| 17 | 292 | (SEQ ID NO:103) GVFRGIQDV | 0.450 |
| 18 | 194 | (SEQ ID NO:218) SVPPPVYGC | 0.405 |
| 19 | 287 | (SEQ ID NO:182) RIHTHGVFR | 0.400 |
| 20 | 263 | (SEQ ID NO:100) GQSNHSTGY | 0.360 |

TABLE VII

Results of BIMAS HLA Peptide Binding Prediction Analysis for Binding of Human WT1 Peptides to Human HLA A68.1

| Rank | Start Position | Subsequence Residue Listing | Score (Estimate of Half Time of Dissociation of a Molecule Containing This Subsequence |
|---|---|---|---|
| 1 | 100 | (SEQ ID NO:84) FTGTAGACR | 100.000 |
| 2 | 386 | (SEQ ID NO:128) KTCQRKFSR | 50.000 |
| 3 | 368 | (SEQ ID NO:60) DQLKRHQRR | 30.000 |
| 4 | 312 | (SEQ ID NO:190) RSASETSEK | 18.000 |
| 5 | 337 | (SEQ ID NO:141) LSHLQMHSR | 15.000 |
| 6 | 364 | (SEQ ID NO:83) FSRSDQLKR | 15.000 |
| 7 | 409 | (SEQ ID NO:232) TSEKPFSCR | 15.000 |
| 8 | 299 | (SEQ ID NO:63) DVRRVPGVA | 12.000 |
| 9 | 4 | (SEQ ID NO:62) DVRDLNALL | 12.000 |
| 10 | 118 | (SEQ ID NO:216) SQASSGQAR | 10.000 |
| 11 | 343 | (SEQ ID NO:111) HSRKHTGEK | 9.000 |
| 12 | 169 | (SEQ ID NO:36) AQFPNHSFK | 9.000 |
| 13 | 292 | (SEQ ID NO:103) GVFRGIQDV | 8.000 |
| 14 | 325 | (SEQ ID NO:44) CAYPGCNKR | 7.500 |
| 15 | 425 | (SEQ ID NO:75) FARSDELVR | 7.500 |
| 16 | 354 | (SEQ ID NO:162) QCDFKDCER | 7.500 |
| 17 | 324 | (SEQ ID NO:142) MCAYPGCNK | 6.000 |
| 18 | 251 | (SEQ ID NO:28) AAGSSSSVK | 6.000 |
| 19 | 379 | (SEQ ID NO:104) GVKPFQCKT | 6.000 |
| 20 | 137 | (SEQ ID NO:47) CLESQPAIR | 5.000 |

TABLE VIII

Results of BIMAS HLA Peptide Binding Prediction Analysis for Binding of Human WT1 Peptides to Human HLA A 1101

| Rank | Start Position | Subsequence Residue Listing | Score (Estimate of Half Time of Dissociation of a Molecule Containing This Subsequence) |
|---|---|---|---|
| 1 | 386 | (SEQ ID NO:128) KTCQRKFSR | 1.800 |
| 2 | 169 | (SEQ ID NO:36) AQFPNHSFK | 1.200 |
| 3 | 436 | (SEQ ID NO:148) NMHQRNMTK | 0.800 |
| 4 | 391 | (SEQ ID NO:120) KFSRSDHLK | 0.600 |
| 5 | 373 | (SEQ ID NO:109) HQRRHTGVK | 0.600 |
| 6 | 383 | (SEQ ID NO:80) FQCKTCQRK | 0.600 |
| 7 | 363 | (SEQ ID NO:178) RFSRSDQLK | 0.600 |
| 8 | 240 | (SEQ ID NO:168) QMNLGATLK | 0.400 |
| 9 | 287 | (SEQ ID NO:182) RIHTHGVFR | 0.240 |
| 10 | 100 | (SEQ ID NO:84) FTGTAGACR | 0.200 |
| 11 | 324 | (SEQ ID NO:142) MCAYPGCNK | 0.200 |
| 12 | 251 | (SEQ ID NO:28) AAGSSSSVK | 0.200 |
| 13 | 415 | (SEQ ID NO:201) SCRWPSCQK | 0.200 |
| 14 | 118 | (SEQ ID NO:216) SQASSGQAR | 0.120 |
| 15 | 292 | (SEQ ID NO:103) GVFRGIQDV | 0.120 |
| 16 | 137 | (SEQ ID NO:47) CLESQPAIR | 0.080 |
| 17 | 425 | (SEQ ID NO:75) FARSDELVR | 0.080 |
| 18 | 325 | (SEQ ID NO:44) CAYPGCNKR | 0.080 |
| 19 | 312 | (SEQ ID NO:190) RSASETSEK | 0.060 |
| 20 | 65 | (SEQ ID NO:156)K PPPPHSFI | 0.060 |

TABLE IX

Results of BIMAS HLA Peptide Binding Prediction Analysis for Binding of Human WT1 Peptides to Human HLA A 3101

| Rank | Start Position | Subsequence Residue Listing | Score (Estimate of Half Time of Disassociation of a Molecule Containing This Subsequence) |
|---|---|---|---|
| 1 | 386 | (SEQ ID NO:128) KTCQRKFSR | 9.000 |
| 2 | 287 | (SEQ ID NO:182) RIHTHGVFR | 6.000 |
| 3 | 137 | (SEQ ID NO:47) CLESQPAIR | 2.000 |
| 4 | 118 | (SEQ ID NO:216) SQASSGQAR | 2.000 |
| 5 | 368 | (SEQ ID NO:60) DQLKRHQRR | 1.200 |
| 6 | 100 | (SEQ ID NO:84) FTGTAGACR | 1.000 |
| 7 | 293 | (SEQ ID NO:238) VFRGIQDVR | 0.600 |
| 8 | 325 | (SEQ ID NO:44) CAYPGCNKR | 0.600 |
| 9 | 169 | (SEQ ID NO:36) AQFPNHSFK | 0.600 |
| 10 | 279 | (SEQ ID NO:155) PILCGAQYR | 0.400 |
| 11 | 436 | (SEQ ID NO:148) NMHQRNMTK | 0.400 |
| 12 | 425 | (SEQ ID NO:75) FARSDELVR | 0.400 |
| 13 | 32 | (SEQ ID NO:37) AQWAPVLDF | 0.240 |
| 14 | 240 | (SEQ ID NO:168) QMNLGATLK | 0.200 |
| 15 | 354 | (SEQ ID NO:162) QCDFKDCER | 0.200 |
| 16 | 373 | (SEQ ID NO:109) HQRRHTGVK | 0.200 |
| 17 | 383 | (SEQ ID NO:80) FQCKTCQRK | 0.200 |
| 18 | 313 | (SEQ ID NO:197) SASETSEKR | 0.200 |
| 19 | 358 | (SEQ ID NO:118) KDCERRFSR | 0.180 |
| 20 | 391 | (SEQ ID NO:120) KFSRSDHLK | 0.180 |

TABLE X

Results of BIMAS HLA Peptide Binding Prediction Analysis for Binding of Human WT1 Peptides to Human HLA A 3302

| Rank | Start Position | Subsequence Residue Listing | Score (Estimate of Half Time of Disassociation of a Molecule Containing This Subsequence) |
|---|---|---|---|
| 1 | 337 | (SEQ ID NO:141) LSHLQMHSR | 15.000 |
| 2 | 409 | (SEQ ID NO:232) TSEKPFSCR | 15.000 |
| 3 | 364 | (SEQ ID NO:83) FSRSDQLKR | 15.000 |
| 4 | 137 | (SEQ ID NO:47) CLESQPAIR | 9.000 |
| 5 | 368 | (SEQ ID NO:60) DQLKRHQRR | 9.000 |
| 6 | 287 | (SEQ ID NO:182) RIHTHGVFR | 4.500 |
| 7 | 210 | (SEQ ID NO:223) TGSQALLLR | 3.000 |
| 8 | 425 | (SEQ ID NO:75) FARSDELVR | 3.000 |
| 9 | 313 | (SEQ ID NO:197) SASETSEKR | 3.000 |
| 10 | 293 | (SEQ ID NO:238) VFRGIQDVR | 3.000 |
| 11 | 354 | (SEQ ID NO:162) QCDFKDCER | 3.000 |
| 12 | 100 | (SEQ ID NO:84) FTGTAGACR | 3.000 |
| 13 | 118 | (SEQ ID NO:216) SQASSGQAR | 3.000 |
| 14 | 325 | (SEQ ID NO:44) CAYPGCNKR | 3.000 |
| 15 | 207 | (SEQ ID NO:61) DSCTGSQAL | 1.500 |
| 16 | 139 | (SEQ ID NO:72) ESQPAIRNQ | 1.500 |
| 17 | 299 | (SEQ ID NO:63) DVRRVPGVA | 1.500 |
| 18 | 419 | (SEQ ID NO:159) PSCQKKFAR | 1.500 |
| 19 | 272 | (SEQ ID NO:71) ESDNHTTPI | 1.500 |
| 20 | 4 | (SEQ ID NO:62) DVRDLNALL | 1.500 |

TABLE XI

Results of BIMAS HLA Peptide Binding Prediction Analysis for Binding of Human WT1 Peptides to Human HLA B14

| Rank | Start Position | Subsequence Residue Listing | Score (Estimate of Half Time of Disassociation of a Molecule Containing This Subsequence) |
|---|---|---|---|
| 1 | 362 | RRFSRSDQL (SEQ ID NO:187) | 1000.000 |
| 2 | 332 | KRYFKLSHL (SEQ ID NO:127) | 300.000 |
| 3 | 423 | KKFARSDEL (SEQ ID NO:122) | 150.000 |
| 4 | 390 | RKFSRSDHL (SEQ ID NO:183) | 150.000 |
| 5 | 439 | QRNMTKLQL (SEQ ID NO:173) | 20.000 |
| 6 | 329 | GCNKRYFKL (SEQ ID NO:90) | 10.000 |
| 7 | 10 | ALLPAVPSL (SEQ ID NO:34) | 10.000 |
| 8 | 180 | DPMGQQGSL (SEQ ID NO:59) | 9.000 |
| 9 | 301 | RRVPGVAPT (SEQ ID NO:189) | 6.000 |
| 10 | 126 | RMFPNAPYL (SEQ ID NO:185) | 5.000 |
| 11 | 371 | KRHQRRHTG (SEQ ID NO:126) | 5.000 |
| 12 | 225 | NLYQMTSQL (SEQ ID NO:147) | 5.000 |
| 13 | 144 | IRNQGYSTV (SEQ ID NO:117) | 4.000 |
| 14 | 429 | DELVRHHNM (SEQ ID NO:53) | 3.000 |
| 15 | 437 | MHQRNMTKL (SEQ ID NO:143) | 3.000 |
| 16 | 125 | ARMFPNAPY (SEQ ID NO:38) | 3.000 |
| 17 | 239 | NQMNLGATL (SEQ ID NO:151) | 3.000 |
| 18 | 286 | YRIHTHGVF (SEQ ID NO:252) | 3.000 |
| 19 | 174 | HSFKHEDPM (SEQ ID NO:110) | 3.000 |
| 20 | 372 | RHQRRHTGV (SEQ ID NO:181) | 3.000 |

TABLE XII

Results of BIMAS HLA Peptide Binding Prediction Analysis for Binding of Human WT1 Peptides to Human HLA B40

| Rank | Start Position | Subsequence Residue Listing | Score (Estimate of Half Time of Disassociation of a Molecule Containing This Subsequence) |
|---|---|---|---|
| 1 | 81 | AEPHEEQCL (SEQ ID NO:30) | 40.000 |
| 2 | 429 | DELVRHHNM (SEQ ID NO:53) | 24.000 |
| 3 | 410 | SEKPFSCRW (SEQ ID NO:207) | 20.000 |
| 4 | 318 | SEKRPFMCA (SEQ ID NO:208) | 15.000 |
| 5 | 233 | LECMTWNQM (SEQ ID NO:131) | 12.000 |
| 6 | 3 | SDVRDLNAL (SEQ ID NO:206) | 10.000 |
| 7 | 349 | GEKPYQCDF (SEQ ID NO:91) | 8.000 |
| 8 | 6 | RDLNALLPA (SEQ ID NO:177) | 5.000 |
| 9 | 85 | EEQCLSAFT (SEQ ID NO:65) | 4.000 |
| 10 | 315 | SETSEKRPF (SEQ ID NO:209) | 4.000 |

TABLE XII-continued

Results of BIMAS HLA Peptide Binding Prediction Analysis for Binding of Human WT1 Peptides to Human HLA B40

| Rank | Start Position | Subsequence Residue Listing | Score (Estimate of Half Time of Disassociation of a Molecule Containing This Subsequence) |
|---|---|---|---|
| 11 | 261 | TEGQSNHST (SEQ ID NO:221) | 4.000 |
| 12 | 23 | GCALPVSGA (SEQ ID NO:89) | 3.000 |
| 13 | 38 | LDFAPPGAS (SEQ ID NO:130) | 3.000 |
| 14 | 273 | SDNHTTPIL (SEQ ID NO:204) | 2.500 |
| 15 | 206 | TDSCTGSQA (SEQ ID NO:220) | 2.500 |
| 16 | 24 | CALPVSGAA (SEQ ID NO:43) | 2.000 |
| 17 | 98 | GQFTGTAGA (SEQ ID NO:99) | 2.000 |
| 18 | 30 | GAAQWAPVL (SEQ ID NO:86) | 2.000 |
| 19 | 84 | HEEQCLSAF (SEQ ID NO:107) | 2.000 |
| 20 | 26 | LPVSGAAQW (SEQ ID NO:138) | 2.000 |

TABLE XIII

Results of BIMAS HLA Peptide Binding Prediction Analysis for Binding of Human WT1 Peptides to Human HLA B60

| Rank | Start Position | Subsequence Residue Listing | Score (Estimate of Half Time of Disassociation of a Molecule Containing This Subsequence) |
|---|---|---|---|
| 1 | 81 | AEPHEEQCL (SEQ ID NO:30) | 160.000 |
| 2 | 3 | SDVRDLNAL (SEQ ID NO:206) | 40.000 |
| 3 | 429 | DELVRHHNM (SEQ ID NO:53) | 40.000 |
| 4 | 233 | LECMTWNQM (SEQ ID NO:131) | 22.000 |
| 5 | 273 | SDNHTTPIL (SEQ ID NO:204) | 20.000 |
| 6 | 209 | CTGSQALLL (SEQ ID NO:52) | 8.000 |
| 7 | 30 | GAAQWAPVL (SEQ ID NO:86) | 8.000 |
| 8 | 318 | SEKRPFMCA (SEQ ID NO:208) | 8.000 |
| 9 | 180 | DPMGQQGSL (SEQ ID NO:59) | 8.000 |
| 10 | 138 | LESQPAIRN (SEQ ID NO:132) | 5.280 |
| 11 | 239 | NQMNLGATL (SEQ ID NO:151) | 4.400 |
| 12 | 329 | GCNKRYFKL (SEQ ID NO:90) | 4.400 |
| 13 | 130 | NAPYLPSCL (SEQ ID NO:144) | 4.400 |
| 14 | 85 | EEQCLSAFT (SEQ ID NO:65) | 4.400 |
| 15 | 208 | SCTGSQALL (SEQ ID NO:202) | 4.000 |
| 16 | 207 | DSCTGSQAL (SEQ ID NO:61) | 4.000 |
| 17 | 218 | RTPYSSDNL (SEQ ID NO:194) | 4.000 |
| 18 | 261 | TEGQSNHST (SEQ ID NO:221) | 4.000 |

TABLE XIII-continued

Results of BIMAS HLA Peptide Binding Prediction Analysis for Binding of Human WT1 Peptides to Human HLA B60

| Rank | Start Position | Subsequence Residue Listing | Score (Estimate of Half Time of Disassociation of a Molecule Containing This Subsequence) |
|---|---|---|---|
| 19 | 18 | LGGGGGCAL (SEQ ID NO:134) | 4.000 |
| 20 | 221 | YSSDNLYQM (SEQ ID NO:253) | 2.200 |

TABLE XIV

Results of BIMAS HLA Peptide Binding Prediction Analysis for Binding of Human WT1 Peptides to Human HLA B61

| Rank | Start Position | Subsequence Residue Listing | Score (Estimate of Half Time of Disassociation of a Molecule Containing This Subsequence) |
|---|---|---|---|
| 1 | 318 | SEKRPFMCA (SEQ ID NO:208) | 20.000 |
| 2 | 429 | DELVRHHNM (SEQ ID NO:53) | 16.000 |
| 3 | 298 | QDVRRVPGV (SEQ ID NO:164) | 10.000 |
| 4 | 81 | AEPHEEQCL (SEQ ID NO:30) | 8.000 |
| 5 | 233 | LECMTWNQM (SEQ ID NO:131) | 8.000 |
| 6 | 6 | RDLNALLPA (SEQ ID NO:177) | 5.500 |
| 7 | 85 | EEQCLSAFT (SEQ ID NO:65) | 4.000 |
| 8 | 261 | TEGQSNHST (SEQ ID NO:221) | 4.000 |
| 9 | 206 | TDSCTGSQA (SEQ ID NO:220) | 2.500 |
| 10 | 295 | RGIQDVRRV (SEQ ID NO:179) | 2.200 |
| 11 | 3 | SDVRDLNAL (SEQ ID NO:206) | 2.000 |
| 12 | 250 | VAAGSSSSV (SEQ ID NO:236) | 2.000 |
| 13 | 29 | SGAAQWAPV (SEQ ID NO:21 1) | 2.000 |
| 14 | 315 | SETSEKRPF (SEQ ID NO:209) | 1.600 |
| 15 | 138 | LESQPAIRN (SEQ ID NO:132) | 1.200 |
| 16 | 244 | GATLKGVAA (SEQ ID NO:88) | 1.100 |
| 17 | 20 | GGGGCALPV (SEQ ID NO:92) | 1.100 |
| 18 | 440 | RNMTKLQLA (SEQ ID NO:186) | 1.100 |
| 19 | 23 | GCALPVSGA (SEQ ID NO:89) | 1.100 |
| 20 | 191 | QQYSVPPPV (SEQ ID NO:171) | 1.000 |

TABLE XV

Results of BIMAS HLA Peptide Binding Prediction Analysis for Binding of Human WT1 Peptides to Human HLA B62

| Rank | Start Position | Subsequence Residue Listing | Score (Estimate of Half Time of Disassociation of a Molecule Containing This Subsequence) |
|---|---|---|---|
| 1 | 146 | NQGYSTVTF (SEQ ID NO:150) | 211.200 |
| 2 | 32 | AQWAPVLDF (SEQ ID NO:37) | 96.000 |

TABLE XV-continued

Results of BIMAS HLA Peptide Binding Prediction Analysis for Binding of Human WT1 Peptides to Human HLA B62

| Rank | Start Position | Subsequence Residue Listing | Score (Estimate of Half Time of Disassociation of a Molecule Containing This Subsequence) |
|---|---|---|---|
| 3 | 263 | GQSNHSTGY (SEQ ID NO:100) | 96.000 |
| 4 | 88 | CLSAFTVHF (SEQ ID NO:48) | 96.000 |
| 5 | 17 | SLGGGGGCA (SEQ ID NO:215) | 9.600 |
| 6 | 239 | NQMNLGATL (SEQ ID NO:151) | 8.800 |
| 7 | 191 | QQYSVPPPV (SEQ ID NO:171) | 8.000 |
| 8 | 98 | GQFTGTAGA (SEQ ID NO:99) | 8.000 |
| 9 | 384 | QCKTCQRKF (SEQ ID NO:163) | 6.000 |
| 10 | 40 | FAPPGASAY (SEQ ID NO:74) | 4.800 |
| 11 | 227 | YQMTSQLEC (SEQ ID NO:251) | 4.800 |
| 12 | 187 | SLGEQQYSV (SEQ ID NO:214) | 4.400 |
| 13 | 86 | EQCLSAFTV (SEQ ID NO:69) | 4.400 |
| 14 | 152 | VTFDGTPSY (SEQ ID NO:244) | 4.400 |
| 15 | 101 | TGTAGACRY (SEQ ID NO:224) | 4.000 |
| 16 | 242 | NLGATLKGV (SEQ ID NO:146) | 4.000 |
| 17 | 92 | FTVHFSGQF (SEQ ID NO:85) | 4.000 |
| 18 | 7 | DLNALLPAV (SEQ ID NO:58) | 4.000 |
| 19 | 123 | GQARMFPNA (SEQ ID NO:98) | 4.000 |
| 20 | 280 | ILCGAQYRI (SEQ ID NO:116) | 3.120 |

TABLE XVI

Results of BIMAS HLA Peptide Binding Prediction Analysis for Binding of Human WT1 Peptides to Human HLA B7

| Rank | Start Position | Subsequence Residue Listing | Score (Estimate of Half Time of Disassociation of a Molecule Containing This Subsequence) |
|---|---|---|---|
| 1 | 180 | DPMGQQGSL (SEQ ID NO:59) | 240.000 |
| 2 | 4 | DVRDLNALL (SEQ ID NO:62) | 200.000 |
| 3 | 302 | RVPGVAPTL (SEQ ID NO:195) | 20.000 |
| 4 | 30 | GAAQWAPVL (SEQ ID NO:86) | 12.000 |
| 5 | 239 | NQMNLGATL (SEQ ID NO:151) | 12.000 |
| 6 | 130 | NAPYLPSCL (SEQ ID NO:144) | 12.000 |
| 7 | 10 | ALLPAVPSL (SEQ ID NO:34) | 12.000 |
| 8 | 299 | DVRRVPGVA (SEQ ID NO:63) | 5.000 |
| 9 | 208 | SCTGSQALL (SEQ ID NO:202) | 4.000 |
| 10 | 303 | VPGVAPTLV (SEQ ID NO:242) | 4.000 |
| 11 | 18 | LGGGGGCAL (SEQ ID NO:134) | 4.000 |
| 12 | 218 | RTPYSSDNL (SEQ ID NO:194) | 4.000 |

TABLE XVI-continued

Results of BIMAS HLA Peptide Binding Prediction Analysis for Binding of Human WT1 Peptides to Human HLA B7

| Rank | Start Position | Subsequence Residue Listing | Score (Estimate of Half Time of Disassociation of a Molecule Containing This Subsequence) |
|---|---|---|---|
| 13 | 207 | DSCTGSQAL (SEQ ID NO:61) | 4.000 |
| 14 | 209 | CTGSQALLL (SEQ ID NO:52) | 4.000 |
| 15 | 329 | GCNKRYFKL (SEQ ID NO:90) | 4.000 |
| 16 | 235 | CMTWNQMNL (SEQ ID NO:49) | 4.000 |
| 17 | 441 | NMTKLQLAL (SEQ ID NO:149) | 4.000 |
| 18 | 126 | RMFPNAPYL (SEQ ID NO:185) | 4.000 |
| 19 | 225 | NLYQMTSQL (SEQ ID NO:147) | 4.000 |
| 20 | 143 | AIRNQGYST (SEQ ID NO:33) | 3.000 |

TABLE XVII

Results of BIMAS HLA Peptide Binding Prediction Analysis for Binding of Human WT1 Peptides to Human HLA B8

| Rank | Start Position | Subsequence Residue Listing | Score (Estimate of Half Time of Disassociation of a Molecule Containing This Subsequence) |
|---|---|---|---|
| 1 | 329 | GCNKRYFKL (SEQ ID NO:90) | 16.000 |
| 2 | 4 | DVRDLNALL (SEQ ID NO:62) | 12.000 |
| 3 | 316 | ETSEKLRPFM(SEQ ID NO:73) | 3.000 |
| 4 | 180 | DPMGQQGSL (SEQ ID NO:59) | 1.600 |
| 5 | 208 | SCTGSQALL (SEQ ID NO:202) | 0.800 |
| 6 | 130 | NAPYLPSCL (SEQ ID NO:144) | 0.800 |
| 7 | 244 | GATLKGVAA (SEQ ID NO:88) | 0.800 |
| 8 | 30 | GAAQWAPVL (SEQ ID NO:86) | 0.800 |
| 9 | 299 | DVRRVPGVA (SEQ ID NO:63) | 0.400 |
| 10 | 420 | SCQKKFARS (SEQ ID NO:200) | 0.400 |
| 11 | 387 | TCQRKFSRS (SEQ ID NO:219) | 0.400 |
| 12 | 225 | NLYQMTSQL (SEQ ID NO:147) | 0.400 |
| 13 | 141 | QPAIRNQGY (SEQ ID NO:170) | 0.400 |
| 14 | 10 | ALLPAVPSL (SEQ ID NO:34) | 0.400 |
| 15 | 207 | DSCTGSQAL (SEQ ID NO:61) | 0.400 |
| 16 | 384 | QCKTCQRKF (SEQ ID NO:163) | 0.400 |
| 17 | 136 | SCLESQPAI (SEQ ID NO:198) | 0.300 |
| 18 | 347 | HTGEKPYQC (SEQ ID NO:112) | 0.300 |
| 19 | 401 | HTRTHTGKT (SEQ ID NO:114) | 0.200 |
| 20 | 332 | KRYFKLSHL (SEQ ID NO:127) | 0.200 |

TABLE XVIII

Results of BIMAS HLA Peptide Binding Prediction Analysis for Binding of Human WT1 Peptides to Human HLA B 2702

| Rank | Start Position | Subsequence Residue Listing | Score (Estimate of Half Time of Disassociation of a Molecule Containing This Subsequence) |
|---|---|---|---|
| 1 | 332 | KRYFKLSHL (SEQ ID NO:127) | 900.000 |
| 2 | 362 | RRFSRSDQL (SEQ ID NO:187) | 900.000 |
| 3 | 286 | YRIHTHGVF (SEQ ID NO:252) | 200.000 |
| 4 | 125 | ARMFPNAPY (SEQ ID NO:38) | 200.000 |
| 5 | 375 | RRHTGVKPF (SEQ ID NO:188) | 180.000 |
| 6 | 32 | AQWAPVLDF (SEQ ID NO:37) | 100.000 |
| 7 | 301 | RRVPGVAPT (SEQ ID NO:189) | 60.000 |
| 8 | 439 | QRNMTKLQL (SEQ ID NO:173) | 60.000 |
| 9 | 126 | RMFPNAPYL (SEQ ID NO:185) | 22.500 |
| 10 | 426 | ARSDELVRH (SEQ ID NO:39) | 20.000 |
| 11 | 146 | NQGYSTVTF (SEQ ID NO:150) | 20.000 |
| 12 | 144 | IRNQGYSTV (SEQ ID NO:117) | 20.000 |
| 13 | 389 | QRKFSRSDH (SEQ ID NO:172) | 20.000 |
| 14 | 263 | GQSNHSTGY (SEQ ID NO:100) | 20.000 |
| 15 | 416 | CRWPSCQKK (SEQ ID NO:50) | 20.000 |
| 16 | 191 | QQYSVPPPV (SEQ ID NO:171) | 10.000 |
| 17 | 217 | LRTPYSSDN (SEQ ID NO:140) | 10.000 |
| 18 | 107 | CRYGPFGPP (SEQ ID NO:51) | 10.000 |
| 19 | 98 | GQFTGTAGA (SEQ ID NO:99) | 10.000 |
| 20 | 239 | NQMNLGATL (SEQ ID NO:151) | 6.000 |

TABLE XIX

Results of BIMAS HLA Peptide Binding Prediction Analysis for Binding of Human WT1 Peptides to Human HLA B 2705

| Rank | Start Position | Subsequence Residue Listing | Score (Estimate of Half Time of Disassociation of a Molecule Containing This Subsequence) |
|---|---|---|---|
| 1 | 332 | KRYFKLSHL (SEQ ID NO:127) | 30000.000 |
| 2 | 362 | RRFSRSDQL (SEQ ID NO:187) | 30000.000 |
| 3 | 416 | CRWPSCQKK (SEQ ID NO:50) | 10000.000 |
| 4 | 439 | QRNMTKLQL (SEQ ID NO:173) | 2000.000 |
| 5 | 286 | YRIHTHGVF (SEQ ID NO:252) | 1000.000 |
| 6 | 125 | ARMFPNAPY (SEQ ID NO:38) | 1000.000 |
| 7 | 294 | FRGIQDVRR (SEQ ID NO:81) | 1000.000 |
| 8 | 432 | VRHHNMHQR (SEQ ID NO:243) | 1000.000 |
| 9 | 169 | AQFPNHSFK (SEQ ID NO:36) | 1000.000 |

TABLE XIX-continued

Results of BIMAS HLA Peptide Binding Prediction Analysis for Binding of Human WT1 Peptides to Human HLA B 2705

| Rank | Start Position | Subsequence Residue Listing | Score (Estimate of Half Time of Disassociation of a Molecule Containing This Subsequence) |
|---|---|---|---|
| 10 | 375 | RRHTGVKPF (SEQ ID NO:188) | 900.000 |
| 11 | 126 | RMFPNAPYL (SEQ ID NO:185) | 750.000 |
| 12 | 144 | IRNQGYSTV (SEQ ID NO:117) | 600.000 |
| 13 | 301 | RRVPGVAPT (SEQ ID NO:189) | 600.000 |
| 14 | 32 | AQWAPVLDF (SEQ ID NO:37) | 500.000 |
| 15 | 191 | QQYSVPPPV (SEQ ID NO:171) | 300.000 |
| 16 | 373 | HQRRHTGVK (SEQ ID NO:109) | 200.000 |
| 17 | 426 | ARSDELVRH (SEQ ID NO:39) | 200.000 |
| 18 | 383 | FQCKTCQRK (SEQ ID NO:80) | 200.000 |
| 19 | 239 | NQMNLGATL (SEQ ID NO:151) | 200.000 |
| 20 | 389 | QRKFSRSDH (SEQ ID NO:172) | 200.000 |

TABLE XX

Results of BIMAS HLA Peptide Binding Prediction Analysis for Binding of Human WT1 Peptides to Human HLA B 3501

| Rank | Start Position | Subsequence Residue Listing | Score (Estimate of Half Time of Disassociation of a Molecule Containing This Subsequence) |
|---|---|---|---|
| 1 | 278 | TPILCGAQY (SEQ ID NO:227) | 40.000 |
| 2 | 141 | QPAIRNQGY (SEQ ID NO:170) | 40.000 |
| 3 | 219 | TPYSSDNLY (SEQ ID NO:231) | 40.000 |
| 4 | 327 | YPGCNKRYF (SEQ ID NO:250) | 20.000 |
| 5 | 163 | TPSHHAAQF (SEQ ID NO:228) | 20.000 |
| 6 | 180 | DPMGQQGSL (SEQ ID NO:59) | 20.000 |
| 7 | 221 | YSSDNLYQM (SEQ ID NO:253) | 20.000 |
| 8 | 26 | LPVSGAAQW (SEQ ID NO:138) | 10.000 |
| 9 | 174 | HSFKjHEDPM(SEQ ID NO:110) | 10.000 |
| 10 | 82 | EPHEEQCLS (SEQ ID NO:68) | 6.000 |
| 11 | 213 | QALLLRTPY (SEQ ID NO:160) | 6.000 |
| 12 | 119 | QASSGQALRM(SEQ ID NO:161) | 6.000 |
| 13 | 4 | DVRDLNALL (SEQ ID NO:62) | 6.000 |
| 14 | 40 | FAPPGASAY (SEQ ID NO:74) | 6.000 |
| 15 | 120 | ASSGQARMF (SEQ ID NO:40) | 5.000 |
| 16 | 207 | DSCTGSQAL (SEQ ID NO:61) | 5.000 |
| 17 | 303 | VPGVAPTLV (SEQ ID NO:242) | 4.000 |

TABLE XX-continued

| Results of BIMAS HLA Peptide Binding Prediction Analysis for Binding of Human WT1 Peptides to Human HLA B 3501 | | | |
|---|---|---|---|
| Rank | Start Position | Subsequence Residue Listing | Score (Estimate of Half Time of Disassociation of a Molecule Containing This Subsequence) |
| 18 | 316 | ETSEKRPFM (SEQ ID NO:73) | 4.000 |
| 19 | 152 | VTFDGTPSY (SEQ ID NO:244) | 4.000 |
| 20 | 412 | KPFSCRWPS (SEQ ID NO:123) | 4.000 |

TABLE XXI

| Results of BIMAS HLA Peptide Binding Prediction Analysis for Binding of Human WT1 Peptides to Human HLA B 3701 | | | |
|---|---|---|---|
| Rank | Start Position | Subsequence Residue Listing | Score (Estimate of Half Time of Disassociation of a Molecule Containing This Subsequence) |
| 1 | 3 | (SEQ ID NO:206) SDVRDLNAL | 40.000 |
| 2 | 273 | (SEQ ID NO:204) SDNHTTPIL | 40.000 |
| 3 | 81 | (SEQ ID NO:30) AEPHEEQCL | 10.000 |
| 4 | 298 | (SEQ ID NO:164) QDVRRVPGV | 8.000 |
| 5 | 428 | (SEQ ID NO:203) SDELVRHHN | 6.000 |
| 6 | 85 | (SEQ ID NO:65) EEQCLSAFT | 5.000 |
| 7 | 208 | (SEQ ID NO:202) SCTGSQALL | 5.000 |
| 8 | 4 | (SEQ ID NO:62) DVRDLNALL | 5.000 |
| 9 | 209 | (SEQ ID NO:52) CTGSQALLL | 5.000 |
| 10 | 38 | (SEQ ID NO:130) LDFAPPGAS | 4.000 |
| 11 | 223 | (SEQ ID NO:205) SDNLYQMTS | 4.000 |
| 12 | 179 | (SEQ ID NO:64) EDPMGQQGS | 4.000 |
| 13 | 206 | (SEQ ID NO:220) TDSCTGSQA | 4.000 |
| 14 | 6 | (SEQ ID NO:177) RDLNALLPA | 4.000 |
| 15 | 84 | (SEQ ID NO:107) HEEQCLSAF | 2.000 |
| 16 | 233 | (SEQ ID NO:131) LECMTWNQM | 2.000 |
| 17 | 429 | (SEQ ID NO:53) DELVRHHNM | 2.000 |

TABLE XXI-continued

| Results of BIMAS HLA Peptide Binding Prediction Analysis for Binding of Human WT1 Peptides to Human HLA B 3701 | | | |
|---|---|---|---|
| Rank | Start Position | Subsequence Residue Listing | Score (Estimate of Half Time of Disassociation of a Molecule Containing This Subsequence) |
| 18 | 315 | (SEQ ID NO:209) SETSEKRPF | 2.000 |
| 19 | 349 | (SEQ ID NO:91) GEKPYQCDF | 2.000 |
| 20 | 302 | (SEQ ID NO:195) RVPGVAPTL | 1.500 |

TABLE XXII

| Results of BIMAS HLA Peptide Binding Prediction Analysis for Binding of Human WT1 Peptides to Human HLA B 3801 | | | |
|---|---|---|---|
| Rank | Start Position | Subsequence Residue Listing | Score (Estimate of Half Time of Disassociation of a Molecule Containing This Subsequence) |
| 1 | 437 | (SEQ ID NO:143) MHQRNMTKL | 36.000 |
| 2 | 434 | (SEQ ID NO:108) HHNMHQRNM | 6.000 |
| 3 | 372 | (SEQ ID NO:181) RHQRRHTGV | 6.000 |
| 4 | 180 | (SEQ ID NO:59) DPMGQQGSL | 4.000 |
| 5 | 433 | (SEQ ID NO:180) RHHNMHQRN | 3.900 |
| 6 | 165 | (SEQ ID NO:213) SHHAAQFPN | 3.900 |
| 7 | 202 | (SEQ ID NO:45) CHTPTDSCT | 3.000 |
| 8 | 396 | (SEQ ID NO:57) DHLKTHTRT | 3.000 |
| 9 | 161 | (SEQ ID NO:94) GHTPSHHAA | 3.000 |

TABLE XXII-continued

Results of BIMAS HLA Peptide Binding Prediction Analysis for Binding of Human WT1 Peptides to Human HLA B 3801

| Rank | Start Position | Subsequence Residue Listing | Score (Estimate of Half Time of Dissociation of a Molecule Containing This Subsequence) |
|---|---|---|---|
| 10 | 302 | (SEQ ID NO:195) RVPGVAPTL | 2.600 |
| 11 | 417 | (SEQ ID NO:196) RWPSCQKKF | 2.400 |
| 12 | 327 | (SEQ ID NO:250) YPGCNKRYF | 2.400 |
| 13 | 208 | (SEQ ID NO:202) SCTGSQALL | 2.000 |
| 14 | 163 | (SEQ ID NO:228) TPSHHAAQF | 2.000 |
| 15 | 120 | (SEQ ID NO:40) ASSGQARMF | 2.000 |
| 16 | 18 | (SEQ ID NO:134) LGGGGGCAL | 2.000 |
| 17 | 177 | (SEQ ID NO:121) KHEDPMGQQ | 1.800 |
| 18 | 83 | (SEQ ID NO:154) PHEEQCLSA | 1.800 |
| 19 | 10 | (SEQ ID NO:34) ALLPAVPSL | 1.300 |
| 20 | 225 | (SEQ ID NO:147) NLYQMTSQL | 1.300 |

TABLE XXIII

Results of BIMAS HLA Peptide Binding Prediction Analysis for Binding of Human WT1 Peptides to Human HLA B 3901

| Rank | Start Position | Subsequence Residue Listing | Score (Estimate of Half Time of Dissociation of a Molecule Containing This Subsequence) |
|---|---|---|---|
| 1 | 437 | (SEQ ID NO:143) MHQRNMTKL | 135.000 |
| 2 | 332 | (SEQ ID NO:127) KRYFKLSHL | 45.000 |
| 3 | 434 | (SEQ ID NO:108) HHNMHQRNM | 30.000 |
| 4 | 362 | (SEQ ID NO:187) RRFSRSDQL | 30.000 |
| 5 | 372 | (SEQ ID NO:181) RHQRRHTGV | 30.000 |
| 6 | 10 | (SEQ ID NO:34) ALLPAVPSL | 9.000 |
| 7 | 439 | (SEQ ID NO:173) QRNMTKLQL | 7.500 |

TABLE XXIII-continued

Results of BIMAS HLA Peptide Binding Prediction Analysis for Binding of Human WT1 Peptides to Human HLA B 3901

| Rank | Start Position | Subsequence Residue Listing | Score (Estimate of Half Time of Dissociation of a Molecule Containing This Subsequence) |
|---|---|---|---|
| 8 | 390 | (SEQ ID NO:183) RKFSRSDHL | 6.000 |
| 9 | 396 | (SEQ ID NO:57) DHLKTHTRT | 6.000 |
| 10 | 239 | (SEQ ID NO:151) NQMNLGATL | 6.000 |
| 11 | 423 | (SEQ ID NO:122) KKFARSDEL | 6.000 |
| 12 | 126 | (SEQ ID NO:185) RMFPNAPYL | 6.000 |
| 13 | 225 | (SEQ ID NO:147) NLYQMTSQL | 6.000 |
| 14 | 180 | (SEQ ID NO:59) DPMGQQGSL | 6.000 |
| 15 | 144 | (SEQ ID NO:117) IRNQGYSTV | 5.000 |
| 16 | 136 | (SEQ ID NO:198) SCLESQPAI | 4.000 |
| 17 | 292 | (SEQ ID NO:103) GVFRGIQDV | 3.000 |
| 18 | 302 | (SEQ ID NO:195) RVPGVAPTL | 3.000 |
| 19 | 208 | (SEQ ID NO:202) SCTGSQALL | 3.000 |
| 20 | 207 | (SEQ ID NO:61) DSCTGSQAL | 3.000 |

TABLE XXIV

Results of BIMAS HLA Peptide Binding Prediction Analysis for Binding of Human WT1 Peptides to Human HLA B 3902

| Rank | Start Position | Subsequence Residue Listing | Score (Estimate of Half Time of Dissociation of a Molecule Containing This Subsequence) |
|---|---|---|---|
| 1 | 239 | (SEQ ID NO:151) NQMNLGATL | 24.000 |
| 2 | 390 | (SEQ ID NO:183) RKFSRSDHL | 20.000 |
| 3 | 423 | (SEQ ID NO:122) KKFARSDEL | 20.000 |
| 4 | 32 | (SEQ ID NO:37) AQWAPVLDF | 5.000 |
| 5 | 146 | (SEQ ID NO:150) NQGYSTVTF | 5.000 |
| 6 | 130 | (SEQ ID NO:144) NAPYLPSCL | 2.400 |

TABLE XXIV-continued

Results of BIMAS HLA Peptide Binding Prediction Analysis for Binding of Human WT1 Peptides to Human HLA B 3902

| Rank | Start Position | Subsequence Residue Listing | Score (Estimate of Half Time of Dissociation of a Molecule Containing This Subsequence) |
|---|---|---|---|
| 7 | 225 | (SEQ ID NO:147) NLYQMTSQL | 2.400 |
| 8 | 30 | (SEQ ID NO:86) GAAQWAPVL | 2.400 |
| 9 | 441 | (SEQ ID NO:149) NMTKLQLAL | 2.400 |
| 10 | 302 | (SEQ ID NO:195) RVPGVAPTL | 2.400 |
| 11 | 126 | (SEQ ID NO:185) RMFPNAPYL | 2.000 |
| 12 | 218 | (SEQ ID NO:194) RTPYSSDNL | 2.000 |
| 13 | 209 | (SEQ ID NO:52) CTGSQALLL | 2.000 |
| 14 | 332 | (SEQ ID NO:127) KRYFKLSHL | 2.000 |
| 15 | 180 | (SEQ ID NO:59) DPMGQQGSL | 2.000 |
| 16 | 437 | (SEQ ID NO:143) MHQRNMTKL | 2.000 |
| 17 | 207 | (SEQ ID NO:61) DSCTGSQAL | 2.000 |
| 18 | 208 | (SEQ ID NO:202) SCTGSQALL | 2.000 |
| 19 | 329 | (SEQ ID NO:90) GCNKRYFKL | 2.000 |
| 20 | 10 | (SEQ ID NO:34) ALLPAVPSL | 2.000 |

TABLE XXV

Results of BIMAS HLA Peptide Binding Prediction Analysis for Binding of Human WT1 Peptides to Human HLA B 4403

| Rank | Start Position | Subsequence Residue Listing | Score (Estimate of Half Time of Dissociation of a Molecule Containing This Subsequence) |
|---|---|---|---|
| 1 | 315 | (SEQ ID NO:209) SETSEKRPF | 80.000 |
| 2 | 349 | (SEQ ID NO:91) GEKPYQCDF | 80.000 |
| 3 | 84 | (SEQ ID NO:107) HEEQCLSAF | 60.000 |
| 4 | 410 | (SEQ ID NO:207) SEKPFSCRW | 48.000 |

TABLE XXV-continued

Results of BIMAS HLA Peptide Binding Prediction Analysis for Binding of Human WT1 Peptides to Human HLA B 4403

| Rank | Start Position | Subsequence Residue Listing | Score (Estimate of Half Time of Dissociation of a Molecule Containing This Subsequence) |
|---|---|---|---|
| 5 | 429 | (SEQ ID NO:53) DELVRHHNM | 24.000 |
| 6 | 278 | (SEQ ID NO:227) TPILCGAQY | 15.000 |
| 7 | 141 | (SEQ ID NO:170) QPAIRNQGY | 9.000 |
| 8 | 40 | (SEQ ID NO:74) FAPPGASAY | 9.000 |
| 9 | 213 | (SEQ ID NO:160) 9.000 QALLLRTPY | |
| 10 | 318 | (SEQ ID NO:208) SEKRPFMCA | 8.000 |
| 11 | 81 | (SEQ ID NO:30) AEPHEEQCL | 8.000 |
| 12 | 152 | (SEQ ID NO:244) VTFDGTPSY | 4.500 |
| 13 | 101 | (SEQ ID NO:224) TGTAGACRY | 4.500 |
| 14 | 120 | (SEQ ID NO:40) ASSGQARMF | 4.500 |
| 15 | 261 | (SEQ ID NO:221) TEGQSNHST | 4.000 |
| 16 | 85 | (SEQ ID NO:65) EEQCLSAFT | 4.000 |
| 17 | 233 | (SEQ ID NO:131) LECMTWNQM | 4.000 |
| 18 | 104 | (SEQ ID NO:31) AGACRYGPF | 4.000 |
| 19 | 3 | (SEQ ID NO:206) SDVRDLNAL | 3.000 |
| 20 | 185 | (SEQ ID NO:166) QGSLGEQQY | 3.000 |

TABLE XXVI

Results of BIMAS HLA Peptide Binding Prediction Analysis for Binding of Human WT1 Peptides to Human HLA B 5101

| RanK | Start Position | Subsequence Residue Listing | Score (Estimate of Half Time of Dissociation of a Molecule Containing This Subsequence) |
|---|---|---|---|
| 1 | 303 | (SEQ ID NO:242) VPGVAPTLV | 314.600 |
| 2 | 180 | (SEQ ID NO:59) DPMGQQGSL | 242.000 |

TABLE XXVI-continued

Results of BIMAS HLA Peptide Binding Prediction Analysis for Binding of Human WT1 Peptides to Human HLA B 5101

| RanK | Start Position | Subsequence Residue Listing | Score (Estimate of Half Time of Disassociation of a Molecule Containing This Subsequence) |
|---|---|---|---|
| 3 | 250 | (SEQ ID NO:236) VAAGSSSSV | 157.300 |
| 4 | 130 | (SEQ ID NO:144) NAPYLPSCL | 50.000 |
| 5 | 30 | (SEQ ID NO:86) GAAQWAPVL | 50.000 |
| 6 | 20 | (SEQ ID NO:92) GGGGCALPV | 44.000 |
| 7 | 64 | (SEQ ID NO:157) PPPPPHSFI | 40.000 |
| 8 | 29 | (SEQ ID NO:211) SGAAQWAPV | 40.000 |
| 9 | 18 | (SEQ ID NO:134) LGGGGGCAL | 31.460 |
| 10 | 295 | (SEQ ID NO:179) RGIQDVRRV | 22.000 |
| 11 | 119 | (SEQ ID NO:161) QASSGQARM | 18.150 |
| 12 | 418 | (SEQ ID NO:246) WPSCQKKFA | 12.100 |
| 13 | 82 | (SEQ ID NO:68) EPHEEQCLS | 12.100 |
| 14 | 110 | (SEQ ID NO:96) GPFGPPPPS | 11.000 |
| 15 | 272 | (SEQ ID NO:71) ESDNHTTPI | 8.000 |
| 16 | 306 | (SEQ ID NO:237) VAPTLVRSA | 7.150 |
| 17 | 280 | (SEQ ID NO:116) ILCGAQYRI | 6.921 |
| 18 | 219 | (SEQ ID NO:231) TPYSSDNLY | 6.600 |
| 19 | 128 | (SEQ ID NO:79) FPNAPYLPS | 6.500 |
| 20 | 204 | (SEQ ID NO:230) TPTDSCTGS | 6.050 |

TABLE XXVII

Results of BIMAS HLA Peptide Binding Prediction Analysis for Binding of Human WT1 Peptides to Human HLA B 5102

| Rank | Start Position | Subsequence Residue Listing | Score (Estimate of Half Time of Disassociation of a Molecule Containing This Subsequence) |
|---|---|---|---|
| 1 | 295 | (SEQ ID NO:179) RGIQDVRRV | 290.400 |
| 2 | 303 | (SEQ ID NO:242) VPGVAPTLV | 200.000 |
| 3 | 180 | (SEQ ID NO:59) DPMGQQGSL | 133.100 |
| 4 | 250 | (SEQ ID NO:236) VAAGSSSSV | 110.000 |
| 5 | 30 | (SEQ ID NO:86) GAAQWAPVL | 55.000 |
| 6 | 130 | (SEQ ID NO:144) NAPYLPSCL | 50.000 |
| 7 | 20 | (SEQ ID NO:92) GGGGCALPV | 44.000 |
| 8 | 29 | (SEQ ID NO:211) SGAAQWAPV | 44.000 |
| 9 | 64 | (SEQ ID NO:157) PPPPPHSFI | 40.000 |
| 10 | 119 | (SEQ ID NO:161) QASSGQARM | 36.300 |
| 11 | 110 | (SEQ ID NO:96) GPFGPPPPS | 27.500 |
| 12 | 412 | (SEQ ID NO:123) KPFSCRWPS | 25.000 |
| 13 | 18 | (SEQ ID NO:134) LGGGGGCAL | 24.200 |
| 14 | 24 | (SEQ ID NO:43) CALPVSGAA | 16.500 |
| 15 | 219 | (SEQ ID NO:231) TPYSSDNLY | 15.000 |
| 16 | 292 | (SEQ ID NO:103) GVFRGIQDV | 14.641 |
| 17 | 136 | (SEQ ID NO:198) SCLESQPAI | 14.520 |
| 18 | 418 | (SEQ ID NO:246) WPSCQKKFA | 12.100 |
| 19 | 269 | (SEQ ID NO:225) TGYESDNHT | 11.000 |
| 20 | 351 | (SEQ ID NO:124) RPYQCDFKD | 11.000 |

TABLE XXVIII

Results of BIMAS HLA Peptide Binding Prediction Analysis for Binding of Human WT1 Peptides to Human HLA B 5201

| Rank | Start Position | Subsequence Residue Listing | Score (Estimate of Half Time of Dissasociation of a Molecule Containing This Subsequence) |
|---|---|---|---|
| 1 | 191 | (SEQ ID NO:171) QQYSVPPPV | 100.000 |
| 2 | 32 | (SEQ ID NO:37) AQWAPVLDF | 30.000 |
| 3 | 243 | (SEQ ID NO:133) LGATLKGVA | 16.500 |
| 4 | 303 | (SEQ ID NO:242) VPGVAPTLV | 13.500 |
| 5 | 86 | (SEQ ID NO:69) EQCLSAFTV | 12.000 |
| 6 | 295 | (SEQ ID NO:179) RGIQDVRRV | 10.000 |
| 7 | 98 | (SEQ ID NO:99) GQFTGTAGA | 8.250 |
| 8 | 292 | (SEQ ID NO:103) GVFRGIQDV | 8.250 |
| 9 | 29 | (SEQ ID NO:211) SGAAQWAPV | 6.000 |
| 10 | 146 | (SEQ ID NO:150) NQGYSTVTF | 5.500 |
| 11 | 20 | (SEQ ID NO:92) GGGGCALPV | 5.000 |
| 12 | 239 | (SEQ ID NO:151) NQMNLGATL | 4.000 |
| 13 | 64 | (SEQ ID NO:157) PPPPPHSFI | 3.600 |
| 14 | 273 | (SEQ ID NO:204) SDNHTTPIL | 3.300 |
| 15 | 286 | (SEQ ID NO:252) YRIHTHGVF | 3.000 |
| 16 | 269 | (SEQ ID NO:225) TGYESDNHT | 3.000 |
| 17 | 406 | (SEQ ID NO:222) TGKTSEKPF | 2.750 |
| 18 | 327 | (SEQ ID NO:250) YPGCNKRYF | 2.750 |
| 19 | 7 | (SEQ ID NO:58) DLNALLPAV | 2.640 |
| 20 | 104 | (SEQ ID NO:31) AGACRYGPF | 2.500 |

TABLE XXIX

Results of BIMAS HLA Peptide Binding Prediction Analysis for Binding of Human WT1 Peptides to Human HLA B 5801

| Rank | Start Position | Subsequence Residue Listing | Score (Estimate of Half Time of Dissasociation of a Molecule Containing This Subsequence) |
|---|---|---|---|
| 1 | 230 | (SEQ ID NO:234) TSQLECMTW | 96.800 |
| 2 | 92 | (SEQ ID NO:85) FTVHFSGQF | 60.000 |
| 3 | 120 | (SEQ ID NO:40) ASSGQARMF | 40.000 |
| 4 | 168 | (SEQ ID NO:29) AAQFPNHSF | 20.000 |
| 5 | 408 | (SEQ ID NO:129) KTSEKPFSC | 12.000 |
| 6 | 394 | (SEQ ID NO:192) RSDHLKTHT | 9.900 |
| 7 | 276 | (SEQ ID NO:115) HTTPILCGA | 7.200 |
| 8 | 218 | (SEQ ID NO:194) RTPYSSDNL | 6.600 |
| 9 | 152 | (SEQ ID NO:244) VTFDGTPSY | 6.000 |
| 10 | 40 | (SEQ ID NO:74) FAPPGASAY | 6.000 |
| 11 | 213 | (SEQ ID NO:160) QALLLRTPY | 4.500 |
| 12 | 347 | (SEQ ID NO:112) HTGEKPYQC | 4.400 |
| 13 | 252 | (SEQ ID NO:32) AGSSSSVKW | 4.400 |
| 14 | 211 | (SEQ ID NO:102) GSQALLLRT | 4.356 |
| 15 | 174 | (SEQ ID NO:110) HSFKHEDPM | 4.000 |
| 16 | 317 | (SEQ ID NO:233) TSEKRPFMC | 4.000 |
| 17 | 26 | (SEQ ID NO:138) LPVSGAAQW | 4.000 |
| 18 | 289 | (SEQ ID NO:113) HTHGVFRGI | 3.600 |
| 19 | 222 | (SEQ ID NO:217) SSDNLYQMT | 3.300 |
| 20 | 96 | (SEQ ID NO:82) FSGQFTGTA | 3.300 |

TABLE XXX

Results of BIMAS HLA Peptide Binding Prediction Analysis for Binding of Human WT1 Peptides to Human HLA CW0301

| Rank | Start Position | Subsequence Residue Listing | Score (Estimate of Half Time of Disassociation of a Molecule Containing This Subsequence) |
|---|---|---|---|
| 1 | 10 | (SEQ ID NO:34) ALLPAVPSL | 100.000 |
| 2 | 332 | (SEQ ID NO:127) KRYFKLSHL | 48.000 |
| 3 | 126 | (SEQ ID NO:185) RMFPNAPYL | 36.000 |
| 4 | 3 | (SEQ ID NO:206) SDVRDLNAL | 30.000 |
| 5 | 239 | (SEQ ID NO:151) NQMNLGATL | 24.000 |
| 6 | 225 | (SEQ ID NO:147) NLYQMTSQL | 24.000 |
| 7 | 180 | (SEQ ID NO:59) DPMGQQGSL | 20.000 |
| 8 | 362 | (SEQ ID NO:187) RRFSRSDQL | 12.000 |
| 9 | 329 | (SEQ ID NO:90) GCNKRYFKL | 10.000 |
| 10 | 286 | (SEQ ID NO:252) YRIHTHGVF | 10.000 |
| 11 | 301 | (SEQ ID NO:189) RRVPGVAPT | 10.000 |
| 12 | 24 | (SEQ ID NO:43) CALPVSGAA | 10.000 |
| 13 | 136 | (SEQ ID NO:198) SCLESQPAI | 7.500 |
| 14 | 437 | (SEQ ID NO:143) MHQRNMTKL | 7.200 |
| 15 | 390 | (SEQ ID NO:183) RKFSRSDHL | 6.000 |
| 16 | 423 | (SEQ ID NO:122) KKFARSDEL | 6.000 |
| 17 | 92 | (SEQ ID NO:85) FTVHFSGQF | 5.000 |
| 18 | 429 | (SEQ ID NO:53) DELVRHHNM | 5.000 |
| 19 | 130 | (SEQ ID NO:144) NAPYLPSCL | 4.800 |
| 20 | 30 | (SEQ ID NO:86) GAAQWAPVL | 4.000 |

TABLE XXXI

Results of BIMAS HLA Peptide Binding Prediction Analysis for Binding of Human WT1 Peptides to Human HLA CW0401

| Rank | Start Position | Subsequence Residue Listing | Score (Estimate of Half Time of Disassociation of a Molecule Containing This Subsequence) |
|---|---|---|---|
| 1 | 356 | DFKDCERRF (SEQ ID NO:55) | 120.000 |
| 2 | 334 | YFKLSHLQM (SEQ ID NO:248) | 100.000 |
| 3 | 180 | DPMGQQGSL (SEQ ID NO:59) | 88.000 |
| 4 | 163 | TPSHHAAQF (SEQ ID NO:228) | 52.800 |
| 5 | 327 | YPGCNKRYF (SEQ ID NO:250) | 40.000 |
| 6 | 285 | QYRIHTHGV (SEQ ID NO:175) | 27.500 |
| 7 | 424 | KFARSDELV (SEQ ID NO:119) | 25.000 |
| 8 | 326 | AYPGCNKRY (SEQ ID NO:42) | 25.000 |
| 9 | 192 | QYSVPPPVY (SEQ ID NO:176) | 25.000 |
| 10 | 417 | RWPSCQKKF (SEQ ID NO:196) | 22.000 |
| 11 | 278 | TPILCGAQY (SEQ ID NO:227) | 12.000 |
| 12 | 10 | ALLPAVPSL (SEQ ID NO:34) | 11.616 |
| 13 | 141 | QPAIRNQGY (SEQ ID NO:170) | 11.000 |

TABLE XXXI-continued

Results of BIMAS HLA Peptide Binding Prediction Analysis for Binding of Human WT1 Peptides to Human HLA CW0401

| Rank | Start Position | Subsequence Residue Listing | Score (Estimate of Half Time of Disassociation of a Molecule Containing This Subsequence) |
|---|---|---|---|
| 14 | 303 | VPGVAPTLV (SEQ ID NO:242) | 11.000 |
| 15 | 219 | TPYSSDNLY (SEQ ID NO:231) | 10.000 |
| 16 | 39 | DFAPPGASA (SEQ ID NO:54) | 7.920 |
| 17 | 99 | QFTGTAGAC (SEQ ID NO:165) | 6.000 |
| 18 | 4 | DVRDLNALL (SEQ ID NO:62) | 5.760 |
| 19 | 70 | SFIKQEPSW (SEQ ID NO:210) | 5.500 |
| 20 | 63 | PPPPPPHSF (SEQ ID NO:158) | 5.280 |

TABLE XXXII

Results of BIMAS HLA Peptide Binding Prediction Analysis for Binding of Human WT1 Peptides to Human HLA CW0602

| Rank | Start Position | Subsequence Residue Listing | Score (Estimate of Half Time of Disassociation of a Molecule Containing This Subsequence) |
|---|---|---|---|
| 1 | 332 | KRYFKLSHL (SEQ ID NO:127) | 9.680 |
| 2 | 239 | NQMNLGATL (SEQ ID NO:151) | 6.600 |
| 3 | 130 | NAPYLPSCL (SEQ ID NO:144) | 6.600 |
| 4 | 7 | DLNALLPAV (SEQ ID NO:58) | 6.000 |
| 5 | 441 | NMTKLQLAL (SEQ ID NO:149) | 6.000 |
| 6 | 225 | NLYQMTSQL (SEQ ID NO:147) | 6.000 |
| 7 | 4 | DVRDLNALL (SEQ ID NO:62) | 6.000 |
| 8 | 3 | SDVRDLNAL (SEQ ID NO:206) | 4.400 |
| 9 | 10 | ALLPAVPSL (SEQ ID NO:34) | 4.000 |
| 10 | 213 | QALLLRTPY (SEQ ID NO:160) | 3.300 |
| 11 | 319 | EKRPFMCAY (SEQ ID NO:67) | 3.000 |
| 12 | 30 | GAAQWAPVL (SEQ ID NO:86) | 2.200 |
| 13 | 242 | NLGATLKGV (SEQ ID NO:146) | 2.200 |
| 14 | 292 | GVFRGIQDV (SEQ ID NO:103) | 2.200 |
| 15 | 207 | DSCTGSQAL (SEQ ID NO:61) | 2.200 |
| 16 | 362 | RRFSRSDQL (SEQ ID NO:187) | 2.200 |
| 17 | 439 | QRNMTKLQL (SEQ ID NO:173) | 2.200 |
| 18 | 295 | RGIQDVRRV (SEQ ID NO:179) | 2.200 |
| 19 | 423 | KKFARSDEL (SEQ ID NO:122) | 2.200 |
| 20 | 180 | DPMGQQGSL (SEQ ID NO:59) | 2.200 |

TABLE XXXIII

| Results of BIMAS HLA Peptide Binding Prediction Analysis for Binding of Human WT1 Peptides to Human HLA CW0702 | | | |
|---|---|---|---|
| Rank | Start Position | Subsequence Residue Listing | Score (Estimate of Half Time of Disassociation of a Molecule Containing This Subsequence) |
| 1 | 319 | EKRPFMCAY (SEQ ID NO:67) | 26.880 |
| 2 | 326 | AYPGCNKRY (SEQ ID NO:42) | 24.000 |
| 3 | 40 | FAPPGASAY (SEQ ID NO:74) | 14.784 |
| 4 | 192 | QYSVPPPVY (SEQ ID NO:176) | 12.000 |
| 5 | 278 | TPILCGAQY (SEQ ID NO:227) | 12.000 |
| 6 | 219 | TPYSSDNLY (SEQ ID NO:231) | 12.000 |
| 7 | 213 | QALLLRTPY (SEQ ID NO:160) | 8.800 |
| 8 | 125 | ARMFPNAPY (SEQ ID NO:38) | 8.000 |
| 9 | 327 | YPGCNKRYF (SEQ ID NO:250) | 6.600 |
| 10 | 152 | VTFDGTPSY (SEQ ID NO:244) | 5.600 |
| 11 | 141 | QPAIRNQGY (SEQ ID NO:170) | 4.800 |
| 12 | 345 | RKHTGEKPY (SEQ ID NO:184) | 4.000 |
| 13 | 185 | QGSLGEQQY (SEQ ID NO:166) | 4.000 |
| 14 | 101 | TGTAGACRY (SEQ ID NO:224) | 4.000 |
| 15 | 375 | RRHTGVKPF (SEQ ID NO:188) | 4.000 |
| 16 | 263 | GQSNHSTGY (SEQ ID NO:100) | 4.000 |
| 17 | 163 | TPSHHAAQF (SEQ ID NO:228) | 3.000 |
| 18 | 33 | QWAPVLDFA (SEQ ID NO:174) | 2.688 |
| 19 | 130 | NAPYLPSCL (SEQ ID NO:144) | 2.640 |
| 20 | 84 | HEEQCLSAF (SEQ ID NO:107) | 2.400 |

TABLE XXXIV

| Results of BIMAS HLA Peptide Binding Prediction Analysis for Binding of Human WT1 Peptides to Mouse MHC Class I Db | | | |
|---|---|---|---|
| Rank | Start Position | Subsequence Residue Listing | Score (Estimate of Half Time of Disassociation of a Molecule Containing This Subsequence) |
| 1 | 235 | CMTWNQMNL (SEQ ID NO:49) | 5255.712 |
| 2 | 126 | RMFPNAPYL (SEQ ID NO:185) | 1990.800 |
| 3 | 221 | YSSDNLYQM (SEQ ID NO:253) | 930.000 |
| 4 | 228 | QMTSQLECM (SEQ ID NO:169) | 33.701 |
| 5 | 239 | NQMNLGATL (SEQ ID NO:151) | 21.470 |
| 6 | 441 | NMTKLQLAL (SEQ ID NO:149) | 19.908 |
| 7 | 437 | MHQRNMTKL (SEQ ID NO:143) | 19.837 |
| 8 | 136 | SCLESQPAI (SEQ ID NO:198) | 11.177 |
| 9 | 174 | HSFKHEDPM (SEQ ID NO:110) | 10.800 |

TABLE XXXIV-continued

Results of BIMAS HLA Peptide Binding Prediction Analysis for Binding of Human WT1 Peptides to Mouse MHC Class I Db

| Rank | Start Position | Subsequence Residue Listing | Score (Estimate of Half Time of Disassociation of a Molecule Containing This Subsequence) |
|---|---|---|---|
| 10 | 302 | RVPGVAPTL (SEQ ID NO:195) | 10.088 |
| 11 | 130 | NAPYLPSCL (SEQ ID NO:144) | 8.400 |
| 12 | 10 | ALLPAVPSL (SEQ ID NO:34) | 5.988 |
| 13 | 208 | SCTGSQALL (SEQ ID NO:202) | 4.435 |
| 14 | 209 | CTGSQALLL (SEQ ID NO:52) | 3.548 |
| 15 | 238 | WNQMNLGAT (SEQ ID NO:245) | 3.300 |
| 16 | 218 | RTPYSSDNL (SEQ ID NO:194) | 3.185 |
| 17 | 24 | CALPVSGAA (SEQ ID NO:43) | 2.851 |
| 18 | 18 | LGGGGGCAL (SEQ ID NO:134) | 2.177 |
| 19 | 142 | PAIRNQGYS (SEQ ID NO:152) | 2.160 |
| 20 | 30 | GAAQWAPVL (SEQ ID NO:86) | 1.680 |

TABLE XXXV

Results of BIMAS HLA Peptide Binding Prediction Analysis for Binding of Human WT1 Peptides to Mouse MHC Class I Dd

| Rank | Start Position | Subsequence Residue Listing | Score (Estimate of Half Time of Disassociation of a Molecule Containing This Subsequence) |
|---|---|---|---|
| 1 | 112 | FGPPPPSQA (SEQ ID NO:76) | 48.000 |
| 2 | 122 | SGQARMFPN (SEQ ID NO:212) | 36.000 |
| 3 | 104 | AGACRYGPF (SEQ ID NO:31) | 30.000 |
| 4 | 218 | RTPYSSDNL (SEQ ID NO:194) | 28.800 |
| 5 | 130 | NAPYLPSCL (SEQ ID NO:144) | 20.000 |
| 6 | 302 | RVPGVAPTL (SEQ ID NO:195) | 20.000 |
| 7 | 18 | LGGGGGCAL (SEQ ID NO:134) | 20.000 |
| 8 | 81 | AEPHEEQCL (SEQ ID NO:30) | 10.000 |
| 9 | 29 | SGAAQWAPV (SEQ ID NO:211) | 7.200 |
| 10 | 423 | KKFARSDEL (SEQ ID NO:122) | 7.200 |
| 11 | 295 | RGIQDVRRV (SEQ ID NO:179) | 7.200 |
| 12 | 390 | RKFSRSDHL (SEQ ID NO:183) | 6.000 |
| 13 | 332 | KRYFKLSHL (SEQ ID NO:127) | 6.000 |
| 14 | 362 | RRFSRSDQL (SEQ ID NO:187) | 6.000 |
| 15 | 417 | RWPSCQKKF (SEQ ID NO:196) | 6.000 |
| 16 | 160 | YGHTPSHHA (SEQ ID NO:249) | 6.000 |
| 17 | 20 | GGGGCALPV (SEQ ID NO:92) | 6.000 |
| 18 | 329 | GCNKRYFKL (SEQ ID NO:90) | 5.000 |

TABLE XXXV-continued

Results of BIMAS HLA Peptide Binding Prediction Analysis for Binding of Human WT1 Peptides to Mouse MHC Class I Dd

| Rank | Start Position | Subsequence Residue Listing | Score (Estimate of Half Time of Disassociation of a Molecule Containing This Subsequence) |
|---|---|---|---|
| 19 | 372 | RHQRRHTGV (SEQ ID NO:181) | 4.500 |
| 20 | 52 | GGPAPPPAP (SEQ ID NO:93) | 4.000 |

TABLE XXXVI

Results of BIMAS HLA Peptide Binding Prediction Analysis for Binding of Human WT1 Peptides to Mouse MHC Class I Kb

| Rank | Start Position | Subsequence Residue Listing | Score (Estimate of Half Time of Disassociation of a Molecule Containing This Subsequence) |
|---|---|---|---|
| 1 | 329 | GCNKRYFKL (SEQ ID NO:90) | 24.000 |
| 2 | 225 | NLYQMTSQL (SEQ ID NO:147) | 10.000 |
| 3 | 420 | SCQKKFARS (SEQ ID NO:200) | 3.960 |
| 4 | 218 | RTPYSSDNL (SEQ ID NO:194) | 3.630 |
| 5 | 437 | MHQRNMTKL (SEQ ID NO:143) | 3.600 |
| 6 | 387 | TCQRKFSRS (SEQ ID NO:219) | 3.600 |
| 7 | 302 | RVPGVAPTL (SEQ ID NO:195) | 3.300 |
| 8 | 130 | NAPYLPSCL (SEQ ID NO:144) | 3.000 |
| 9 | 289 | HTHGVFRGI (SEQ ID NO:113) | 3.000 |
| 10 | 43 | PGASAYGSL (SEQ ID NO:153) | 2.400 |
| 11 | 155 | DGTPSYGHT (SEQ ID NO:56) | 2.400 |
| 12 | 273 | SDNHTTPIL (SEQ ID NO:204) | 2.200 |
| 13 | 126 | RMFPNAPYL (SEQ ID NO:185) | 2.200 |
| 14 | 128 | FPNAPYLPS (SEQ ID NO:79) | 2.000 |
| 15 | 3 | SDVRDLNAL (SEQ ID NO:206) | 1.584 |
| 16 | 207 | DSCTGSQAL (SEQ ID NO:61) | 1.584 |
| 17 | 332 | KRYFKLSHL (SEQ ID NO:127) | 1.500 |
| 18 | 18 | LGGGGGCAL (SEQ ID NO: 134) | 1.320 |
| 19 | 233 | LECMTWNQM (SEQ ID NO:131) | 1.320 |
| 20 | 441 | NMTKLQLAL (SEQ ID NO:149) | 1.200 |

TABLE XXXVII

Results of BIMAS HLA Peptide Binding Prediction Analysis for Binding of Human WT1 Peptides to Mouse MHC Class I Kd

| Rank | Start Position | Subsequence Residue Listing | Score (Estimate of Half Time of Disassociation of a Molecule Containing This Subsequence) |
|---|---|---|---|
| 1 | 285 | QYRIHTHGV (SEQ ID NO:175) | 600.000 |
| 2 | 424 | KFARSDELV (SEQ ID NO:119) | 288.000 |

TABLE XXXVII-continued

Results of BIMAS HLA Peptide Binding Prediction Analysis for Binding of Human WT1 Peptides to Mouse MHC Class I Kd

| Rank | Start Position | Subsequence Residue Listing | Score (Estimate of Half Time of Disassociation of a Molecule Containing This Subsequence) |
|---|---|---|---|
| 3 | 334 | YFKLSHLQM (SEQ ID NO:248) | 120.000 |
| 4 | 136 | SCLESQPTI (SEQ ID NO:199) | 115.200 |
| 5 | 239 | NQMNLGATL (SEQ ID NO:151) | 115.200 |
| 6 | 10 | ALLPAVSSL (SEQ ID NO:35) | 115.200 |
| 7 | 47 | AYGSLGGPA (SEQ ID NO:41) | 86.400 |
| 8 | 180 | DPMGQQGSL (SEQ ID NO:59) | 80.000 |
| 9 | 270 | GYESDNHTA (SEQ ID NO:105) | 72.000 |
| 10 | 326 | AYPGCNKRY (SEQ ID NO:42) | 60.000 |
| 11 | 192 | QYSVPPPVY (SEQ ID NO:176) | 60.000 |
| 12 | 272 | ESDNHTAPI (SEQ ID NO:70) | 57.600 |
| 13 | 289 | HTHGVFRGI (SEQ ID NO:113) | 57.600 |
| 14 | 126 | DVRDLNALL (SEQ ID NO:62) | 57.600 |
| 15 | 4 | CTGSQALLL (SEQ ID NO:52) | 57.600 |
| 16 | 208 | SCTGSQALL (SEQ ID NO:202) | 48.000 |
| 17 | 441 | NMTKLQLAL (SEQ ID NO:149) | 48.000 |
| 18 | 207 | DSCTGSQAL (SEQ ID NO:61) | 48.000 |
| 19 | 130 | NAPYLPSCL (SEQ ID NO:144) | 48.000 |
| 20 | 235 | CMTWNQMNL (SEQ ID NO:49) | 48.000 |

TABLE XXXVIII

Results of BIMAS HLA Peptide Binding Prediction Analysis for Binding of Human WT1 Peptides to Mouse MHC Class I Kk

| Rank | Start Position | Subsequence Residue Listing | Score (Estimate of Half Time of Disassociation of a Molecule Containing This Subsequence) |
|---|---|---|---|
| 1 | 81 | AEPHEEQCL (SEQ ID NO:30) | 40.000 |
| 2 | 85 | EEQCLSAFT (SEQ ID NO:65) | 40.000 |
| 3 | 429 | DELVRHHNM (SEQ ID NO:53) | 20.000 |
| 4 | 315 | SETSEKRPF (SEQ ID NO:209) | 20.000 |
| 5 | 261 | TEGQSNHST (SEQ ID NO:221) | 20.000 |
| 6 | 410 | SEKPFSCRW (SEQ ID NO:207) | 10.000 |
| 7 | 272 | ESDNHTTPI (SEQ ID NO:71) | 10.000 |
| 8 | 318 | SEKRPFMCA (SEQ ID NO:208) | 10.000 |
| 9 | 138 | LESQPAIRN (SEQ ID NO:132) | 10.000 |
| 10 | 233 | LECMTWNQM (SEQ ID NO:131) | 10.000 |
| 11 | 298 | QDVRRVPGV (SEQ ID NO:164) | 10.000 |

TABLE XXXVIII-continued

Results of BIMAS HLA Peptide Binding Prediction Analysis for Binding of Human WT1 Peptides to Mouse MHC Class I Kk

| Rank | Start Position | Subsequence Residue Listing | Score (Estimate of Half Time of Disassociation of a Molecule Containing This Subsequence) |
|---|---|---|---|
| 12 | 84 | HEEQCLSAF (SEQ ID NO:107) | 10.000 |
| 13 | 349 | GEKPYQCDF (SEQ ID NO:91) | 10.000 |
| 14 | 289 | HTHGVFRGI (SEQ ID NO:113) | 10.000 |
| 15 | 179 | EDPMGQQGS (SEQ ID NO:64) | 8.000 |
| 16 | 136 | SCLESQPAI (SEQ ID NO:198) | 5.000 |
| 17 | 280 | ILCGAQYRI (SEQ ID NO:116) | 5.000 |
| 18 | 273 | SDNHTTPIL (SEQ ID NO:204) | 4.000 |
| 19 | 428 | SDELVRHHN (SEQ ID NO:203) | 4.000 |
| 20 | 3 | SDVRDLNAL (SEQ ID NO:206) | 4.000 |

TABLE XXXIX

Results of BIMAS HLA Peptide Binding Prediction Analysis for Binding of Human WT1 Peptides to Mouse MHC Class I Ld

| Rank | Start Position | Subsequence Residue Listing | Score (Estimate of Half Time of Disassociation of a Molecule Containing This Subsequence) |
|---|---|---|---|
| 1 | 163 | TPSHHAAQF (SEQ ID NO:228) | 360.000 |
| 2 | 327 | YPGCNKRYF (SEQ ID NO:250) | 300.000 |
| 3 | 180 | DPMGQQGSL (SEQ ID NO:59) | 150.000 |
| 4 | 26 | LPVSGAAQW (SEQ ID NO:138) | 93.600 |
| 5 | 278 | TPILCGAQY (SEQ ID NO:227) | 72.000 |
| 6 | 141 | QPAIRNQGY (SEQ ID NO:170) | 60.000 |
| 7 | 219 | TPYSSDNLY (SEQ ID NO:231) | 60.000 |
| 8 | 303 | VPGVAPTLV (SEQ ID NO:242) | 60.000 |
| 9 | 120 | ASSGQARMF (SEQ ID NO:40) | 50.000 |
| 10 | 63 | PPPPPPHSF (SEQ ID NO:158) | 45.000 |
| 11 | 113 | GPPPPSQAS (SEQ ID NO:97) | 45.000 |
| 12 | 157 | TPSYGHTPS (SEQ ID NO:229) | 39.000 |
| 13 | 207 | DSCTGSQAL (SEQ ID NO:61) | 32.500 |
| 14 | 110 | GPFGPPPPS (SEQ ID NO:96) | 30.000 |
| 15 | 82 | EPHEEQCLS (SEQ ID NO:68) | 30.000 |
| 16 | 412 | KPFSCRWPS (SEQ ID NO:123) | 30.000 |
| 17 | 418 | WPSCQKKFA (SEQ ID NO:246) | 30.000 |
| 18 | 221 | YSSDNLYQM (SEQ ID NO:253) | 30.000 |
| 19 | 204 | TPTDSCTGS (SEQ ID NO:230) | 30.000 |
| 20 | 128 | FPNAPYLPS (SEQ ID NO:79) | 30.000 |

TABLE XL

Results of BIMAS HLA Peptide Binding Prediction Analysis for Binding of Human WT1 Peptides to Cattle HLA A20

| Rank | Start Position | Subsequence Residue Listing | Score (Estimate of Half Time of Disassociation of a Molecule Containing This Subsequence) |
|---|---|---|---|
| 1 | 350 | EKPYQCDFK (SEQ ID NO:66) | 1000.00 |
| 2 | 319 | EKRPFMCAY (SEQ ID NO:67) | 500.000 |
| 3 | 423 | KKFARSDEL (SEQ ID NO:122) | 500.000 |
| 4 | 345 | RKHTGEKPY (SEQ ID NO:184) | 500.000 |
| 5 | 390 | RKFSRSDHL (SEQ ID NO:183) | 500.000 |
| 6 | 137 | CLESQPAIR (SEQ ID NO:47) | 120.000 |
| 7 | 380 | VKPFQCKTC (SEQ ID NO:239) | 100.000 |
| 8 | 407 | GKTSEKPFS (SEQ ID NO:95) | 100.000 |
| 9 | 335 | FKLSHLQMH (SEQ ID NO:78) | 100.000 |
| 10 | 247 | LKGVAAGSS (SEQ ID NO:135) | 100.000 |
| 11 | 370 | LKRHQRRHT (SEQ ID NO:136) | 100.000 |
| 12 | 258 | VKWTEGQSN (SEQ ID NO:240) | 100.000 |
| 13 | 398 | LKTHTRTHT (SEQ ID NO:137) | 100.000 |
| 14 | 331 | NKRYFKLSH (SEQ ID NO:145) | 100.000 |
| 15 | 357 | FKDCERRFS (SEQ ID NO:77) | 100.000 |
| 16 | 385 | CKTCQRKFS (SEQ ID NO:46) | 100.000 |
| 17 | 294 | FRGIQDVRR (SEQ ID NO:81) | 80.000 |
| 18 | 368 | DQLKRHQRR (SEQ ID NO:60) | 80.000 |
| 19 | 432 | VRHHNMHQR (SEQ ID NO:243) | 80.000 |
| 20 | 118 | SQASSGQAR (SEQ ID NO:216) | 80.000 |

TABLE XLI

Results of BIMAS HLA Peptide Binding Prediction Analysis for Binding of Mouse WT1 Peptides to Mouse MHC Class I A_0201

| Rank | Start Position | Subsequence Residue Listing | Score (Estimate of Half Time of Disassociation of a Molecule Containing This Subsequence) |
|---|---|---|---|
| 1 | 126 | RMFPNAPYL (SEQ ID NO:293) | 313.968 |
| 2 | 187 | SLGEQQYSV (SEQ ID NO:299) | 285.163 |
| 3 | 10 | ALLPAVSSL (SEQ ID NO:255) | 181.794 |
| 4 | 225 | NLYQMTSQL (SEQ ID NO:284) | 68.360 |
| 5 | 292 | GVFRGIQDV (SEQ ID NO:270) | 51.790 |
| 6 | 93 | TLHFSGQFT (SEQ ID NO:302) | 40.986 |
| 7 | 191 | QQYSVPPPV (SEQ ID NO:290) | 22.566 |
| 8 | 280 | ILCGAQYRI (SEQ ID NO:274) | 17.736 |
| 9 | 441 | NMTKLHVAL (SEQ ID NO:285) | 15.428 |

TABLE XLI-continued

Results of BIMAS HLA Peptide Binding Prediction Analysis for Binding of Mouse WT1 Peptides to Mouse MHC Class I A_0201

| Rank | Start Position | Subsequence Residue Listing | Score (Estimate of Half Time of Disassociation of a Molecule Containing This Subsequence) |
|---|---|---|---|
| 10 | 235 | CMTWNQMNL (SEQ ID NO:258) | 15.428 |
| 11 | 7 | DLNALLPAV (SEQ ID NO:261) | 11.998 |
| 12 | 242 | NLGATLKGM (SEQ ID NO:283) | 11.426 |
| 13 | 227 | YQMTSQLEC (SEQ ID NO:307) | 8.573 |
| 14 | 239 | NQMNLGATL (SEQ ID NO:286) | 8.014 |
| 15 | 309 | TLVRSASET (SEQ ID NO:303) | 7.452 |
| 16 | 408 | KTSEKPFSC (SEQ ID NO:277) | 5.743 |
| 17 | 340 | LQMHSRKHT (SEQ ID NO:280) | 4.752 |
| 18 | 228 | QMTSQLECM (SEQ ID NO:289) | 4.044 |
| 19 | 37 | VLDFAPPGA (SEQ ID NO:304) | 3.378 |
| 20 | 302 | RVSGVAPTL (SEQ ID NO:295) | 1.869 |

TABLE XLII

Results of BIMAS HLA Peptide Binding Prediction Analysis for Binding of Mouse WT1 Peptides to Mouse MHC Class I Db

| Rank | Start Position | Subsequence Residue Listing | Score (Estimate of Half Time of Disassociation of a Molecule Containing This Subsequence) |
|---|---|---|---|
| 1 | 221 | YSSDNLYQM (SEQ ID NO:308) | 312.000 |
| 2 | 126 | RMFPNAPYL (SEQ ID NO:293) | 260.000 |
| 3 | 235 | CMTWNQMNL (SEQ ID NO:258) | 260.000 |
| 4 | 437 | MHQRNMTKL (SEQ ID NO:281) | 200.000 |
| 5 | 238 | WNQMNLGAT (SEQ ID NO:305) | 12.000 |
| 6 | 130 | NAPYLPSCL (SEQ ID NO:282) | 8.580 |
| 7 | 3 | SDVRDLNAL (SEQ ID NO:298) | 7.920 |
| 8 | 136 | SCLESQPTI (SEQ ID NO:296) | 7.920 |
| 9 | 81 | AEPHEEQCL (SEQ ID NO:254) | 6.600 |
| 10 | 10 | ALLPAVSSL (SEQ ID NO:255) | 6.600 |
| 11 | 218 | RTPYSSDNL (SEQ ID NO:294) | 6.000 |
| 12 | 441 | NMTKLHVAL (SEQ ID NO:285) | 3.432 |
| 13 | 228 | QMTSQLECM (SEQ ID NO:289) | 3.120 |
| 14 | 174 | HSFKHEDPM (SEQ ID NO:272) | 3.120 |
| 15 | 242 | NLGATLKGM (SEQ ID NO:283) | 2.640 |
| 16 | 261 | TEGQSNHGI (SEQ ID NO:301) | 2.640 |
| 17 | 225 | NLYQMTSQL (SEQ ID NO:284) | 2.640 |
| 18 | 207 | DSCTGSQAL (SEQ ID NO:263) | 2.600 |

TABLE XLII-continued

Results of BIMAS HLA Peptide Binding Prediction Analysis for Binding of Mouse WT1 Peptides to Mouse MHC Class I Db

| Rank | Start Position | Subsequence Residue Listing | Score (Estimate of Half Time of Disassociation of a Molecule Containing This Subsequence) |
|---|---|---|---|
| 19 | 119 | QASSGQARM (SEQ ID NO:288) | 2.600 |
| 20 | 18 | LGGGGGCGL (SEQ ID NO:279) | 2.600 |

TABLE XLIII

Results of BIMAS HLA Peptide Binding Prediction Analysis for Binding of Mouse WT1 Peptides to Mouse MHC Class I Kb

| Rank | Start Position | Subsequence Residue Listing | Score (Estimate of Half Time of Disassociation of a Molecule Containing This Subsequence) |
|---|---|---|---|
| 1 | 329 | GCNKRYFKL (SEQ ID NO:268) | 24.000 |
| 2 | 225 | NLYQMTSQL (SEQ ID NO:284) | 10.000 |
| 3 | 420 | SCQKKFARS (SEQ ID NO:297) | 3.960 |
| 4 | 218 | RTPYSSDNL (SEQ ID NO:294) | 3.630 |
| 5 | 437 | MHQRNMTKL (SEQ ID NO:281) | 3.600 |
| 6 | 387 | TCQRKFSRS (SEQ ID NO:300) | 3.600 |
| 7 | 289 | HTHGVFRGI (SEQ ID NO:273) | 3.000 |
| 8 | 130 | NAPYLPSCL (SEQ ID NO:282) | 3.000 |
| 9 | 43 | PGASAYGSL (SEQ ID NO:287) | 2.400 |
| 10 | 155 | DGAPSYGHT (SEQ ID NO:260) | 2.400 |
| 11 | 126 | RMFPNAPYL (SEQ ID NO:293) | 2.200 |
| 12 | 128 | FPNAPYLPS (SEQ ID NO:267) | 2.000 |
| 13 | 207 | DSCTGSQAL (SEQ ID NO:263) | 1.584 |
| 14 | 3 | SDVRDLNAL (SEQ ID NO:298) | 1.584 |
| 15 | 332 | KRYFKLSHL (SEQ ID NO:276) | 1.500 |
| 16 | 233 | LECMTWNQM (SEQ ID NO:278) | 1.320 |
| 17 | 18 | LGGGGGCGL (SEQ ID NO:279) | 1.320 |
| 18 | 242 | NLGATLKGM (SEQ ID NO:283) | 1.200 |
| 19 | 123 | GQARMFPNA (SEQ ID NO:269) | 1.200 |
| 20 | 441 | NMTKLHVAL (SEQ ID NO:285) | 1.200 |

TABLE XLIV

Results of BIMAS HLA Peptide Binding Prediction Analysis for Binding of Mouse WT1 Peptides to Mouse MHC Class I Kd

| Rank | Start Position | Subsequence Residue Listing | Score (Estimate of Half Time of Disassociation of a Molecule Containing This Subsequence) |
|---|---|---|---|
| 1 | 285 | QYRIHTHGV (SEQ ID NO:291) | 600.000 |
| 2 | 424 | KFARSDELV (SEQ ID NO:275) | 288.000 |

TABLE XLIV-continued

Results of BIMAS HLA Peptide Binding Prediction Analysis for Binding of Mouse WT1 Peptides to Mouse MHC Class I Kd

| Rank | Start Position | Subsequence Residue Listing | Score (Estimate of Half Time of Disassociation of a Molecule Containing This Subsequence) |
|---|---|---|---|
| 3 | 334 | YFKLSHLQM (SEQ ID NO:306) | 120.000 |
| 4 | 136 | SCLESQPTI (SEQ ID NO:296) | 115.200 |
| 5 | 239 | NQMNLGATL (SEQ ID NO:286) | 115.200 |
| 6 | 10 | ALLPAVSSL (SEQ ID NO:255) | 115.200 |
| 7 | 47 | AYGSLGGPA (SEQ ID NO:256) | 86.400 |
| 8 | 180 | DPMGQQGSL (SEQ ID NO:262) | 80.000 |
| 9 | 270 | GYESDNHTA (SEQ ID NO:271) | 72.000 |
| 10 | 192 | QYSVPPPVY (SEQ ID NO:292) | 60.000 |
| 11 | 326 | AYPGCNKRY (SEQ ID NO:257) | 60.000 |
| 12 | 289 | HTHGVFRGI (SEQ ID NO:273) | 57.600 |
| 13 | 4 | DVRDLNALL (SEQ ID NO:264) | 57.600 |
| 14 | 126 | RMFPNAPYL (SEQ ID NO:293) | 57.600 |
| 15 | 209 | CTGSQALLL (SEQ ID NO:259) | 48.000 |
| 16 | 86 | EQCLSAFTL (SEQ ID NO:265) | 48.000 |
| 17 | 302 | RVSGVAPTL (SEQ ID NO:295) | 48.000 |
| 18 | 218 | RTPYSSDNL (SEQ ID NO:294) | 48.000 |
| 19 | 272 | ESDNHTAPI (SEQ ID NO:266) | 48.000 |
| 20 | 225 | NLYQMTSQL (SEQ ID NO:284) | 48.000 |

TABLE XLV

Results of TSites Peptide Binding Prediction Analysis for Human WT1 Peptides Capable of Eliciting a Helper T cell Response

| Peptide | Sequence | |
|---|---|---|
| p6-23 | RDLNALLPAVPSLGGGG | (SEQ ID NO:1) |
| p30-35 | GAAQWA | (SEQ ID NO:309) |
| p45-56 | ASAYGSLGGPAP | (SEQ ID NO:310) |
| p91-105 | AFTVHFSGQFTGTAG | (SEQ ID NO:311) |
| p117-139 | PSQASSGQARMFPNAPYLPSCLE | (SEQ ID NO:2) |
| p167-171 | HAAQF | (SEQ ID NO:312) |
| 202-233 | CHTPTDSCTGSQALLLRTPYSSDNLYQMTSQL | (SEQ ID NO:313) |
| p244-262 | GATLKGVAAGSSSSVKWTE | (SEQ ID NO:4) |

TABLE XLV-continued

Results of TSites Peptide Binding Prediction Analysis for Human WT1 Peptides Capable of Eliciting a Helper T cell Response

| Peptide | Sequence | |
|---|---|---|
| p287-318 | RIHTHGVFRGIQDVRRVPGVAPTLVRSASETS | (SEQ ID NO:314) |
| p333-336 | RYFK | (SEQ ID NO:315) |
| p361-374 | ERRFSRSDQLKRHQ | (SEQ ID NO:316) |
| p389-410 | QRKFSRSDHLKTHTRTHTGKTS | (SEQ ID NO:317) |
| p421-441 | CQKKFARSDELVRHHNMHQRN | (SEQ ID NO:318) |

Certain CTL peptides (shown in Table XLVI) were selected for further study. For each peptide in Table XLVI, scores obtained using BIMAS HLA peptide Binding prediction analysis are provided.

TABLE XLVI

| WT1 Peptide Sequences and HLA Peptide Binding Predictions | | |
|---|---|---|
| Peptide | Sequence | Comments |
| p329-337 | GCNKRYFKL (SEQ ID NOs:90 and 268) | Score 24,000 |
| p225-233 | NLYQMTSQL (SEQ ID NOs:147 and 284) | binds also to class II and HLA A2, Kd, score 10,000 |
| p235-243 | CMTWNQMNL (SEQ ID NOs:49 and 258) | binds also to HLA A2, score 5,255,712 |
| p126-134 | RMFPNAPYL (SEQ ID NOs:185 and 293) | binds also to Kd, class II and HLA A2, score 1,990, 800 |
| p221-229 | YSSDNLYQM (SEQ ID NOs:253 and 308) | binds also to Ld, score 312,000 |
| p228-236 | QMTSQLECM (SEQ ID NOs: 169 and 289) | score 3,120 |
| p239-247 | NQMNLGATL (SEQ ID NOs: 151 and 286) | binds also to HLA A 0201, Kd, score 8,015 |
| mouse p136-144 | SCLESQPTI (SEQ ID NO:296) | binds also to Kd, 1mismatch to human |
| human p136-144 | SCLESQPAI (SEQ ID NO:198) | score 7,920 |
| mouse p10-18 | ALLPAVSSL (SEQ ID NO:255) | binds also to Kd, HLA A2, 1 mismatch to human |
| human p10-18 | ALLPAVPSL (SEQ ID NO:34) | score 6,600 |

Peptide binding to C57B1/6 murine MHC was confirmed using the leukemia cell line RMA-S, as described by Ljunggren et al., *Nature* 346:476-480, 1990. In brief, RMA-S cells were cultured for 7 hours at 26° C. in complete medium supplemented with 1% FCS. A total of $10^6$ RMA-S cells were added into each well of a 24-well plate and incubated either alone or with the designated peptide (25 ug/ml) for 16 hours at 26° C. and additional 3 hours at 37° C. in complete medium. Cells were then washed three times and stained with fluorescein isothiocyanate-conjugated anti $D^b$ or anti-$K^b$ antibody (PharMingen, San Diego, Calif.). Labeled cells were washed twice, resuspended and fixed in 500 ul of PBS with 1% paraformaldehyde and analyzed for fluorescence intensity in a flow cytometer (Becton-Dickinson FACSCALIBUR™). The percentage of increase of $D^b$ or $K^b$ molecules on the surface of the RMA-S cells was measured by increased mean fluorescent intensity of cells incubated with peptide compared with that of cells incubated in medium alone.

Mice were immunized with the peptides capable of binding to murine class I MHC. Following immunization, spleen cells were stimulated in vitro and tested for the ability to lyse targets incubated with WT1 peptides. CTL were evaluated with a standard chromium release assay (Chen et al., *Cancer Res.* 54:1065-1070, 1994). $10^6$ target cells were incubated at 37° C. with 150 μCi of sodium $^{51}Cr$ for 90 minutes, in the presence or absence of specific peptides. Cells were washed three times and resuspended in RPMI with 5% fetal bovine serum. For the assay, $10^4$ $^{51}Cr$-labeled target cells were incubated with different concentrations of effector cells in a final volume of 200 μl in U-bottomed 96-well plates. Supernatants were removed after 4 to 7 hours at 37° C., and the percentage specific lysis was determined by the formula:

% specific lysis=100×(experimental release−spontaneous release)/(maximum release−spontaneous release).

Figure 9A:
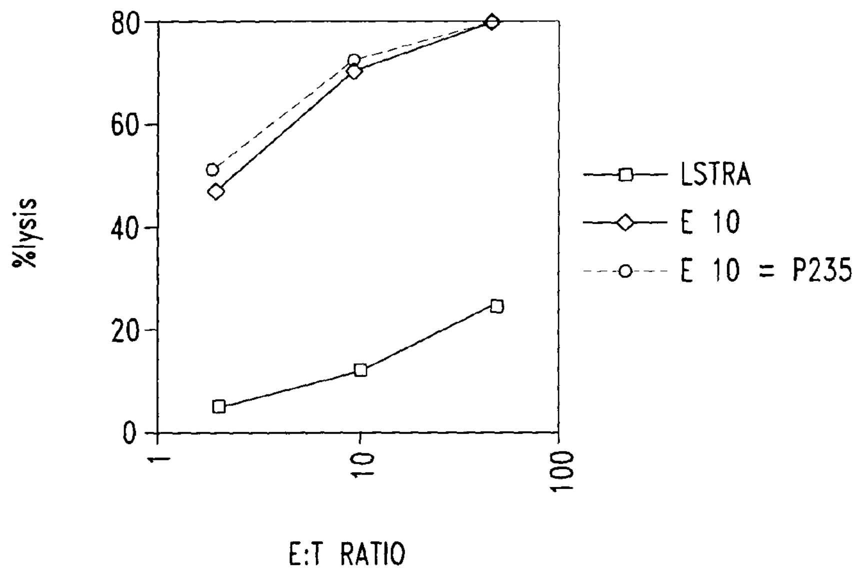
FIGS. 9A and 9B are graphs illustrating the elicitation of WT1 peptide-specific CTL in mice immunized with WT1 peptides.
Figure 9B:
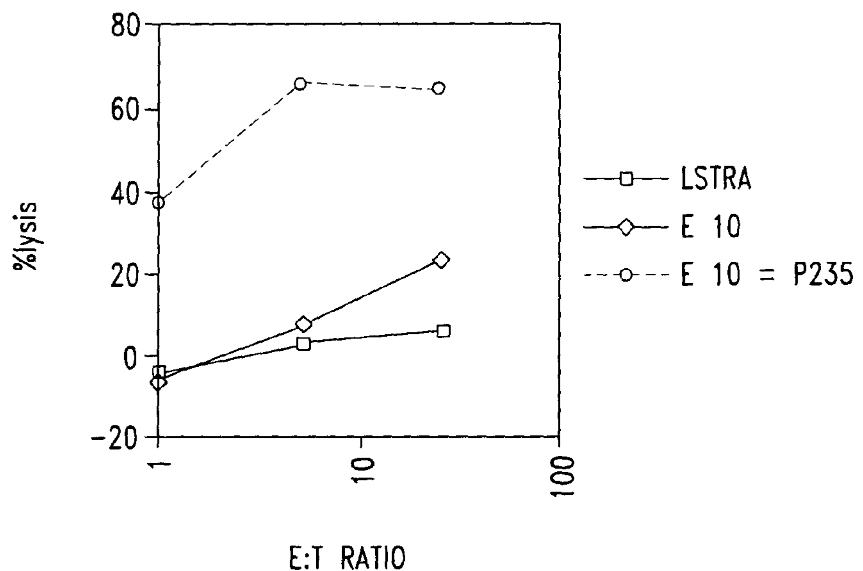
Figure 10A:
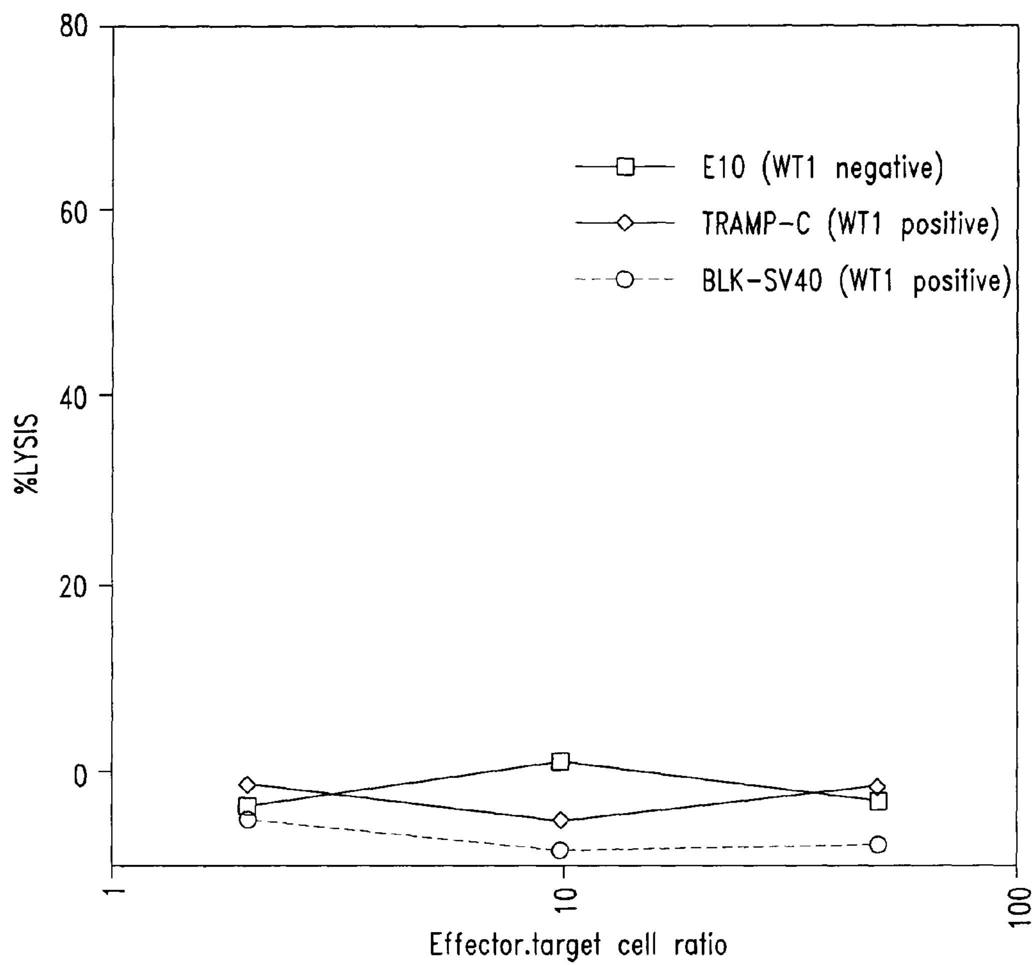
FIGS. 10A-10D are graphs illustrating the elicitation of WT1 specific CTL, which kill WT1 positive tumor cell lines but do not kill WT1 negative cell lines, following vaccination of B6 mice with WT1 peptide P117.
Figure 10B:
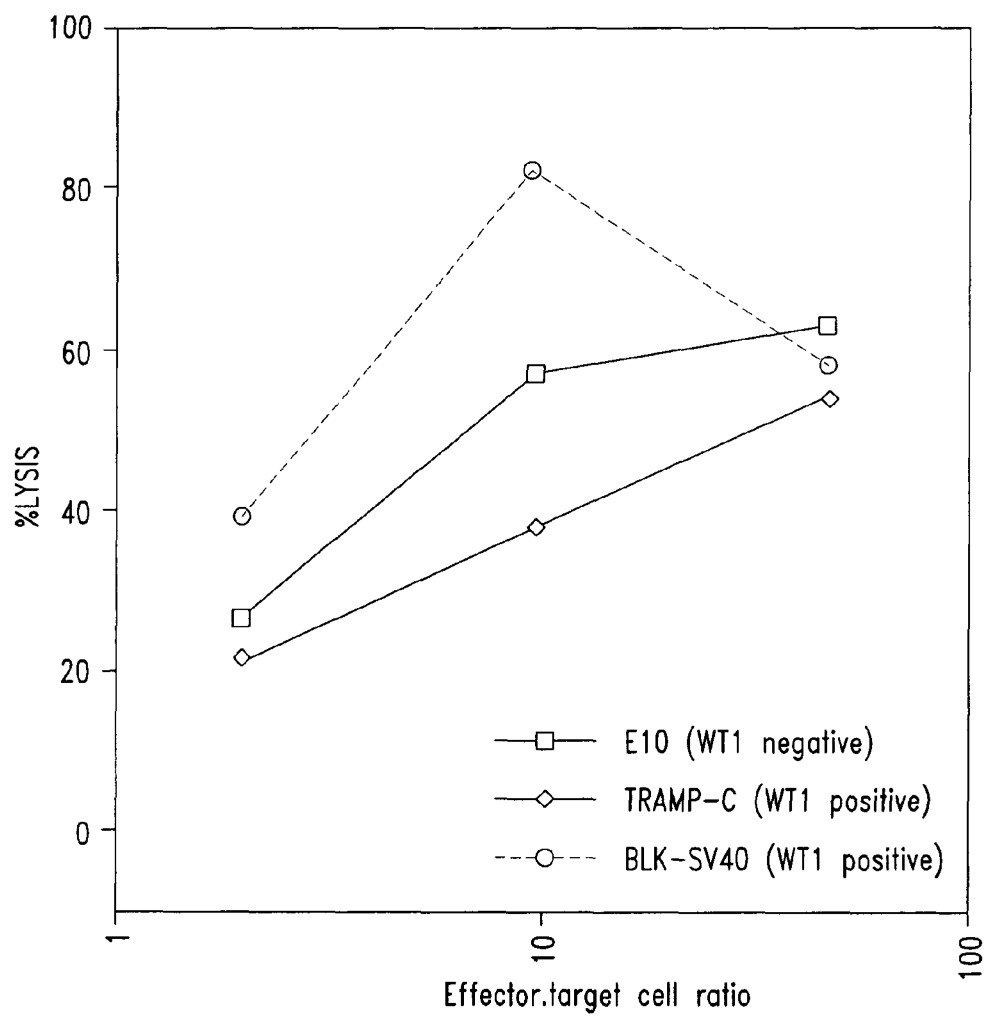
Figure 10C:
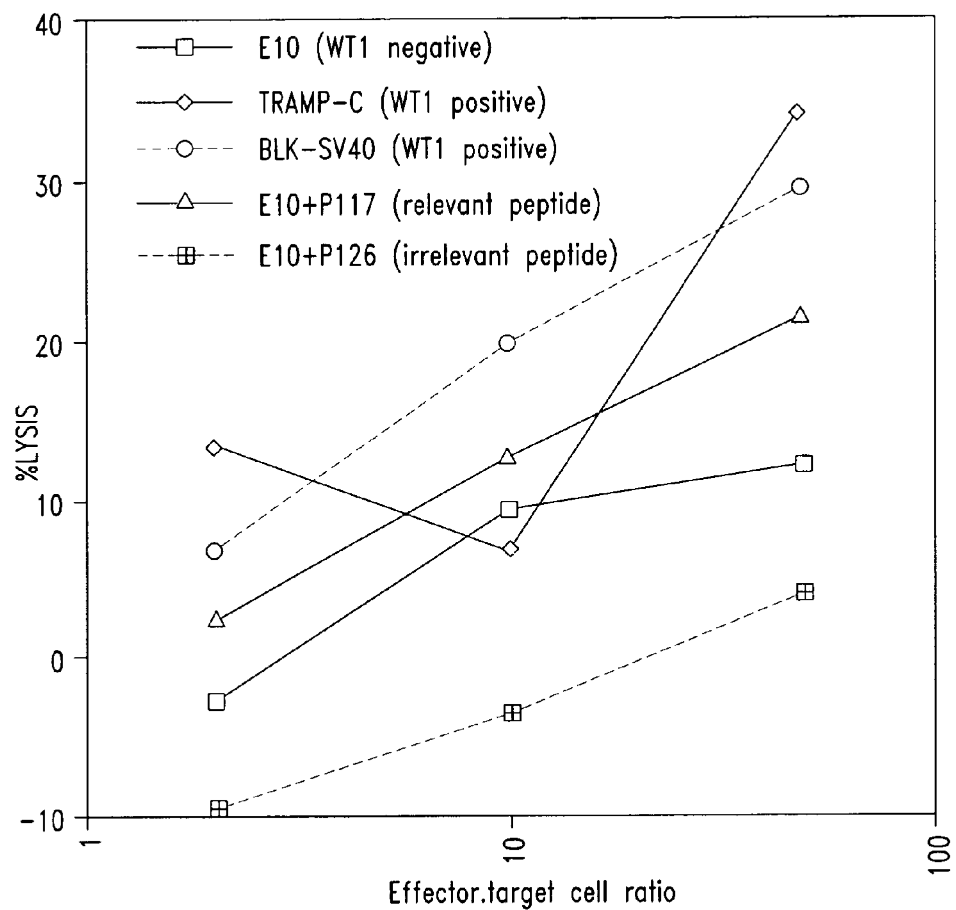
Figure 10D:
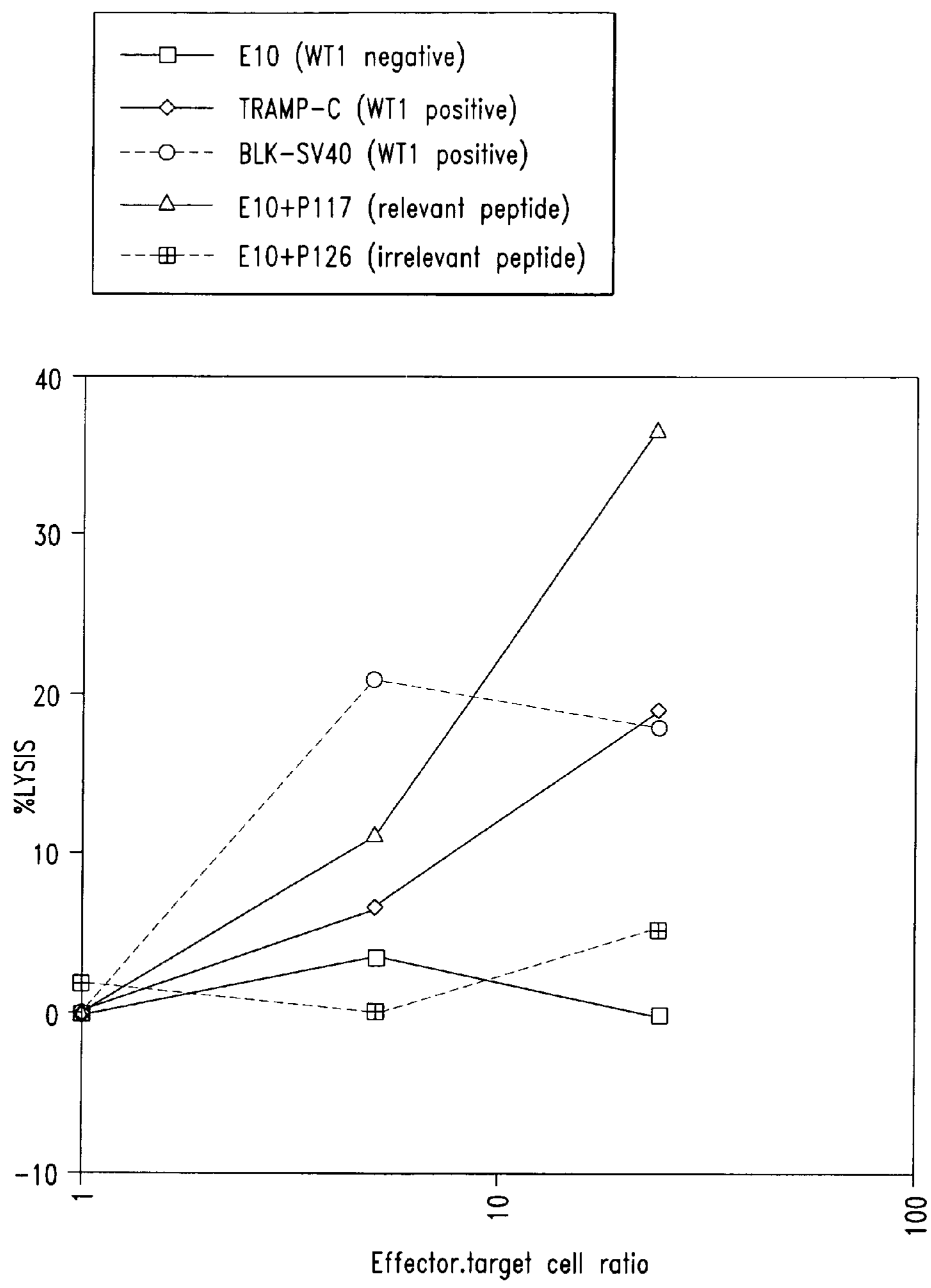

The results, presented in Table XLVII, show that some WT1 peptides can bind to class I MHC molecules, which is essential for generating CTL. Moreover, several of the peptides were able to elicit peptide specific CTL (FIGS. 9A and 9B), as determined using chromium release assays. Following immunization to CTL peptides p10-18 human, p136-144 human, p136-144 mouse and p235-243, peptide specific CTL lines were generated and clones were established. These results indicate that peptide specific CTL can kill malignant cells expressing WT1.

TABLE XLVII

| Binding of WT1 CTL Peptides to mouse B6 class I antigens | |
|---|---|
| Peptide | Binding Affinity to Mouse MHC Class I |
| Positive control | 91% |
| negative control | 0.5.–1.3% |
| p235–243 | 33.6% |
| p136–144 mouse | 27.9% |
| p136–144 human | 52% |
| p10–18: human | 2.2% |
| p225–233 | 5.8% |
| p329–337 | 1.2% |
| p126–134 | 0.9% |
| p221–229 | 0.8% |
| p228–236 | 1.2% |
| p239–247 | 1% |

Example 5

Use of a WT1 Polypeptide to Elicit WT1 Specific CTL in Mice

This Example illustrates the ability of a representative WT1 polypeptide to elicit CTL immunity capable of killing WT1 positive tumor cell lines.

P117-139, a peptide with motifs appropriate for binding to class I and class II MHC, was identified as described above using TSITES and BIMAS HLA peptide binding prediction analyses. Mice were immunized as described in Example 3. Following immunization, spleen cells were stimulated in vitro and tested for the ability to lyse targets incubated with WT1 peptides, as well as WT1 positive and negative tumor cells. CTL were evaluated with a standard chromium release assay. The results, presented in FIGS. 10A-10D, show that P117 can elicit WT1 specific CTL capable of killing WT1 positive tumor cells, whereas no killing of WT1 negative cells was observed. These results demonstrate that peptide specific CTL in fact kill malignant cells expressing WT1 and that vaccine and T cell therapy are effective against malignancies that express WT1.

Similar immunizations were performed using the 9-mer class I MHC binding peptides p136-144, p225-233, p235-243 as well as the 23-mer peptide p117-139. Following immunization, spleen cells were stimulated in vitro with each of the 4 peptides and tested for ability to lyse targets incubated with WT1 peptides. CTL were generated specific for p136-144, p235-243 and p117-139, but not for p225-233. CTL data for p235-243 and p117-139 are presented in FIGS. 11A and 11B. Data for peptides p136-144 and p225-233 are not depicted.

Figure 11B:
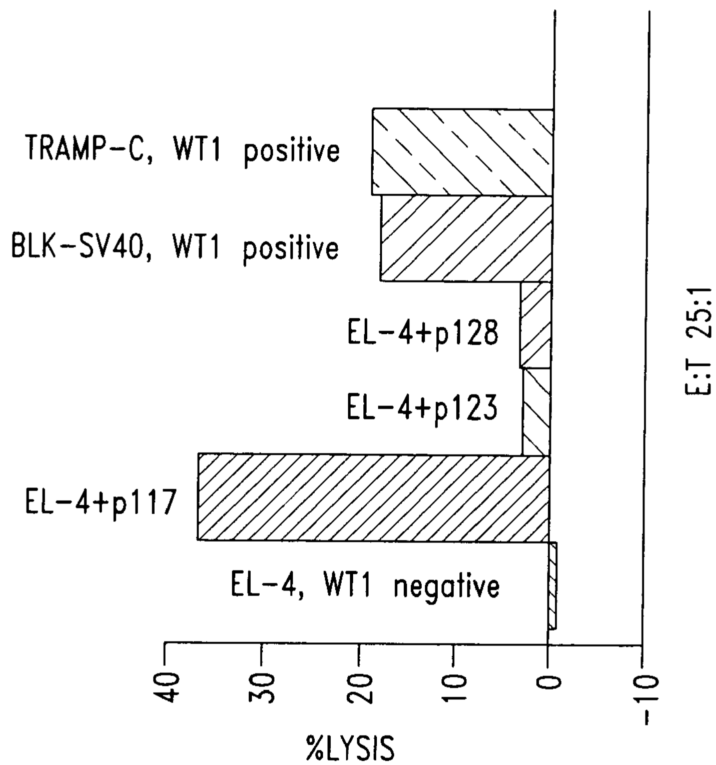
FIGS. 11A and 11B are histograms illustrating the ability of representative peptide P117-139 specific CTL to lyse WT1 positive tumor cells. Three weeks after the third immunization, spleen cells of mice that had been inoculated with the peptides p235-243 or p117-139 were stimulated in vitro with the relevant peptide and tested for ability to lyse targets incubated with WT1 peptides as well as WT1 positive and negative tumor cells. The bars represent the mean % specific lysis in chromium release assays performed in triplicate with an E:T ratio of 25:1.
Figure 11A:
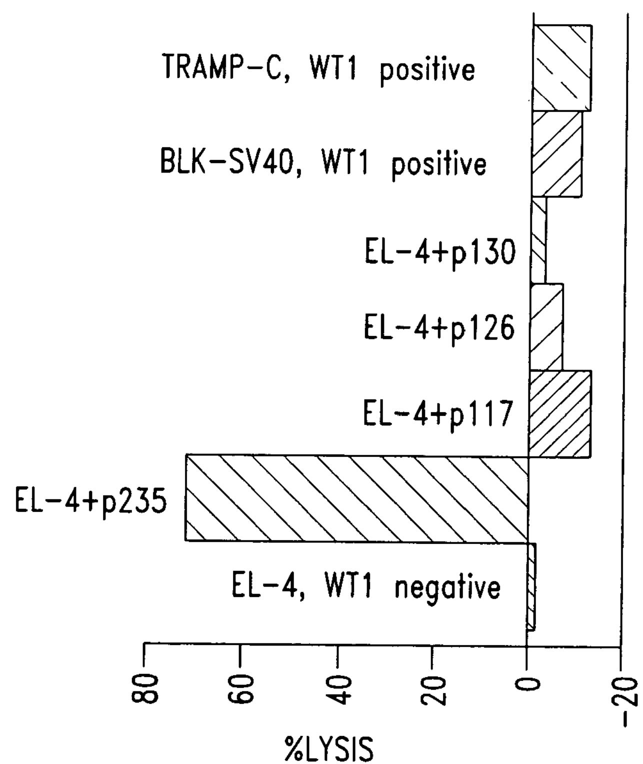

CTL lysis demands that the target WT1 peptides are endogenously processed and presented in association with tumor cell class I MHC molecules. The above WT1 peptide specific CTL were tested for ability to lyse WT1 positive versus negative tumor cell lines. CTL specific for p235-243 lysed targets incubated with the p235-243 peptides, but failed to lyse cell lines that expressed WT 1 proteins (FIG. 11A). By marked contrast, CTL specific for p117-139 lysed targets incubated with p117-139 peptides and also lysed malignant cells expressing WT1 (FIG. 11B). As a negative control, CTL specific for p117-139 did not lyse WT1 negative EL-4 (also referred to herein as E10).

Figures 12A, 12B:
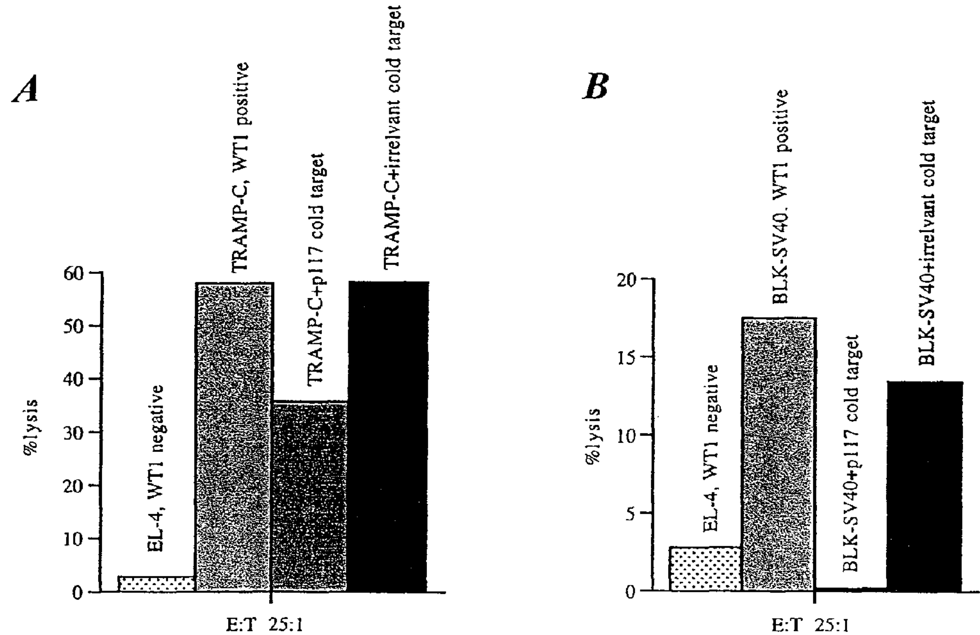
FIGS. 12A and 12B are histograms illustrating the specificity of lysis of WT1 positive tumor cells, as demonstrated by cold target inhibition. The bars represent the mean % specific lysis in chromium release assays performed in triplicate with an E:T ratio of 25:1.

Specificity of WT1 specific lysis was confirmed by cold target inhibition (FIGS. 12A-12B). Effector cells were plated for various effector: target ratios in 96-well U-bottom plates. A ten-fold excess (compared to hot target) of the indicated peptide-coated target without $^{51}$Cr labeling was added. Finally, $10^4$ $^{51}$Cr-labeled target cells per well were added and the plates incubated at 37° C. for 4 hours. The total volume per well was 200 µl.

Lysis of TRAMP-C by p117-139 specific CTL was blocked from 58% to 36% by EL-4 incubated with the relevant peptide p117-139, but not with EL-4 incubated with an irrelevant peptide (FIG. 12A). Similarly, lysis of BLK-SV40 was blocked from 18% to 0% by EL-4 incubated with the relevant peptide p117-139 (FIG. 12B). Results validate that WT1 peptide specific CTL specifically kill malignant cells by recognition of processed WT1.

Figure 13A:
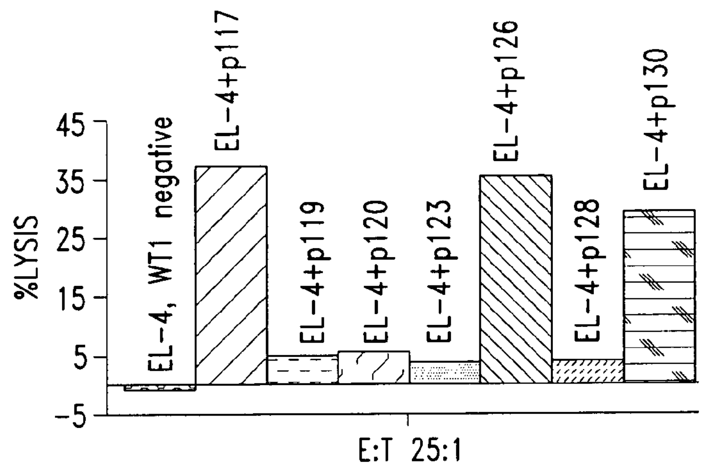
FIGS. 13A-13C are histograms depicting an evaluation of the 9 mer CTL epitope within p117-139. The p117-139 tumor specific CTL line was tested against peptides within aa117-139 containing or lacking an appropriate H-$2^b$ class I binding motif and following restimulation with p126-134 or p130-138. The bars represent the mean % specific lysis in chromium release assays performed in triplicate with an E:T ratio of 25:1.

Several segments with putative CTL motifs are contained within p117-139. To determine the precise sequence of the CTL epitope all potential 9-mer peptides within p117-139 were synthesized (Table XLVIII). Two of these peptides (p126-134 and p130-138) were shown to bind to H-$2^b$ class I molecules (Table XLVIII). CTL generated by immunization with p117-139 lysed targets incubated with p126-134 and p130-138, but not the other 9-mer peptides within p117-139 (FIG. 13A).

Figure 13B:
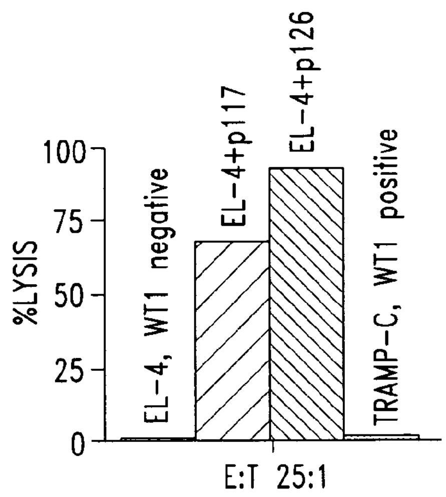
Figure 13C:
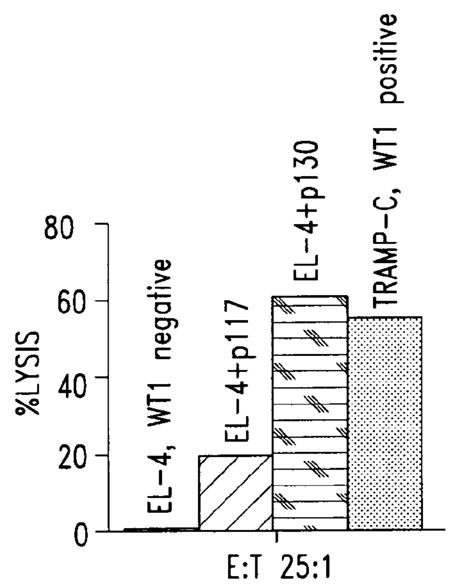
Figure 14:
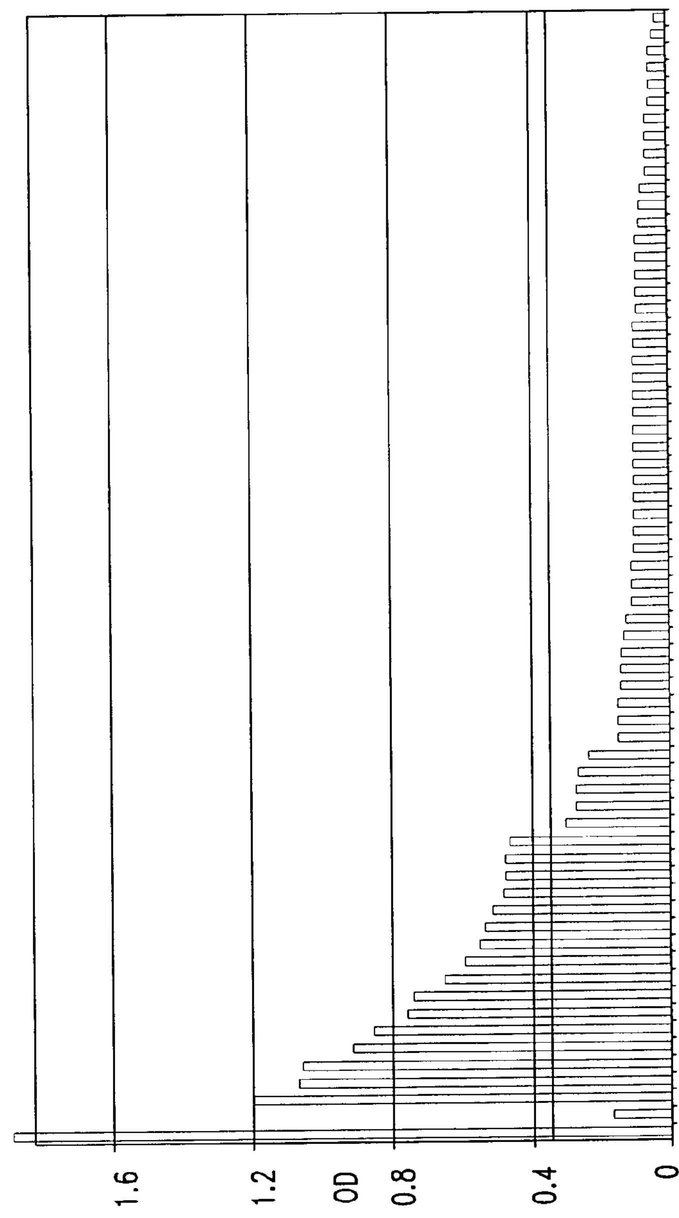
FIG. 14 depicts serum antibody reactivity to WT1 in 63 patients with AML. Reactivity of serum antibody to WT1/N-terminus protein was evaluated by ELISA in patients with AML. The first and second lanes represent the positive and negative controls, respectively. The first and second lanes represent the positive and negative controls, respectively. Commercially obtained WT1 specific antibody WT180 was used for the positive control. The next 63 lanes represent results using sera from each individual patient. The OD values depicted were from ELISA using a 1:500 serum dilution. The figure includes cumulative data from 3 separate experiments.
Figure 15:
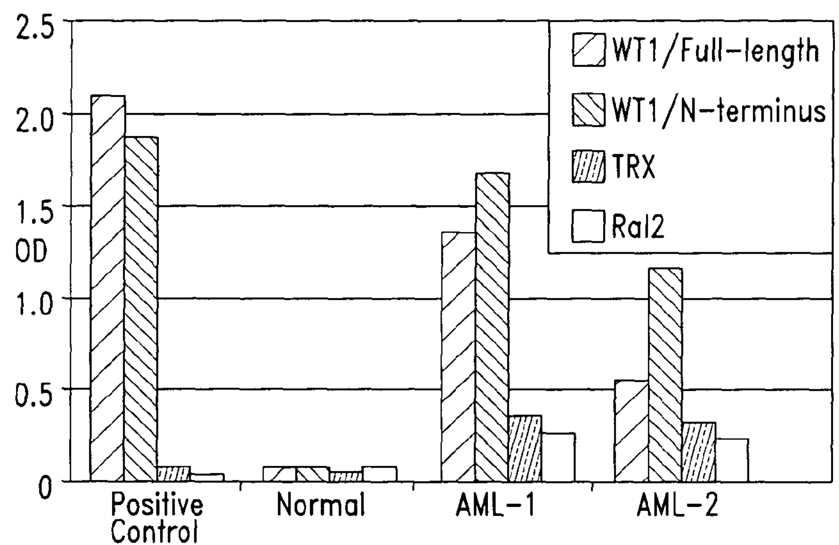
FIG. 15 depicts serum antibody reactivity to WT1 proteins and control proteins in 2 patients with AML. Reactivity of serum antibody to WT1/full-length, WT1N-terminus, TRX and Ra12 proteins was evaluated by ELISA in 2 patients with AML. The OD values depicted were from ELISA using a 1:500 serum dilution. AML-1 and AML-2 denote serum from 2 of the individual patients in FIG. 1 with demonstrated antibody reactivity to WT1/full-length. The WT1 full-length protein was expressed as a fusion protein with Ra12. The WT1/N-terminus protein was expressed as a fusion protein with TRX. The control Ra12 and TRX proteins were purified in a similar manner. The results confirm that the serum antibody reactivity against the WT1 fusion proteins is directed against the WT1 portions of the protein.

The p117-139 specific CTL line was restimulated with either p126-134 or p130-138. Following restimulation with p126-134 or p130-138, both T cell lines demonstrated peptide specific lysis, but only p130-138 specific CTL showed lysis of a WT1 positive tumor cell line (FIGS. 13B and 13C). Thus, p130-138 appears to be the naturally processed epitope.

TABLE XLVIII

Binding of WT1 CTL 9mer Peptides within p117-139 to mouse B6 class I antigens

| Peptide | Binding Affinity to Mouse MHC Class I |
|---|---|
| P117-125 PSQASSGQA (SEQ ID NO:221) | 2% |
| P118-126 SQASSGQAR (SEQ ID NO:216) | 2% |
| P119-127 QASSGQARM (SEQ ID Nos:161 and 288) | 2% |
| P120-128 ASSGQARMF (SEQ ID NO:40 | 1% |
| P121-129 SSGQARMFP (SEQ ID NO:222) | 1% |
| P122-130 SGQARMFPN (SEQ ID NO:212) | 1% |
| P123-131 GQARMFPNA (SEQ ID Nos:98 and 269) | 1% |
| P124-132 QARMFPNAP (SEQ ID NO:223) | 1% |
| P125-133 ARMFPNAPY (SEQ ID NO:38) | 1% |
| P126-134 RMFPNAPYL (SEQ ID NOs:185 and 293) | 79% |
| P127-135 MFPNAPYLP (SEQ ID NO:224) | 2% |
| P128-136 FPNAPYLPS (SEQ ID NOs:79 and 267) | 1% |
| P129-137 PNAPYLPSC (SEQ ID NO:225) | 1% |
| P130-138 NAPYLPSCL (SEQ ID NOs:144 and 282) | 79% |
| P131-139 APYLPSCLE (SEQ ID NO:226) | 1% |

Example 6

Identification of WT1 Specific mRNA in Mouse Tumor Cell Lines

This Example illustrates the use of RT-PCR to detect WT1 specific mRNA in cells and cell lines.

Mononuclear cells were isolated by density gradient centrifugation, and were immediately frozen and stored at −80° C. until analyzed by RT-PCR for the presence of WT1 specific mRNA. RT-PCR was generally performed as described by Fraizer et al., *Blood* 86:4704-4706, 1995. Total RNA was extracted from $10^7$ cells according to standard procedures. RNA pellets were resuspended in 25 μL diethylpyrocarbonate treated water and used directly for reverse transcription. The zinc-finger region (exons 7 to 10) was amplified by PCR as a 330 bp mouse cDNA. Amplification was performed in a thermocycler during one or, when necessary, two sequential rounds of PCR. AMPLITAQ® DNA Polymerase (Perkin Elmer Cetus, Norwalk, Conn.), 2.5 mM $MgCl_2$ and 20 pmol of each primer in a total reaction volume of 50 μl were used. Twenty μL aliquots of the PCR products were electrophoresed on 2% agarose gels stained with ethidium bromide. The gels were photographed with POLAROID® film (Polaroid 667, Polaroid Ltd., Hertfordshire, England). Precautions against cross contamination were taken following the recommendations of Kwok and Higuchi, *Nature* 339:237-238, 1989. Negative controls included the cDNA- and PCR-reagent mixes with water instead of cDNA in each experiment. To avoid false negatives, the presence of intact RNA and adequate cDNA generation was evaluated for each sample by a control PCR using β-actin primers. Samples that did not amplify with these primers were excluded from analysis.

Primers for amplification of WT1 in mouse cell lines were: P115: 1458-1478: 5' CCC AGG CTG CAA TAA GAG ATA 3' (forward primer; SEQ ID NO:21); and P116: 1767-1787: 5' ATG TTG TGA TGG CGG ACC AAT 3' (reverse primer; SEQ ID NO:22) (see Inoue et al, *Blood* 88:2267-2278, 1996; Fraizer et al., *Blood* 86:4704-4706, 1995).

Beta Actin primers used in the control reactions were: 5' GTG GGG CGC CCC AGG CAC CA 3' (sense primer; SEQ ID NO:23); and 5' GTC CTT AAT GTC ACG CAC GAT TTC 3' (antisense primer; SEQ ID NO:24)

Primers for use in amplifying human WT1 include: P117: 954-974: 5' GGC ATC TGA GAC CAG TGA GAA 3' (SEQ ID NO:25); and P118: 1434-1414: 5' GAG AGT CAG ACT TGA AAG CAGT 3' (SEQ ID NO:5). For nested RT-PCR, primers may be: P119: 1023-1043: 5' GCT GTC CCA CTT ACA GAT GCA 3' (SEQ ID NO:26); and P120: 1345-1365: 5' TCA AAG CGC CAG CTG GAG TTT 3' (SEQ ID NO:27).

Table XLVIII shows the results of WT1 PCR analysis of mouse tumor cell lines. Within Table IV, (+++) indicates a strong WT1 PCR amplification product in the first step RT PCR, (++) indicates a WT1 amplification product that is detectable by first step WT1 RT PCR, (+) indicates a product that is detectable only in the second step of WT1 RT PCR, and (−) indicates WT1 PCR negative.

TABLE XLIX

Detection of WT1 mRNA in Mouse Tumor Cell Lines

| Cell Line | WT1 mRNA |
|---|---|
| K562 (human leukemia; ATCC): Positive control; (Lozzio and Lozzio, Blood 45:321–334, 1975) | + + + |
| TRAMPC (SV40 transformed prostate, B6); Foster et al., Cancer Res. 57:3325–3330, 1997 | + + + |
| BLK-SV40 HD2 (SV40-transf. fibroblast, B6; ATCC); Nature 276:510–511, 1978 | + + |
| CTLL (T-cell, B6; ATCC); Gillis, Nature 268:154–156, 1977) | + |
| FM (FBL-3 subline, leukemia, B6); Glynn and Fefer, Cancer Res. 28:434–439, 1968 | + |
| BALB 3T3 (ATCC); Aaroston and Todaro, J. Cell. Physiol. 72:141-148, 1968 | + |
| S49.1 (Lymphoma, T-cell like, B/C; ATCC); Horibata and Harris, Exp. Cell. Res. 60:61, 1970 | + |
| BNL CL.2 (embryonic liver, B/C; ATCC); Nature 276:510–511, 1978 | + |
| MethA (sarcoma, B/C); Old et al., Ann. NY Acad. Sci. 101:80–106, 1962 | – |
| P3.6.2.8.1 (myeloma, B/C; ATCC); Proc. Natl. Acad. Sci. USA 66:344, 1970 | – |
| P2N (leukemia, DBA/2; ATCC); Melling et al., J. Immunol. 117:1267–1274, 1976 | – |
| BCL1 (lymphoma, B/C; ATCC); Slavin and Strober, Nature 272:624–626, 1977 | – |
| LSTRA (lymphoma, B/C); Glynn et al., Cancer Res. 28:434–439, 1968 | – |
| E10/EL-4 (lymphoma, B6); Glynn et al., Cancer Res. 28:434–439, 1968 | – |

Example 7

Expression in *E. coli* of WT1 Trx Fusion Construct

The truncated open reading frame of WT1 (WT1B) was PCR amplified with the following primers:

Forward Primer starting at amino acid 2

P-37 (SEQ ID NO:347) 5' ggctccgacgtgcgggacctg 3' Tm 64° C.

Reverse Primer creating EcoRI site after stop codon

P-23 (SEQ ID NO:348) 5' gaattctcaaagcgccagctggagtttggt 3' Tm 63° C.

The PCR was performed under the following conditions:

10 μl 10× Pfu buffer

1 μl 10 mM dNTPs

2 μl 10 μM each oligo

83 μL sterile water 1.5 μl Pfu DNA polymerase (Stratagene, La Jolla, Calif.)

50 ng DNA (pPDM FL WT1)

| | | |
|---|---|---|
| 96° C. 2 minutes | | |
| 96° C. 20 seconds | 63° C. 15 seconds | 72° C. 3 minutes × 40 cycles |
| 72° C. 4 minutes | | |

The PCR product was digested with EcoRI restriction enzyme, gel purified and then cloned into pTrx 2H vector (a modified pET28 vector with a Trx fusion on the N-terminal and two His tags surrounding the Trx fusion. After the Trx fusion there exists protease cleavage sites for thrombin and enterokinase). The pTrx2H construct was digested with StuI and EcoRI restriction enzymes. The correct constructs were confirmed by DNA sequence analysis and then transformed into BL21 (DE3) pLys S and BL21 (DE3) CodonPlus expression host cells.

Example 8

Expression in *E. coli* of WT1 A His Tag Fusion Constructs

The N-terminal open reading frame of WT1 (WT1A) was PCR amplified with the following primers:

Forward Primer starting at amino acid 2

P-37 (SEQ ID NO. 349) 5'ggctccgacgtgcgggacctg 3' Tm 64° C.

Reverse Primer creating EcoRI site after an artificial stop codon put after amino acid 249.

PDM-335 (SEQ ID NO.350) 5'gaattctcaaagcgccagctggagtttggt 3' Tm 64° C.

The PCR was performed under the following conditions:

10 μl 10× Pfu buffer
1 μl 10 mM dNTPs
2 μl 10 μM each oligo
83 μL sterile water
1.5 μl Pfu DNA polymerase (Stratagene, La Jolla, Calif.)
50 ng DNA (pPDM FL WT1)

| | | |
|---|---|---|
| 96° C. 2 minutes | | |
| 96° C. 20 seconds | 63° C. 15 seconds | 72° C. 1 minute 20 seconds × 40 cycles |
| 72° C. 4 minutes | | |

The PCR product was digested with EcoRI restriction enzyme, gel purified and then cloned into pPDM, a modified pET28 vector with a His tag in frame, which had been digested with Eco72I and EcoRI restriction enzymes. The PCR product was also transformed into pTrx 2H vector. The pTrx2H construct was digested with StuI and EcoRI restriction enzymes. The correct constructs were confirmed by DNA sequence analysis and then transformed into BL21 (DE3) pLys S and BL21 (DE3) CodonPlus expression host cells.

Example 9

Expression in *E. coli* of WT1 B His Tag Fusion Constructs

The truncated open reading frame of WT1 (WT1A) was PCR amplified with the following primers:

Forward Primer starting at amino acid 250

PDM-346 (SEQ ID NO.351) 5' cacagcacagggtacgagagc 3' Tm 58° C.

Reverse Primer creating EcoRI site after stop codon

P-23 (SEQ ID NO.352) 5'gaattctcaaagcgccagctggagtttggt 3' Tm 63° C.

The PCR was performed under the following conditions:

10 μl 10× Pfu buffer
1 μl 10 mM dNTPs
2 μl 10 μM each oligo
83 μL sterile water
1.5 μl Pfu DNA polymerase (Stratagene, La Jolla, Calif.)
50 ng DNA (pPDM FL WT1)

| | | |
|---|---|---|
| 96° C. 2 minutes | | |
| 96° C. 20 seconds | 63° C. 15 seconds | 72° C. 1 minute 30 seconds × 40 cycles |
| 72° C. 4 minutes | | |

The PCR product was digested with EcoRI restriction enzyme, gel purified and then cloned into pPDM, a modified pET28 vector with a His tag in frame, which had been digested with Eco72I and EcoRI restriction enzymes. The PCR product was also transformed into pTrx 2H vector. The pTrx 2H construct was digested with StuI and EcoRI restriction enzymes. The correct constructs were confirmed by DNA sequence analysis and then transformed into BL21 (DE3) pLys S and BL21 (DE3) CodonPlus expression host cells.

For Examples 7-9, the following SEQ ID NOs. are disclosed:

SEQ ID NO. 327 is the determined cDNA sequence for Trx_WT1_B

SEQ ID NO. 328 is the determined cDNA sequence for Trx_WT1_A

SEQ ID NO. 329 is the determined cDNA sequence for Trx_WT1

SEQ ID NO. 330 is the determined cDNA sequence for WT1_A

SEQ ID NO. 331 is the determined cDNA sequence for WT1_B

SEQ ID NO. 332 is the predicted amino acid sequence encoded by SEQ ID No. 327

SEQ ID NO. 333 is the predicted amino acid sequence encoded by SEQ ID No. 328

SEQ ID NO. 334 is the predicted amino acid sequence encoded by SEQ ID No. 329

SEQ ID NO. 335 is the predicted amino acid sequence encoded by SEQ ID No. 330

SEQ ID NO. 336 is the predicted amino acid sequence encoded by SEQ ID No. 331

Example 10

Truncated Forms of WT1 Expressed in *E. coli*

Three reading frames of WT1 were amplified by PCR using the following primers:

```
For WT1 Tr2:
PDM-441 (SEQ ID NO.348) 5' cacgaagaacagtgcctgagcgcattcac 3' Tm 63° C.

PDM-442 (SEQ ID NO.349) 5' ccggcgaattcatcagtataaattgtcactgc 3' TM 62° C.

For WT1 Tr3:
PDM-443 (SEQ ID NO.350) 5' caggctttgctgctgaggacgccc 3' Tm 64° C.

PDM-444 (SEQ ID NO.351) 5' cacggagaattcatcactggtatggtttctcacc Tm 64° C.

For WT1 Tr4:
PDM-445 (SEQ ID NO.352) 5' cacagcaggaagcacactggtgagaaac 3' Tm 63° C.

PDM-446 (SEQ ID NO.353) 5' ggatatctgcagaattctcaaagcgccagc 3' TM 63° C.
```

The PCR was performed under the following conditions:

10 μl 10× Pfu buffer
1 μl 10 mM dNTPs
2 μl 10 μM each oligo
83 μL sterile water
1.5 μl Pfu DNA polymerase (Stratagene, La Jolla, Calif.)
50 ng DNA (pPDM FL WT1)

| | | |
|---|---|---|
| 96° C. 2 minutes | | |
| 96° C. 20 seconds | 63° C. 15 seconds | 72° C. 30 seconds × 40 cycles |
| 72° C. 4 minutes | | |

The PCR product was digested with EcoRI and cloned into pPDM His (a modified pET28 vector with a His tag in frame on the 5' end) which has been digested with Eco72I and EcoRI. The constructs were confirmed to be correct through sequence analysis and transformed into BL21 pLys S and BL21 CONDONPLUS® cells or BLR pLys S and BL21-CODONPLUS® cells.

Example 11

WT1 C (Amino Acids 76-437) and WT1 D (Amino Acids 91-437) Expression in *E. coli*

The WT1 C reading frame was amplified by PCR using the following primers:

PDM-504 (SEQ ID NO.359) 5' cactccttcatcaaacaggaac 3' Tm 61° C.

PDM-446 (SEQ ID NO.360) 5' ggatatctgcagaattct-caaagcgccagc 3' Tm 63° C.

The PCR was performed under the following conditions:

10 μl 10× Pfu buffer
1 μl 10 mM dNTPs
2 μl 10 μM each oligo
83 μL sterile water
1.5 μl Pfu DNA polymerase (Stratagene, La Jolla, Calif.)
50 ng DNA (pPDM FL WT1)

| | | |
|---|---|---|
| 96° C. 2 minutes | | |
| 96° C. 20 seconds | 63° C. 15 seconds | 72° C. 2 minutes × 40 cycles |
| 72° C. 4 minutes | | |

The PCR product was digested with EcoRI and cloned into pPDM His which had been digested with Eco72I and EcoRI. The sequence was confirmed through sequence analysis and then transformed into BLR pLys S and BLR which is co-transformed with CODONPLUS® RP.

Example 12

Synthetic Production of WT1 Tr-1 by Annealing Overlapping Oligos

This example was performed to determine the effect of changing proline codon usage on expression.

The following pairs of oligos were annealed:

```
1. PDM-505 (SEQ ID NO.356) 5' ggttccgacgtgcgggacctgaacgcactgctg 3'

   PDM-506 (SEQ ID NO.357) 5' ctgccggcagcagtgcgttcaggtcccgcacgtcggaacc 3'

2. PDM-507 (SEQ ID NO.358) 5' ccggcagttccatccctgggtggcggtggaggctg 3'

   PDM-508 (SEQ ID NO.359) 5' cggcagtgcgcagcctccaccgccacccagggatggaa 3'

3. PDM-509 (SEQ ID NO.360) 5' cgcactgccggttagcggtgcagcacagtgggctc 3'

   PDM-510 (SEQ ID NO.361) 5' cagaactggagcccactgtgctgcaccgctaac 3'

4. PDM-511 (SEQ ID NO.362) 5' cagttctggacttcgcaccgcctggtgcatccgcatac 3'

   PDM-512 (SEQ ID NO.363) 5' cagggaaccgtatgcggatgcaccaggcggtgcgaagtc 3'

5. PDM-513 (SEQ ID NO.364) 5' ggttccctgggtggtccagcacctccgcccgcaacgcc 3'

   PDM-514 (SEQ ID NO.365) 5' ggcggtgggggcgttgcgggcggaggtgctggaccacc 3'

6. PDM-515 (SEQ ID NO.366) 5' cccaccgcctccaccgcccccgcactccttcatcaaacag 3'

   PDM-516 (SEQ ID NO.367) 5' ctaggttcctgtttgatgaaggagtgcgggggcggtgga 3'

7. PDM-517 (SEQ ID NO.368) 5' gaacctagctggggtggtgcagaaccgcacgaagaaca 3'

   PDM-518 (SEQ ID NO.369) 5' ctcaggcactgttcttcgtgcggttctgcaccaccccag 3'

8. PDM-519 (SEQ ID NO.370) 5' gtgcctgagcgcattctgagaattctgcagat 3'

   PDM-520 (SEQ ID NO.371) 5' gtgtgatggatatctgcagaattctcagaatgcg 3'
```

Each oligo pair was separately combined then annealed. The pairs were then ligated together and one μl of ligation mix was used for PCR conditions below:

10 μl 10× Pfu buffer
1 μl 10 mM dNTPs
2 μl 10 μM each oligo
83 μL sterile water
1.5 μl Pfu DNA polymerase (Stratagene, La Jolla, Calif.)

| | | |
|---|---|---|
| 96° C. 2 minutes | | |
| 96° C. 20 seconds | 63° C. 15 seconds | 72° C. 30 seconds × 40 cycles |
| 72° C. 4 minutes | | |

The PCR product was digested with EcoRI and cloned into pPDM His which had been digested with Eco72I and EcoRI. The sequence was confirmed and then transformed into BLR pLys S and BLR which is co-transformed with CODON-PLUS® RP.

For examples 10-12, the following SEQ ID NOs. are disclosed:

SEQ ID NO:337 is the determined cDNA sequence for WT1_Tr1

SEQ ID NO:338 is the determined cDNA sequence for WT1_Tr2

SEQ ID NO:339 is the determined cDNA sequence for WT1_Tr3

SEQ ID NO:340 is the determined cDNA sequence for WT1_Tr4

SEQ ID NO:341 is the determined cDNA sequence for WT1_C

SEQ ID NO:342 is the predicted amino acid sequence encoded by SEQ ID NO:337

SEQ ID NO:343 is the predicted amino acid sequence encoded by SEQ ID NO:338

SEQ ID NO:344 is the predicted amino acid sequence encoded by SEQ ID NO:339

SEQ ID NO:345 is the predicted amino acid sequence encoded by SEQ ID NO:340

SEQ ID NO:346 is the predicted amino acid sequence encoded by SEQ ID NO:341

The WT1 C sequence represents a polynucleotide having the coding regions of TR2, TR3 and TR4.

The WT1 TR-1 synthetic sequence represents a polynucleotide in which alternative codons for proline were substituted for the native codons, producing a polynucleotide capable of expressing WT1 TR-1 in *E. coli.*

Example 13

Evaluation of the Systemic Histopathological and Toxicological Effects of WT1 Immunization in Mice The purpose of this example is to analyze the immunogenicity and potential systemic histopathological and toxicological effects of WT1 protein immunization in a multiple dose titration in mice.

The experimental design for immunization of mice with WT1 protein is outlined in Table L.

TABLE L

Experimental Design of WT1 Immunization in Mice

| Histology Group | Corixa Group | Treatment Description | Dose Level | Total No. (Females) |
|---|---|---|---|---|
| 1 | 0 | No treatment | 0 | 4 |
| 2 | 1.1 | MPL-SE (adjuvants alone), 6x, 1 week apart | 10 ug | 4 |
| 3 | 1.2 | MPL-SE, 3x, 2 weeks apart | 10 ug | 4 |
| 4 | 2.1 | Ra12-WT1 + MPL-SE, 6x | 25 ug | 4 |
| 5 | 2.2 | Ra12-WT1 + MPL-SE, 3x | 25 ug | 4 |
| 6 | 3.1 | Ra12-WT1 + MPL-SE, 6x | 100 ug | 4 |
| 7 | 3.2 | Ra12-WT1 + MPL-SE, 3x | 100 ug | 4 |
| 8 | 4.1 | Ra12-WT1 + MPL-SE, 6x | 1000 ug | 4 |
| 9 | 4.2 | Ra12-WT1 + MPL-SE, 3x | 1000 ug | 4 |

Figure 20A:
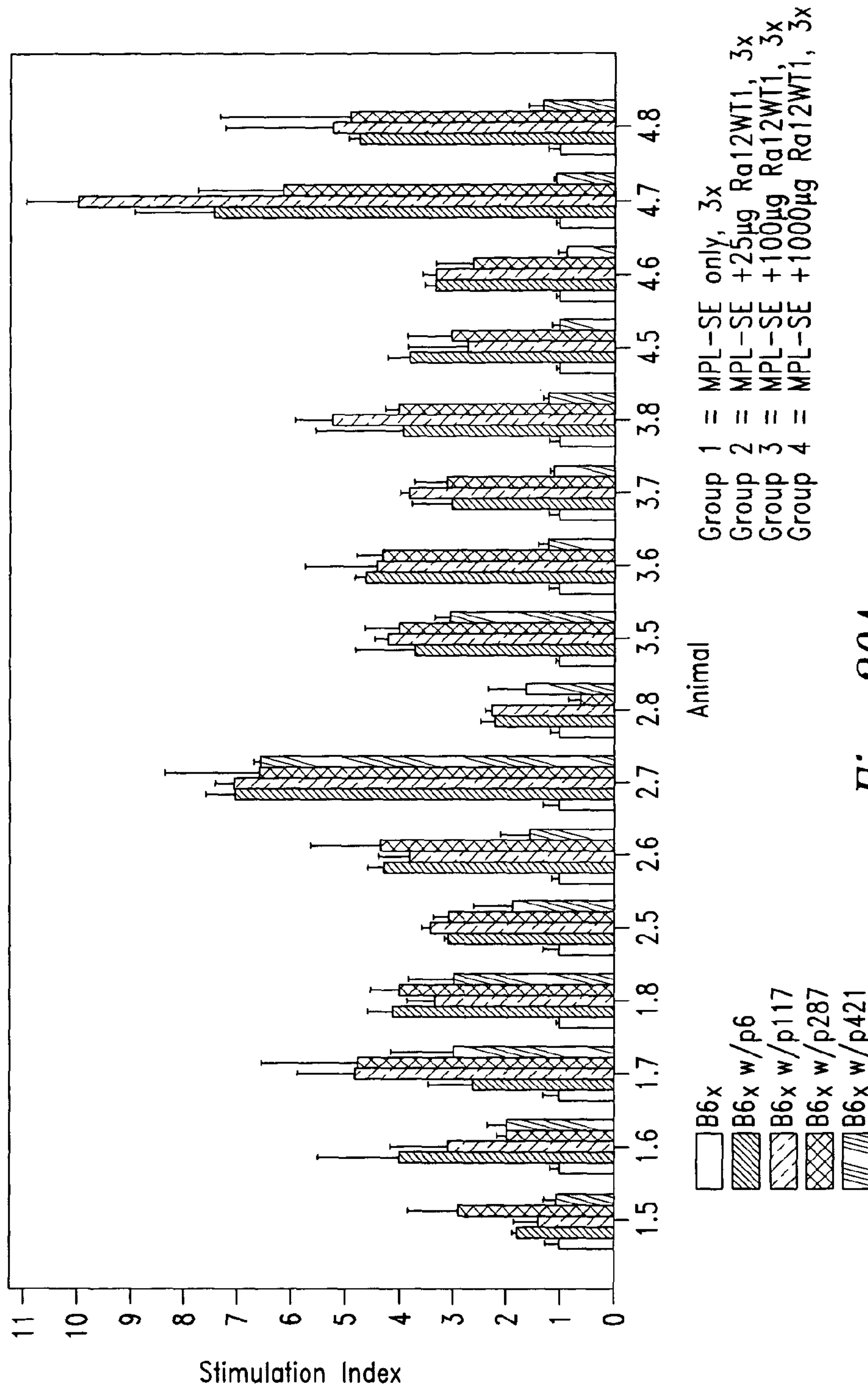
FIG. 20 is a bar graph of the proliferative T-cell responses in mice immunized with WT1 protein.
Figure 20B:
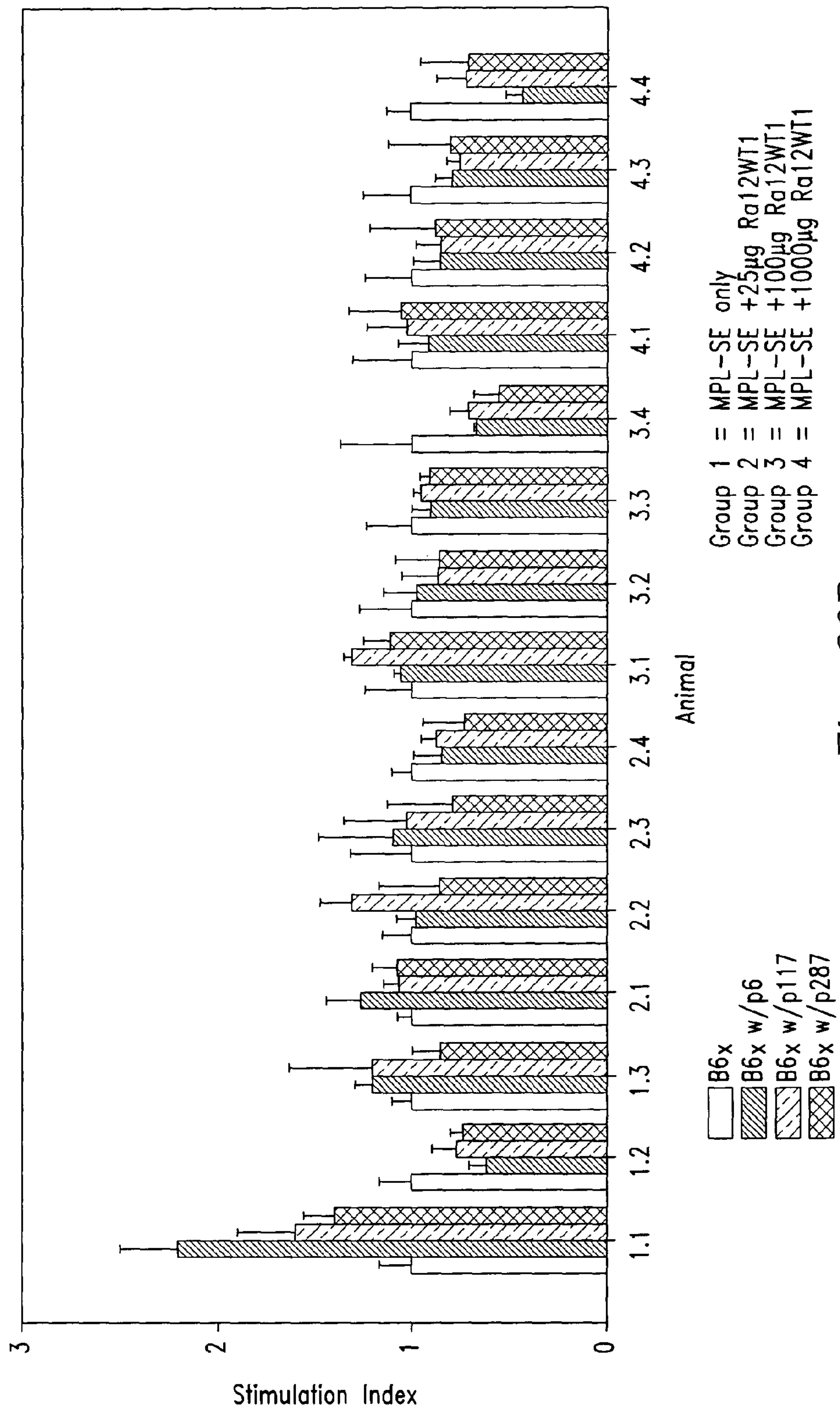

Vaccination to WT1 protein using MPL®-SE as adjuvant, in a multiple dose titration study (doses ranging from 25 μg, 100 μg to 1000 μg WT1 protein) in female C57/B6 mice elicited a strong WT1-specific antibody response (FIG. 19) and cellular T-cell responses (FIG. 20).

No systemic histopathological or toxicological effects of inununization with WT1 protein was observed. No histological evidence for toxicity was seen in the following tissues: adrenal gland, brain, cecum, colon, duodenum, eye, femur and marrow, gall bladder, heart, ileum, jejunum, kidney, larynx, lacrimal gland, liver, lung, lymph node, muscle, esophagus, ovary, pancreas, parathyroid, salivary gland, sternum and marrow, spleen, stomach, thymus, trachea, thyroid, urinary bladder and uterus.

Special emphasis was put on evaluation of potential hematopoietic toxicity. The myeloid/erythroid ratio in sternum and femur marrow was normal. All evaluable blood cell counts and blood chemistry (BUN, creatinine, bilirubin, albumin, globulin) were within the normal range (Table LI).

Given that existent immunity to WT1 is present in some patients with leukemia and that vaccination to WT1 protein can elicit WT1 specific Ab and cellular T-cell responses in mice without toxicity to normal tissues, these experiments validate WT1as a tumor/leukemia vaccine.

TABLE LI

Clinical Chemistry and Hematology Analysis

Table LI: WT1 Dose Titration Study
Clinical Chemistry and Hematology Analysis

| Animal # | K/uL WBC | M/uL RBC | g/dl Hg. | % HCT | fL MCV | pg MCH | % MCHC |
|---|---|---|---|---|---|---|---|
| Normal | 5.4–16.0 | 6.7–12.5 | 10.2–16.6 | 32–54 | 31–62 | 9.2–20.8 | 22.0–35.5 |
| Group 1 | | | | | | | |
| 1 (0) | 5.6 | 8.41 | 12.8 | 43.5 | 53 | 15.2 | 29.4 |
| 2 (0) | 5.5 | 9.12 | 13.4 | 47.5 | 53 | 14.7 | 28.2 |

TABLE LI-continued

| | | | | | | | |
|---|---|---|---|---|---|---|---|
| 3 (0) | 7.5 | 9.22 | 13.5 | 48 | 54 | 14.7 | 28.1 |
| 4 (0) | 3.9 | 9.27 | 13.6 | 46 | 52 | 14.7 | 29.6 |
| Mean | 5.6 | 9.0 | 13.3 | 46.3 | 53.0 | 14.8 | 28.8 |
| STD | 1.5 | 0.4 | 0.4 | 2.0 | 0.8 | 0.3 | 0.8 |
| Group 2 | | | | | | | |
| 5 (1.5) | 6.6 | 9 | 13.1 | 46 | 54 | 14.5 | 28.5 |
| 6 (1.6) | 5.2 | 8.58 | 12.6 | 44 | 53 | 14.7 | 28.6 |
| 7 (1.7) | 7.8 | 9.21 | 13.6 | 46 | 53 | 14.7 | 29.6 |
| 8 (1.8) | 6.3 | NA | NA | 41 | NA | NA | NA |
| Mean | 6.5 | 8.9 | 13.1 | 44.3 | 53.3 | 14.6 | 28.9 |
| STD | 1.1 | 0.3 | 0.5 | 2.4 | 0.6 | 0.1 | 0.6 |
| Group 3 | | | | | | | |
| 9 (2.5) | 8.3 | 9.16 | 13.6 | 50.3 | 55 | 14.9 | 27.1 |
| 10 (2.6) | 5 | 8.78 | 13 | 44.2 | 50 | 14.8 | 29.3 |
| 11 (2.7) | 4 | 8.94 | 13.2 | 48.3 | 54 | 14.7 | 27.3 |
| 12 (2.8) | 8.2 | NA | NA | 41 | NA | NA | NA |
| Mean | 6.4 | 9.0 | 13.3 | 46.0 | 53.0 | 14.8 | 27.9 |
| STD | 2.2 | 0.2 | 0.3 | 4.2 | 2.6 | 0.1 | 1.2 |
| Group 4 | | | | | | | |
| 13 (3.5) | 6.1 | 8.82 | 13.1 | 46 | 54 | 14.9 | 28.5 |
| 14 (3.6) | 6.1 | 8.64 | 12.9 | 46 | 54 | 15 | 28 |
| 15 (3.7) | 9.3 | 8.93 | 13.2 | 48 | 55 | 14.8 | 27.5 |
| 16 (3.8) | 4.8 | 8.19 | 12.6 | 44 | 55 | 15.3 | 28.6 |
| Mean | 6.6 | 8.6 | 13.0 | 46.0 | 54.5 | 15.0 | 28.2 |
| STD | 1.9 | 0.3 | 0.3 | 1.6 | 0.6 | 0.2 | 0.5 |
| Group 5 | | | | | | | |
| 17 (4.5) | 3.1 | 8.48 | 12.6 | 46 | 54 | 14.9 | 27.5 |
| 18 (4.6) | 5.7 | 9.12 | 13.7 | 48 | 54 | 15 | 28.5 |
| 19 (4.7) | 5.3 | 8.58 | 13 | 44.5 | 55 | 15.2 | 29.2 |
| 20 (4.8) | 5.3 | NA | NA | 40 | NA | NA | NA |
| Mean | 4.9 | 8.7 | 13.1 | 44.6 | 54.3 | 15.0 | 28.4 |
| STD | 1.2 | 0.3 | 0.6 | 3.4 | 0.6 | 0.2 | 0.9 |
| Group 6 | | | | | | | |
| 21 (1.1) | 3.5 | 9.36 | 13.5 | 37.6 | 40 | 14.4 | 35.9 |
| 22 (1.2) | 6.9 | 8.93 | 13.6 | 37.3 | 42 | 15.3 | 36.6 |
| 23 (1.3) | 3.6 | 8.3 | 12.5 | 35.3 | 43 | 15.1 | 35.5 |
| 24 (1.4) | NA | NA | NA | NA | NA | NA | NA |
| Mean | 4.7 | 8.9 | 13.2 | 36.7 | 41.7 | 14.9 | 36.0 |
| STD | 1.9 | 0.5 | 0.6 | 1.3 | 1.5 | 0.5 | 0.6 |
| Group 7 | | | | | | | |
| 25 (2.1) | 4 | NA | NA | 40 | NA | NA | NA |
| 26 (2.2) | 7.4 | 9.12 | 13.2 | 38.5 | 42 | 14.5 | 34.3 |
| 27 (2.3) | 4.5 | 8.19 | 12.1 | 34.5 | 42 | 14.8 | 35.1 |
| 28 (2.4) | 5.8 | 8.25 | 12.3 | 34.1 | 41 | 14.9 | 36.1 |
| Mean | 5.4 | 8.5 | 12.5 | 36.8 | 41.7 | 14.7 | 35.2 |
| STD | 1.5 | 0.5 | 0.6 | 2.9 | 0.6 | 0.2 | 0.9 |
| Group 8 | | | | | | | |
| 29 (3.1) | 5.1 | 8.53 | 12.6 | 34.9 | 41 | 14.7 | 36 |
| 30 (3.2) | 7.6 | 8.42 | 13 | 36.1 | 43 | 15.4 | 35.9 |
| 31 (3.3) | 3.4 | 8.45 | 12.6 | 34.9 | 41 | 14.9 | 36.1 |
| 32 (3.4) | 6.1 | 8.11 | 12.3 | 34.8 | 43 | 15.2 | 35.5 |
| Mean | 5.6 | 8.4 | 12.6 | 35.2 | 42.0 | 15.1 | 35.9 |
| STD | 1.8 | 0.2 | 0.3 | 0.6 | 1.2 | 0.3 | 0.3 |
| Group 9 | | | | | | | |
| 33 (4.1) | NA | NA | NA | NA | NA | NA | NA |
| 34 (4.2) | 4.5 | 8.63 | 12.8 | 36.2 | 42 | 14.8 | 35.2 |
| 35 (4.3) | 3.9 | 8.85 | 13 | 36.6 | 41 | 14.7 | 35.6 |
| 36 (4.4) | 4.7 | 8.14 | 12.3 | 33.8 | 42 | 15.1 | 36.3 |
| Mean | 4.4 | 8.5 | 12.7 | 35.5 | 41.7 | 14.9 | 35.7 |
| STD | 0.4 | 0.4 | 0.4 | 1.5 | 0.6 | 0.2 | 0.6 |

| Animal # | yes/no Plt. clump | K/uL Platelets | Abs. Baso | Abs. Eos | Abs. Bands | Abs. Polys | Abs. Lymph | Abs. Mono |
|---|---|---|---|---|---|---|---|---|
| Normal | no | 150-1500 | 0.0-0.15 K/uL | 0.0-0.51 K/uL | 0.0-0.32 K/uL | 8.0-42.9 K/uL | 8.0-18.0 K/uL | 0.0-1.5 K/uL |
| Group 1 | | | | | | | | |
| 1 (0) | yes | 726 | 0 | 56 | 0 | 336 | 5208 | 0 |
| 2 (0) | no | 860 | 0 | 0 | 0 | 55 | 5445 | 0 |

TABLE LI-continued

| | | | | | | | | |
|---|---|---|---|---|---|---|---|---|
| 3 (0) | no | 875 | 0 | 375 | 0 | 525 | 6525 | 75 |
| 4 (0) | yes | 902 | 0 | 0 | 0 | 156 | 3744 | 0 |
| Mean | | 840.8 | 0.0 | 107.8 | 0.0 | 268.0 | 5230.5 | 18.8 |
| STD | | 78.4 | 0.0 | 180.1 | 0.0 | 207.0 | 1144.8 | 37.5 |
| Group 2 | | | | | | | | |
| 5 (1.5) | no | 1193 | 0 | 132 | 0 | 792 | 5214 | 462 |
| 6 (1.6) | no | 1166 | 0 | 52 | 0 | 624 | 4472 | 52 |
| 7 (1.7) | no | 1087 | 0 | 234 | 0 | 1170 | 6396 | 0 |
| 8 (1.8) | yes | NA | 0 | 126 | 0 | 126 | 5922 | 126 |
| Mean | | 1148.7 | 0.0 | 136.0 | 0.0 | 678.0 | 5501.0 | 160.0 |
| STD | | 55.1 | 0.0 | 74.8 | 0.0 | 433.1 | 840.5 | 207.9 |
| Group 3 | | | | | | | | |
| 9 (2.5) | no | 705 | 0 | 166 | 0 | 664 | 7387 | 83 |
| 10 (2.6) | no | 1140 | 0 | 150 | 0 | 500 | 4350 | 0 |
| 11 (2.7) | no | 952 | 0 | 120 | 0 | 680 | 3200 | 0 |
| 12 (2.8) | yes | NA | 0 | 164 | 0 | 656 | 7216 | 164 |
| Mean | | 932.3 | 0.0 | 150.0 | 0.0 | 625.0 | 5538.3 | 61.8 |
| STD | | 218.2 | 0.0 | 21.2 | 0.0 | 83.9 | 2090.6 | 78.6 |
| Group 4 | | | | | | | | |
| 13 (3.5) | no | 785 | 0 | 488 | 0 | 732 | 4636 | 244 |
| 14 (3.6) | yes | 973 | 0 | 0 | 0 | 488 | 5307 | 305 |
| 15 (3.7) | yes | 939 | 0 | 465 | 0 | 558 | 7812 | 465 |
| 16 (3.8) | yes | 1622 | 0 | 192 | 0 | 480 | 4080 | 48 |
| Mean | | 1079.8 | 0.0 | 286.3 | 0.0 | 564.5 | 5458.8 | 265.5 |
| STD | | 370.6 | 0.0 | 233.4 | 0.0 | 117.0 | 1647.1 | 172.4 |
| Group 5 | | | | | | | | |
| 17 (4.5) | no | 892 | 0 | 31 | 0 | 620 | 2449 | 0 |
| 18 (4.6) | yes | 966 | 57 | 114 | 0 | 855 | 4674 | 0 |
| 19 (4.7) | yes | 883 | 0 | 53 | 0 | 742 | 4452 | 53 |
| 20 (4.8) | yes | NA | 0 | 106 | 0 | 53 | 5141 | 0 |
| Mean | | 913.7 | 14.3 | 76.0 | 0.0 | 567.5 | 4179.0 | 13.3 |
| STD | | 45.5 | 28.5 | 40.4 | 0.0 | 356.2 | 1188.5 | 26.5 |
| Group 6 | | | | | | | | |
| 21 (1.1) | yes | 784 | 0 | 35 | 0 | 385 | 2870 | 210 |
| 22 (1.2) | yes | 806 | 0 | 69 | 0 | 207 | 6486 | 138 |
| 23 (1.3) | yes | 790 | 0 | 180 | 0 | 396 | 2988 | 36 |
| 24 (1.4) | NA | NA | NA | NA | NA | NA | NA | NA |
| Mean | | 793.3 | 0.0 | 94.7 | 0.0 | 329.3 | 4114.7 | 128.0 |
| STD | | 11.4 | 0.0 | 75.8 | 0.0 | 106.1 | 2054.5 | 87.4 |
| Group 7 | | | | | | | | |
| 25 (2.1) | yes | NA | 0 | 80 | 0 | 200 | 3720 | 0 |
| 26 (2.2) | yes | 753 | 0 | 0 | 0 | 518 | 6734 | 148 |
| 27 (2.3) | yes | 725 | 0 | 90 | 0 | 225 | 4140 | 45 |
| 28 (2.4) | yes | 792 | 0 | 232 | 0 | 754 | 4814 | 0 |
| Mean | | 756.7 | 0.0 | 100.5 | 0.0 | 424.3 | 4852.0 | 48.3 |
| STD | | 33.7 | 0.0 | 96.5 | 0.0 | 263.0 | 1333.1 | 69.8 |
| Group 8 | | | | | | | | |
| 29 (3.1) | yes | 784 | 0 | 153 | 0 | 561 | 4233 | 153 |
| 30 (3.2) | yes | 512 | 0 | 152 | 0 | 304 | 6992 | 152 |
| 31 (3.3) | yes | 701 | 0 | 0 | 0 | 238 | 3094 | 68 |
| 32 (3.4) | yes | 631 | 0 | 305 | 0 | 305 | 5368 | 122 |
| Mean | | 657.0 | 0.0 | 152.5 | 0.0 | 352.0 | 4921.8 | 123.8 |
| STD | | 115.1 | 0.0 | 124.5 | 0.0 | 142.8 | 1663.3 | 39.9 |
| Group 9 | | | | | | | | |
| 33 (4.1) | NA | NA | NA | NA | NA | NA | NA | NA |
| 34 (4.2) | yes | 724 | 0 | 125 | 0 | 540 | 3780 | 45 |
| 35 (4.3) | yes | 758 | 0 | 117 | 0 | 429 | 3315 | 39 |
| 36 (4.4) | yes | 808 | 0 | 47 | 0 | 329 | 4089 | 235 |
| Mean | | 763.3 | 0.0 | 96.3 | 0.0 | 432.7 | 3728.0 | 106.3 |
| STD | | 42.3 | 0.0 | 42.9 | 0.0 | 105.5 | 389.6 | 111.5 |

| Animal # | mg/dl BUN | mg/dl Creatinine | g/dl T. protein | g/dl Albumin | g/dl Globulin | mg/dl T. Bilirubin |
|---|---|---|---|---|---|---|
| Normal | 13.9–28.3 | 0.3–1.0 | 4.0–8.6 | 2.5–4.8 | 1.5–3.8 | 0.10–0.90 |
| Group 1 | | | | | | |
| 1 (0) | NA | NA | NA | NA | NA | NA |
| 2 (0) | 28 | 0.5 | 4.9 | 3.7 | 1.2 | 0.3 |

TABLE LI-continued

| | | | | | | |
|---|---|---|---|---|---|---|
| 3 (0) | 25 | 0.5 | 4.9 | 3.8 | 1.1 | 0.2 |
| 4 (0) | 27 | 0.5 | 4.7 | 3.7 | 1 | 0.2 |
| Mean | 26.7 | 0.5 | 4.8 | 3.7 | 1.1 | 0.2 |
| STD | 1.5 | 0.0 | 0.1 | 0.1 | 0.1 | 0.1 |
| Group 2 | | | | | | |
| 5 (1.5) | 34 | 0.5 | 4.6 | 3.6 | 1 | 0.2 |
| 6 (1.6) | 31 | 0.4 | 4.6 | 3.3 | 1.3 | 0.2 |
| 7 (1.7) | 34 | 0.6 | 4.9 | 4 | 0.9 | 0.3 |
| 8 (1.8) | NA | NA | NA | NA | NA | NA |
| Mean | 33.0 | 0.5 | 4.7 | 3.6 | 1.1 | 0.2 |
| STD | 1.7 | 0.1 | 0.2 | 0.4 | 0.2 | 0.1 |
| Group 3 | | | | | | |
| 9 (2.5) | NA | NA | NA | NA | NA | NA |
| 10 (2.6) | 33 | 0.5 | 4.6 | 3.6 | 1 | 0.3 |
| 11 (2.7) | NA | NA | NA | NA | NA | NA |
| 12 (2.8) | 31 | 0.5 | 4.8 | 3.7 | 1.1 | 0.2 |
| Mean | 32.0 | 0.5 | 4.7 | 3.7 | 1.1 | 0.3 |
| STD | 1.4 | 0.0 | 0.1 | 0.1 | 0.1 | 0.1 |
| Group 4 | | | | | | |
| 13 (3.5) | 32 | 0.7 | 4.6 | 3.4 | 1.2 | 0.2 |
| 14 (3.6) | 34 | 0.4 | 4.8 | 3.8 | 1 | 0.2 |
| 15 (3.7) | 30 | 0.4 | 4.7 | 3.4 | 1.3 | 0.2 |
| 16 (3.8) | 24 | 0.3 | 5.1 | 3.8 | 1.3 | 0.2 |
| Mean | 30.0 | 0.5 | 4.8 | 3.6 | 1.2 | 0.2 |
| STD | 4.3 | 0.2 | 0.2 | 0.2 | 0.1 | 0.0 |
| Group 5 | | | | | | |
| 17 (4.5) | 22 | 0.4 | 4.6 | 3.3 | 1.3 | 0.2 |
| 18 (4.6) | 31 | 0.5 | 4.9 | 3.7 | 1.2 | 0.2 |
| 19 (4.7) | 23 | 0.6 | 4.8 | 3.6 | 1.2 | 0.2 |
| 20 (4.8) | 28 | 0.5 | 4.5 | 3.4 | 1.1 | 0.2 |
| Mean | 26.0 | 0.5 | 4.7 | 3.5 | 1.2 | 0.2 |
| STD | 4.2 | 0.1 | 0.2 | 0.2 | 0.1 | 0.0 |
| Group 6 | | | | | | |
| 21 (1.1) | 28 | 0.3 | 5.1 | 3.4 | 1.7 | 0.2 |
| 22 (1.2) | 36 | 0.3 | 5.1 | 3.8 | 1.3 | 0.2 |
| 23 (1.3) | 32 | 0.4 | 4.9 | 3.5 | 1.4 | 0.1 |
| 24 (1.4) | NA | NA | NA | NA | NA | NA |
| Mean | 32.0 | 0.3 | 5.0 | 3.6 | 1.5 | 0.2 |
| STD | 4.0 | 0.1 | 0.1 | 0.2 | 0.2 | 0.1 |
| Group 7 | | | | | | |
| 25 (2.1) | 32 | 0.2 | 5 | 3.4 | 1.6 | 0.2 |
| 26 (2.2) | 24 | 0.3 | 4.2 | 2.8 | 1.4 | 0.1 |
| 27 (2.3) | 28 | 0.3 | 4.8 | 3.2 | 1.6 | 0.2 |
| 28 (2.4) | 27 | 0.3 | 5 | 3.4 | 1.6 | 0.1 |
| Mean | 27.8 | 0.3 | 4.8 | 3.2 | 1.6 | 0.2 |
| STD | 3.3 | 0.0 | 0.4 | 0.3 | 0.1 | 0.1 |
| Group 8 | | | | | | |
| 29 (3.1) | 32 | 0.3 | 4.9 | 3.3 | 1.6 | 0.2 |
| 30 (3.2) | NA | NA | NA | NA | NA | NA |
| 31 (3.3) | 18 | 0.3 | 4.8 | 3.1 | 1.7 | 0.2 |
| 32 (3.4) | 26 | 0.2 | 4.2 | 2.9 | 1.3 | 0 |
| Mean | 25.3 | 0.3 | 4.6 | 3.1 | 1.5 | 0.1 |
| STD | 7.0 | 0.1 | 0.4 | 0.2 | 0.2 | 0.1 |
| Group 9 | | | | | | |
| 33 (4.1) | 25 | 0.2 | 4.1 | 2.7 | 1.4 | 0.3 |
| 34 (4.2) | NA | NA | NA | NA | NA | NA |
| 35 (4.3) | 23 | 0.2 | 4.7 | 3.1 | 1.6 | 0.2 |
| 36 (4.4) | 29 | 0.3 | 4.7 | 3.2 | 1.5 | 0.3 |
| Mean | 25.7 | 0.2 | 4.5 | 3.0 | 1.5 | 0.3 |
| STD | 3.1 | 0.1 | 0.3 | 0.3 | 0.1 | 0.1 |

Abbreviations: WBC: white blood cells; RBC: red blood cells; Hg.: hemoglobin; HCT: hematocrit; MCV: Mean corpuscular volume; MCH: mean corpuscular hemoglobin; MCHC: mean corpuscular hemoglobin concentration; Plt.: platelets; Abs.: Absolute; Baso: basophils; Eos: eosinophils; Abs. Bands: immature neutrophils; Polys: polymorphonuclear cells; Lymph: lymphocytes; Mono: monocytes; BUN: blood urea nitrogen.

Example 14

Elicitation of Human WT1-specific T-cell Responses by Whole Gene in vitro Priming This example demonstrates that WT1 specific T-cell responses can be generated from the blood of normal individuals.

Figure 23:
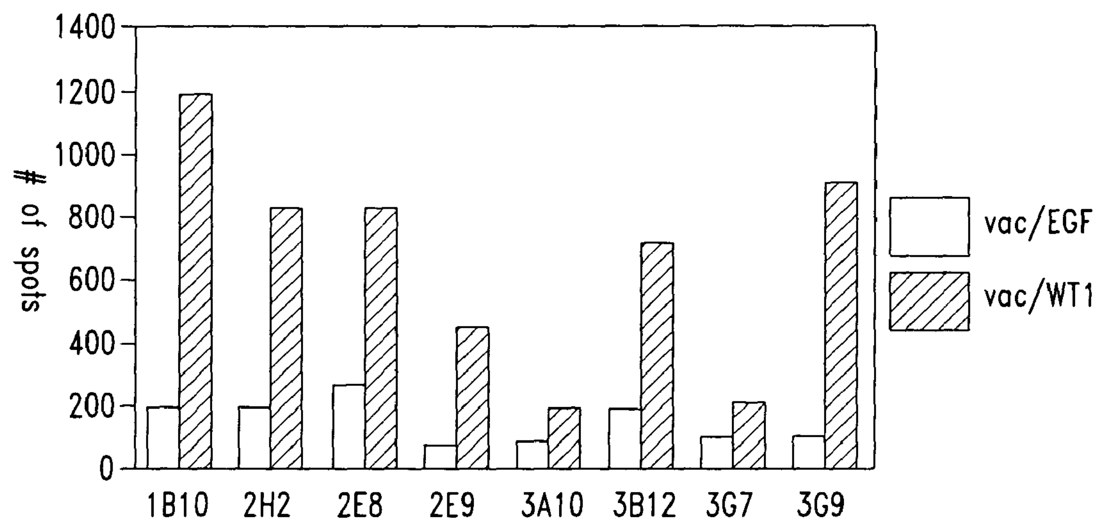
FIG. 23 is a graph of an IFN-gamma ELISPOT assay showing that WT1 whole gene in vitro priming elicits WT1 specific T-cell responses.

Dendritic cells (DC) were differentiated from monocyte cultures derived from PBMC of normal donors by growth for 4-10 days in RPMI medium containing 10% human serum, 50 ng/ml GMCSF and 30 ng/ml IL-4. Following culture, DC were infected 16 hours with recombinant WT1-expressing vaccinia virus at an M.O.I. of 5, or for 3 days with recombinant WT1-expressing adenovirus at an M.O.I. of 10 (FIGS. 21 and 22). Vaccinia virus was inactivated by U.V. irradiation. CD8+ T-cells were isolated by positive selection using magnetic beads, and priming cultures were initiated in 96-well plates. Cultures were restimulated every 7-10 days using autologous dendritic cells adeno or vaccinia infected to express WT1. Following 3-6 stimulation cycles, CD8+ lines could be identified that specifically produced interferon-gamma when stimulated with autologous-WT1-expressing dendritic cells or fibroblasts. The WT1-specific activity of these lines could be maintained following additional stimulation cycles. These lines were demonstrated to specifically recognize adeno or vaccinia WT1 infected autologous dendritic cells but not adeno or vaccinia EGFP-infected autologous dendritic cells by Elispot assays (FIG. 23).

Example 15

Formulation of RA12-WT1 for Injection: Use of Excipients to Stabilize Lyophilized Product This example describes the formulation that allows the complete solubilization of lyophilized Ra12-WT1.

The following formulation allowed for the recombinant protein Ra12-WT1 to be dissolved into an aqueous medium after being lyophylized to dryness:

Recombinant Ra12-WT1 concentration: 0.5-1.0 mg/ml; Buffer: 10-20 mM Ethanolamine, pH 10.0; 1.0-5.0 mM Cysteine; 0.05% TWEEN®-80 (Polysorbate-80); Sugar: 10% Trehalose (T5251, Sigma, MO) 10% Maltose (M9171, Sigma, MO) 10% Sucrose (S7903, Sigma, MO) 10% Fructose (F2543, Sigma, MO) 10% Glucose (G7528, Sigma, MO).

The lyophilized protein with the sugar excipient was found to dissolve significantly more than without the sugar excipient. Analysis by coomassie stained SDS-PAGE showed no signs of remaining solids in the dissolved material.

Example 16

Formulation of a WT1 Protein Vaccine

This example describes the induction of WT1-specific immune responses following immunization with WT1 protein and 2 different adjuvant formulations.

According to this example, WT1 protein in combination with MPL®-SE induces a strong Ab and Interferon-γ (IFN-γ) response to WT1. Described in detail below are the methods used to induce WT1 specific immune responses following WT1 protein immunization using MPL®-SE or ENHANZYN® as adjuvant in C57/B6 mice.

C57BL/6 mice were immunized with 20 μg rRa12-WT1 combined with either MPL®-SE or ENHANZYN® adjuvants. One group of control mice was immunized with rRa12-WT1 without adjuvant and one group was immunized with saline alone. Three intramuscular (IM) immunizations were given, three weeks apart. Spleens and sera were harvested 2 weeks post-final immunization. Sera were analyzed for antibody responses by ELISA on plates coated with Ra12-WT1 fusion, Ra12 or WT1TRX. Similar levels of IgG2a and IgG1 antibody titers were observed in mice immunized with Ra12-WT1+MPL®-SE and Ra12-WT1+ENHANZYN®. Mice immunized with rRa12-WT1 without adjuvant showed lower levels of IgG2a antibodies.

CD4 responses were assessed by measuring Interferon-γ production following stimulation of splenocytes in vitro with rRa12-WT1, rRa12 or with WT1 peptides p6, p117 and p287. Both adjuvants improved the CD4 responses over mice immunized with rRA12-WT1 alone. Additionally, the results indicate that rRA12-WT1+MPL®-SE induced a stronger CD4 response than did rRA12-WT1+ENHANZYN®. IFN-γ OD readings ranged from 1.4-1.6 in the mice immunized with rRA12-WT1+MPL®-SE as compared to 1-1.2 in the mice immunized with rRA12-WT1+ENHANZYN®. Peptide responses were only observed against p117, and then only in mice immunized with rRa12-WT1+MPL®-SE. Strong IFN-γ responses to the positive control, ConA, were observed in all mice. Only responses to ConA were observed in the negative control mice immunized with saline indicating that the responses were specific to rRA12-WT1.

Example 17

Construction of a Randomly Mutated WT1 Library

The nucleic acid sequence of human WT1 was randomly mutated using a polymerase chain reaction method in the presence of 8-oxo dGTP and dPTP (journal of Molecular Biology 1996; 255:589-603). The complete unspliced human WT1 gene is disclosed in SEQ ID NO:380 and the corresponding protein sequence is set forth in SEQ ID NO:404. A splice variant of WT1 was used as a template for the PCR reactions and is disclosed in SEQ ID NOs:381 (DNA) and 408 (protein). Conditions were selected so that the frequency of nucleic acid alterations led to a targeted change in the amino acid sequence, usually 5-30% of the PCR product. The mutated PCR product was then amplified in the absence of the nucleotide analogues using the four normal dNTPs. This PCR product was subcloned into mammalian expression vectors and viral vectors for immunization. This library, therefore, contains a mixed population of randomly mutated WT1 clones. Several clones were selected and sequenced. The mutated WT1 variant DNA sequences are disclosed in SEQ ID NOs: 377-379 and the predicted amino acid sequences of the variants are set forth in SEQ ID NOs:405-407. These altered sequences, and others from the library, can be used as immunogens to induce stronger T cell responses against WT1 protein in cancer cells.

Example 18

Construction of WT1-LAMP Fusions

A tripartite fusion was constructed using the polymerase chain reaction and synthetic oligonucleotides containing the desired junctions of human lysosomal associated membrane protein-1 (LAMP-1) and a splice variant of the human WT1 sequence. The splice variant of WT1 and the LAMP-1 sequence used for these fusions are disclosed in SEQ ID NOs:381 and 383. Specifically, the signal peptide of LAMP-1

(base pairs 1-87 of LAMP) was fused to the 5-prime end of the human WT1 open reading frame (1,290 base pairs in length), then the transmembrane and cytoplasmic domain of LAMP-1 (base pairs 1161 to 1281 of LAMP) was fused to the 3-prime end of the WT1 sequence. The sequence of the resulting WT1-LAMP construct is set forth in SEQ ID NO:382 (DNA) and SEQ ID NO:409 (protein). The construct was designed so that when it is expressed in eukaryotic cells, the signal peptide directs the protein to the endoplasmic reticulum (ER) where the localization signals in the transmembrane and cytoplasmic domain of LAMP-1 direct transport of the fusion protein to the lysosomal location where peptides are loaded on to Class II MHC molecules.

Example 19

Construction of WT1-Ubiquitin Fusions for Enhanced MHC Class I Presentation

The human ubiquitin open reading frame (SEQ ID NO:384) was mutated such that the nucleotides encoding the last amino acid encode an alanine instead of a glycine. This mutated open reading frame was cloned in frame just upstream of the first codon of a splice variant of human WT1 (SEQ ID NOs:381 and 408, DNA and protein, respectively). The G->A mutation prevents co-translational cleavage of the nacent protein by the proteases that normally process polyubiquitin during translation. The DNA and predicted amino acid sequence for the resulting contruct are set forth in SEQ ID NOs:385 and 410, respectively. The resulting protein demonstrated decreased cellular cytotoxicity when it was expressed in human cells. Whereas it was not possible to generate stable lines expressing native WT1, cell lines expressing the fusion protein were readily obtained. The resulting protein is predicted to be targeted to the proteosome by virtue of the added ubiquitin molecule. This should result in more efficient recognition of the protein by WT1 specific CD8+ T cells.

Example 20

Construction of an Adenovirus Vector Expressing Human WT1

A splice variant of human WT1 (SEQ ID NO:381) was cloned into an E1 and E3 deleted adenovirus serotype 5 vector. The expression of the WT1 gene is controlled by the CMV promoter mediating high levels of WT1 protein expression. Infection of human cells with this reagent leads to a high level of expression of the WT1 protein. The antigenic nature of the adenoviral proteins introduced into the host cell during and produced at low levels subsequent to infection can act to increase immune surveillance and immune recognition of WT1 as an immunological target. This vector can be also used to generate immune responses against the WT1 protein when innoculated into human subjects. If these subjects are positive for WT1 expressing tumor cells the immune response could have a theraputic or curative effect on the course of the disease.

Example 21

Construction of a Vaccinia Virus Vector Expressing Human WT1

A splice variant of the full length human WT1 gene (SEQ ID NO:381) was cloned into the thymidine kinase locus of the Western Reserve strain of the vaccinia virus using the pSC11 shuttle vector. The WT1 gene is under the control of a hybrid vaccinia virus promoter that mediates gene expression throughout the course of vaccinia virus infection. This reagent can be used to express the WT1 protein in human cells in vivo or in vitro. WT1 is a self protein that is overexpressed on some human tumor cells. Thus, immunological responses to WT1 delivered as a protein are unlikely to lead to Major Histocompatibility Class I (MHC class I)-mediated recognition of WT1. However, expression of the protein in the intracellular compartment by the vaccinia virus vector will allow high level MHC class I presentation and recognition of the WT1 protein by CD8+ T cells. Expression of the WT1 protein by the vaccinia virus vector will also lead to presentation of WT1 peptides in the context of MHC class II and thus to recognition by CD4+ T cells.

The uses of this invention include its use as a cancer vaccine. Immunization of human subjects bearing WT1 positive tumors could lead to a theraputic or curative response. The expression of WT1 within the cell will lead to recognition of the protein by both CD4 and CD8 positive T cells.

Example 22

Generation of WT1-specific CD8+ T-cell Clones using Whole Gene Priming

Dendritic cells (DC) were differentiated from monocyte cultures derived from PBMC of normal donors by growth for 4-6 days in RPMI medium containing 10% human serum, 50 ng/ml GM-CSF and 30 ng/ml IL-4. Following culture, DC were infected 16 hours with recombinant WT1-expressing vaccinia virus (described in Example 21) at a multiplicity of infection (MOI) of 5 or for 3 days with recombinat WT1-expressing adenovirus at an MOI of 10. Vaccinia virus was inactivated by U.V. irradiation. CD8+ T-cells were isolated by negative depletion using magnetic beads, and priming cultures were initiated in 96-well plates. Cultures were restimulated every 7-10 days using autologous dendritic cells infected with adeno or vaccinia virus engineered to express WT1. Following 4-5 stimulation cycles, CD8+ T-cell lines could be identified that specifically produced interferon-gamma when stimulated with autologous-WT1 expressing dendritic cells or fibroblasts. These lines were cloned and demonstrated to specifically recognize WT1 transduced autologous fibroblasts but not EGFP transduced fibroblasts by Elispot assays.

The Wilms' tumor (WT1) gene participates in leukemogenesis and is overexpressed in most human leukemias as well as in several solid tumors. Previous studies in humans have demonstrated the presence of WT1 specific antibody (Ab) responses in 16/63 (25%) of AML and in 15/81 (19%) of CML patients studied. Previous studies in mice have shown that WT1 peptide based vaccines elicit WT1 specific Ab, Th and CTL responses. The use of peptides as vaccines in humans is limited by their HLA restriction and the tendency to elicit peptide specific responses and only in a minority of patients tumor specific CTL. The advantages of whole gene immunization are that several helper and CTL epitopes can be included in a single vaccine, thus not restricting the vaccine to specific HLA types. The data disclosed herein demonstrate the induction of WT1 specific immune responses using whole gene in vitro priming. and that WT1 specific CD8+ T-cell clones can be generated. Given that existent immunity to WT1 is present in some patients with leukemia and that murine and human WT1 are 96% identical at the amino acid level and vaccination to WT1 protein, DNA or peptides can elicit WT1 specific Ab, and cellular T-cell responses in mice without toxicity to normal tissues in mice, these human in vitro priming experiments provide further validation of WT1 as a tumor/leukemia vaccine. Furthermore, the ability to generate WT1 specific CD8+ T-cell clones may lead to the treatment of malignancies associated with WT1 overexpression using genetically engineered T-cells.

Example 23

Recombinant Constructs for Clinical Manufacturing of WT1

Five constructs were made as described in detail below, for the production of clinical grade WT1.

Design of Ra12/WT-E (SEQ ID NOs:388 (cDNA) and 391 (protein)) and WT-1 E (SEQ ID NOs:386 (cDNA) and 395 (protein)) with No His tag:

The WT-1 E reading frame was PCR amplified with the following primers for the non-His non fusion construct:

PDM-780 (SEQ ID NO:396) 5' gacgaaagcatatgcactccttcatcaaac 3' Tm 60° C.

PDM-779 (SEQ ID NO:397) 5' cgcgtgaattcatcactgaatgcctctgaag 3' Tm 63° C.

The following PCR cycling conditions were used: 10 μl 10× Pfu buffer, 1 μl 10 mM dNTPs, 2 μl 10 μM each oligo, 83 μl sterile water 1.5 μl Pfu DNA polymerase (Stratagene, La Jolla, Calif.), 50 ηg DNA (pPDMRa12 WT-1 No His). The reaction was denatured initially at 96° C. for 2 minutes, followed by 40 cylces of 96° C. for 20 seconds, 62° C. for 15 seconds, and 72° C. for 1 minute and 40 seconds. This was followed by a final extension of 72° C. for 4 minutes. The PCR product was digested with NdeI and EcoRI and cloned into pPDM His (a modified pET28 vector) that had been digested with NdeI and EcoRI. The construct was confirmed through sequence analysis and then transformed into BLR (DE3) pLys S and HMS 174 (DE3) pLys S cells. This construct—pPDM WT-1 E was then digested with NcoI and XbaI and used as the vector backbone for the NcoI and XbaI insert from pPDM Ra12 WT-1 F (see below). The construct was confirmed through sequence analysis and then transformed into BLR (DE3) pLys S and HMS 174 (DE3) pLys S cells. Protein expression was confirmed by Coomassie stained SDS-PAGE and N-terminal protein sequence analysis.

Design of Ra12-WT-1-F (a.a. 1-281) with No His tag (SEQ ID NOs:389 (cDNA) and 393 (protein)):

The Ra12 WT-1 reading frame was PCR amplified with the following primers:

PDM-777 (SEQ ID NO:398) 5' cgataagcatatgacggccgcgtccgataac 3' Tm 66° C.

PDM-779 (SEQ ID NO:399) 5' cgcgtgaattcatcactgaatgcctctgaag 3' Tm 63° C.

The following PCR cycling conditions were used: 10 μl 10× Pfu buffer, 1 μl 10 mM dNTPs, 2 μl 10 μM each oligo, 83 μl sterile water 1.5 μl Pfu DNA polymerase (Stratagene, La Jolla, Calif.), 50 θg DNA (pPDMRa12 WT-1 No His). The reaction was denatured initially at 96° C. for 2 minutes, followed by 40 cylces of 96° C. for 20 seconds, 58° C. for 15 seconds, and 72° C. for 3 minutes. This was followed by a final extension of 72° C. for 4 minutes. The PCR product was digested with NdeI and cloned into pPDM His that had been digested with NdeI and Eco72I. The sequence was confirmed through sequence analysis and then transformed into BLR (DE3) pLys S and HMS 174 (DE3) pLysS cells. Protein expression was confirmed by Coomassie stained SDS-PAGE and N-terminal protein sequence analysis.

Design of Ra12-WT-1 with No His tag (SEQ ID NOs:390 (cDNA) and 392 (protein)):

The Ra12 WT-1 reading frame was PCR amplified with the following primers:

PDM-777 (SEQ ID NO:400) 5' cgataagcatatgacggccgcgtccgataac 3' Tm 66° C.

PDM-778 (SEQ ID NO:401) 5' gtctgcagcggccgctcaaagcgccagc 3' Tm 70° C.

The following PCR cycling conditions were used: 10 μl 10× Pfu buffer, 1 μl 10 mM dNTPs, 2 μl 10 μM each oligo, 83 μl sterile water 1.5 μl Pfu DNA polymerase (Stratagene, La Jolla, Calif.), 50 ηg DNA (pPDMRa12 WT-1 No His). The reaction was denatured initially at 96° C. for 2 minutes, followed by 40 cylces of 96° C. for 20 seconds, 68° C. for 15 seconds, and 72° C. for 2 minutes and 30 seconds. This was followed by a final extension of 72° C. for 4 minutes. The PCR product was digested with NotI and NdeI and cloned into pPDM His that had been digested with NdeI and NotI. The sequence was confirmed through sequence analysis and then transformed into BLR (DE3) pLys S and HMS 174 (DE3) pLysS cells. Protein expression was confirmed by Coomassie stained SDS-PAGE and N-terminal protein sequence analysis.

Design of WT-1 C (a.a. 69-430) in *E. coli* without His tag (SEQ ID NOs:387 (cDNA) and 394 (protein)):

The WT-1 C reading frame was PCR amplified with the following primers:

PDM-780 (SEQ ID NO:402) 5' gacgaaagcatatgcactccttcatcaaac 3' Tm 60° C.

PDM-778 (SEQ ID NO:403) 5' gtctgcagcggccgctcaaagcgccagc 3' Tm 70° C.

The following PCR cycling conditions were used: 10 μl 10× Pfu buffer, 1 μl 10 mM dNTPs, 2 μl 10 μM each oligo, 83 μl sterile water 1.5 μl Pfu DNA polymerase (Stratagene, La Jolla, Calif.), 50 ηg DNA (pPDMRa12 WT-1 No His). The reaction was denatured initially at 96° C. for 2 minutes, followed by 40 cylces of 96° C. for 20 seconds, 62° C. for 15 seconds, and 72° C. for 2 minutes. This was followed by a final extension of 72° C. for 4 minutes. The PCR product was digested with NdeI and cloned into pPDM His that had been digested with NdeI and Eco72I. The sequence was confirmed through sequence analysis and then transformed into BLR (DE3) pLys S and HMS 174 (DE3) pLys S cells. Protein expression was confirmed by Coomassie stained SDS-PAGE and N-terminal protein sequence analysis.

Example 24

Generation of WT1-specific CD8$^+$ T Cell Clones using Whole Gene Priming and Identification of an HLA-A2-restricted WT1 Epitope In this example, Adeno and Vaccinia virus delivery vehicles were used to generate WT1-specific T cell lines. A T cell clone from the line was shown to be specific for WT1 and further, the epitope recognized by this clone was identified.

Dendritic cells (DC) were differentiated from monocyte cultures derived from PBMC of normal donors by growth for 4-6 days in RPMI medium containing 10% human serum, 50 ng/ml GM-CSF and 30 ng/ml IL-4. Following culture, DC were infected 16 hours with recombinant WT1-expressing vaccinia virus at a multiplicity of infection (MOI) of 5 or for 2-3 days with recombinant WT1-expressing adeno virus at an MOI of 3-10. Vaccinia virus was inactivated by U.V. irradiation. CD8+ T-cells were isolated by negative depletion using antibodies to CD4, CD14, CD16, CD19 and CD56+ cells, followed by magnetic beads specific for the Fc portion of these Abs.

Priming cultures were initiated in 96-well plates. Cultures were restimulated every 7-14 days using autologous dendritic cells infected with adeno or vaccinia virus engineered to express WT1. Following 4-5 stimulation cycles, CD8+ T cell lines could be identified that specifically produced interferon-γ(IFN-γ) when stimulated with autologous-WT1 expressing dendritic cells or fibroblasts. These lines were cloned and demonstrated to specifically recognize WT1 transduced autologous fibroblasts but not control transduced fibroblasts by Elispot assays.

To further analyze HLA restriction of these WT1 specific CD8+ T-cell clones, fibroblasts derived from an additional donor (D475), sharing only the HLA-A2 allele with the donor (D349) from which the T-cell clone was established, were transduced with WT1. ELISPOT analysis demonstrated recognition of these D475 target cells by the T-cell clone. To farther demonstrate HLA A2 restriction and demonstrate that this epitope is expressed by tumor cells "naturally" overxpressing WT1 (as part of their malignant transformation), the leukemia cell line K562 was tested. K562 was transduced with the HLA A2 molecule, and HLA-A2 negative K562 cells were used as controls for nonspecific IFN-γ release. ELISPOT analysis demonstrated that the T cells recognized the A2 positive K562 cell line, but not the A2 negative K562 cells. Further proof of specificity and HLA-A2 restriction of the recognition was documented by HLA-A2 antibody blocking experiments.

To further define the WT1 epitope, 4 truncated WT1 retroviral constructs were generated. Donor 475 fibroblasts were then transduced with these constructs. ELISPOT assays demonstrated recognition of D475 fibroblasts transduced with the WT1 Tr1 construct (aa2-aa92), thus demonstrating that the WT1 epitope is localized within the first 91 N-terminal amino acids of the WT1 protein. To fine map the epitope, 15 mer peptides of the WT1 protein, overlapping by 11 amino acids, were synthesized. The WT1 specific T-cell clone recognized two overlapping 15 mer peptides, peptide 9 (QWAPVLDFAPPGASA) (SEQ ID NO: 412) and peptide 10 (VLDFAPPGASAYGSL) (SEQ ID NO: 413). To further characterize the minimal epitope recognized, shared 9 mer and 10 mer peptides of the 15 mers (5 total) were used to analyse the specificity of the clone. The clone specifically recognized the 9 mer, VLDFAPPGA (SEQ ID NO:241), and the 10 mer, VLDFAPPGAS (SEQ ID NO:411).

Example 25

Cloning and Sequence of TCR Alpha and Beta Chains Derived from a CD8 T Cell Specific for WT1

T cell receptor (TCR) alpha and beta chains from CD8+ T cell clones specific for WT1 are cloned. Sequence analysis is carried to demonstrate the family origin of the alpha and beta chains of the TCR. Additionally, unique diversity and joining segments (contributing to the specificity of the response) are identified.

Total mRNA from $2\times10^6$ cells from a WT1 specific CD8+ T cell clone is isolated using TRIZOL® reagent and cDNA is synthesized using READY-TO-GO® kits (Pharmacia). To determine Vα and Vβ sequences in a clone, a panel of Vα and Vβ subtype specific primers are synthesized (based on primer sequences generated by Clontech, Palo Alto, Calif.) and used in RT-PCR reactions with cDNA generated from each clone. The RT-PCR reactions demonstrate which Vβ and Vα sequence is expressed by each clone.

To clone the full-length TCR alpha and beta chains from a clone, primers are designed that span the initiator and terminator-coding TCR nucleotides. Standard 35 cycle RT-PCR reactions are established using cDNA synthesized from the CTL clone and the above primers using the proofreading thermostable polymerase PWO (Roche, Basel, Switzerland). The resultant specific bands (~850 bp for alpha and ~950 for beta) are ligated into the PCR blunt vector (Invitrogen, Carlsbad, Calif.) and transformed into *E. coli*. *E. coli* transformed with plasmids containing full-length alpha and beta chains are identified, and large scale preparations of the corresponding plasmids are generated. Plasmids containing full-length TCR alpha and beta chains are then sequenced using standard methods. The diversity-joining (DJ) region that contributes to the specificity of the TCR is thus determined.

Example 26

WT1 Specific CD8+ T-cell Clone Lyses WT1-expressing Leukemic Blasts

The CD8+ T cell clone intially disclosed in Example 24 that recognizes peptide sequence VLDFAPPGA (human WT1 residues 37-45; SEQ ID NO:241) was further tested for the ability to kill (lyse) WT1 expressing leukemia target cells in an HLA A2 restricted fashion. K562 target cells transduced with the HLA A2 molecule, GFP, A2Kb, or untransduced, were used in a standard 4.5 hour $^{51}$Chromium release assay with effector to target cell (E:T) ratios of 25:1 and 5:1. At an E:T ratio of 25:1, the CD8+ T-cell clone lysed the K562/A2 and K562/A2Kb cells (40% and 49% specific lysis, respectively) while the control GFP transduced and the K562 cells were not lysed. At an E:T of 5:1, specific lysis of the K562/A2 and K562/A2 Kb cells was 21% and 24%, respectively. Thus, this CD8+ T cell clone recognizes and lyses leukemic cells expressing WT1 in an HLA-A2-restricted fashion. The ability to generate WT1 specific CD8+ T-cell clones has utility in the treatment of malignancies associated with WT1 overexpression using genetically engineered T-cells.

Example 27

Construction of HLA-A2-peptide-MHC Tetrameric Complexes

This example describes the cloning and expression of soluble HLA-A2 in insect cells, and the purification and assembly of HLA-A2 into fluorescent, multivalent peptide-MHC tetramer complexes for the detection and isolation of antigen-specific CD8 T cells.

This system is similar to that developed and described by Altman, et al. (Altman, J., et al., Science, 1996 274(5284): 94-6) in that soluble HLA-A2 was singly biotinylated at a birA recognition sequence and was subsequently assembled into multimers on a phycoerythrin-conjugated streptavidin scaffolding. The materials described herein differ in that the HLA-A2 was expressed in a glycosylated, soluble form from insect cells and the heterodimer was purified using an anti-human class I MHC antibody affinity column.

The HLA-A2 heavy chain gene, appended with the birA biotinylation sequence, and the human beta-2-microglobulin gene were cloned into the baculovirus expression vector pFASTBAC-dual. Upon infection of insect cells the genes were concomitantly transcribed from divergent promoters and fully assembled, glycosylated soluble HLA-A2 heterodimer was secreted into the growth medium. The infected insect cells were cultured in cell factories for 4 days at 21° C. before the supernatants were harvested. HLA-A2 production was monitored by a capture ELISA employing the W6/32 and biotinylated B9.12.1 antibodies. HLA-A2 was purified from the culture supernatant to >90% purity in one step by affinity chromatography using 2 anti-human class I MHC monoclonal antibodies linked to Sepharose beads. The antibodies used were PA2.1 and W6/32. Purified HLA-A2 was singly biotinylated on the birA recognition sequence on the C-terminus of the heavy chain using the commercially available birA enzyme. The efficiency of biotinylation was evaluated essentially as described (Crawford et al (1998) Immunity June;8(6):675-82), and the material was further purified by size exclusion chromatography (SEC). Phycoerythrin-conjugated streptavidin was saturated with bio-HLA-A2 and the mulivalent staining reagent was purified from free HLA-A2 by SEC. HLA-A2 tetramer was incubated for 48 hours at room temperature with a 10-fold molar excess of Her-2/neu E75 peptide or Influenza matrix MI peptide before the specific T cell clones were stained at 4° C. for 30 minutes in the presence of peptide loaded tetramer and anti-CD8 antibody. Results indicated that the tetramers incubated in the presence of molar excess of the M1 58-66 M1 influenza peptide specifically stained an influenza-specific T cell clone and the tetramers incubated with an excess of the Her-2/neu E75 peptide specifically stained the Her-2/new specific T cell clone.

Example 28

Detection of WT1 Specific T-cells using WT1 MHC-Peptide Tetramers

HLA-A2 tetramers described in Example 27 were incubated with a molar excess of the WT1 p37-45 peptide (VLDFAPPGA) (human WT1 residues 37-45; SEQ ID NO:241) previously shown in Example 24 to be restricted by HLA-A2. This tetramer was used to stain the WT1-specific CD8+ T cell clone described in Example 24. This clone was shown to specifically recognize the p37-45 epitope. When the tetramers were incubated with an excess of p37-45 peptide, they specifically stained the CD8+ T cell clone while those tetramers incubated with an excess of irrelevant HLA-A2 peptides (Her2/neu, WT1p38-46, WT1 p39-47), the tetramers did not stain the CD8+ T cell clone. Thus, the WT1p37-45-specific CD8+ T cell clone is specifically recognized by the HLA-A2-p37-45 peptide MHC tetramer.

A WT1-specific T cell line generated as described in Example 24 was then stained with the HLA-A2-p37-45, irrelevant Her2/neu or WT1p37-46 tetramers. The HLA-A2-p37-45 tetramers stained 1% of the total population of this WT1-specific T cell line and 7% of the gated CD8+ population while the control HLA-A2-p37-46 tetramer stained at the same background levels as the control HLA-A2-Her2/neu tetramers.

These results indicate that MHC-peptide tetramers are a highly sensitive and specific tool for detecting WT1 specific immune responses. The peptide-MHC tetramers can be used for early detection of WT1 associated malignancies, monitoring WT1-specific responses, and for monitoring minimal residual disease. Detection of WT1 specific T-cells by tetramer staining is also a useful tool to identify groups within a patient population suffering from a WT1 asssociated disease at a higher risk for relapse or disease progression.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed:

1. An isolated polypeptide consisting of the amino acid sequence of SEQ ID NO:333.

2. A composition comprising the polypeptide of claim 1 in combination with a pharmaceutically acceptable carrier or excipient.

3. A composition comprising the polypeptide according to claim 1 and monophosphoryl lipid A.

4. A composition comprising the polypeptide of claim 1 in combination with a non-specific immune response enhancer.

5. The composition according to claim 4 wherein the non-specific immune response enhancer preferentially enhances a T cell response in a patient.

6. The composition according to claim 3, further comprising an aluminum salt.

7. A composition comprising the polypeptide according to claim 1 and 3-de-O-acylated monophosphoryl lipid A.

8. The composition according to claim 7, further comprising an aluminum salt.

9. A composition comprising the polypeptide according to claim 1 and an adjuvant containing monophosphoryl lipid A.

* * * * *

```
                             SEQUENCE LISTING


<160> NUMBER OF SEQ ID NOS: 413

<210> SEQ ID NO 1
<211> LENGTH: 17
<212> TYPE: PRT
<213> ORGANISM: Homo sapien

<400> SEQUENCE: 1

Arg Asp Leu Asn Ala Leu Leu Pro Ala Val Pro Ser Leu Gly Gly Gly
 1               5                  10                  15

Gly


<210> SEQ ID NO 2
<211> LENGTH: 23
<212> TYPE: PRT
<213> ORGANISM: Homo sapien

<400> SEQUENCE: 2

Pro Ser Gln Ala Ser Ser Gly Gln Ala Arg Met Phe Pro Asn Ala Pro
 1               5                  10                  15

Tyr Leu Pro Ser Cys Leu Glu
            20


<210> SEQ ID NO 3
<211> LENGTH: 23
<212> TYPE: PRT
```

<213> ORGANISM: Mus musculus

<400> SEQUENCE: 3

Pro Ser Gln Ala Ser Ser Gly Gln Ala Arg Met Phe Pro Asn Ala Pro
 1               5                  10                  15

Tyr Leu Pro Ser Cys Leu Glu
            20

<210> SEQ ID NO 4
<211> LENGTH: 19
<212> TYPE: PRT
<213> ORGANISM: Homo sapien

<400> SEQUENCE: 4

Gly Ala Thr Leu Lys Gly Val Ala Ala Gly Ser Ser Ser Ser Val Lys
 1               5                  10                  15

Trp Thr Glu

<210> SEQ ID NO 5
<211> LENGTH: 22
<212> TYPE: DNA
<213> ORGANISM: Artificial Sequence
<220> FEATURE:
<223> OTHER INFORMATION: Primer for use in amplifying human WT1

<400> SEQUENCE: 5
gagagtcaga cttgaaagca gt 22

<210> SEQ ID NO 6
<211> LENGTH: 20
<212> TYPE: DNA
<213> ORGANISM: Artificial Sequence
<220> FEATURE:
<223> OTHER INFORMATION: Primer for use in amplifying human WT1

<400> SEQUENCE: 6
ctgagcctca gcaaatgggc 20

<210> SEQ ID NO 7
<211> LENGTH: 27
<212> TYPE: DNA
<213> ORGANISM: Artificial Sequence
<220> FEATURE:
<223> OTHER INFORMATION: Primer for use in amplifying human WT1

<400> SEQUENCE: 7
gagcatgcat gggctccgac gtgcggg 27

<210> SEQ ID NO 8
<211> LENGTH: 25
<212> TYPE: DNA
<213> ORGANISM: Artificial Sequence
<220> FEATURE:
<223> OTHER INFORMATION: Primer for use in amplifying human WT1

<400> SEQUENCE: 8
ggggtaccca ctgaacggtc cccga 25

<210> SEQ ID NO 9
<211> LENGTH: 18
<212> TYPE: DNA
<213> ORGANISM: Artificial Sequence
<220> FEATURE:
<223> OTHER INFORMATION: Primer for use in amplifying mouse WT1

<400> SEQUENCE: 9
tccgagccgc acctcatg 18

<210> SEQ ID NO 10
<211> LENGTH: 18
<212> TYPE: DNA
<213> ORGANISM: Artificial Sequence
<220> FEATURE:
<223> OTHER INFORMATION: Primer for use in amplifying mouse WT1

<400> SEQUENCE: 10
gcctgggatg ctggactg 18

<210> SEQ ID NO 11
<211> LENGTH: 27
<212> TYPE: DNA
<213> ORGANISM: Artificial Sequence
<220> FEATURE:
<223> OTHER INFORMATION: Primer for use in amplifying mouse WT1

<400> SEQUENCE: 11
gagcatgcga tgggttccga cgtgcgg 27

<210> SEQ ID NO 12
<211> LENGTH: 29
<212> TYPE: DNA
<213> ORGANISM: Artificial Sequence
<220> FEATURE:
<223> OTHER INFORMATION: Primer for use in amplifying mouse WT1

<400> SEQUENCE: 12
ggggtacctc aaagcgccac gtggagttt 29

<210> SEQ ID NO 13
<211> LENGTH: 17
<212> TYPE: PRT
<213> ORGANISM: Mus musculus

<400> SEQUENCE: 13

Arg Asp Leu Asn Ala Leu Leu Pro Ala Val Ser Ser Leu Gly Gly Gly
1 5 10 15

Gly

<210> SEQ ID NO 14
<211> LENGTH: 19
<212> TYPE: PRT
<213> ORGANISM: Mus musculus

<400> SEQUENCE: 14

Gly Ala Thr Leu Lys Gly Met Ala Ala Gly Ser Ser Ser Ser Val Lys
1 5 10 15

Trp Thr Glu

<210> SEQ ID NO 15
<211> LENGTH: 15
<212> TYPE: PRT
<213> ORGANISM: Homo sapien

<400> SEQUENCE: 15

Arg Ile His Thr His Gly Val Phe Arg Gly Ile Gln Asp Val Arg
1 5 10 15

<210> SEQ ID NO 16
<211> LENGTH: 15
<212> TYPE: PRT

<213> ORGANISM: Mus musculus

<400> SEQUENCE: 16

Arg Ile His Thr His Gly Val Phe Arg Gly Ile Gln Asp Val Arg
1 5 10 15

<210> SEQ ID NO 17
<211> LENGTH: 14
<212> TYPE: PRT
<213> ORGANISM: Mus musculus

<400> SEQUENCE: 17

Val Arg Arg Val Ser Gly Val Ala Pro Thr Leu Val Arg Ser
1 5 10

<210> SEQ ID NO 18
<211> LENGTH: 14
<212> TYPE: PRT
<213> ORGANISM: Homo sapien

<400> SEQUENCE: 18

Val Arg Arg Val Pro Gly Val Ala Pro Thr Leu Val Arg Ser
1 5 10

<210> SEQ ID NO 19
<211> LENGTH: 15
<212> TYPE: PRT
<213> ORGANISM: Homo sapien

<400> SEQUENCE: 19

Cys Gln Lys Lys Phe Ala Arg Ser Asp Glu Leu Val Arg His His
1 5 10 15

<210> SEQ ID NO 20
<211> LENGTH: 15
<212> TYPE: PRT
<213> ORGANISM: Mus musculus

<400> SEQUENCE: 20

Cys Gln Lys Lys Phe Ala Arg Ser Asp Glu Leu Val Arg His His
1 5 10 15

<210> SEQ ID NO 21
<211> LENGTH: 21
<212> TYPE: DNA
<213> ORGANISM: Artificial Sequence
<220> FEATURE:
<223> OTHER INFORMATION: sense primer for amplification of WT1 in mouse cell lines

<400> SEQUENCE: 21
cccaggctgc aataagagat a 21

<210> SEQ ID NO 22
<211> LENGTH: 21
<212> TYPE: DNA
<213> ORGANISM: Artificial Sequence
<220> FEATURE:
<223> OTHER INFORMATION: antisense primer for amplification of WT1 in mouse cell lines

<400> SEQUENCE: 22
atgttgtgat ggcggaccaa t 21

<210> SEQ ID NO 23
<211> LENGTH: 20

<212> TYPE: DNA
<213> ORGANISM: Artificial Sequence
<220> FEATURE:
<223> OTHER INFORMATION: sense Beta Actin primer used in the control reactions

<400> SEQUENCE: 23
gtggggcgcc ccaggcacca 20

<210> SEQ ID NO 24
<211> LENGTH: 24
<212> TYPE: DNA
<213> ORGANISM: Artificial Sequence
<220> FEATURE:
<223> OTHER INFORMATION: antisense Beta Actin primer used in the control reactions

<400> SEQUENCE: 24
gtccttaatg ctacgcacga tttc 24

<210> SEQ ID NO 25
<211> LENGTH: 21
<212> TYPE: DNA
<213> ORGANISM: Artificial Sequence
<220> FEATURE:
<223> OTHER INFORMATION: Primer for use in amplifying human WT1

<400> SEQUENCE: 25
ggcatctgag accagtgaga a 21

<210> SEQ ID NO 26
<211> LENGTH: 21
<212> TYPE: DNA
<213> ORGANISM: Artificial Sequence
<220> FEATURE:
<223> OTHER INFORMATION: Primer for use in nested RT-PCR

<400> SEQUENCE: 26
gctgtcccac ttacagatgc a 21

<210> SEQ ID NO 27
<211> LENGTH: 21
<212> TYPE: DNA
<213> ORGANISM: Artificial Sequence
<220> FEATURE:
<223> OTHER INFORMATION: Primer for use in nested RT-PCR

<400> SEQUENCE: 27
tcaaagcgcc agctggagtt t 21

<210> SEQ ID NO 28
<211> LENGTH: 9
<212> TYPE: PRT
<213> ORGANISM: Homo sapien

<400> SEQUENCE: 28

Ala Ala Gly Ser Ser Ser Ser Val Lys
1 5

<210> SEQ ID NO 29
<211> LENGTH: 9
<212> TYPE: PRT
<213> ORGANISM: Homo sapien

<400> SEQUENCE: 29

Ala Ala Gln Phe Pro Asn His Ser Phe
1 5

<210> SEQ ID NO 30
<211> LENGTH: 9
<212> TYPE: PRT
<213> ORGANISM: Homo sapien

<400> SEQUENCE: 30

Ala Glu Pro His Glu Glu Gln Cys Leu
1 5

<210> SEQ ID NO 31
<211> LENGTH: 9
<212> TYPE: PRT
<213> ORGANISM: Homo sapien

<400> SEQUENCE: 31

Ala Gly Ala Cys Arg Tyr Gly Pro Phe
1 5

<210> SEQ ID NO 32
<211> LENGTH: 9
<212> TYPE: PRT
<213> ORGANISM: Homo sapien

<400> SEQUENCE: 32

Ala Gly Ser Ser Ser Ser Val Lys Trp
1 5

<210> SEQ ID NO 33
<211> LENGTH: 9
<212> TYPE: PRT
<213> ORGANISM: Homo sapien

<400> SEQUENCE: 33

Ala Ile Arg Asn Gln Gly Tyr Ser Thr
1 5

<210> SEQ ID NO 34
<211> LENGTH: 9
<212> TYPE: PRT
<213> ORGANISM: Homo sapien

<400> SEQUENCE: 34

Ala Leu Leu Pro Ala Val Pro Ser Leu
1 5

<210> SEQ ID NO 35
<211> LENGTH: 9
<212> TYPE: PRT
<213> ORGANISM: Homo sapien

<400> SEQUENCE: 35

Ala Leu Leu Pro Ala Val Ser Ser Leu
1 5

<210> SEQ ID NO 36
<211> LENGTH: 9
<212> TYPE: PRT
<213> ORGANISM: Homo sapien

<400> SEQUENCE: 36

Ala Gln Phe Pro Asn His Ser Phe Lys
1 5

<210> SEQ ID NO 37

<211> LENGTH: 9
<212> TYPE: PRT
<213> ORGANISM: Homo sapien

<400> SEQUENCE: 37

Ala Gln Trp Ala Pro Val Leu Asp Phe
1 5

<210> SEQ ID NO 38
<211> LENGTH: 9
<212> TYPE: PRT
<213> ORGANISM: Homo sapien

<400> SEQUENCE: 38

Ala Arg Met Phe Pro Asn Ala Pro Tyr
1 5

<210> SEQ ID NO 39
<211> LENGTH: 9
<212> TYPE: PRT
<213> ORGANISM: Homo sapien

<400> SEQUENCE: 39

Ala Arg Ser Asp Glu Leu Val Arg His
1 5

<210> SEQ ID NO 40
<211> LENGTH: 9
<212> TYPE: PRT
<213> ORGANISM: Homo sapien

<400> SEQUENCE: 40

Ala Ser Ser Gly Gln Ala Arg Met Phe
1 5

<210> SEQ ID NO 41
<211> LENGTH: 9
<212> TYPE: PRT
<213> ORGANISM: Homo sapien

<400> SEQUENCE: 41

Ala Tyr Gly Ser Leu Gly Gly Pro Ala
1 5

<210> SEQ ID NO 42
<211> LENGTH: 9
<212> TYPE: PRT
<213> ORGANISM: Homo sapien

<400> SEQUENCE: 42

Ala Tyr Pro Gly Cys Asn Lys Arg Tyr
1 5

<210> SEQ ID NO 43
<211> LENGTH: 9
<212> TYPE: PRT
<213> ORGANISM: Homo sapien

<400> SEQUENCE: 43

Cys Ala Leu Pro Val Ser Gly Ala Ala
1 5

<210> SEQ ID NO 44
<211> LENGTH: 9
<212> TYPE: PRT
<213> ORGANISM: Homo sapien

<400> SEQUENCE: 44

Cys Ala Tyr Pro Gly Cys Asn Lys Arg
1 5

<210> SEQ ID NO 45
<211> LENGTH: 9
<212> TYPE: PRT
<213> ORGANISM: Homo sapien

<400> SEQUENCE: 45

Cys His Thr Pro Thr Asp Ser Cys Thr
1 5

<210> SEQ ID NO 46
<211> LENGTH: 9
<212> TYPE: PRT
<213> ORGANISM: Homo sapien

<400> SEQUENCE: 46

Cys Lys Thr Cys Gln Arg Lys Phe Ser
1 5

<210> SEQ ID NO 47
<211> LENGTH: 9
<212> TYPE: PRT
<213> ORGANISM: Homo sapien

<400> SEQUENCE: 47

Cys Leu Glu Ser Gln Pro Ala Ile Arg
1 5

<210> SEQ ID NO 48
<211> LENGTH: 9
<212> TYPE: PRT
<213> ORGANISM: Homo sapien

<400> SEQUENCE: 48

Cys Leu Ser Ala Phe Thr Val His Phe
1 5

<210> SEQ ID NO 49
<211> LENGTH: 9
<212> TYPE: PRT
<213> ORGANISM: Homo sapien

<400> SEQUENCE: 49

Cys Met Thr Trp Asn Gln Met Asn Leu
1 5

<210> SEQ ID NO 50
<211> LENGTH: 9
<212> TYPE: PRT
<213> ORGANISM: Homo sapien

<400> SEQUENCE: 50

Cys Arg Trp Pro Ser Cys Gln Lys Lys
1 5

<210> SEQ ID NO 51
<211> LENGTH: 9
<212> TYPE: PRT
<213> ORGANISM: Homo sapien

<400> SEQUENCE: 51

```
Cys Arg Tyr Gly Pro Phe Gly Pro Pro
 1               5


<210> SEQ ID NO 52
<211> LENGTH: 9
<212> TYPE: PRT
<213> ORGANISM: Homo sapien

<400> SEQUENCE: 52

Cys Thr Gly Ser Gln Ala Leu Leu Leu
 1               5


<210> SEQ ID NO 53
<211> LENGTH: 9
<212> TYPE: PRT
<213> ORGANISM: Homo sapien

<400> SEQUENCE: 53

Asp Glu Leu Val Arg His His Asn Met
 1               5


<210> SEQ ID NO 54
<211> LENGTH: 9
<212> TYPE: PRT
<213> ORGANISM: Homo sapien

<400> SEQUENCE: 54

Asp Phe Ala Pro Pro Gly Ala Ser Ala
 1               5


<210> SEQ ID NO 55
<211> LENGTH: 9
<212> TYPE: PRT
<213> ORGANISM: Homo sapien

<400> SEQUENCE: 55

Asp Phe Lys Asp Cys Glu Arg Arg Phe
 1               5


<210> SEQ ID NO 56
<211> LENGTH: 9
<212> TYPE: PRT
<213> ORGANISM: Homo sapien

<400> SEQUENCE: 56

Asp Gly Thr Pro Ser Tyr Gly His Thr
 1               5


<210> SEQ ID NO 57
<211> LENGTH: 9
<212> TYPE: PRT
<213> ORGANISM: Homo sapien

<400> SEQUENCE: 57

Asp His Leu Lys Thr His Thr Arg Thr
 1               5


<210> SEQ ID NO 58
<211> LENGTH: 9
<212> TYPE: PRT
<213> ORGANISM: Homo sapien

<400> SEQUENCE: 58

Asp Leu Asn Ala Leu Leu Pro Ala Val
 1               5
```

<210> SEQ ID NO 59
<211> LENGTH: 9
<212> TYPE: PRT
<213> ORGANISM: Homo sapien

<400> SEQUENCE: 59

Asp Pro Met Gly Gln Gln Gly Ser Leu
1 5

<210> SEQ ID NO 60
<211> LENGTH: 9
<212> TYPE: PRT
<213> ORGANISM: Homo sapien

<400> SEQUENCE: 60

Asp Gln Leu Lys Arg His Gln Arg Arg
1 5

<210> SEQ ID NO 61
<211> LENGTH: 9
<212> TYPE: PRT
<213> ORGANISM: Homo sapien

<400> SEQUENCE: 61

Asp Ser Cys Thr Gly Ser Gln Ala Leu
1 5

<210> SEQ ID NO 62
<211> LENGTH: 9
<212> TYPE: PRT
<213> ORGANISM: Homo sapien

<400> SEQUENCE: 62

Asp Val Arg Asp Leu Asn Ala Leu Leu
1 5

<210> SEQ ID NO 63
<211> LENGTH: 9
<212> TYPE: PRT
<213> ORGANISM: Homo sapien

<400> SEQUENCE: 63

Asp Val Arg Arg Val Pro Gly Val Ala
1 5

<210> SEQ ID NO 64
<211> LENGTH: 9
<212> TYPE: PRT
<213> ORGANISM: Homo sapien

<400> SEQUENCE: 64

Glu Asp Pro Met Gly Gln Gln Gly Ser
1 5

<210> SEQ ID NO 65
<211> LENGTH: 9
<212> TYPE: PRT
<213> ORGANISM: Homo sapien

<400> SEQUENCE: 65

Glu Glu Gln Cys Leu Ser Ala Phe Thr
1 5

<210> SEQ ID NO 66
<211> LENGTH: 9

<212> TYPE: PRT
<213> ORGANISM: Homo sapien

<400> SEQUENCE: 66

Glu Lys Pro Tyr Gln Cys Asp Phe Lys
1 5

<210> SEQ ID NO 67
<211> LENGTH: 9
<212> TYPE: PRT
<213> ORGANISM: Homo sapien

<400> SEQUENCE: 67

Glu Lys Arg Pro Phe Met Cys Ala Tyr
1 5

<210> SEQ ID NO 68
<211> LENGTH: 9
<212> TYPE: PRT
<213> ORGANISM: Homo sapien

<400> SEQUENCE: 68

Glu Pro His Glu Glu Gln Cys Leu Ser
1 5

<210> SEQ ID NO 69
<211> LENGTH: 9
<212> TYPE: PRT
<213> ORGANISM: Homo sapien

<400> SEQUENCE: 69

Glu Gln Cys Leu Ser Ala Phe Thr Val
1 5

<210> SEQ ID NO 70
<211> LENGTH: 9
<212> TYPE: PRT
<213> ORGANISM: Homo sapien

<400> SEQUENCE: 70

Glu Ser Asp Asn His Thr Ala Pro Ile
1 5

<210> SEQ ID NO 71
<211> LENGTH: 9
<212> TYPE: PRT
<213> ORGANISM: Homo sapien

<400> SEQUENCE: 71

Glu Ser Asp Asn His Thr Thr Pro Ile
1 5

<210> SEQ ID NO 72
<211> LENGTH: 9
<212> TYPE: PRT
<213> ORGANISM: Homo sapien

<400> SEQUENCE: 72

Glu Ser Gln Pro Ala Ile Arg Asn Gln
1 5

<210> SEQ ID NO 73
<211> LENGTH: 9
<212> TYPE: PRT
<213> ORGANISM: Homo sapien

<400> SEQUENCE: 73

Glu Thr Ser Glu Lys Arg Pro Phe Met
1 5

<210> SEQ ID NO 74
<211> LENGTH: 9
<212> TYPE: PRT
<213> ORGANISM: Homo sapien

<400> SEQUENCE: 74

Phe Ala Pro Pro Gly Ala Ser Ala Tyr
1 5

<210> SEQ ID NO 75
<211> LENGTH: 9
<212> TYPE: PRT
<213> ORGANISM: Homo sapien

<400> SEQUENCE: 75

Phe Ala Arg Ser Asp Glu Leu Val Arg
1 5

<210> SEQ ID NO 76
<211> LENGTH: 9
<212> TYPE: PRT
<213> ORGANISM: Homo sapien

<400> SEQUENCE: 76

Phe Gly Pro Pro Pro Pro Ser Gln Ala
1 5

<210> SEQ ID NO 77
<211> LENGTH: 9
<212> TYPE: PRT
<213> ORGANISM: Homo sapien

<400> SEQUENCE: 77

Phe Lys Asp Cys Glu Arg Arg Phe Ser
1 5

<210> SEQ ID NO 78
<211> LENGTH: 9
<212> TYPE: PRT
<213> ORGANISM: Homo sapien

<400> SEQUENCE: 78

Phe Lys Leu Ser His Leu Gln Met His
1 5

<210> SEQ ID NO 79
<211> LENGTH: 9
<212> TYPE: PRT
<213> ORGANISM: Homo sapien

<400> SEQUENCE: 79

Phe Pro Asn Ala Pro Tyr Leu Pro Ser
1 5

<210> SEQ ID NO 80
<211> LENGTH: 9
<212> TYPE: PRT
<213> ORGANISM: Homo sapien

<400> SEQUENCE: 80

Phe Gln Cys Lys Thr Cys Gln Arg Lys 1 5

<210> SEQ ID NO 81
<211> LENGTH: 9
<212> TYPE: PRT
<213> ORGANISM: Homo sapien

<400> SEQUENCE: 81

Phe Arg Gly Ile Gln Asp Val Arg Arg
1 5

<210> SEQ ID NO 82
<211> LENGTH: 9
<212> TYPE: PRT
<213> ORGANISM: Homo sapien

<400> SEQUENCE: 82

Phe Ser Gly Gln Phe Thr Gly Thr Ala
1 5

<210> SEQ ID NO 83
<211> LENGTH: 9
<212> TYPE: PRT
<213> ORGANISM: Homo sapien

<400> SEQUENCE: 83

Phe Ser Arg Ser Asp Gln Leu Lys Arg
1 5

<210> SEQ ID NO 84
<211> LENGTH: 9
<212> TYPE: PRT
<213> ORGANISM: Homo sapien

<400> SEQUENCE: 84

Phe Thr Gly Thr Ala Gly Ala Cys Arg
1 5

<210> SEQ ID NO 85
<211> LENGTH: 9
<212> TYPE: PRT
<213> ORGANISM: Homo sapien

<400> SEQUENCE: 85

Phe Thr Val His Phe Ser Gly Gln Phe
1 5

<210> SEQ ID NO 86
<211> LENGTH: 9
<212> TYPE: PRT
<213> ORGANISM: Homo sapien

<400> SEQUENCE: 86

Gly Ala Ala Gln Trp Ala Pro Val Leu
1 5

<210> SEQ ID NO 87
<211> LENGTH: 9
<212> TYPE: PRT
<213> ORGANISM: Homo sapien

<400> SEQUENCE: 87

Gly Ala Glu Pro His Glu Glu Gln Cys
1 5

<210> SEQ ID NO 88
<211> LENGTH: 9
<212> TYPE: PRT
<213> ORGANISM: Homo sapien

<400> SEQUENCE: 88

Gly Ala Thr Leu Lys Gly Val Ala Ala
1 5

<210> SEQ ID NO 89
<211> LENGTH: 9
<212> TYPE: PRT
<213> ORGANISM: Homo sapien

<400> SEQUENCE: 89

Gly Cys Ala Leu Pro Val Ser Gly Ala
1 5

<210> SEQ ID NO 90
<211> LENGTH: 9
<212> TYPE: PRT
<213> ORGANISM: Homo sapien

<400> SEQUENCE: 90

Gly Cys Asn Lys Arg Tyr Phe Lys Leu
1 5

<210> SEQ ID NO 91
<211> LENGTH: 9
<212> TYPE: PRT
<213> ORGANISM: Homo sapien

<400> SEQUENCE: 91

Gly Glu Lys Pro Tyr Gln Cys Asp Phe
1 5

<210> SEQ ID NO 92
<211> LENGTH: 9
<212> TYPE: PRT
<213> ORGANISM: Homo sapien

<400> SEQUENCE: 92

Gly Gly Gly Gly Cys Ala Leu Pro Val
1 5

<210> SEQ ID NO 93
<211> LENGTH: 9
<212> TYPE: PRT
<213> ORGANISM: Homo sapien

<400> SEQUENCE: 93

Gly Gly Pro Ala Pro Pro Pro Ala Pro
1 5

<210> SEQ ID NO 94
<211> LENGTH: 9
<212> TYPE: PRT
<213> ORGANISM: Homo sapien

<400> SEQUENCE: 94

Gly His Thr Pro Ser His His Ala Ala
1 5

<210> SEQ ID NO 95
<211> LENGTH: 9
<212> TYPE: PRT

<213> ORGANISM: Homo sapien

<400> SEQUENCE: 95

Gly Lys Thr Ser Glu Lys Pro Phe Ser
1 5

<210> SEQ ID NO 96
<211> LENGTH: 9
<212> TYPE: PRT
<213> ORGANISM: Homo sapien

<400> SEQUENCE: 96

Gly Pro Phe Gly Pro Pro Pro Pro Ser
1 5

<210> SEQ ID NO 97
<211> LENGTH: 9
<212> TYPE: PRT
<213> ORGANISM: Homo sapien

<400> SEQUENCE: 97

Gly Pro Pro Pro Pro Ser Gln Ala Ser
1 5

<210> SEQ ID NO 98
<211> LENGTH: 9
<212> TYPE: PRT
<213> ORGANISM: Homo sapien

<400> SEQUENCE: 98

Gly Gln Ala Arg Met Phe Pro Asn Ala
1 5

<210> SEQ ID NO 99
<211> LENGTH: 9
<212> TYPE: PRT
<213> ORGANISM: Homo sapien

<400> SEQUENCE: 99

Gly Gln Phe Thr Gly Thr Ala Gly Ala
1 5

<210> SEQ ID NO 100
<211> LENGTH: 9
<212> TYPE: PRT
<213> ORGANISM: Homo sapien

<400> SEQUENCE: 100

Gly Gln Ser Asn His Ser Thr Gly Tyr
1 5

<210> SEQ ID NO 101
<211> LENGTH: 9
<212> TYPE: PRT
<213> ORGANISM: Homo sapien

<400> SEQUENCE: 101

Gly Ser Asp Val Arg Asp Leu Asn Ala
1 5

<210> SEQ ID NO 102
<211> LENGTH: 9
<212> TYPE: PRT
<213> ORGANISM: Homo sapien

<400> SEQUENCE: 102

Gly Ser Gln Ala Leu Leu Leu Arg Thr
1 5

<210> SEQ ID NO 103
<211> LENGTH: 9
<212> TYPE: PRT
<213> ORGANISM: Homo sapien

<400> SEQUENCE: 103

Gly Val Phe Arg Gly Ile Gln Asp Val
1 5

<210> SEQ ID NO 104
<211> LENGTH: 9
<212> TYPE: PRT
<213> ORGANISM: Homo sapien

<400> SEQUENCE: 104

Gly Val Lys Pro Phe Gln Cys Lys Thr
1 5

<210> SEQ ID NO 105
<211> LENGTH: 9
<212> TYPE: PRT
<213> ORGANISM: Homo sapien

<400> SEQUENCE: 105

Gly Tyr Glu Ser Asp Asn His Thr Ala
1 5

<210> SEQ ID NO 106
<211> LENGTH: 9
<212> TYPE: PRT
<213> ORGANISM: Homo sapien

<400> SEQUENCE: 106

Gly Tyr Glu Ser Asp Asn His Thr Thr
1 5

<210> SEQ ID NO 107
<211> LENGTH: 9
<212> TYPE: PRT
<213> ORGANISM: Homo sapien

<400> SEQUENCE: 107

His Glu Glu Gln Cys Leu Ser Ala Phe
1 5

<210> SEQ ID NO 108
<211> LENGTH: 9
<212> TYPE: PRT
<213> ORGANISM: Homo sapien

<400> SEQUENCE: 108

His His Asn Met His Gln Arg Asn Met
1 5

<210> SEQ ID NO 109
<211> LENGTH: 9
<212> TYPE: PRT
<213> ORGANISM: Homo sapien

<400> SEQUENCE: 109

His Gln Arg Arg His Thr Gly Val Lys
1 5

<210> SEQ ID NO 110
<211> LENGTH: 9
<212> TYPE: PRT
<213> ORGANISM: Homo sapien

<400> SEQUENCE: 110

His Ser Phe Lys His Glu Asp Pro Met
1 5

<210> SEQ ID NO 111
<211> LENGTH: 9
<212> TYPE: PRT
<213> ORGANISM: Homo sapien

<400> SEQUENCE: 111

His Ser Arg Lys His Thr Gly Glu Lys
1 5

<210> SEQ ID NO 112
<211> LENGTH: 9
<212> TYPE: PRT
<213> ORGANISM: Homo sapien

<400> SEQUENCE: 112

His Thr Gly Glu Lys Pro Tyr Gln Cys
1 5

<210> SEQ ID NO 113
<211> LENGTH: 9
<212> TYPE: PRT
<213> ORGANISM: Homo sapien

<400> SEQUENCE: 113

His Thr His Gly Val Phe Arg Gly Ile
1 5

<210> SEQ ID NO 114
<211> LENGTH: 9
<212> TYPE: PRT
<213> ORGANISM: Homo sapien

<400> SEQUENCE: 114

His Thr Arg Thr His Thr Gly Lys Thr
1 5

<210> SEQ ID NO 115
<211> LENGTH: 9
<212> TYPE: PRT
<213> ORGANISM: Homo sapien

<400> SEQUENCE: 115

His Thr Thr Pro Ile Leu Cys Gly Ala
1 5

<210> SEQ ID NO 116
<211> LENGTH: 9
<212> TYPE: PRT
<213> ORGANISM: Homo sapien

<400> SEQUENCE: 116

Ile Leu Cys Gly Ala Gln Tyr Arg Ile
1 5

<210> SEQ ID NO 117

<211> LENGTH: 9
<212> TYPE: PRT
<213> ORGANISM: Homo sapien

<400> SEQUENCE: 117

Ile Arg Asn Gln Gly Tyr Ser Thr Val
1 5

<210> SEQ ID NO 118
<211> LENGTH: 9
<212> TYPE: PRT
<213> ORGANISM: Homo sapien

<400> SEQUENCE: 118

Lys Asp Cys Glu Arg Arg Phe Ser Arg
1 5

<210> SEQ ID NO 119
<211> LENGTH: 9
<212> TYPE: PRT
<213> ORGANISM: Homo sapien

<400> SEQUENCE: 119

Lys Phe Ala Arg Ser Asp Glu Leu Val
1 5

<210> SEQ ID NO 120
<211> LENGTH: 9
<212> TYPE: PRT
<213> ORGANISM: Homo sapien

<400> SEQUENCE: 120

Lys Phe Ser Arg Ser Asp His Leu Lys
1 5

<210> SEQ ID NO 121
<211> LENGTH: 9
<212> TYPE: PRT
<213> ORGANISM: Homo sapien

<400> SEQUENCE: 121

Lys His Glu Asp Pro Met Gly Gln Gln
1 5

<210> SEQ ID NO 122
<211> LENGTH: 9
<212> TYPE: PRT
<213> ORGANISM: Homo sapien

<400> SEQUENCE: 122

Lys Lys Phe Ala Arg Ser Asp Glu Leu
1 5

<210> SEQ ID NO 123
<211> LENGTH: 9
<212> TYPE: PRT
<213> ORGANISM: Homo sapien

<400> SEQUENCE: 123

Lys Pro Phe Ser Cys Arg Trp Pro Ser
1 5

<210> SEQ ID NO 124
<211> LENGTH: 9
<212> TYPE: PRT
<213> ORGANISM: Homo sapien

<400> SEQUENCE: 124

Lys Pro Tyr Gln Cys Asp Phe Lys Asp
1 5

<210> SEQ ID NO 125
<211> LENGTH: 9
<212> TYPE: PRT
<213> ORGANISM: Homo sapien

<400> SEQUENCE: 125

Lys Gln Glu Pro Ser Trp Gly Gly Ala
1 5

<210> SEQ ID NO 126
<211> LENGTH: 9
<212> TYPE: PRT
<213> ORGANISM: Homo sapien

<400> SEQUENCE: 126

Lys Arg His Gln Arg Arg His Thr Gly
1 5

<210> SEQ ID NO 127
<211> LENGTH: 9
<212> TYPE: PRT
<213> ORGANISM: Homo sapien

<400> SEQUENCE: 127

Lys Arg Tyr Phe Lys Leu Ser His Leu
1 5

<210> SEQ ID NO 128
<211> LENGTH: 9
<212> TYPE: PRT
<213> ORGANISM: Homo sapien

<400> SEQUENCE: 128

Lys Thr Cys Gln Arg Lys Phe Ser Arg
1 5

<210> SEQ ID NO 129
<211> LENGTH: 9
<212> TYPE: PRT
<213> ORGANISM: Homo sapien

<400> SEQUENCE: 129

Lys Thr Ser Glu Lys Pro Phe Ser Cys
1 5

<210> SEQ ID NO 130
<211> LENGTH: 9
<212> TYPE: PRT
<213> ORGANISM: Homo sapien

<400> SEQUENCE: 130

Leu Asp Phe Ala Pro Pro Gly Ala Ser
1 5

<210> SEQ ID NO 131
<211> LENGTH: 9
<212> TYPE: PRT
<213> ORGANISM: Homo sapien

<400> SEQUENCE: 131

Leu Glu Cys Met Thr Trp Asn Gln Met
 1               5

<210> SEQ ID NO 132
<211> LENGTH: 9
<212> TYPE: PRT
<213> ORGANISM: Homo sapien

<400> SEQUENCE: 132

Leu Glu Ser Gln Pro Ala Ile Arg Asn
 1               5

<210> SEQ ID NO 133
<211> LENGTH: 9
<212> TYPE: PRT
<213> ORGANISM: Homo sapien

<400> SEQUENCE: 133

Leu Gly Ala Thr Leu Lys Gly Val Ala
 1               5

<210> SEQ ID NO 134
<211> LENGTH: 9
<212> TYPE: PRT
<213> ORGANISM: Homo sapien

<400> SEQUENCE: 134

Leu Gly Gly Gly Gly Gly Cys Ala Leu
 1               5

<210> SEQ ID NO 135
<211> LENGTH: 9
<212> TYPE: PRT
<213> ORGANISM: Homo sapien

<400> SEQUENCE: 135

Leu Lys Gly Val Ala Ala Gly Ser Ser
 1               5

<210> SEQ ID NO 136
<211> LENGTH: 9
<212> TYPE: PRT
<213> ORGANISM: Homo sapien

<400> SEQUENCE: 136

Leu Lys Arg His Gln Arg Arg His Thr
 1               5

<210> SEQ ID NO 137
<211> LENGTH: 9
<212> TYPE: PRT
<213> ORGANISM: Homo sapien

<400> SEQUENCE: 137

Leu Lys Thr His Thr Arg Thr His Thr
 1               5

<210> SEQ ID NO 138
<211> LENGTH: 9
<212> TYPE: PRT
<213> ORGANISM: Homo sapien

<400> SEQUENCE: 138

Leu Pro Val Ser Gly Ala Ala Gln Trp
 1               5

<210> SEQ ID NO 139
<211> LENGTH: 9
<212> TYPE: PRT
<213> ORGANISM: Homo sapien

<400> SEQUENCE: 139

Leu Gln Met His Ser Arg Lys His Thr
1 5

<210> SEQ ID NO 140
<211> LENGTH: 9
<212> TYPE: PRT
<213> ORGANISM: Homo sapien

<400> SEQUENCE: 140

Leu Arg Thr Pro Tyr Ser Ser Asp Asn
1 5

<210> SEQ ID NO 141
<211> LENGTH: 9
<212> TYPE: PRT
<213> ORGANISM: Homo sapien

<400> SEQUENCE: 141

Leu Ser His Leu Gln Met His Ser Arg
1 5

<210> SEQ ID NO 142
<211> LENGTH: 9
<212> TYPE: PRT
<213> ORGANISM: Homo sapien

<400> SEQUENCE: 142

Met Cys Ala Tyr Pro Gly Cys Asn Lys
1 5

<210> SEQ ID NO 143
<211> LENGTH: 9
<212> TYPE: PRT
<213> ORGANISM: Homo sapien

<400> SEQUENCE: 143

Met His Gln Arg Asn Met Thr Lys Leu
1 5

<210> SEQ ID NO 144
<211> LENGTH: 9
<212> TYPE: PRT
<213> ORGANISM: Homo sapien

<400> SEQUENCE: 144

Asn Ala Pro Tyr Leu Pro Ser Cys Leu
1 5

<210> SEQ ID NO 145
<211> LENGTH: 9
<212> TYPE: PRT
<213> ORGANISM: Homo sapien

<400> SEQUENCE: 145

Asn Lys Arg Tyr Phe Lys Leu Ser His
1 5

<210> SEQ ID NO 146
<211> LENGTH: 9

<212> TYPE: PRT
<213> ORGANISM: Homo sapien

<400> SEQUENCE: 146

Asn Leu Gly Ala Thr Leu Lys Gly Val
1 5

<210> SEQ ID NO 147
<211> LENGTH: 9
<212> TYPE: PRT
<213> ORGANISM: Homo sapien

<400> SEQUENCE: 147

Asn Leu Tyr Gln Met Thr Ser Gln Leu
1 5

<210> SEQ ID NO 148
<211> LENGTH: 9
<212> TYPE: PRT
<213> ORGANISM: Homo sapien

<400> SEQUENCE: 148

Asn Met His Gln Arg Asn Met Thr Lys
1 5

<210> SEQ ID NO 149
<211> LENGTH: 9
<212> TYPE: PRT
<213> ORGANISM: Homo sapien

<400> SEQUENCE: 149

Asn Met Thr Lys Leu Gln Leu Ala Leu
1 5

<210> SEQ ID NO 150
<211> LENGTH: 9
<212> TYPE: PRT
<213> ORGANISM: Homo sapien

<400> SEQUENCE: 150

Asn Gln Gly Tyr Ser Thr Val Thr Phe
1 5

<210> SEQ ID NO 151
<211> LENGTH: 9
<212> TYPE: PRT
<213> ORGANISM: Homo sapien

<400> SEQUENCE: 151

Asn Gln Met Asn Leu Gly Ala Thr Leu
1 5

<210> SEQ ID NO 152
<211> LENGTH: 9
<212> TYPE: PRT
<213> ORGANISM: Homo sapien

<400> SEQUENCE: 152

Pro Ala Ile Arg Asn Gln Gly Tyr Ser
1 5

<210> SEQ ID NO 153
<211> LENGTH: 9
<212> TYPE: PRT
<213> ORGANISM: Homo sapien

<400> SEQUENCE: 153

Pro Gly Ala Ser Ala Tyr Gly Ser Leu
1 5

<210> SEQ ID NO 154
<211> LENGTH: 9
<212> TYPE: PRT
<213> ORGANISM: Homo sapien

<400> SEQUENCE: 154

Pro His Glu Glu Gln Cys Leu Ser Ala
1 5

<210> SEQ ID NO 155
<211> LENGTH: 9
<212> TYPE: PRT
<213> ORGANISM: Homo sapien

<400> SEQUENCE: 155

Pro Ile Leu Cys Gly Ala Gln Tyr Arg
1 5

<210> SEQ ID NO 156
<211> LENGTH: 9
<212> TYPE: PRT
<213> ORGANISM: Homo sapien

<400> SEQUENCE: 156

Pro Pro Pro Pro His Ser Phe Ile Lys
1 5

<210> SEQ ID NO 157
<211> LENGTH: 9
<212> TYPE: PRT
<213> ORGANISM: Homo sapien

<400> SEQUENCE: 157

Pro Pro Pro Pro Pro His Ser Phe Ile
1 5

<210> SEQ ID NO 158
<211> LENGTH: 9
<212> TYPE: PRT
<213> ORGANISM: Homo sapien

<400> SEQUENCE: 158

Pro Pro Pro Pro Pro Pro His Ser Phe
1 5

<210> SEQ ID NO 159
<211> LENGTH: 9
<212> TYPE: PRT
<213> ORGANISM: Homo sapien

<400> SEQUENCE: 159

Pro Ser Cys Gln Lys Lys Phe Ala Arg
1 5

<210> SEQ ID NO 160
<211> LENGTH: 9
<212> TYPE: PRT
<213> ORGANISM: Homo sapien

<400> SEQUENCE: 160

Gln Ala Leu Leu Leu Arg Thr Pro Tyr 1 5

<210> SEQ ID NO 161
<211> LENGTH: 9
<212> TYPE: PRT
<213> ORGANISM: Homo sapien

<400> SEQUENCE: 161

Gln Ala Ser Ser Gly Gln Ala Arg Met
1 5

<210> SEQ ID NO 162
<211> LENGTH: 9
<212> TYPE: PRT
<213> ORGANISM: Homo sapien

<400> SEQUENCE: 162

Gln Cys Asp Phe Lys Asp Cys Glu Arg
1 5

<210> SEQ ID NO 163
<211> LENGTH: 9
<212> TYPE: PRT
<213> ORGANISM: Homo sapien

<400> SEQUENCE: 163

Gln Cys Lys Thr Cys Gln Arg Lys Phe
1 5

<210> SEQ ID NO 164
<211> LENGTH: 9
<212> TYPE: PRT
<213> ORGANISM: Homo sapien

<400> SEQUENCE: 164

Gln Asp Val Arg Arg Val Pro Gly Val
1 5

<210> SEQ ID NO 165
<211> LENGTH: 9
<212> TYPE: PRT
<213> ORGANISM: Homo sapien

<400> SEQUENCE: 165

Gln Phe Thr Gly Thr Ala Gly Ala Cys
1 5

<210> SEQ ID NO 166
<211> LENGTH: 9
<212> TYPE: PRT
<213> ORGANISM: Homo sapien

<400> SEQUENCE: 166

Gln Gly Ser Leu Gly Glu Gln Gln Tyr
1 5

<210> SEQ ID NO 167
<211> LENGTH: 9
<212> TYPE: PRT
<213> ORGANISM: Homo sapien

<400> SEQUENCE: 167

Gln Leu Glu Cys Met Thr Trp Asn Gln
1 5

<210> SEQ ID NO 168
<211> LENGTH: 9
<212> TYPE: PRT
<213> ORGANISM: Homo sapien

<400> SEQUENCE: 168

Gln Met Asn Leu Gly Ala Thr Leu Lys
1 5

<210> SEQ ID NO 169
<211> LENGTH: 9
<212> TYPE: PRT
<213> ORGANISM: Homo sapien

<400> SEQUENCE: 169

Gln Met Thr Ser Gln Leu Glu Cys Met
1 5

<210> SEQ ID NO 170
<211> LENGTH: 9
<212> TYPE: PRT
<213> ORGANISM: Homo sapien

<400> SEQUENCE: 170

Gln Pro Ala Ile Arg Asn Gln Gly Tyr
1 5

<210> SEQ ID NO 171
<211> LENGTH: 9
<212> TYPE: PRT
<213> ORGANISM: Homo sapien

<400> SEQUENCE: 171

Gln Gln Tyr Ser Val Pro Pro Pro Val
1 5

<210> SEQ ID NO 172
<211> LENGTH: 9
<212> TYPE: PRT
<213> ORGANISM: Homo sapien

<400> SEQUENCE: 172

Gln Arg Lys Phe Ser Arg Ser Asp His
1 5

<210> SEQ ID NO 173
<211> LENGTH: 9
<212> TYPE: PRT
<213> ORGANISM: Homo sapien

<400> SEQUENCE: 173

Gln Arg Asn Met Thr Lys Leu Gln Leu
1 5

<210> SEQ ID NO 174
<211> LENGTH: 9
<212> TYPE: PRT
<213> ORGANISM: Homo sapien

<400> SEQUENCE: 174

Gln Trp Ala Pro Val Leu Asp Phe Ala
1 5

<210> SEQ ID NO 175
<211> LENGTH: 9
<212> TYPE: PRT

<213> ORGANISM: Homo sapien

<400> SEQUENCE: 175

Gln Tyr Arg Ile His Thr His Gly Val
 1               5

<210> SEQ ID NO 176
<211> LENGTH: 9
<212> TYPE: PRT
<213> ORGANISM: Homo sapien

<400> SEQUENCE: 176

Gln Tyr Ser Val Pro Pro Pro Val Tyr
 1               5

<210> SEQ ID NO 177
<211> LENGTH: 9
<212> TYPE: PRT
<213> ORGANISM: Homo sapien

<400> SEQUENCE: 177

Arg Asp Leu Asn Ala Leu Leu Pro Ala
 1               5

<210> SEQ ID NO 178
<211> LENGTH: 9
<212> TYPE: PRT
<213> ORGANISM: Homo sapien

<400> SEQUENCE: 178

Arg Phe Ser Arg Ser Asp Gln Leu Lys
 1               5

<210> SEQ ID NO 179
<211> LENGTH: 9
<212> TYPE: PRT
<213> ORGANISM: Homo sapien

<400> SEQUENCE: 179

Arg Gly Ile Gln Asp Val Arg Arg Val
 1               5

<210> SEQ ID NO 180
<211> LENGTH: 9
<212> TYPE: PRT
<213> ORGANISM: Homo sapien

<400> SEQUENCE: 180

Arg His His Asn Met His Gln Arg Asn
 1               5

<210> SEQ ID NO 181
<211> LENGTH: 9
<212> TYPE: PRT
<213> ORGANISM: Homo sapien

<400> SEQUENCE: 181

Arg His Gln Arg Arg His Thr Gly Val
 1               5

<210> SEQ ID NO 182
<211> LENGTH: 9
<212> TYPE: PRT
<213> ORGANISM: Homo sapien

<400> SEQUENCE: 182

Arg Ile His Thr His Gly Val Phe Arg
1 5

<210> SEQ ID NO 183
<211> LENGTH: 9
<212> TYPE: PRT
<213> ORGANISM: Homo sapien

<400> SEQUENCE: 183

Arg Lys Phe Ser Arg Ser Asp His Leu
1 5

<210> SEQ ID NO 184
<211> LENGTH: 9
<212> TYPE: PRT
<213> ORGANISM: Homo sapien

<400> SEQUENCE: 184

Arg Lys His Thr Gly Glu Lys Pro Tyr
1 5

<210> SEQ ID NO 185
<211> LENGTH: 9
<212> TYPE: PRT
<213> ORGANISM: Homo sapien

<400> SEQUENCE: 185

Arg Met Phe Pro Asn Ala Pro Tyr Leu
1 5

<210> SEQ ID NO 186
<211> LENGTH: 9
<212> TYPE: PRT
<213> ORGANISM: Homo sapien

<400> SEQUENCE: 186

Arg Asn Met Thr Lys Leu Gln Leu Ala
1 5

<210> SEQ ID NO 187
<211> LENGTH: 9
<212> TYPE: PRT
<213> ORGANISM: Homo sapien

<400> SEQUENCE: 187

Arg Arg Phe Ser Arg Ser Asp Gln Leu
1 5

<210> SEQ ID NO 188
<211> LENGTH: 9
<212> TYPE: PRT
<213> ORGANISM: Homo sapien

<400> SEQUENCE: 188

Arg Arg His Thr Gly Val Lys Pro Phe
1 5

<210> SEQ ID NO 189
<211> LENGTH: 9
<212> TYPE: PRT
<213> ORGANISM: Homo sapien

<400> SEQUENCE: 189

Arg Arg Val Pro Gly Val Ala Pro Thr
1 5

<210> SEQ ID NO 190
<211> LENGTH: 9
<212> TYPE: PRT
<213> ORGANISM: Homo sapien

<400> SEQUENCE: 190

Arg Ser Ala Ser Glu Thr Ser Glu Lys
1               5

<210> SEQ ID NO 191
<211> LENGTH: 9
<212> TYPE: PRT
<213> ORGANISM: Homo sapien

<400> SEQUENCE: 191

Arg Ser Asp Glu Leu Val Arg His His
1               5

<210> SEQ ID NO 192
<211> LENGTH: 9
<212> TYPE: PRT
<213> ORGANISM: Homo sapien

<400> SEQUENCE: 192

Arg Ser Asp His Leu Lys Thr His Thr
1               5

<210> SEQ ID NO 193
<211> LENGTH: 9
<212> TYPE: PRT
<213> ORGANISM: Homo sapien

<400> SEQUENCE: 193

Arg Ser Asp Gln Leu Lys Arg His Gln
1               5

<210> SEQ ID NO 194
<211> LENGTH: 9
<212> TYPE: PRT
<213> ORGANISM: Homo sapien

<400> SEQUENCE: 194

Arg Thr Pro Tyr Ser Ser Asp Asn Leu
1               5

<210> SEQ ID NO 195
<211> LENGTH: 9
<212> TYPE: PRT
<213> ORGANISM: Homo sapien

<400> SEQUENCE: 195

Arg Val Pro Gly Val Ala Pro Thr Leu
1               5

<210> SEQ ID NO 196
<211> LENGTH: 9
<212> TYPE: PRT
<213> ORGANISM: Homo sapien

<400> SEQUENCE: 196

Arg Trp Pro Ser Cys Gln Lys Lys Phe
1               5

<210> SEQ ID NO 197

<211> LENGTH: 9
<212> TYPE: PRT
<213> ORGANISM: Homo sapien

<400> SEQUENCE: 197

Ser Ala Ser Glu Thr Ser Glu Lys Arg
1 5

<210> SEQ ID NO 198
<211> LENGTH: 9
<212> TYPE: PRT
<213> ORGANISM: Homo sapien

<400> SEQUENCE: 198

Ser Cys Leu Glu Ser Gln Pro Ala Ile
1 5

<210> SEQ ID NO 199
<211> LENGTH: 9
<212> TYPE: PRT
<213> ORGANISM: Homo sapien

<400> SEQUENCE: 199

Ser Cys Leu Glu Ser Gln Pro Thr Ile
1 5

<210> SEQ ID NO 200
<211> LENGTH: 9
<212> TYPE: PRT
<213> ORGANISM: Homo sapien

<400> SEQUENCE: 200

Ser Cys Gln Lys Lys Phe Ala Arg Ser
1 5

<210> SEQ ID NO 201
<211> LENGTH: 9
<212> TYPE: PRT
<213> ORGANISM: Homo sapien

<400> SEQUENCE: 201

Ser Cys Arg Trp Pro Ser Cys Gln Lys
1 5

<210> SEQ ID NO 202
<211> LENGTH: 9
<212> TYPE: PRT
<213> ORGANISM: Homo sapien

<400> SEQUENCE: 202

Ser Cys Thr Gly Ser Gln Ala Leu Leu
1 5

<210> SEQ ID NO 203
<211> LENGTH: 9
<212> TYPE: PRT
<213> ORGANISM: Homo sapien

<400> SEQUENCE: 203

Ser Asp Glu Leu Val Arg His His Asn
1 5

<210> SEQ ID NO 204
<211> LENGTH: 9
<212> TYPE: PRT
<213> ORGANISM: Homo sapien

<400> SEQUENCE: 204

Ser Asp Asn His Thr Thr Pro Ile Leu
1 5

<210> SEQ ID NO 205
<211> LENGTH: 9
<212> TYPE: PRT
<213> ORGANISM: Homo sapien

<400> SEQUENCE: 205

Ser Asp Asn Leu Tyr Gln Met Thr Ser
1 5

<210> SEQ ID NO 206
<211> LENGTH: 9
<212> TYPE: PRT
<213> ORGANISM: Homo sapien

<400> SEQUENCE: 206

Ser Asp Val Arg Asp Leu Asn Ala Leu
1 5

<210> SEQ ID NO 207
<211> LENGTH: 9
<212> TYPE: PRT
<213> ORGANISM: Homo sapien

<400> SEQUENCE: 207

Ser Glu Lys Pro Phe Ser Cys Arg Trp
1 5

<210> SEQ ID NO 208
<211> LENGTH: 9
<212> TYPE: PRT
<213> ORGANISM: Homo sapien

<400> SEQUENCE: 208

Ser Glu Lys Arg Pro Phe Met Cys Ala
1 5

<210> SEQ ID NO 209
<211> LENGTH: 9
<212> TYPE: PRT
<213> ORGANISM: Homo sapien

<400> SEQUENCE: 209

Ser Glu Thr Ser Glu Lys Arg Pro Phe
1 5

<210> SEQ ID NO 210
<211> LENGTH: 9
<212> TYPE: PRT
<213> ORGANISM: Homo sapien

<400> SEQUENCE: 210

Ser Phe Ile Lys Gln Glu Pro Ser Trp
1 5

<210> SEQ ID NO 211
<211> LENGTH: 9
<212> TYPE: PRT
<213> ORGANISM: Homo sapien

<400> SEQUENCE: 211

Ser Gly Ala Ala Gln Trp Ala Pro Val
1 5

<210> SEQ ID NO 212
<211> LENGTH: 9
<212> TYPE: PRT
<213> ORGANISM: Homo sapien

<400> SEQUENCE: 212

Ser Gly Gln Ala Arg Met Phe Pro Asn
1 5

<210> SEQ ID NO 213
<211> LENGTH: 9
<212> TYPE: PRT
<213> ORGANISM: Homo sapien

<400> SEQUENCE: 213

Ser His His Ala Ala Gln Phe Pro Asn
1 5

<210> SEQ ID NO 214
<211> LENGTH: 9
<212> TYPE: PRT
<213> ORGANISM: Homo sapien

<400> SEQUENCE: 214

Ser Leu Gly Glu Gln Gln Tyr Ser Val
1 5

<210> SEQ ID NO 215
<211> LENGTH: 9
<212> TYPE: PRT
<213> ORGANISM: Homo sapien

<400> SEQUENCE: 215

Ser Leu Gly Gly Gly Gly Gly Cys Ala
1 5

<210> SEQ ID NO 216
<211> LENGTH: 9
<212> TYPE: PRT
<213> ORGANISM: Homo sapien

<400> SEQUENCE: 216

Ser Gln Ala Ser Ser Gly Gln Ala Arg
1 5

<210> SEQ ID NO 217
<211> LENGTH: 9
<212> TYPE: PRT
<213> ORGANISM: Homo sapien

<400> SEQUENCE: 217

Ser Ser Asp Asn Leu Tyr Gln Met Thr
1 5

<210> SEQ ID NO 218
<211> LENGTH: 9
<212> TYPE: PRT
<213> ORGANISM: Homo sapien

<400> SEQUENCE: 218

Ser Val Pro Pro Pro Val Tyr Gly Cys
1 5

<210> SEQ ID NO 219
<211> LENGTH: 9
<212> TYPE: PRT
<213> ORGANISM: Homo sapien

<400> SEQUENCE: 219

Thr Cys Gln Arg Lys Phe Ser Arg Ser
1 5

<210> SEQ ID NO 220
<211> LENGTH: 9
<212> TYPE: PRT
<213> ORGANISM: Homo sapien

<400> SEQUENCE: 220

Thr Asp Ser Cys Thr Gly Ser Gln Ala
1 5

<210> SEQ ID NO 221
<211> LENGTH: 9
<212> TYPE: PRT
<213> ORGANISM: Homo sapien

<400> SEQUENCE: 221

Thr Glu Gly Gln Ser Asn His Ser Thr
1 5

<210> SEQ ID NO 222
<211> LENGTH: 9
<212> TYPE: PRT
<213> ORGANISM: Homo sapien

<400> SEQUENCE: 222

Thr Gly Lys Thr Ser Glu Lys Pro Phe
1 5

<210> SEQ ID NO 223
<211> LENGTH: 9
<212> TYPE: PRT
<213> ORGANISM: Homo sapien

<400> SEQUENCE: 223

Thr Gly Ser Gln Ala Leu Leu Leu Arg
1 5

<210> SEQ ID NO 224
<211> LENGTH: 9
<212> TYPE: PRT
<213> ORGANISM: Homo sapien

<400> SEQUENCE: 224

Thr Gly Thr Ala Gly Ala Cys Arg Tyr
1 5

<210> SEQ ID NO 225
<211> LENGTH: 9
<212> TYPE: PRT
<213> ORGANISM: Homo sapien

<400> SEQUENCE: 225

Thr Gly Tyr Glu Ser Asp Asn His Thr
1 5

<210> SEQ ID NO 226
<211> LENGTH: 9

<212> TYPE: PRT
<213> ORGANISM: Homo sapien

<400> SEQUENCE: 226

Thr Leu Val Arg Ser Ala Ser Glu Thr
 1               5

<210> SEQ ID NO 227
<211> LENGTH: 9
<212> TYPE: PRT
<213> ORGANISM: Homo sapien

<400> SEQUENCE: 227

Thr Pro Ile Leu Cys Gly Ala Gln Tyr
 1               5

<210> SEQ ID NO 228
<211> LENGTH: 9
<212> TYPE: PRT
<213> ORGANISM: Homo sapien

<400> SEQUENCE: 228

Thr Pro Ser His His Ala Ala Gln Phe
 1               5

<210> SEQ ID NO 229
<211> LENGTH: 9
<212> TYPE: PRT
<213> ORGANISM: Homo sapien

<400> SEQUENCE: 229

Thr Pro Ser Tyr Gly His Thr Pro Ser
 1               5

<210> SEQ ID NO 230
<211> LENGTH: 9
<212> TYPE: PRT
<213> ORGANISM: Homo sapien

<400> SEQUENCE: 230

Thr Pro Thr Asp Ser Cys Thr Gly Ser
 1               5

<210> SEQ ID NO 231
<211> LENGTH: 9
<212> TYPE: PRT
<213> ORGANISM: Homo sapien

<400> SEQUENCE: 231

Thr Pro Tyr Ser Ser Asp Asn Leu Tyr
 1               5

<210> SEQ ID NO 232
<211> LENGTH: 9
<212> TYPE: PRT
<213> ORGANISM: Homo sapien

<400> SEQUENCE: 232

Thr Ser Glu Lys Pro Phe Ser Cys Arg
 1               5

<210> SEQ ID NO 233
<211> LENGTH: 9
<212> TYPE: PRT
<213> ORGANISM: Homo sapien

<400> SEQUENCE: 233

Thr Ser Glu Lys Arg Pro Phe Met Cys
1 5

<210> SEQ ID NO 234
<211> LENGTH: 9
<212> TYPE: PRT
<213> ORGANISM: Homo sapien

<400> SEQUENCE: 234

Thr Ser Gln Leu Glu Cys Met Thr Trp
1 5

<210> SEQ ID NO 235
<211> LENGTH: 9
<212> TYPE: PRT
<213> ORGANISM: Homo sapien

<400> SEQUENCE: 235

Thr Val His Phe Ser Gly Gln Phe Thr
1 5

<210> SEQ ID NO 236
<211> LENGTH: 9
<212> TYPE: PRT
<213> ORGANISM: Homo sapien

<400> SEQUENCE: 236

Val Ala Ala Gly Ser Ser Ser Ser Val
1 5

<210> SEQ ID NO 237
<211> LENGTH: 9
<212> TYPE: PRT
<213> ORGANISM: Homo sapien

<400> SEQUENCE: 237

Val Ala Pro Thr Leu Val Arg Ser Ala
1 5

<210> SEQ ID NO 238
<211> LENGTH: 9
<212> TYPE: PRT
<213> ORGANISM: Homo sapien

<400> SEQUENCE: 238

Val Phe Arg Gly Ile Gln Asp Val Arg
1 5

<210> SEQ ID NO 239
<211> LENGTH: 9
<212> TYPE: PRT
<213> ORGANISM: Homo sapien

<400> SEQUENCE: 239

Val Lys Pro Phe Gln Cys Lys Thr Cys
1 5

<210> SEQ ID NO 240
<211> LENGTH: 9
<212> TYPE: PRT
<213> ORGANISM: Homo sapien

<400> SEQUENCE: 240

Val Lys Trp Thr Glu Gly Gln Ser Asn

```
 1               5


<210> SEQ ID NO 241
<211> LENGTH: 9
<212> TYPE: PRT
<213> ORGANISM: Homo sapien

<400> SEQUENCE: 241

Val Leu Asp Phe Ala Pro Pro Gly Ala
 1               5


<210> SEQ ID NO 242
<211> LENGTH: 9
<212> TYPE: PRT
<213> ORGANISM: Homo sapien

<400> SEQUENCE: 242

Val Pro Gly Val Ala Pro Thr Leu Val
 1               5


<210> SEQ ID NO 243
<211> LENGTH: 9
<212> TYPE: PRT
<213> ORGANISM: Homo sapien

<400> SEQUENCE: 243

Val Arg His His Asn Met His Gln Arg
 1               5


<210> SEQ ID NO 244
<211> LENGTH: 9
<212> TYPE: PRT
<213> ORGANISM: Homo sapien

<400> SEQUENCE: 244

Val Thr Phe Asp Gly Thr Pro Ser Tyr
 1               5


<210> SEQ ID NO 245
<211> LENGTH: 9
<212> TYPE: PRT
<213> ORGANISM: Homo sapien

<400> SEQUENCE: 245

Trp Asn Gln Met Asn Leu Gly Ala Thr
 1               5


<210> SEQ ID NO 246
<211> LENGTH: 9
<212> TYPE: PRT
<213> ORGANISM: Homo sapien

<400> SEQUENCE: 246

Trp Pro Ser Cys Gln Lys Lys Phe Ala
 1               5


<210> SEQ ID NO 247
<211> LENGTH: 9
<212> TYPE: PRT
<213> ORGANISM: Homo sapien

<400> SEQUENCE: 247

Trp Thr Glu Gly Gln Ser Asn His Ser
 1               5
```

<210> SEQ ID NO 248
<211> LENGTH: 9
<212> TYPE: PRT
<213> ORGANISM: Homo sapien

<400> SEQUENCE: 248

Tyr Phe Lys Leu Ser His Leu Gln Met
1 5

<210> SEQ ID NO 249
<211> LENGTH: 9
<212> TYPE: PRT
<213> ORGANISM: Homo sapien

<400> SEQUENCE: 249

Tyr Gly His Thr Pro Ser His His Ala
1 5

<210> SEQ ID NO 250
<211> LENGTH: 9
<212> TYPE: PRT
<213> ORGANISM: Homo sapien

<400> SEQUENCE: 250

Tyr Pro Gly Cys Asn Lys Arg Tyr Phe
1 5

<210> SEQ ID NO 251
<211> LENGTH: 9
<212> TYPE: PRT
<213> ORGANISM: Homo sapien

<400> SEQUENCE: 251

Tyr Gln Met Thr Ser Gln Leu Glu Cys
1 5

<210> SEQ ID NO 252
<211> LENGTH: 9
<212> TYPE: PRT
<213> ORGANISM: Homo sapien

<400> SEQUENCE: 252

Tyr Arg Ile His Thr His Gly Val Phe
1 5

<210> SEQ ID NO 253
<211> LENGTH: 9
<212> TYPE: PRT
<213> ORGANISM: Homo sapien

<400> SEQUENCE: 253

Tyr Ser Ser Asp Asn Leu Tyr Gln Met
1 5

<210> SEQ ID NO 254
<211> LENGTH: 9
<212> TYPE: PRT
<213> ORGANISM: Mus musculus

<400> SEQUENCE: 254

Ala Glu Pro His Glu Glu Gln Cys Leu
1 5

<210> SEQ ID NO 255
<211> LENGTH: 9
<212> TYPE: PRT

<213> ORGANISM: Mus musculus

<400> SEQUENCE: 255

Ala Leu Leu Pro Ala Val Ser Ser Leu
1 5

<210> SEQ ID NO 256
<211> LENGTH: 9
<212> TYPE: PRT
<213> ORGANISM: Mus musculus

<400> SEQUENCE: 256

Ala Tyr Gly Ser Leu Gly Gly Pro Ala
1 5

<210> SEQ ID NO 257
<211> LENGTH: 9
<212> TYPE: PRT
<213> ORGANISM: Mus musculus

<400> SEQUENCE: 257

Ala Tyr Pro Gly Cys Asn Lys Arg Tyr
1 5

<210> SEQ ID NO 258
<211> LENGTH: 9
<212> TYPE: PRT
<213> ORGANISM: Mus musculus

<400> SEQUENCE: 258

Cys Met Thr Trp Asn Gln Met Asn Leu
1 5

<210> SEQ ID NO 259
<211> LENGTH: 9
<212> TYPE: PRT
<213> ORGANISM: Mus musculus

<400> SEQUENCE: 259

Cys Thr Gly Ser Gln Ala Leu Leu Leu
1 5

<210> SEQ ID NO 260
<211> LENGTH: 9
<212> TYPE: PRT
<213> ORGANISM: Mus musculus

<400> SEQUENCE: 260

Asp Gly Ala Pro Ser Tyr Gly His Thr
1 5

<210> SEQ ID NO 261
<211> LENGTH: 9
<212> TYPE: PRT
<213> ORGANISM: Mus musculus

<400> SEQUENCE: 261

Asp Leu Asn Ala Leu Leu Pro Ala Val
1 5

<210> SEQ ID NO 262
<211> LENGTH: 9
<212> TYPE: PRT
<213> ORGANISM: Mus musculus

<400> SEQUENCE: 262

Asp Pro Met Gly Gln Gln Gly Ser Leu
1 5

<210> SEQ ID NO 263
<211> LENGTH: 9
<212> TYPE: PRT
<213> ORGANISM: Mus musculus

<400> SEQUENCE: 263

Asp Ser Cys Thr Gly Ser Gln Ala Leu
1 5

<210> SEQ ID NO 264
<211> LENGTH: 9
<212> TYPE: PRT
<213> ORGANISM: Mus musculus

<400> SEQUENCE: 264

Asp Val Arg Asp Leu Asn Ala Leu Leu
1 5

<210> SEQ ID NO 265
<211> LENGTH: 9
<212> TYPE: PRT
<213> ORGANISM: Mus musculus

<400> SEQUENCE: 265

Glu Gln Cys Leu Ser Ala Phe Thr Leu
1 5

<210> SEQ ID NO 266
<211> LENGTH: 9
<212> TYPE: PRT
<213> ORGANISM: Mus musculus

<400> SEQUENCE: 266

Glu Ser Asp Asn His Thr Ala Pro Ile
1 5

<210> SEQ ID NO 267
<211> LENGTH: 9
<212> TYPE: PRT
<213> ORGANISM: Mus musculus

<400> SEQUENCE: 267

Phe Pro Asn Ala Pro Tyr Leu Pro Ser
1 5

<210> SEQ ID NO 268
<211> LENGTH: 9
<212> TYPE: PRT
<213> ORGANISM: Mus musculus

<400> SEQUENCE: 268

Gly Cys Asn Lys Arg Tyr Phe Lys Leu
1 5

<210> SEQ ID NO 269
<211> LENGTH: 9
<212> TYPE: PRT
<213> ORGANISM: Mus musculus

<400> SEQUENCE: 269

Gly Gln Ala Arg Met Phe Pro Asn Ala
1 5

<210> SEQ ID NO 270
<211> LENGTH: 9
<212> TYPE: PRT
<213> ORGANISM: Mus musculus

<400> SEQUENCE: 270

Gly Val Phe Arg Gly Ile Gln Asp Val
1 5

<210> SEQ ID NO 271
<211> LENGTH: 9
<212> TYPE: PRT
<213> ORGANISM: Mus musculus

<400> SEQUENCE: 271

Gly Tyr Glu Ser Asp Asn His Thr Ala
1 5

<210> SEQ ID NO 272
<211> LENGTH: 9
<212> TYPE: PRT
<213> ORGANISM: Mus musculus

<400> SEQUENCE: 272

His Ser Phe Lys His Glu Asp Pro Met
1 5

<210> SEQ ID NO 273
<211> LENGTH: 9
<212> TYPE: PRT
<213> ORGANISM: Mus musculus

<400> SEQUENCE: 273

His Thr His Gly Val Phe Arg Gly Ile
1 5

<210> SEQ ID NO 274
<211> LENGTH: 9
<212> TYPE: PRT
<213> ORGANISM: Mus musculus

<400> SEQUENCE: 274

Ile Leu Cys Gly Ala Gln Tyr Arg Ile
1 5

<210> SEQ ID NO 275
<211> LENGTH: 9
<212> TYPE: PRT
<213> ORGANISM: Mus musculus

<400> SEQUENCE: 275

Lys Phe Ala Arg Ser Asp Glu Leu Val
1 5

<210> SEQ ID NO 276
<211> LENGTH: 9
<212> TYPE: PRT
<213> ORGANISM: Mus musculus

<400> SEQUENCE: 276

Lys Arg Tyr Phe Lys Leu Ser His Leu
1 5

<210> SEQ ID NO 277

<211> LENGTH: 9
<212> TYPE: PRT
<213> ORGANISM: Mus musculus

<400> SEQUENCE: 277

Lys Thr Ser Glu Lys Pro Phe Ser Cys
1 5

<210> SEQ ID NO 278
<211> LENGTH: 9
<212> TYPE: PRT
<213> ORGANISM: Mus musculus

<400> SEQUENCE: 278

Leu Glu Cys Met Thr Trp Asn Gln Met
1 5

<210> SEQ ID NO 279
<211> LENGTH: 9
<212> TYPE: PRT
<213> ORGANISM: Mus musculus

<400> SEQUENCE: 279

Leu Gly Gly Gly Gly Gly Cys Gly Leu
1 5

<210> SEQ ID NO 280
<211> LENGTH: 9
<212> TYPE: PRT
<213> ORGANISM: Mus musculus

<400> SEQUENCE: 280

Leu Gln Met His Ser Arg Lys His Thr
1 5

<210> SEQ ID NO 281
<211> LENGTH: 9
<212> TYPE: PRT
<213> ORGANISM: Mus musculus

<400> SEQUENCE: 281

Met His Gln Arg Asn Met Thr Lys Leu
1 5

<210> SEQ ID NO 282
<211> LENGTH: 9
<212> TYPE: PRT
<213> ORGANISM: Mus musculus

<400> SEQUENCE: 282

Asn Ala Pro Tyr Leu Pro Ser Cys Leu
1 5

<210> SEQ ID NO 283
<211> LENGTH: 9
<212> TYPE: PRT
<213> ORGANISM: Mus musculus

<400> SEQUENCE: 283

Asn Leu Gly Ala Thr Leu Lys Gly Met
1 5

<210> SEQ ID NO 284
<211> LENGTH: 9
<212> TYPE: PRT
<213> ORGANISM: Mus musculus

<400> SEQUENCE: 284

Asn Leu Tyr Gln Met Thr Ser Gln Leu
1 5

<210> SEQ ID NO 285
<211> LENGTH: 9
<212> TYPE: PRT
<213> ORGANISM: Mus musculus

<400> SEQUENCE: 285

Asn Met Thr Lys Leu His Val Ala Leu
1 5

<210> SEQ ID NO 286
<211> LENGTH: 9
<212> TYPE: PRT
<213> ORGANISM: Mus musculus

<400> SEQUENCE: 286

Asn Gln Met Asn Leu Gly Ala Thr Leu
1 5

<210> SEQ ID NO 287
<211> LENGTH: 9
<212> TYPE: PRT
<213> ORGANISM: Mus musculus

<400> SEQUENCE: 287

Pro Gly Ala Ser Ala Tyr Gly Ser Leu
1 5

<210> SEQ ID NO 288
<211> LENGTH: 9
<212> TYPE: PRT
<213> ORGANISM: Mus musculus

<400> SEQUENCE: 288

Gln Ala Ser Ser Gly Gln Ala Arg Met
1 5

<210> SEQ ID NO 289
<211> LENGTH: 9
<212> TYPE: PRT
<213> ORGANISM: Mus musculus

<400> SEQUENCE: 289

Gln Met Thr Ser Gln Leu Glu Cys Met
1 5

<210> SEQ ID NO 290
<211> LENGTH: 9
<212> TYPE: PRT
<213> ORGANISM: Mus musculus

<400> SEQUENCE: 290

Gln Gln Tyr Ser Val Pro Pro Pro Val
1 5

<210> SEQ ID NO 291
<211> LENGTH: 9
<212> TYPE: PRT
<213> ORGANISM: Mus musculus

<400> SEQUENCE: 291

Gln Tyr Arg Ile His Thr His Gly Val
1 5

<210> SEQ ID NO 292
<211> LENGTH: 9
<212> TYPE: PRT
<213> ORGANISM: Mus musculus

<400> SEQUENCE: 292

Gln Tyr Ser Val Pro Pro Pro Val Tyr
1 5

<210> SEQ ID NO 293
<211> LENGTH: 9
<212> TYPE: PRT
<213> ORGANISM: Mus musculus

<400> SEQUENCE: 293

Arg Met Phe Pro Asn Ala Pro Tyr Leu
1 5

<210> SEQ ID NO 294
<211> LENGTH: 9
<212> TYPE: PRT
<213> ORGANISM: Mus musculus

<400> SEQUENCE: 294

Arg Thr Pro Tyr Ser Ser Asp Asn Leu
1 5

<210> SEQ ID NO 295
<211> LENGTH: 9
<212> TYPE: PRT
<213> ORGANISM: Mus musculus

<400> SEQUENCE: 295

Arg Val Ser Gly Val Ala Pro Thr Leu
1 5

<210> SEQ ID NO 296
<211> LENGTH: 9
<212> TYPE: PRT
<213> ORGANISM: Mus musculus

<400> SEQUENCE: 296

Ser Cys Leu Glu Ser Gln Pro Thr Ile
1 5

<210> SEQ ID NO 297
<211> LENGTH: 9
<212> TYPE: PRT
<213> ORGANISM: Mus musculus

<400> SEQUENCE: 297

Ser Cys Gln Lys Lys Phe Ala Arg Ser
1 5

<210> SEQ ID NO 298
<211> LENGTH: 9
<212> TYPE: PRT
<213> ORGANISM: Mus musculus

<400> SEQUENCE: 298

Ser Asp Val Arg Asp Leu Asn Ala Leu
1 5

<210> SEQ ID NO 299
<211> LENGTH: 9
<212> TYPE: PRT
<213> ORGANISM: Mus musculus

<400> SEQUENCE: 299

Ser Leu Gly Glu Gln Gln Tyr Ser Val
1 5

<210> SEQ ID NO 300
<211> LENGTH: 9
<212> TYPE: PRT
<213> ORGANISM: Mus musculus

<400> SEQUENCE: 300

Thr Cys Gln Arg Lys Phe Ser Arg Ser
1 5

<210> SEQ ID NO 301
<211> LENGTH: 9
<212> TYPE: PRT
<213> ORGANISM: Mus musculus

<400> SEQUENCE: 301

Thr Glu Gly Gln Ser Asn His Gly Ile
1 5

<210> SEQ ID NO 302
<211> LENGTH: 9
<212> TYPE: PRT
<213> ORGANISM: Mus musculus

<400> SEQUENCE: 302

Thr Leu His Phe Ser Gly Gln Phe Thr
1 5

<210> SEQ ID NO 303
<211> LENGTH: 9
<212> TYPE: PRT
<213> ORGANISM: Mus musculus

<400> SEQUENCE: 303

Thr Leu Val Arg Ser Ala Ser Glu Thr
1 5

<210> SEQ ID NO 304
<211> LENGTH: 9
<212> TYPE: PRT
<213> ORGANISM: Mus musculus

<400> SEQUENCE: 304

Val Leu Asp Phe Ala Pro Pro Gly Ala
1 5

<210> SEQ ID NO 305
<211> LENGTH: 9
<212> TYPE: PRT
<213> ORGANISM: Mus musculus

<400> SEQUENCE: 305

Trp Asn Gln Met Asn Leu Gly Ala Thr
1 5

<210> SEQ ID NO 306
<211> LENGTH: 9

<212> TYPE: PRT
<213> ORGANISM: Mus musculus

<400> SEQUENCE: 306

Tyr Phe Lys Leu Ser His Leu Gln Met
1 5

<210> SEQ ID NO 307
<211> LENGTH: 9
<212> TYPE: PRT
<213> ORGANISM: Mus musculus

<400> SEQUENCE: 307

Tyr Gln Met Thr Ser Gln Leu Glu Cys
1 5

<210> SEQ ID NO 308
<211> LENGTH: 9
<212> TYPE: PRT
<213> ORGANISM: Mus musculus

<400> SEQUENCE: 308

Tyr Ser Ser Asp Asn Leu Tyr Gln Met
1 5

<210> SEQ ID NO 309
<211> LENGTH: 6
<212> TYPE: PRT
<213> ORGANISM: Homo sapien

<400> SEQUENCE: 309

Gly Ala Ala Gln Trp Ala
1 5

<210> SEQ ID NO 310
<211> LENGTH: 12
<212> TYPE: PRT
<213> ORGANISM: Homo sapien

<400> SEQUENCE: 310

Ala Ser Ala Tyr Gly Ser Leu Gly Gly Pro Ala Pro
1 5 10

<210> SEQ ID NO 311
<211> LENGTH: 15
<212> TYPE: PRT
<213> ORGANISM: Homo sapien

<400> SEQUENCE: 311

Ala Phe Thr Val His Phe Ser Gly Gln Phe Thr Gly Thr Ala Gly
1 5 10 15

<210> SEQ ID NO 312
<211> LENGTH: 5
<212> TYPE: PRT
<213> ORGANISM: Homo sapien

<400> SEQUENCE: 312

His Ala Ala Gln Phe
1 5

<210> SEQ ID NO 313
<211> LENGTH: 32
<212> TYPE: PRT
<213> ORGANISM: Homo sapien

<400> SEQUENCE: 313

Cys His Thr Pro Thr Asp Ser Cys Thr Gly Ser Gln Ala Leu Leu Leu
1 5 10 15

Arg Thr Pro Tyr Ser Ser Asp Asn Leu Tyr Gln Met Thr Ser Gln Leu
20 25 30

<210> SEQ ID NO 314
<211> LENGTH: 32
<212> TYPE: PRT
<213> ORGANISM: Homo sapien

<400> SEQUENCE: 314

Arg Ile His Thr His Gly Val Phe Arg Gly Ile Gln Asp Val Arg Arg
1 5 10 15

Val Pro Gly Val Ala Pro Thr Leu Val Arg Ser Ala Ser Glu Thr Ser
20 25 30

<210> SEQ ID NO 315
<211> LENGTH: 4
<212> TYPE: PRT
<213> ORGANISM: Homo sapien

<400> SEQUENCE: 315

Arg Tyr Phe Lys
1

<210> SEQ ID NO 316
<211> LENGTH: 14
<212> TYPE: PRT
<213> ORGANISM: Homo sapien

<400> SEQUENCE: 316

Glu Arg Arg Phe Ser Arg Ser Asp Gln Leu Lys Arg His Gln
1 5 10

<210> SEQ ID NO 317
<211> LENGTH: 22
<212> TYPE: PRT
<213> ORGANISM: Homo sapien

<400> SEQUENCE: 317

Gln Arg Lys Phe Ser Arg Ser Asp His Leu Lys Thr His Thr Arg Thr
1 5 10 15

His Thr Gly Lys Thr Ser
20

<210> SEQ ID NO 318
<211> LENGTH: 21
<212> TYPE: PRT
<213> ORGANISM: Homo sapien

<400> SEQUENCE: 318

Cys Gln Lys Lys Phe Ala Arg Ser Asp Glu Leu Val Arg His His Asn
1 5 10 15

Met His Gln Arg Asn
20

<210> SEQ ID NO 319
<211> LENGTH: 449
<212> TYPE: PRT
<213> ORGANISM: Homo sapien

<400> SEQUENCE: 319

```
Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Pro Ala Pro Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430
```

```
Arg His His Asn Met His Gln Arg Asn Met Thr Lys Leu Gln Leu Ala
        435                 440                 445

Leu


<210> SEQ ID NO 320
<211> LENGTH: 449
<212> TYPE: PRT
<213> ORGANISM: Mus musculus

<400> SEQUENCE: 320

Met Gly Ser Asp Val Arg Asp Leu Asn Ala Leu Leu Pro Ala Val Ser
 1               5                  10                  15

Ser Leu Gly Gly Gly Gly Gly Cys Gly Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Pro Ala Pro Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Leu His Phe
                85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Thr Ile
    130                 135                 140

Arg Asn Gln Gly Tyr Ser Thr Val Thr Phe Asp Gly Ala Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Met Ala Ala Gly Ser Ser Ser
                245                 250                 255

Ser Val Lys Trp Thr Glu Gly Gln Ser Asn His Gly Ile Gly Tyr Glu
            260                 265                 270

Ser Asp Asn His Thr Ala Pro Ile Leu Cys Gly Ala Gln Tyr Arg Ile
        275                 280                 285

His Thr His Gly Val Phe Arg Gly Ile Gln Asp Val Arg Arg Val Ser
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350
```

```
Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp His Ser Cys Gln Lys Lys Phe Ala Arg Ser Asp Glu Leu Val
            420                 425                 430

Arg His His Asn Met His Gln Arg Asn Met Thr Lys Leu His Val Ala
        435                 440                 445

Leu


<210> SEQ ID NO 321
<211> LENGTH: 9
<212> TYPE: PRT
<213> ORGANISM: Homo sapien and Mus musculus

<400> SEQUENCE: 321

Pro Ser Gln Ala Ser Ser Gly Gln Ala
 1               5


<210> SEQ ID NO 322
<211> LENGTH: 9
<212> TYPE: PRT
<213> ORGANISM: Homo sapien and Mus musculus

<400> SEQUENCE: 322

Ser Ser Gly Gln Ala Arg Met Phe Pro
 1               5


<210> SEQ ID NO 323
<211> LENGTH: 9
<212> TYPE: PRT
<213> ORGANISM: Homo sapien and Mus musculus

<400> SEQUENCE: 323

Gln Ala Arg Met Phe Pro Asn Ala Pro
 1               5


<210> SEQ ID NO 324
<211> LENGTH: 9
<212> TYPE: PRT
<213> ORGANISM: Homo sapien and Mus musculus

<400> SEQUENCE: 324

Met Phe Pro Asn Ala Pro Tyr Leu Pro
 1               5


<210> SEQ ID NO 325
<211> LENGTH: 9
<212> TYPE: PRT
<213> ORGANISM: Homo sapien and Mus musculus

<400> SEQUENCE: 325

Pro Asn Ala Pro Tyr Leu Pro Ser Cys
 1               5


<210> SEQ ID NO 326
<211> LENGTH: 9
<212> TYPE: PRT
<213> ORGANISM: Homo sapien and Mus musculus
```

<400> SEQUENCE: 326

Ala Pro Tyr Leu Pro Ser Cys Leu Glu
1 5

<210> SEQ ID NO 327
<211> LENGTH: 1029
<212> TYPE: DNA
<213> ORGANISM: Homo sapiens

<400> SEQUENCE: 327

```
atgcagcatc accaccatca ccacatgagc gataaaatta ttcacctgac tgacgacagt     60

tttgacacgg atgtactcaa agcggacggg gcgatcctcg tcgatttctg ggcagagtgg    120

tgcggtccgt gcaaaatgat cgccccgatt ctggatgaaa tcgctgacga atatcagggc    180

aaactgaccg ttgcaaaact gaacatcgat caaaaccctg gcactgcgcc gaaatatggc    240

atccgtggta tcccgactct gctgctgttc aaaaacggtg aagtggcggc aaccaaagtg    300

ggtgcactgt ctaaaggtca gttgaaagag ttcctcgacg ctaacctggc cggttctggt    360

tctggccata tgcagcatca ccaccatcac cacgtgtcta tcgaaggtcg tgctagctct    420

ggtggcagcg gtctggttcc gcgtggtagc tctggttcgg gggacgacga cgacaaatct    480

agtaggcaca gcacagggta cgagagcgat aaccacacaa cgcccatcct ctgcggagcc    540

caatacagaa tacacacgca cggtgtcttc agaggcattc aggatgtgcg acgtgtgcct    600

ggagtagccc cgactcttgt acggtcggca tctgagacca gtgagaaacg ccccttcatg    660

tgtgcttacc caggctgcaa taagagatat tttaagctgt cccacttaca gatgcacagc    720

aggaagcaca ctggtgagaa accataccag tgtgacttca aggactgtga acgaaggttt    780

tttcgttcag accagctcaa aagacaccaa aggagacata caggtgtgaa accattccag    840

tgtaaaactt gtcagcgaaa gttctcccgg tccgaccacc tgaagaccca caccaggact    900

catacaggtg aaaagccctt cagctgtcgg tggccaagtt gtcagaaaaa gtttgcccgg    960

tcagatgaat tagtccgcca tcacaacatg catcagagaa acatgaccaa actccagctg   1020

gcgctttga                                                           1029
```

<210> SEQ ID NO 328
<211> LENGTH: 1233
<212> TYPE: DNA
<213> ORGANISM: Homo sapiens

<400> SEQUENCE: 328

```
atgcagcatc accaccatca ccacatgagc gataaaatta ttcacctgac tgacgacagt     60

tttgacacgg atgtactcaa agcggacggg gcgatcctcg tcgatttctg ggcagagtgg    120

tgcggtccgt gcaaaatgat cgccccgatt ctggatgaaa tcgctgacga atatcagggc    180

aaactgaccg ttgcaaaact gaacatcgat caaaaccctg gcactgcgcc gaaatatggc    240

atccgtggta tcccgactct gctgctgttc aaaaacggtg aagtggcggc aaccaaagtg    300

ggtgcactgt ctaaaggtca gttgaaagag ttcctcgacg ctaacctggc cggttctggt    360

tctggccata tgcagcatca ccaccatcac cacgtgtcta tcgaaggtcg tgctagctct    420

ggtggcagcg gtctggttcc gcgtggtagc tctggttcgg gggacgacga cgacaaatct    480

agtaggggct ccgacgttcg tgacctgaac gcactgctgc cggcagttcc gtccctgggt    540

ggtggtggtg gttgcgcact gccggttagc ggtgcagcac agtgggctcc ggttctggac    600

ttcgcaccgc cgggtgcatc cgcatacggt tccctgggtg gtccggcacc gccgccggca    660
```

-continued

```
ccgccgccgc cgccgccgcc gccgccgcac tccttcatca aacaggaacc gagctggggt    720

ggtgcagaac cgcacgaaga acagtgcctg agcgcattca ccgttcactt ctccggccag    780

ttcactggca cagccggagc ctgtcgctac gggcccttcg gtcctcctcc gcccagccag    840

gcgtcatccg gccaggccag gatgtttcct aacgcgccct acctgcccag ctgcctcgag    900

agccagcccg ctattcgcaa tcagggttac agcacggtca ccttcgacgg gacgcccagc    960

tacggtcaca cgccctcgca ccatgcggcg cagttcccca accactcatt caagcatgag   1020

gatcccatgg gccagcaggg ctcgctgggt gagcagcagt actcggtgcc gcccccggtc   1080

tatggctgcc acacccccac cgacagctgc accggcagcc aggctttgct gctgaggacg   1140

ccctacagca gtgacaattt ataccaaatg acatcccagc ttgaatgcat gacctggaat   1200

cagatgaact taggagccac cttaaagggc tga                                1233
```

<210> SEQ ID NO 329
<211> LENGTH: 1776
<212> TYPE: DNA
<213> ORGANISM: Homo sapiens

<400> SEQUENCE: 329

```
atgcagcatc accaccatca ccacatgagc gataaaatta ttcacctgac tgacgacagt     60

tttgacacgg atgtactcaa agcggacggg gcgatcctcg tcgatttctg ggcagagtgg    120

tgcggtccgt gcaaaatgat cgccccgatt ctggatgaaa tcgctgacga atatcagggc    180

aaactgaccg ttgcaaaact gaacatcgat caaaaccctg gcactgcgcc gaaatatggc    240

atccgtggta tcccgactct gctgctgttc aaaaacggtg aagtggcggc aaccaaagtg    300

ggtgcactgt ctaaaggtca gttgaaagag ttcctcgacg ctaacctggc cggttctggt    360

tctggccata tgcagcatca ccaccatcac cacgtgtcta tcgaaggtcg tgctagctct    420

ggtggcagcg gtctggttcc gcgtggtagc tctggttcgg gggacgacga cgacaaatct    480

agtaggatgg gctccgacgt tcgtgacctg aacgcactgc tgccggcagt tccgtccctg    540

ggtggtggtg gtggttgcgc actgccggtt agcggtgcag cacagtgggc tccggttctg    600

gacttcgcac cgccgggtgc atccgcatac ggttccctgg gtggtccggc accgccgccg    660

gcaccgccgc cgccgccgcc gccgccgccg cactccttca tcaaacagga accgagctgg    720

ggtggtgcag aaccgcacga agaacagtgc ctgagcgcat tcaccgttca cttctccggc    780

cagttcactg gcacagccgg agcctgtcgc tacgggccct tcggtcctcc tccgcccagc    840

caggcgtcat ccggccaggc caggatgttt cctaacgcgc cctacctgcc cagctgcctc    900

gagagccagc ccgctattcg caatcagggt tacagcacgg tcaccttcga cgggacgccc    960

agctacggtc acacgccctc gcaccatgcg gcgcagttcc ccaaccactc attcaagcat   1020

gaggatccca tgggccagca gggctcgctg ggtgagcagc agtactcggt gccgcccccg   1080

gtctatggct gccacacccc caccgacagc tgcaccggca gccaggcttt gctgctgagg   1140

acgccctaca gcagtgacaa tttataccaa atgacatccc agcttgaatg catgacctgg   1200

aatcagatga acttaggagc caccttaaag ggccacagca cagggtacga gagcgataac   1260

cacacaacgc ccatcctctg cggagcccaa tacagaatac acacgcacgg tgtcttcaga   1320

ggcattcagg atgtgcgacg tgtgcctgga gtagccccga ctcttgtacg gtcggcatct   1380

gagaccagtg agaaacgccc cttcatgtgt gcttacccag gctgcaataa gagatatttt   1440

aagctgtccc acttacagat gcacagcagg aagcacactg gtgagaaacc ataccagtgt   1500

gacttcaagg actgtgaacg aaggtttttt cgttcagacc agctcaaaag acaccaaagg   1560
```

```
agacatacag gtgtgaaacc attccagtgt aaaacttgtc agcgaaagtt ctcccggtcc   1620

gaccacctga agacccacac caggactcat acaggtgaaa agcccttcag ctgtcggtgg   1680

ccaagttgtc agaaaaagtt tgcccggtca gatgaattag tccgccatca caacatgcat   1740

cagagaaaca tgaccaaact ccagctggcg ctttga                             1776
```

<210> SEQ ID NO 330
<211> LENGTH: 771
<212> TYPE: DNA
<213> ORGANISM: Homo sapiens

<400> SEQUENCE: 330

```
atgcagcatc accaccatca ccacggctcc gacgttcgtg acctgaacgc actgctgccg     60

gcagttccgt ccctgggtgg tggtggtggt tgcgcactgc cggttagcgg tgcagcacag    120

tgggctccgg ttctggactt cgcaccgccg ggtgcatccg catacggttc cctgggtggt    180

ccggcaccgc cgccggcacc gccgccgccg ccgccgccgc cgccgcactc cttcatcaaa    240

caggaaccga gctggggtgg tgcagaaccg cacgaagaac agtgcctgag cgcattcacc    300

gttcacttct ccggccagtt cactggcaca gccggagcct gtcgctacgg gcccttcggt    360

cctcctccgc ccagccaggc gtcatccggc caggccagga tgtttcctaa cgcgccctac    420

ctgcccagct gcctcgagag ccagcccgct attcgcaatc agggttacag cacggtcacc    480

ttcgacggga cgcccagcta cggtcacacg ccctcgcacc atgcggcgca gttccccaac    540

cactcattca agcatgagga tcccatgggc cagcagggct cgctgggtga gcagcagtac    600

tcggtgccgc ccccggtcta tggctgccac acccccaccg acagctgcac cggcagccag    660

gctttgctgc tgaggacgcc ctacagcagt gacaatttat accaaatgac atcccagctt    720

gaatgcatga cctggaatca gatgaactta ggagccacct taaagggctg a             771
```

<210> SEQ ID NO 331
<211> LENGTH: 567
<212> TYPE: DNA
<213> ORGANISM: Homo sapiens

<400> SEQUENCE: 331

```
atgcagcatc accaccatca ccaccacagc acagggtacg agagcgataa ccacacaacg     60

cccatcctct gcggagccca atacagaata cacacgcacg gtgtcttcag aggcattcag    120

gatgtgcgac gtgtgcctgg agtagccccg actcttgtac ggtcggcatc tgagaccagt    180

gagaaacgcc ccttcatgtg tgcttaccca ggctgcaata agagatattt taagctgtcc    240

cacttacaga tgcacagcag gaagcacact ggtgagaaac cataccagtg tgacttcaag    300

gactgtgaac gaaggttttt tcgttcagac cagctcaaaa gacaccaaag gagacataca    360

ggtgtgaaac cattccagtg taaaacttgt cagcgaaagt tctcccggtc cgaccacctg    420

aagacccaca ccaggactca tacaggtgaa aagcccttca gctgtcggtg gccaagttgt    480

cagaaaaagt ttgcccggtc agatgaatta gtccgccatc acaacatgca tcagagaaac    540

atgaccaaac tccagctggc gctttga                                        567
```

<210> SEQ ID NO 332
<211> LENGTH: 342
<212> TYPE: PRT
<213> ORGANISM: Homo sapiens

<400> SEQUENCE: 332

```
Met Gln His His His His His His Met Ser Asp Lys Ile Ile His Leu
                5                   10                  15
```

```
Thr Asp Asp Ser Phe Asp Thr Asp Val Leu Lys Ala Asp Gly Ala Ile
            20                  25                  30

Leu Val Asp Phe Trp Ala Glu Trp Cys Gly Pro Cys Lys Met Ile Ala
        35                  40                  45

Pro Ile Leu Asp Glu Ile Ala Asp Glu Tyr Gln Gly Lys Leu Thr Val
    50                  55                  60

Ala Lys Leu Asn Ile Asp Gln Asn Pro Gly Thr Ala Pro Lys Tyr Gly
65                  70                  75                  80

Ile Arg Gly Ile Pro Thr Leu Leu Leu Phe Lys Asn Gly Glu Val Ala
                85                  90                  95

Ala Thr Lys Val Gly Ala Leu Ser Lys Gly Gln Leu Lys Glu Phe Leu
            100                 105                 110

Asp Ala Asn Leu Ala Gly Ser Gly Ser Gly His Met Gln His His His
        115                 120                 125

His His His Val Ser Ile Glu Gly Arg Ala Ser Ser Gly Gly Ser Gly
    130                 135                 140

Leu Val Pro Arg Gly Ser Ser Gly Ser Gly Asp Asp Asp Asp Lys Ser
145                 150                 155                 160

Ser Arg His Ser Thr Gly Tyr Glu Ser Asp Asn His Thr Thr Pro Ile
                165                 170                 175

Leu Cys Gly Ala Gln Tyr Arg Ile His Thr His Gly Val Phe Arg Gly
            180                 185                 190

Ile Gln Asp Val Arg Arg Val Pro Gly Val Ala Pro Thr Leu Val Arg
        195                 200                 205

Ser Ala Ser Glu Thr Ser Glu Lys Arg Pro Phe Met Cys Ala Tyr Pro
    210                 215                 220

Gly Cys Asn Lys Arg Tyr Phe Lys Leu Ser His Leu Gln Met His Ser
225                 230                 235                 240

Arg Lys His Thr Gly Glu Lys Pro Tyr Gln Cys Asp Phe Lys Asp Cys
                245                 250                 255

Glu Arg Arg Phe Phe Arg Ser Asp Gln Leu Lys Arg His Gln Arg Arg
            260                 265                 270

His Thr Gly Val Lys Pro Phe Gln Cys Lys Thr Cys Gln Arg Lys Phe
        275                 280                 285

Ser Arg Ser Asp His Leu Lys Thr His Thr Arg Thr His Thr Gly Glu
    290                 295                 300

Lys Pro Phe Ser Cys Arg Trp Pro Ser Cys Gln Lys Lys Phe Ala Arg
305                 310                 315                 320

Ser Asp Glu Leu Val Arg His His Asn Met His Gln Arg Asn Met Thr
                325                 330                 335

Lys Leu Gln Leu Ala Leu
            340
```

<210> SEQ ID NO 333
<211> LENGTH: 410
<212> TYPE: PRT
<213> ORGANISM: Homo sapiens

<400> SEQUENCE: 333

```
Met Gln His His His His His His Met Ser Asp Lys Ile Ile His Leu
                5                   10                  15

Thr Asp Asp Ser Phe Asp Thr Asp Val Leu Lys Ala Asp Gly Ala Ile
            20                  25                  30

Leu Val Asp Phe Trp Ala Glu Trp Cys Gly Pro Cys Lys Met Ile Ala
        35                  40                  45
```

```
Pro Ile Leu Asp Glu Ile Ala Asp Glu Tyr Gln Gly Lys Leu Thr Val
    50                  55                  60

Ala Lys Leu Asn Ile Asp Gln Asn Pro Gly Thr Ala Pro Lys Tyr Gly
65                  70                  75                  80

Ile Arg Gly Ile Pro Thr Leu Leu Leu Phe Lys Asn Gly Glu Val Ala
                85                  90                  95

Ala Thr Lys Val Gly Ala Leu Ser Lys Gly Gln Leu Lys Glu Phe Leu
            100                 105                 110

Asp Ala Asn Leu Ala Gly Ser Gly Ser Gly His Met Gln His His His
        115                 120                 125

His His His Val Ser Ile Glu Gly Arg Ala Ser Ser Gly Gly Ser Gly
    130                 135                 140

Leu Val Pro Arg Gly Ser Ser Gly Ser Gly Asp Asp Asp Asp Lys Ser
145                 150                 155                 160

Ser Arg Gly Ser Asp Val Arg Asp Leu Asn Ala Leu Leu Pro Ala Val
                165                 170                 175

Pro Ser Leu Gly Gly Gly Gly Gly Cys Ala Leu Pro Val Ser Gly Ala
            180                 185                 190

Ala Gln Trp Ala Pro Val Leu Asp Phe Ala Pro Pro Gly Ala Ser Ala
        195                 200                 205

Tyr Gly Ser Leu Gly Gly Pro Ala Pro Pro Pro Ala Pro Pro Pro Pro
    210                 215                 220

Pro Pro Pro Pro Pro His Ser Phe Ile Lys Gln Glu Pro Ser Trp Gly
225                 230                 235                 240

Gly Ala Glu Pro His Glu Glu Gln Cys Leu Ser Ala Phe Thr Val His
                245                 250                 255

Phe Ser Gly Gln Phe Thr Gly Thr Ala Gly Ala Cys Arg Tyr Gly Pro
            260                 265                 270

Phe Gly Pro Pro Pro Pro Ser Gln Ala Ser Ser Gly Gln Ala Arg Met
        275                 280                 285

Phe Pro Asn Ala Pro Tyr Leu Pro Ser Cys Leu Glu Ser Gln Pro Ala
    290                 295                 300

Ile Arg Asn Gln Gly Tyr Ser Thr Val Thr Phe Asp Gly Thr Pro Ser
305                 310                 315                 320

Tyr Gly His Thr Pro Ser His His Ala Ala Gln Phe Pro Asn His Ser
                325                 330                 335

Phe Lys His Glu Asp Pro Met Gly Gln Gln Gly Ser Leu Gly Glu Gln
            340                 345                 350

Gln Tyr Ser Val Pro Pro Pro Val Tyr Gly Cys His Thr Pro Thr Asp
        355                 360                 365

Ser Cys Thr Gly Ser Gln Ala Leu Leu Leu Arg Thr Pro Tyr Ser Ser
    370                 375                 380

Asp Asn Leu Tyr Gln Met Thr Ser Gln Leu Glu Cys Met Thr Trp Asn
385                 390                 395                 400

Gln Met Asn Leu Gly Ala Thr Leu Lys Gly
                405                 410


<210> SEQ ID NO 334
<211> LENGTH: 591
<212> TYPE: PRT
<213> ORGANISM: Homo sapiens

<400> SEQUENCE: 334

Met Gln His His His His His His Met Ser Asp Lys Ile Ile His Leu
                5                   10                  15
```

```
Thr Asp Asp Ser Phe Asp Thr Asp Val Leu Lys Ala Asp Gly Ala Ile
            20                  25                  30

Leu Val Asp Phe Trp Ala Glu Trp Cys Gly Pro Cys Lys Met Ile Ala
        35                  40                  45

Pro Ile Leu Asp Glu Ile Ala Asp Glu Tyr Gln Gly Lys Leu Thr Val
    50                  55                  60

Ala Lys Leu Asn Ile Asp Gln Asn Pro Gly Thr Ala Pro Lys Tyr Gly
65                  70                  75                  80

Ile Arg Gly Ile Pro Thr Leu Leu Leu Phe Lys Asn Gly Glu Val Ala
                85                  90                  95

Ala Thr Lys Val Gly Ala Leu Ser Lys Gly Gln Leu Lys Glu Phe Leu
            100                 105                 110

Asp Ala Asn Leu Ala Gly Ser Gly Ser Gly His Met Gln His His His
        115                 120                 125

His His His Val Ser Ile Glu Gly Arg Ala Ser Ser Gly Gly Ser Gly
    130                 135                 140

Leu Val Pro Arg Gly Ser Ser Gly Ser Gly Asp Asp Asp Asp Lys Ser
145                 150                 155                 160

Ser Arg Met Gly Ser Asp Val Arg Asp Leu Asn Ala Leu Leu Pro Ala
                165                 170                 175

Val Pro Ser Leu Gly Gly Gly Gly Gly Cys Ala Leu Pro Val Ser Gly
            180                 185                 190

Ala Ala Gln Trp Ala Pro Val Leu Asp Phe Ala Pro Pro Gly Ala Ser
        195                 200                 205

Ala Tyr Gly Ser Leu Gly Gly Pro Ala Pro Pro Pro Ala Pro Pro Pro
    210                 215                 220

Pro Pro Pro Pro Pro Pro His Ser Phe Ile Lys Gln Glu Pro Ser Trp
225                 230                 235                 240

Gly Gly Ala Glu Pro His Glu Glu Gln Cys Leu Ser Ala Phe Thr Val
                245                 250                 255

His Phe Ser Gly Gln Phe Thr Gly Thr Ala Gly Ala Cys Arg Tyr Gly
            260                 265                 270

Pro Phe Gly Pro Pro Pro Pro Ser Gln Ala Ser Ser Gly Gln Ala Arg
        275                 280                 285

Met Phe Pro Asn Ala Pro Tyr Leu Pro Ser Cys Leu Glu Ser Gln Pro
    290                 295                 300

Ala Ile Arg Asn Gln Gly Tyr Ser Thr Val Thr Phe Asp Gly Thr Pro
305                 310                 315                 320

Ser Tyr Gly His Thr Pro Ser His His Ala Ala Gln Phe Pro Asn His
                325                 330                 335

Ser Phe Lys His Glu Asp Pro Met Gly Gln Gln Gly Ser Leu Gly Glu
            340                 345                 350

Gln Gln Tyr Ser Val Pro Pro Pro Val Tyr Gly Cys His Thr Pro Thr
        355                 360                 365

Asp Ser Cys Thr Gly Ser Gln Ala Leu Leu Leu Arg Thr Pro Tyr Ser
    370                 375                 380

Ser Asp Asn Leu Tyr Gln Met Thr Ser Gln Leu Glu Cys Met Thr Trp
385                 390                 395                 400

Asn Gln Met Asn Leu Gly Ala Thr Leu Lys Gly His Ser Thr Gly Tyr
                405                 410                 415

Glu Ser Asp Asn His Thr Thr Pro Ile Leu Cys Gly Ala Gln Tyr Arg
            420                 425                 430

Ile His Thr His Gly Val Phe Arg Gly Ile Gln Asp Val Arg Arg Val
```

```
        435                 440                 445

Pro Gly Val Ala Pro Thr Leu Val Arg Ser Ala Ser Glu Thr Ser Glu
    450                 455                 460

Lys Arg Pro Phe Met Cys Ala Tyr Pro Gly Cys Asn Lys Arg Tyr Phe
465                 470                 475                 480

Lys Leu Ser His Leu Gln Met His Ser Arg Lys His Thr Gly Glu Lys
                485                 490                 495

Pro Tyr Gln Cys Asp Phe Lys Asp Cys Glu Arg Arg Phe Phe Arg Ser
            500                 505                 510

Asp Gln Leu Lys Arg His Gln Arg Arg His Thr Gly Val Lys Pro Phe
        515                 520                 525

Gln Cys Lys Thr Cys Gln Arg Lys Phe Ser Arg Ser Asp His Leu Lys
    530                 535                 540

Thr His Thr Arg Thr His Thr Gly Glu Lys Pro Phe Ser Cys Arg Trp
545                 550                 555                 560

Pro Ser Cys Gln Lys Lys Phe Ala Arg Ser Asp Glu Leu Val Arg His
                565                 570                 575

His Asn Met His Gln Arg Asn Met Thr Lys Leu Gln Leu Ala Leu
            580                 585                 590


<210> SEQ ID NO 335
<211> LENGTH: 256
<212> TYPE: PRT
<213> ORGANISM: Homo sapiens

<400> SEQUENCE: 335

Met Gln His His His His His His Gly Ser Asp Val Arg Asp Leu Asn
                5                   10                  15

Ala Leu Leu Pro Ala Val Pro Ser Leu Gly Gly Gly Gly Gly Cys Ala
            20                  25                  30

Leu Pro Val Ser Gly Ala Ala Gln Trp Ala Pro Val Leu Asp Phe Ala
        35                  40                  45

Pro Pro Gly Ala Ser Ala Tyr Gly Ser Leu Gly Gly Pro Ala Pro Pro
    50                  55                  60

Pro Ala Pro Pro Pro Pro Pro Pro Pro Pro Pro His Ser Phe Ile Lys
65                  70                  75                  80

Gln Glu Pro Ser Trp Gly Gly Ala Glu Pro His Glu Glu Gln Cys Leu
                85                  90                  95

Ser Ala Phe Thr Val His Phe Ser Gly Gln Phe Thr Gly Thr Ala Gly
            100                 105                 110

Ala Cys Arg Tyr Gly Pro Phe Gly Pro Pro Pro Pro Ser Gln Ala Ser
        115                 120                 125

Ser Gly Gln Ala Arg Met Phe Pro Asn Ala Pro Tyr Leu Pro Ser Cys
    130                 135                 140

Leu Glu Ser Gln Pro Ala Ile Arg Asn Gln Gly Tyr Ser Thr Val Thr
145                 150                 155                 160

Phe Asp Gly Thr Pro Ser Tyr Gly His Thr Pro Ser His His Ala Ala
                165                 170                 175

Gln Phe Pro Asn His Ser Phe Lys His Glu Asp Pro Met Gly Gln Gln
            180                 185                 190

Gly Ser Leu Gly Glu Gln Gln Tyr Ser Val Pro Pro Pro Val Tyr Gly
        195                 200                 205

Cys His Thr Pro Thr Asp Ser Cys Thr Gly Ser Gln Ala Leu Leu Leu
    210                 215                 220

Arg Thr Pro Tyr Ser Ser Asp Asn Leu Tyr Gln Met Thr Ser Gln Leu
```

```
225                 230                 235                 240

Glu Cys Met Thr Trp Asn Gln Met Asn Leu Gly Ala Thr Leu Lys Gly
                245                 250                 255


<210> SEQ ID NO 336
<211> LENGTH: 188
<212> TYPE: PRT
<213> ORGANISM: Homo sapiens

<400> SEQUENCE: 336

Met Gln His His His His His His His Ser Thr Gly Tyr Glu Ser Asp
                5                   10                  15

Asn His Thr Thr Pro Ile Leu Cys Gly Ala Gln Tyr Arg Ile His Thr
            20                  25                  30

His Gly Val Phe Arg Gly Ile Gln Asp Val Arg Arg Val Pro Gly Val
        35                  40                  45

Ala Pro Thr Leu Val Arg Ser Ala Ser Glu Thr Ser Glu Lys Arg Pro
    50                  55                  60

Phe Met Cys Ala Tyr Pro Gly Cys Asn Lys Arg Tyr Phe Lys Leu Ser
65                  70                  75                  80

His Leu Gln Met His Ser Arg Lys His Thr Gly Glu Lys Pro Tyr Gln
                85                  90                  95

Cys Asp Phe Lys Asp Cys Glu Arg Arg Phe Phe Arg Ser Asp Gln Leu
            100                 105                 110

Lys Arg His Gln Arg Arg His Thr Gly Val Lys Pro Phe Gln Cys Lys
        115                 120                 125

Thr Cys Gln Arg Lys Phe Ser Arg Ser Asp His Leu Lys Thr His Thr
    130                 135                 140

Arg Thr His Thr Gly Glu Lys Pro Phe Ser Cys Arg Trp Pro Ser Cys
145                 150                 155                 160

Gln Lys Lys Phe Ala Arg Ser Asp Glu Leu Val Arg His His Asn Met
                165                 170                 175

His Gln Arg Asn Met Thr Lys Leu Gln Leu Ala Leu
            180                 185


<210> SEQ ID NO 337
<211> LENGTH: 324
<212> TYPE: DNA
<213> ORGANISM: Homo sapiens

<400> SEQUENCE: 337

atgcagcatc accaccatca ccacggttcc gacgtgcggg acctgaacgc actgctgccg     60

gcagttccat ccctgggtgg cggtggaggc tgcgcactgc cggttagcgg tgcagcacag    120

tgggctccag ttctggactt cgcaccgcct ggtgcatccg catacggttc cctgggtggt    180

ccagcacctc cgcccgcaac gcccccaccg cctccaccgc ccccgcactc cttcatcaaa    240

caggaaccta gctggggtgg tgcagaaccg cacgaagaac agtgcctgag cgcattctga    300

gaattctgca gatatccatc acac                                            324


<210> SEQ ID NO 338
<211> LENGTH: 462
<212> TYPE: DNA
<213> ORGANISM: Homo sapiens

<400> SEQUENCE: 338

atgcagcatc accaccatca ccaccacgaa gaacagtgcc tgagcgcatt caccgttcac     60

ttctccggcc agttcactgg cacagccgga gcctgtcgct acgggccctt cggtcctcct    120
```

```
ccgcccagcc aggcgtcatc cggccaggcc aggatgtttc ctaacgcgcc ctacctgccc    180

agctgcctcg agagccagcc cgctattcgc aatcagggtt acagcacggt caccttcgac    240

gggacgccca gctacggtca cacgccctcg caccatgcgg cgcagttccc caaccactca    300

ttcaagcatg aggatcccat gggccagcag ggctcgctgg gtgagcagca gtactcggtg    360

ccgcccccgg tctatggctg ccacaccccc accgacagct gcaccggcag ccaggctttg    420

ctgctgagga cgccctacag cagtgacaat ttatactgat ga                       462
```

<210> SEQ ID NO 339
<211> LENGTH: 405
<212> TYPE: DNA
<213> ORGANISM: Homo sapiens

<400> SEQUENCE: 339

```
atgcagcatc accaccatca ccaccaggct ttgctgctga ggacgcccta cagcagtgac     60

aatttatacc aaatgacatc ccagcttgaa tgcatgacct ggaatcagat gaacttagga    120

gccaccttaa agggccacag cacagggtac gagagcgata accacacaac gcccatcctc    180

tgcggagccc aatacagaat acacacgcac ggtgtcttca gaggcattca ggatgtgcga    240

cgtgtgcctg gagtagcccc gactcttgta cggtcggcat ctgagaccag tgagaaacgc    300

cccttcatgt gtgcttaccc aggctgcaat aagagatatt ttaagctgtc ccacttacag    360

atgcacagca ggaagcacac tggtgagaaa ccataccagt gatga                    405
```

<210> SEQ ID NO 340
<211> LENGTH: 339
<212> TYPE: DNA
<213> ORGANISM: Homo sapiens

<400> SEQUENCE: 340

```
atgcagcatc accaccatca ccaccacagc aggaagcaca ctggtgagaa accataccag     60

tgtgacttca aggactgtga acgaaggttt tttcgttcag accagctcaa aagacaccaa    120

aggagacata caggtgtgaa accattccag tgtaaaactt gtcagcgaaa gttctcccgg    180

tccgaccacc tgaagaccca caccaggact catacaggtg aaaagccctt cagctgtcgg    240

tggccaagtt gtcagaaaaa gtttgcccgg tcagatgaat tagtccgcca tcacaacatg    300

catcagagaa acatgaccaa actccagctg gcgctttga                           339
```

<210> SEQ ID NO 341
<211> LENGTH: 1110
<212> TYPE: DNA
<213> ORGANISM: Homo sapiens

<400> SEQUENCE: 341

```
atgcagcatc accaccatca ccaccactcc ttcatcaaac aggaaccgag ctggggtggt     60

gcagaaccgc acgaagaaca gtgcctgagc gcattcaccg ttcacttctc cggccagttc    120

actggcacag ccggagcctg tcgctacggg cccttcggtc ctcctccgcc cagccaggcg    180

tcatccggcc aggccaggat gtttcctaac gcgccctacc tgcccagctg cctcgagagc    240

cagcccgcta ttcgcaatca gggttacagc acggtcacct tcgacgggac gcccagctac    300

ggtcacacgc cctcgcacca tgcggcgcag ttccccaacc actcattcaa gcatgaggat    360

cccatgggcc agcagggctc gctgggtgag cagcagtact cggtgccgcc cccggtctat    420

ggctgccaca cccccaccga cagctgcacc ggcagccagg ctttgctgct gaggacgccc    480

tacagcagtg acaatttata ccaaatgaca tcccagcttg aatgcatgac ctggaatcag    540
```

```
atgaacttag gagccacctt aaagggccac agcacagggt acgagagcga taaccacaca    600
acgcccatcc tctgcggagc ccaatacaga atacacacgc acggtgtctt cagaggcatt    660
caggatgtgc gacgtgtgcc tggagtagcc ccgactcttg tacggtcggc atctgagacc    720
agtgagaaac gccccttcat gtgtgcttac ccaggctgca ataagagata ttttaagctg    780
tcccacttac agatgcacag caggaagcac actggtgaga aaccatacca gtgtgacttc    840
aaggactgtg aacgaaggtt ttttcgttca gaccagctca aaagacacca aaggagacat    900
acaggtgtga aaccattcca gtgtaaaact tgtcagcgaa agttctcccg gtccgaccac    960
ctgaagaccc acaccaggac tcatacaggt gaaaagccct tcagctgtcg gtggccaagt   1020
tgtcagaaaa agtttgcccg gtcagatgaa ttagtccgcc atcacaacat gcatcagaga   1080
aacatgacca aactccagct ggcgctttga                                    1110
```

```
<210> SEQ ID NO 342
<211> LENGTH: 99
<212> TYPE: PRT
<213> ORGANISM: Homo sapiens

<400> SEQUENCE: 342

Met Gln His His His His His His Gly Ser Asp Val Arg Asp Leu Asn
                5                   10                  15

Ala Leu Leu Pro Ala Val Pro Ser Leu Gly Gly Gly Gly Gly Cys Ala
            20                  25                  30

Leu Pro Val Ser Gly Ala Ala Gln Trp Ala Pro Val Leu Asp Phe Ala
        35                  40                  45

Pro Pro Gly Ala Ser Ala Tyr Gly Ser Leu Gly Gly Pro Ala Pro Pro
    50                  55                  60

Pro Ala Pro Pro Pro Pro Pro Pro Pro Pro Pro His Ser Phe Ile Lys
65                  70                  75                  80

Gln Glu Pro Ser Trp Gly Gly Ala Glu Pro His Glu Glu Gln Cys Leu
                85                  90                  95

Ser Ala Phe


<210> SEQ ID NO 343
<211> LENGTH: 152
<212> TYPE: PRT
<213> ORGANISM: Homo sapiens

<400> SEQUENCE: 343

Met Gln His His His His His His His Glu Glu Gln Cys Leu Ser Ala
                5                   10                  15

Phe Thr Val His Phe Ser Gly Gln Phe Thr Gly Thr Ala Gly Ala Cys
            20                  25                  30

Arg Tyr Gly Pro Phe Gly Pro Pro Pro Pro Ser Gln Ala Ser Ser Gly
        35                  40                  45

Gln Ala Arg Met Phe Pro Asn Ala Pro Tyr Leu Pro Ser Cys Leu Glu
    50                  55                  60

Ser Gln Pro Ala Ile Arg Asn Gln Gly Tyr Ser Thr Val Thr Phe Asp
65                  70                  75                  80

Gly Thr Pro Ser Tyr Gly His Thr Pro Ser His His Ala Ala Gln Phe
                85                  90                  95

Pro Asn His Ser Phe Lys His Glu Asp Pro Met Gly Gln Gln Gly Ser
            100                 105                 110

Leu Gly Glu Gln Gln Tyr Ser Val Pro Pro Pro Val Tyr Gly Cys His
        115                 120                 125
```

```
Thr Pro Thr Asp Ser Cys Thr Gly Ser Gln Ala Leu Leu Leu Arg Thr
    130                 135                 140

Pro Tyr Ser Ser Asp Asn Leu Tyr
145                 150


<210> SEQ ID NO 344
<211> LENGTH: 133
<212> TYPE: PRT
<213> ORGANISM: Homo sapiens

<400> SEQUENCE: 344

Met Gln His His His His His His Gln Ala Leu Leu Leu Arg Thr Pro
                5                   10                  15

Tyr Ser Ser Asp Asn Leu Tyr Gln Met Thr Ser Gln Leu Glu Cys Met
            20                  25                  30

Thr Trp Asn Gln Met Asn Leu Gly Ala Thr Leu Lys Gly His Ser Thr
        35                  40                  45

Gly Tyr Glu Ser Asp Asn His Thr Thr Pro Ile Leu Cys Gly Ala Gln
    50                  55                  60

Tyr Arg Ile His Thr His Gly Val Phe Arg Gly Ile Gln Asp Val Arg
65                  70                  75                  80

Arg Val Pro Gly Val Ala Pro Thr Leu Val Arg Ser Ala Ser Glu Thr
                85                  90                  95

Ser Glu Lys Arg Pro Phe Met Cys Ala Tyr Pro Gly Cys Asn Lys Arg
            100                 105                 110

Tyr Phe Lys Leu Ser His Leu Gln Met His Ser Arg Lys His Thr Gly
        115                 120                 125

Glu Lys Pro Tyr Gln
    130


<210> SEQ ID NO 345
<211> LENGTH: 112
<212> TYPE: PRT
<213> ORGANISM: Homo sapiens

<400> SEQUENCE: 345

Met Gln His His His His His His His Ser Arg Lys His Thr Gly Glu
                5                   10                  15

Lys Pro Tyr Gln Cys Asp Phe Lys Asp Cys Glu Arg Arg Phe Phe Arg
            20                  25                  30

Ser Asp Gln Leu Lys Arg His Gln Arg Arg His Thr Gly Val Lys Pro
        35                  40                  45

Phe Gln Cys Lys Thr Cys Gln Arg Lys Phe Ser Arg Ser Asp His Leu
    50                  55                  60

Lys Thr His Thr Arg Thr His Thr Gly Glu Lys Pro Phe Ser Cys Arg
65                  70                  75                  80

Trp Pro Ser Cys Gln Lys Lys Phe Ala Arg Ser Asp Glu Leu Val Arg
                85                  90                  95

His His Asn Met His Gln Arg Asn Met Thr Lys Leu Gln Leu Ala Leu
            100                 105                 110


<210> SEQ ID NO 346
<211> LENGTH: 369
<212> TYPE: PRT
<213> ORGANISM: Homo sapiens

<400> SEQUENCE: 346

Met Gln His His His His His His His Ser Phe Ile Lys Gln Glu Pro
```

```
                5                   10                  15

Ser Trp Gly Gly Ala Glu Pro His Glu Glu Gln Cys Leu Ser Ala Phe
            20                  25                  30

Thr Val His Phe Ser Gly Gln Phe Thr Gly Thr Ala Gly Ala Cys Arg
        35                  40                  45

Tyr Gly Pro Phe Gly Pro Pro Pro Pro Ser Gln Ala Ser Ser Gly Gln
    50                  55                  60

Ala Arg Met Phe Pro Asn Ala Pro Tyr Leu Pro Ser Cys Leu Glu Ser
65                  70                  75                  80

Gln Pro Ala Ile Arg Asn Gln Gly Tyr Ser Thr Val Thr Phe Asp Gly
                85                  90                  95

Thr Pro Ser Tyr Gly His Thr Pro Ser His His Ala Ala Gln Phe Pro
            100                 105                 110

Asn His Ser Phe Lys His Glu Asp Pro Met Gly Gln Gln Gly Ser Leu
        115                 120                 125

Gly Glu Gln Gln Tyr Ser Val Pro Pro Pro Val Tyr Gly Cys His Thr
    130                 135                 140

Pro Thr Asp Ser Cys Thr Gly Ser Gln Ala Leu Leu Leu Arg Thr Pro
145                 150                 155                 160

Tyr Ser Ser Asp Asn Leu Tyr Gln Met Thr Ser Gln Leu Glu Cys Met
                165                 170                 175

Thr Trp Asn Gln Met Asn Leu Gly Ala Thr Leu Lys Gly His Ser Thr
            180                 185                 190

Gly Tyr Glu Ser Asp Asn His Thr Thr Pro Ile Leu Cys Gly Ala Gln
        195                 200                 205

Tyr Arg Ile His Thr His Gly Val Phe Arg Gly Ile Gln Asp Val Arg
    210                 215                 220

Arg Val Pro Gly Val Ala Pro Thr Leu Val Arg Ser Ala Ser Glu Thr
225                 230                 235                 240

Ser Glu Lys Arg Pro Phe Met Cys Ala Tyr Pro Gly Cys Asn Lys Arg
                245                 250                 255

Tyr Phe Lys Leu Ser His Leu Gln Met His Ser Arg Lys His Thr Gly
            260                 265                 270

Glu Lys Pro Tyr Gln Cys Asp Phe Lys Asp Cys Glu Arg Arg Phe Phe
        275                 280                 285

Arg Ser Asp Gln Leu Lys Arg His Gln Arg Arg His Thr Gly Val Lys
    290                 295                 300

Pro Phe Gln Cys Lys Thr Cys Gln Arg Lys Phe Ser Arg Ser Asp His
305                 310                 315                 320

Leu Lys Thr His Thr Arg Thr His Thr Gly Glu Lys Pro Phe Ser Cys
                325                 330                 335

Arg Trp Pro Ser Cys Gln Lys Lys Phe Ala Arg Ser Asp Glu Leu Val
            340                 345                 350

Arg His His Asn Met His Gln Arg Asn Met Thr Lys Leu Gln Leu Ala
        355                 360                 365

Leu
```

<210> SEQ ID NO 347
<211> LENGTH: 21
<212> TYPE: DNA
<213> ORGANISM: Artificial Sequence
<220> FEATURE:
<223> OTHER INFORMATION: Sense primer

<400> SEQUENCE: 347
ggctccgacg tgcgggacct g 21

<210> SEQ ID NO 348
<211> LENGTH: 30
<212> TYPE: DNA
<213> ORGANISM: Artificial Sequence
<220> FEATURE:
<223> OTHER INFORMATION: Anti-sense Primer

<400> SEQUENCE: 348
gaattctcaa agcgccagct ggagtttggt 30

<210> SEQ ID NO 349
<211> LENGTH: 21
<212> TYPE: DNA
<213> ORGANISM: Artificial Sequence
<220> FEATURE:
<223> OTHER INFORMATION: Sense Primer

<400> SEQUENCE: 349
ggctccgacg tgcgggacct g 21

<210> SEQ ID NO 350
<211> LENGTH: 30
<212> TYPE: DNA
<213> ORGANISM: Artificial Sequence
<220> FEATURE:
<223> OTHER INFORMATION: Anti-sense Primer

<400> SEQUENCE: 350
gaattctcaa agcgccagct ggagtttggt 30

<210> SEQ ID NO 351
<211> LENGTH: 21
<212> TYPE: DNA
<213> ORGANISM: Artificial Sequence
<220> FEATURE:
<223> OTHER INFORMATION: Sense Primer

<400> SEQUENCE: 351
cacagcacag ggtacgagag c 21

<210> SEQ ID NO 352
<211> LENGTH: 30
<212> TYPE: DNA
<213> ORGANISM: Artificial Sequence
<220> FEATURE:
<223> OTHER INFORMATION: Anti-sense Primer

<400> SEQUENCE: 352
gaattctcaa agcgccagct ggagtttggt 30

<210> SEQ ID NO 353
<211> LENGTH: 29
<212> TYPE: DNA
<213> ORGANISM: Artificial Sequence
<220> FEATURE:
<223> OTHER INFORMATION: PCR Primer

<400> SEQUENCE: 353
cacgaagaac agtgcctgag cgcattcac 29

<210> SEQ ID NO 354
<211> LENGTH: 32
<212> TYPE: DNA
<213> ORGANISM: Artificial Sequence
<220> FEATURE:

<223> OTHER INFORMATION: PCR Primer

<400> SEQUENCE: 354
ccggcgaatt catcagtata aattgtcact gc 32

<210> SEQ ID NO 355
<211> LENGTH: 24
<212> TYPE: DNA
<213> ORGANISM: Artificial Sequence
<220> FEATURE:
<223> OTHER INFORMATION: PCR Primer

<400> SEQUENCE: 355
caggctttgc tgctgaggac gccc 24

<210> SEQ ID NO 356
<211> LENGTH: 34
<212> TYPE: DNA
<213> ORGANISM: Artificial Sequence
<220> FEATURE:
<223> OTHER INFORMATION: PCR Primer

<400> SEQUENCE: 356
cacggagaat tcatcactgg tatggtttct cacc 34

<210> SEQ ID NO 357
<211> LENGTH: 28
<212> TYPE: DNA
<213> ORGANISM: Artificial Sequence
<220> FEATURE:
<223> OTHER INFORMATION: PCR Primer

<400> SEQUENCE: 357
cacagcagga agcacactgg tgagaaac 28

<210> SEQ ID NO 358
<211> LENGTH: 30
<212> TYPE: DNA
<213> ORGANISM: Artificial Sequence
<220> FEATURE:
<223> OTHER INFORMATION: PCR Primer

<400> SEQUENCE: 358
ggatatctgc agaattctca aagcgccagc 30

<210> SEQ ID NO 359
<211> LENGTH: 22
<212> TYPE: DNA
<213> ORGANISM: Artificial Sequence
<220> FEATURE:
<223> OTHER INFORMATION: PCR Primer

<400> SEQUENCE: 359
cactccttca tcaaacagga ac 22

<210> SEQ ID NO 360
<211> LENGTH: 30
<212> TYPE: DNA
<213> ORGANISM: Artificial Sequence
<220> FEATURE:
<223> OTHER INFORMATION: PCR Primer

<400> SEQUENCE: 360
ggatatctgc agaattctca aagcgccagc 30

<210> SEQ ID NO 361

<211> LENGTH: 33
<212> TYPE: DNA
<213> ORGANISM: Artificial Sequence
<220> FEATURE:
<223> OTHER INFORMATION: Oligonucleotide

<400> SEQUENCE: 361
ggttccgacg tgcgggacct gaacgcactg ctg 33

<210> SEQ ID NO 362
<211> LENGTH: 40
<212> TYPE: DNA
<213> ORGANISM: Artificial Sequence
<220> FEATURE:
<223> OTHER INFORMATION: Oligonucleotide

<400> SEQUENCE: 362
ctgccggcag cagtgcgttc aggtcccgca cgtcggaacc 40

<210> SEQ ID NO 363
<211> LENGTH: 35
<212> TYPE: DNA
<213> ORGANISM: Artificial Sequence
<220> FEATURE:
<223> OTHER INFORMATION: Oligonucleotide

<400> SEQUENCE: 363
ccggcagttc catccctggg tggcggtgga ggctg 35

<210> SEQ ID NO 364
<211> LENGTH: 38
<212> TYPE: DNA
<213> ORGANISM: Artificial Sequence
<220> FEATURE:
<223> OTHER INFORMATION: Oligonucleotide

<400> SEQUENCE: 364
cggcagtgcg cagcctccac cgccacccag ggatggaa 38

<210> SEQ ID NO 365
<211> LENGTH: 35
<212> TYPE: DNA
<213> ORGANISM: Artificial Sequence
<220> FEATURE:
<223> OTHER INFORMATION: Oligonucleotide

<400> SEQUENCE: 365
cgcactgccg gttagcggtg cagcacagtg ggctc 35

<210> SEQ ID NO 366
<211> LENGTH: 33
<212> TYPE: DNA
<213> ORGANISM: Artificial Sequence
<220> FEATURE:
<223> OTHER INFORMATION: Oligonucleotide

<400> SEQUENCE: 366
cagaactgga gcccactgtg ctgcaccgct aac 33

<210> SEQ ID NO 367
<211> LENGTH: 38
<212> TYPE: DNA
<213> ORGANISM: Artificial Sequence
<220> FEATURE:
<223> OTHER INFORMATION: Oligonucleotide

<400> SEQUENCE: 367
cagttctgga cttcgcaccg cctggtgcat ccgcatac 38

<210> SEQ ID NO 368
<211> LENGTH: 39
<212> TYPE: DNA
<213> ORGANISM: Artificial Sequence
<220> FEATURE:
<223> OTHER INFORMATION: Oligonucleotide

<400> SEQUENCE: 368
cagggaaccg tatgcggatg caccaggcgg tgcgaagtc 39

<210> SEQ ID NO 369
<211> LENGTH: 38
<212> TYPE: DNA
<213> ORGANISM: Artificial Sequence
<220> FEATURE:
<223> OTHER INFORMATION: Oligonucleotide

<400> SEQUENCE: 369
ggttccctgg gtggtccagc acctccgccc gcaacgcc 38

<210> SEQ ID NO 370
<211> LENGTH: 38
<212> TYPE: DNA
<213> ORGANISM: Artificial Sequence
<220> FEATURE:
<223> OTHER INFORMATION: Oligonucleotide

<400> SEQUENCE: 370
ggcggtgggg gcgttgcggg cggaggtgct ggaccacc 38

<210> SEQ ID NO 371
<211> LENGTH: 40
<212> TYPE: DNA
<213> ORGANISM: Artificial Sequence
<220> FEATURE:
<223> OTHER INFORMATION: Oligonucleotide

<400> SEQUENCE: 371
cccaccgcct ccaccgcccc cgcactcctt catcaaacag 40

<210> SEQ ID NO 372
<211> LENGTH: 39
<212> TYPE: DNA
<213> ORGANISM: Artificial Sequence
<220> FEATURE:
<223> OTHER INFORMATION: Oligonucleotide

<400> SEQUENCE: 372
ctaggttcct gtttgatgaa ggagtgcggg ggcggtgga 39

<210> SEQ ID NO 373
<211> LENGTH: 38
<212> TYPE: DNA
<213> ORGANISM: Artificial Sequence
<220> FEATURE:
<223> OTHER INFORMATION: Oligonucleotide

<400> SEQUENCE: 373
gaacctagct ggggtggtgc agaaccgcac gaagaaca 38

<210> SEQ ID NO 374
<211> LENGTH: 39
<212> TYPE: DNA
<213> ORGANISM: Artificial Sequence
<220> FEATURE:

<223> OTHER INFORMATION: Oligonucleotide

<400> SEQUENCE: 374
ctcaggcact gttcttcgtg cggttctgca ccaccccag 39

<210> SEQ ID NO 375
<211> LENGTH: 32
<212> TYPE: DNA
<213> ORGANISM: Artificial Sequence
<220> FEATURE:
<223> OTHER INFORMATION: Oligonucleotide

<400> SEQUENCE: 375
gtgcctgagc gcattctgag aattctgcag at 32

<210> SEQ ID NO 376
<211> LENGTH: 34
<212> TYPE: DNA
<213> ORGANISM: Artificial Sequence
<220> FEATURE:
<223> OTHER INFORMATION: Oligonucleotide

<400> SEQUENCE: 376
gtgtgatgga tatctgcaga attctcagaa tgcg 34

<210> SEQ ID NO 377
<211> LENGTH: 1292
<212> TYPE: DNA
<213> ORGANISM: Homo sapiens
<220> FEATURE:
<221> NAME/KEY: misc_feature
<222> LOCATION: 253,256,517,518,520,521,522,743,753,754,
758
<223> OTHER INFORMATION: n = A,T,C or G

<400> SEQUENCE: 377
atgggctccg acgttcgtga cctgagcgcg ctgctgccgg cagttccgtc cctgggtgat 60
ggtggtggtt gcgcactgcc ggttagcggt gcagcacagt gggctccggt tctggacttc 120
gcaccgccgg gtgcatccgc acacggtccc ctgggtggtc cggcgccgcc gtcggcaccg 180
ccgccgccgc cgccgccgcc gccgcactcc ttcatcaaac agggaccgag ctggggtggc 240
gcggaactgc ackaakaaca gtacctgagc gcgttcaccg ttcactcctc cggtcaggtt 300
cactggcacg gccggggcct gtcgctacgg gcccctcggc ccccctccgc ccagccaggc 360
gtcatccggc caggccagga tgtctcctag cgcgccctgc ctgcccagcc gcctcgagag 420
ccagcccgct acccgcaatc ggggctacag cacggtcacc ttcgacgggg cgtccggcta 480
cggtcacacg ccctcgcacc atgcggcgca gttctcsmar yyactcgtta ggcgtgagga 540
tcccatgggc cagcagggtc cgctgggtga gcagcagtgc tcggcgccgc ccccggcctg 600
tggccgccac acccccgccg acagctgcgc cggcagccag gctttgctgc tgagggcgcc 660
ctgtagcagc gacggtttat accaagtgac gtcccagctt gagtgcatgg cctggagtca 720
gatgagcctc ggggccgcct tamcgggcca cakyacargg tacgagagcg atgatcacac 780
aacgcccggc ctctgcggag cccaatacag aatacacacg cacggtgcct tcaggggcgt 840
tcagggtgtg cgccgtgtgc ctggagtagc cccgactctt gtacggtcgg catctgaggc 900
cagtgaggaa cgccccctca tgtgtgctta cccaggctgc aataggaggt atctgaagct 960
gccccgctta cagatgcacg gtaggaagca cgctggtgag agaccatacc agtgtgactt 1020
caaggactgt ggacggaggt tttctgctc agaccggctc aaaagacacc aggggaggca 1080
tacagatgtg aagccattcc agcgtaagac ctgtcagcga gggttctccc ggcccaacca 1140

```
cctgaagacc cacgccagga ctcatgcagg tgaaaagccc cccagctgtc ggtggtcaga   1200

ttgtcagaga aagcctgccc ggtcaagtga gttggtccgc catcgcgaca tgcatcagag   1260

gggcatgacc gaactccagc tggcgctttg aa                                 1292
```

<210> SEQ ID NO 378
<211> LENGTH: 1291
<212> TYPE: DNA
<213> ORGANISM: Homo sapiens

<400> SEQUENCE: 378

```
atgggctccg acgttcgtga cctaaacgca ctgctgccgg cagttccgtc cccgggtggt     60

ggtggtggtt gcgcactgcc ggttagcggt gcaacacagt gggctccggt tctggacttc    120

gtaccgccgg gtgcgcctgt atgcggttcc ctgggtggcc cggcaccgcc gccagcgccg    180

ccgccgctgc cgccgccgcc gtcgcactcc ttcaccaaac aggaaccgag ttggggtggt    240

acagagccgc acgcaggaca gggccggagc gcactcgtcg ctcactcctc cggccagttc    300

actggcacag ccggagcctg tcgctacggg ccccttcggtc ctcctccgcc cagccaggcg    360

tcatccggcc aggccaggat gtttcctaac gcgccctacc tgcccagctg cctcgagagc    420

cagcccgcta ttcgcaatca gggttacagc acggtcacct tcgacgggac gcccagctac    480

ggtcacacgc cctcgcacca tgcggcgcag ttccccaacc actcatccaa gcatgaggac    540

cccatgggcc agcagggctc gccgggtgag cagcagtact cggcgccgcc cccggtctgc    600

ggctgccgca cccccaccgg cagctgcacc ggcagccagg ctttgctgct gagggcgccc    660

tacagcggtg gcgatctaca ccaaacgaca tcccagcttg gacacatggc ctggaatcag    720

acgaacttag gagccacctt aaagggccac ggcacagggt acgagagcga tgaccacaca    780

acgcccatcc tctgcggaac ccagtacagg atacgcgcgc gcggcgtcct ccggggtact    840

caggatgtgc ggtgtgtgcc tggggtggcc ccgactcttg tgcggtcggc atctgagacc    900

agtgagaagc gccccctcat gtgtgcctac ccaggctgca ataagagaca ctttaagccg    960

tcccgcttgc gggtgcgcgg cagggagcgc actggtgaga aaccatacca gcgcgacttc   1020

aaggaccgtg gacgagggct tctccgtcca gaccagctca aaaggcacca gagggggcat   1080

acaggtgtga aacctctcca gtgtgaagct tgacggcgga ggccccccccg acccggccac   1140

ctgaaggtcc acaccaggac ccatacaggt ggagagccct tcagttgtcg gtggccaagt   1200

tgtcaggaga agtctgcccg gccagatgaa tcagcccgcc gtcataacat gcatcagaga   1260

aacatgacca aactccagct ggcgctttga a                                  1291
```

<210> SEQ ID NO 379
<211> LENGTH: 1281
<212> TYPE: DNA
<213> ORGANISM: Homo sapiens

<400> SEQUENCE: 379

```
atgggctccg acgttcgtga cctgagtgca ttgctaccga cggccccgtc cctgggtggt     60

ggcggtgact gcacactgcc ggttagcggt acagcacagt gggctccggt cccggcctcc    120

gcaccgccgg gcgcatccgc atacgattcc ctgggtggcc cggcaccgcc gccggcgccg    180

ccgccgccgc cgccgccgcc gccgcactcc tgcggcgaac aggggccgag ctggggtggt    240

gcagaaccgc gcgaggggca atgcctgagt gcgcccgccg tccgcttctc cggccggttc    300

accggcacag tcggagcctg tcgctatggg cccctcggtc ctcctccgcc cagccaggcg    360

ccatccggcc agaccaggat gttgcccagc gcgccctatc tgtcgagttg cctcaggagc    420
```

```
cggtccgcta tccgtagtca gggtcgcagc acggcacctt cagcggggcg cccagctatg    480

gcacccaccc tcgcaccacc ggcgcagtcc cactactccc aacatggggt cctacatggg    540

ccagcagggc tcgctgggtg agcagcagta ctcggtgccg cccccggtct atggctgcca    600

cacccccacc gacagctgca ccggcagcca ggctttgctg ctgaggacgc cctacagcag    660

tgacaattta taccaaatga catcccagct tgaatgcatg acctggaatc agatgaactt    720

aggagccacc ttaaagggcc acagcacagg gtacgagagc gataaccaca caacgcccat    780

cctctgcgga gcccaataca gaatacacac gcacggtgtc ttcagaggca ttcaggatgt    840

gcgacgtgtg cctggagtag ccccgactct tgtacggtag cacctgagac cagtgagaac    900

gcccccttggt gtgtgttacc ggggctgcag taaggggtat tttaagccgt cccacttacg    960

ggtgcacagc aggaagcgca ttggtgagac gccacgccag tgcgactcca agggccgtgg   1020

acgagggcct ctccgttcgg gaccagccca agggacacca aaggagacat acaggtacgc   1080

aaccactcca gtgtaaggct tgtcagcgaa ggttcccccg gtccgaccac ctgagggccc   1140

acgccagggc ccacacgggt gggaagcccc tcagctgccg gtggccaagc tgccagagag   1200

ggttcgccca gtcagacgaa ttagtccgtc atcacaacat gtatcagcga aacatgacta   1260

aactccagct ggcgctttga a                                              1281
```

```
<210> SEQ ID NO 380
<211> LENGTH: 3020
<212> TYPE: DNA
<213> ORGANISM: Homo sapiens

<400> SEQUENCE: 380

gttcaaggca gcgcccacac ccgggggctc tccgcaaccc gaccgcctgt ccgctccccc     60

acttcccgcc ctccctccca cctactcatt cacccaccca cccacccaga gccgggacgg    120

cagcccaggc gcccgggccc cgccgtctcc tcgccgcgat cctggacttc ctcttgctgc    180

aggacccggc ttccacgtgt gtcccggagc cggcgtctca gcacacgctc cgctccgggc    240

ctgggtgcct acagcagcca gagcagcagg gagtccggga cccgggcggc atctgggcca    300

agttaggcgc cgccgaggcc agcgctgaac gtctccaggg ccggaggagc cgcggggcgt    360

ccgggtctga gcctcagcaa atgggctccg acgtgcggga cctgaacgcg ctgctgcccg    420

ccgtcccctc cctgggtggc ggcggcggct gtgccctgcc tgtgagcggc gcggcgcagt    480

gggcgccggt gctggacttt gcgcccccgg gcgcttcggc ttacgggtcg ttgggcggcc    540

ccgcgccgcc accggctccg ccgccacccc cgccgccgcc gcctcactcc ttcatcaaac    600

aggagccgag ctggggcggc gcggagccgc acgaggagca gtgcctgagc gccttcactg    660

tccacttttc cggccagttc actggcacag ccggagcctg tcgctacggg cccttcggtc    720

ctcctccgcc cagccaggcg tcatccggcc aggccaggat gtttcctaac gcgccctacc    780

tgcccagctg cctcgagagc cagcccgcta ttcgcaatca gggttacagc acggtcacct    840

tcgacgggac gcccagctac ggtcacacgc cctcgcacca tgcggcgcag ttccccaacc    900

actcattcaa gcatgaggat cccatgggcc agcagggctc gctgggtgag cagcagtact    960

cggtgccgcc cccggtctat ggctgccaca cccccaccga cagctgcacc ggcagccagg   1020

ctttgctgct gaggacgccc tacagcagtg acaatttata ccaaatgaca tcccagcttg   1080

aatgcatgac ctggaatcag atgaacttag gagccacctt aaagggagtt gctgctggga   1140

gctccagctc agtgaaatgg acagaagggc agagcaacca cagcacaggg tacgagagcg   1200

ataaccacac aacgcccatc ctctgcggag cccaatacag aatacacacg cacggtgtct   1260
```

```
tcagaggcat tcaggatgtg cgacgtgtgc ctggagtagc cccgactctt gtacggtcgg   1320
catctgagac cagtgagaaa cgccccttca tgtgtgctta cccaggctgc aataagagat   1380
attttaagct gtcccactta cagatgcaca gcaggaagca cactggtgag aaaccatacc   1440
agtgtgactt caaggactgt gaacgaaggt tttctcgttc agaccagctc aaaagacacc   1500
aaaggagaca tacaggtgtg aaaccattcc agtgtaaaac ttgtcagcga aagttctccc   1560
ggtccgacca cctgaagacc cacaccagga ctcatacagg taaaacaagt gaaaagccct   1620
tcagctgtcg gtggccaagt tgtcagaaaa agtttgcccg gtcagatgaa ttagtccgcc   1680
atcacaacat gcatcagaga aacatgacca aactccagct ggcgctttga ggggtctccc   1740
tcggggaccg ttcagtgtcc caggcagcac agtgtgtgaa ctgctttcaa gtctgactct   1800
ccactcctcc tcactaaaaa ggaaacttca gttgatcttc ttcatccaac ttccaagaca   1860
agataccggt gcttctggaa actaccaggt gtgcctggaa gagttggtct ctgccctgcc   1920
tacttttagt tgactcacag gccctggaga agcagctaac aatgtctggt tagttaaaag   1980
cccattgcca tttggtctgg attttctact gtaagaagag ccatagctga tcatgtcccc   2040
ctgacccttc ccttcttttt ttatgctcgt tttcgctggg gatggaatta ttgtaccatt   2100
ttctatcatg gaatatttat aggccagggc atgtgtatgt gtctgctaat gtaaactttg   2160
tcatggtttc catttactaa cagcaacagc aagaaataaa tcagagagca aggcatcggg   2220
ggtgaatctt gtctaacatt cccgaggtca gccaggctgc taacctggaa agcaggatgt   2280
agttctgcca ggcaactttt aaagctcatg catttcaagc agctgaagaa agaatcagaa   2340
ctaaccagta cctctgtata gaaatctaaa agaattttac cattcagtta attcaatgtg   2400
aacactggca cactgctctt aagaaactat gaagatctga gattttttttg tgtatgtttt   2460
tgactctttt gagtggtaat catatgtgtc tttatagatg tacatacctc cttgcacaaa   2520
tggaggggaa ttcattttca tcactgggac tgtccttagt gtataaaaac catgctggta   2580
tatggcttca agttgtaaaa atgaaagtga ctttaaaaga aaatagggga tggtccagga   2640
tctccactga taagactgtt tttaagtaac ttaaggacct ttgggtctac aagtatatgt   2700
gaaaaaaatg agacttactg ggtgaggaaa tccattgttt aaagatggtc gtgtgtgtgt   2760
gtgtgtgtgt gtgtgtgttg tgttgtgttt tgttttttaa gggagggaat ttattattta   2820
ccgttgcttg aaattactgt gtaaatatat gtctgataat gatttgctct ttgacaacta   2880
aaattaggac tgtataagta ctagatgcat cactgggtgt tgatcttaca agatattgat   2940
gataacactt aaaattgtaa cctgcatttt tcactttgct ctcaattaaa gtctattcaa   3000
aaggaaaaaa aaaaaaaaaa                                                3020
```

<210> SEQ ID NO 381
<211> LENGTH: 1291
<212> TYPE: DNA
<213> ORGANISM: Homo sapiens

<400> SEQUENCE: 381

```
atgggctccg acgttcgtga cctgaacgca ctgctgccgg cagttccgtc cctgggtggt     60
ggtggtggtt gcgcactgcc ggttagcggt gcagcacagt gggctccggt tctggacttc    120
gcaccgccgg gtgcatccgc atacggttcc ctgggtggtc cggcaccgcc gccggcaccg    180
ccgccgccgc cgccgccgcc gccgcactcc ttcatcaaac aggaaccgag ctggggtggt    240
gcagaaccgc acgaagaaca gtgcctgagc gcattcaccg ttcacttctc cggccagttc    300
actggcacag ccggagcctg tcgctacggg ccccttcggtc ctcctccgcc cagccaggcg    360
```

```
tcatccggcc aggccaggat gtttcctaac gcgccctacc tgcccagctg cctcgagagc    420

cagcccgcta ttcgcaatca gggttacagc acggtcacct tcgacgggac gcccagctac    480

ggtcacacgc cctcgcacca tgcggcgcag ttccccaacc actcattcaa gcatgaggat    540

cccatgggcc agcagggctc gctgggtgag cagcagtact cggtgccgcc cccggtctat    600

ggctgccaca cccccaccga cagctgcacc ggcagccagg ctttgctgct gaggacgccc    660

tacagcagtg acaatttata ccaaatgaca tcccagcttg aatgcatgac ctggaatcag    720

atgaacttag gagccacctt aaagggccac agcacagggt acgagagcga taaccacaca    780

acgcccatcc tctgcggagc ccaatacaga atacacacgc acggtgtctt cagaggcatt    840

caggatgtgc gacgtgtgcc tggagtagcc ccgactcttg tacggtcggc atctgagacc    900

agtgagaaac gccccttcat gtgtgcttac ccaggctgca ataagagata ttttaagctg    960

tcccacttac agatgcacag caggaagcac actggtgaga aaccatacca gtgtgacttc   1020

aaggactgtg aacgaaggtt ttttcgttca gaccagctca aaagacacca aaggagacat   1080

acaggtgtga aaccattcca gtgtaaaact tgtcagcgaa agttctcccg gtccgaccac   1140

ctgaagaccc acaccaggac tcatacaggt gaaaagccct tcagctgtcg gtggccaagt   1200

tgtcagaaaa agtttgcccg gtcagatgaa ttagtccgcc atcacaacat gcatcagaga   1260

aacatgacca aactccagct ggcgctttga g                                  1291
```

<210> SEQ ID NO 382
<211> LENGTH: 1491
<212> TYPE: DNA
<213> ORGANISM: Homo sapiens

<400> SEQUENCE: 382

```
atggcggccc ccggcgcccg gcggtcgctg ctcctgctgc tgctggcagg ccttgcacat     60

ggcgcctcag cactctttga ggatctaatg ggctccgacg ttcgtgacct gaacgcactg    120

ctgccggcag ttccgtccct gggtggtggt ggtggttgcg cactgccggt tagcggtgca    180

gcacagtggg ctccggttct ggacttcgca ccgccgggtg catccgcata cggttccctg    240

ggtggtccgg caccgccgcc ggcaccgccg ccgccgccgc cgccgcactc cttcatcaaa    300

caggaaccga gctggggtgg tgcagaaccg cacgaagaac agtgcctgag cgcattcacc    360

gttcacttct ccggccagtt cactggcaca gccggagcct gtcgctacgg gcccttcggt    420

cctcctccgc ccagccaggc gtcatccggc caggccagga tgtttcctaa cgcgccctac    480

ctgcccagct gcctcgagag ccagcccgct attcgcaatc agggttacag cacggtcacc    540

ttcgacggga cgcccagcta cggtcacacg ccctcgcacc atgcggcgca gttccccaac    600

cactcattca agcatgagga tcccatgggc cagcagggct cgctgggtga gcagcagtac    660

tcggtgccgc ccccggtcta tggctgccac acccccaccg acagctgcac cggcagccag    720

gctttgctgc tgaggacgcc ctacagcagt gacaatttat accaaatgac atcccagctt    780

gaatgcatga cctggaatca gatgaactta ggagccacct taaagggcca cagcacaggg    840

tacgagagcg ataaccacac aacgcccatc ctctgcggag cccaatacag aatacacacg    900

cacggtgtct tcagaggcat tcaggatgtg cgacgtgtgc ctggagtagc cccgactctt    960

gtacggtcgg catctgagac cagtgagaaa cgccccttca tgtgtgctta cccaggctgc   1020

aataagagat attttaagct gtcccactta cagatgcaca gcaggaagca cactggtgag   1080

aaaccatacc agtgtgactt caaggactgt gaacgaaggt tttttcgttc agaccagctc   1140

aaaagacacc aaaggagaca tacaggtgtg aaaccattcc agtgtaaaac ttgtcagcga   1200
```

```
aagttctccc ggtccgacca cctgaagacc cacaccagga ctcatacagg tgaaaagccc   1260

ttcagctgtc ggtggccaag ttgtcagaaa aagtttgccc ggtcagatga attagtccgc   1320

catcacaaca tgcatcagag aaacatgacc aaactccagc tggcgcttct taacaacatg   1380

ttgatcccca ttgctgtggg cggtgccctg gcagggctgg tcctcatcgt cctcattgcc   1440

tacctcattg gcaggaagag gagtcacgcc ggctatcaga ccatctagtg a            1491
```

<210> SEQ ID NO 383
<211> LENGTH: 1251
<212> TYPE: DNA
<213> ORGANISM: Homo sapiens

<400> SEQUENCE: 383

```
atggcgcccc gcagcgcccg gcgacccctg ctgctgctac tgcctgttgc tgctgctcgg     60

cctcatgcat tgtcgtcagc agccatgttt atggtgaaaa atggcaacgg gaccgcgtgc    120

ataatggcca acttctctgc tgccttctca gtgaactacg acaccaagag tggccccaag    180

aacatgacct ttgacctgcc atcagatgcc acagtggtgc tcaaccgcag ctcctgtgga    240

aaagagaaca cttctgaccc cagtctcgtg attgcttttg gaagaggaca tacactcact    300

ctcaatttca cgagaaatgc aacacgttac agcgttcagc tcatgagttt tgtttataac    360

ttgtcagaca cacacctttt ccccaatgcg agctccaaag aaatcaagac tgtggaatct    420

ataactgaca tcagggcaga tatagataaa aaatacagat gtgttagtgg cacccaggtc    480

cacatgaaca acgtgaccgt aacgctccat gatgccacca tccaggcgta cctttccaac    540

agcagcttca gcaggggaga gacacgctgt gaacaagaca ggccttcccc aaccacagcg    600

ccccctgcgc cacccagccc ctcgccctca cccgtgccca agagcccctc tgtggacaag    660

tacaacgtga gcggcaccaa cgggacctgc ctgctggcca gcatggggct gcagctgaac    720

ctcacctatg agaggaagga caacacgacg gtgacaaggc ttctcaacat caaccccaac    780

aagacctcgg ccagcgggag ctgcggcgcc cacctggtga ctctggagct gcacagcgag    840

ggcaccaccg tcctgctctt ccagttcggg atgaatgcaa gttctagccg gtttttccta    900

caaggaatcc agttgaatac aattcttcct gacgccagag accctgcctt taaagctgcc    960

aacggctccc tgcgagcgct gcaggccaca gtcggcaatt cctacaagtg caacgcggag   1020

gagcacgtcc gtgtcacgaa ggcgttttca gtcaatatat tcaaagtgtg ggtccaggct   1080

ttcaaggtgg aaggtggcca gtttggctct gtggaggagt gtctgctgga cgagaacagc   1140

acgctgatcc ccatcgctgt gggtggtgcc ctggcggggc tggtcctcat cgtcctcatc   1200

gcctacctcg tcggcaggaa gaggagtcac gcaggctacc agactatcta g            1251
```

<210> SEQ ID NO 384
<211> LENGTH: 228
<212> TYPE: DNA
<213> ORGANISM: Homo sapiens

<400> SEQUENCE: 384

```
atgcagatct tcgtgaagac tctgactggt aagaccatca ccctcgaggt ggagcccagt     60

gacaccatcg agaatgtcaa ggcaaagatc caagataagg aaggcattcc tcctgatcag    120

cagaggttga tctttgccgg aaaacagctg gaagatggtc gtaccctgtc tgactacaac    180

atccagaaag agtccacctt gcacctggta ctccgtctca gaggtggg                 228
```

<210> SEQ ID NO 385
<211> LENGTH: 1515

<212> TYPE: DNA
<213> ORGANISM: Homo sapiens

<400> SEQUENCE: 385

```
atgcagatct tcgtgaagac cctgaccggc aagaccatca ccctggaagt ggagcccagt     60
gacaccatcg aaaatgtgaa ggccaagatc caggataaag aaggcatccc tcccgaccag    120
cagaggctca tctttgcagg caagcagcta gaagatggcc gcactctttc tgactacaac    180
atccagaagg agtcgaccct gcacctggtc cttcgcctga gaggtgccat gggctccgac    240
gttcgtgacc tgaacgcact gctgccggca gttccgtccc tgggtggtgg tggtggttgc    300
gcactgccgg ttagcggtgc agcacagtgg gctccggttc tggacttcgc accgccgggt    360
gcatccgcat acggttccct gggtggtccg gcaccgccgc cggcaccgcc gccgccgccg    420
ccgccgccgc actccttcat caaacaggaa ccgagctggg gtggtgcaga accgcacgaa    480
gaacagtgcc tgagcgcatt caccgttcac ttctccggcc agttcactgg cacagccgga    540
gcctgtcgct acgggccctt cggtcctcct ccgcccagcc aggcgtcatc cggccaggcc    600
aggatgtttc ctaacgcgcc ctatctgccc agctgcctcg agagccagcc cgctattcgc    660
aatcagggtt acagcacggt caccttcgac gggacgccca gctacggtca cacgccctcg    720
caccatgcgg cgcagttccc caaccactca ttcaagcatg aggatcccat gggccagcag    780
ggctcgctgg gtgagcagca gtactcggtg ccgcccccgg tctatggctg ccacaccccc    840
accgacagct gcaccggcag ccaggctttg ctgctgagga cgccctacag cagtgacaat    900
ttataccaaa tgacatccca gcttgaatgc atgacctgga atcagatgaa cttaggagcc    960
accttaaagg gccacagcac agggtacgag agcgataacc acacaacgcc catcctctgc   1020
ggagcccaat acagaataca cacgcacggt gtcttcagag gcattcagga tgtgcgacgt   1080
gtgcctggag tagccccgac tcttgtacgg tcggcatctg agaccagtga gaaacgcccc   1140
ttcatgtgtg cttacccagg ctgcaataag agatatttta agctgtccca cttacagatg   1200
cacagcagga agcacactgg tgagaaacca taccagtgtg acttcaagga ctgtgaacga   1260
aggtttttc gttcagacca gctcaaaaga caccaaagga gacatacagg tgtgaaacca   1320
ttccagtgta aaacttgtca gcgaaagttc tcccggtccg accacctgaa gacccacacc   1380
aggactcata caggtgaaaa gcccttcagc tgtcggtggc caagttgtca gaaaaagttt   1440
gcccggtcag atgaattagt ccgccatcac aacatgcatc agagaaacat gaccaaactc   1500
cagctggcgc tttga                                                    1515
```

<210> SEQ ID NO 386
<211> LENGTH: 648
<212> TYPE: DNA
<213> ORGANISM: Homo sapiens

<400> SEQUENCE: 386

```
atgcactcct tcatcaaaca ggaaccgagc tggggtggtg cagaaccgca cgaagaacag     60
tgcctgagcg cattcaccgt tcacttctcc ggccagttca ctggcacagc cggagcctgt    120
cgctacgggc ccttcggtcc tcctccgccc agccaggcgt catccggcca ggccaggatg    180
tttcctaacg cgccctacct gcccagctgc ctcgagagcc agcccgctat tcgcaatcag    240
ggttacagca cggtcacctt cgacgggacg cccagctacg gtcacacgcc ctcgcaccat    300
gcggcgcagt tccccaacca ctcattcaag catgaggatc ccatgggcca gcagggctcg    360
ctgggtgagc agcagtactc ggtgccgccc ccggtctatg gctgccacac ccccaccgac    420
agctgcaccg gcagccaggc tttgctgctg aggacgccct acagcagtga caatttatac    480
```

caaatgacat cccagcttga atgcatgacc tggaatcaga tgaacttagg agccacctta 540
aagggccaca gcacagggta cgagagcgat aaccacacaa cgcccatcct ctgcggagcc 600
caatacagaa tacacacgca cggtgtcttc agaggcattc agtgatga 648

<210> SEQ ID NO 387
<211> LENGTH: 1089
<212> TYPE: DNA
<213> ORGANISM: Homo sapiens

<400> SEQUENCE: 387
atgcactcct tcatcaaaca ggaaccgagc tggggtggtg cagaaccgca cgaagaacag 60
tgcctgagcg cattcaccgt tcacttctcc ggccagttca ctggcacagc cggagcctgt 120
cgctacgggc ccttcggtcc tcctccgccc agccaggcgt catccggcca ggccaggatg 180
tttcctaacg cgccctacct gcccagctgc ctcgagagcc agcccgctat tcgcaatcag 240
ggttacagca cggtcacctt cgacgggacg cccagctacg gtcacacgcc ctcgcaccat 300
gcggcgcagt tccccaacca ctcattcaag catgaggatc ccatgggcca gcagggctcg 360
ctgggtgagc agcagtactc ggtgccgccc ccggtctatg gctgccacac ccccaccgac 420
agctgcaccg gcagccaggc tttgctgctg aggacgccct acagcagtga caatttatac 480
caaatgacat cccagcttga atgcatgacc tggaatcaga tgaacttagg agccacctta 540
aagggccaca gcacagggta cgagagcgat aaccacacaa cgcccatcct ctgcggagcc 600
caatacagaa tacacacgca cggtgtcttc agaggcattc aggatgtgcg acgtgtgcct 660
ggagtagccc cgactcttgt acggtcggca tctgagacca gtgagaaacg ccccttcatg 720
tgtgcttacc caggctgcaa taagagatat tttaagctgt cccacttaca gatgcacagc 780
aggaagcaca ctggtgagaa accataccag tgtgacttca aggactgtga acgaaggttt 840
tttcgttcag accagctcaa aagacaccaa aggagacata caggtgtgaa accattccag 900
tgtaaaactt gtcagcgaaa gttctcccgg tccgaccacc tgaagaccca caccaggact 960
catacaggtg aaaagccctt cagctgtcgg tggccaagtt gtcagaaaaa gtttgcccgg 1020
tcagatgaat tagtccgcca tcacaacatg catcagagaa acatgaccaa actccagctg 1080
gcgctttga 1089

<210> SEQ ID NO 388
<211> LENGTH: 1035
<212> TYPE: DNA
<213> ORGANISM: Homo sapiens

<400> SEQUENCE: 388
atgacggccg cgtccgataa cttccagctg tcccagggtg ggcagggatt cgccattccg 60
atcgggcagg cgatggcgat cgcgggccag atcaagcttc ccaccgttca tatcgggcct 120
accgccttcc tcggcttggg tgttgtcgac aacaacggca acggcgcacg agtccaacgc 180
gtggtcggga gcgctccggc ggcaagtctc ggcatctcca ccggcgacgt gatcaccgcg 240
gtcgacggcg ctccgatcaa ctcggccacc gcgatggcgg acgcgcttaa cgggcatcat 300
cccggtgacg tcatctcggt gacctggcaa accaagtcgg gcggcacgcg tacagggaac 360
gtgacattgg ccgagggacc cccggccgaa ttccactcct tcatcaaaca ggaaccgagc 420
tggggtggtg cagaaccgca cgaagaacag tgcctgagcg cattcaccgt tcacttctcc 480
ggccagttca ctggcacagc cggagcctgt cgctacgggc ccttcggtcc tcctccgccc 540
agccaggcgt catccggcca ggccaggatg tttcctaacg cgccctacct gcccagctgc 600

```
ctcgagagcc agcccgctat tcgcaatcag ggttacagca cggtcacctt cgacgggacg     660

cccagctacg gtcacacgcc ctcgcaccat gcggcgcagt tccccaacca ctcattcaag     720

catgaggatc ccatgggcca gcagggctcg ctgggtgagc agcagtactc ggtgccgccc     780

ccggtctatg gctgccacac ccccaccgac agctgcaccg gcagccaggc tttgctgctg     840

aggacgccct acagcagtga caatttatac caaatgacat cccagcttga atgcatgacc     900

tggaatcaga tgaacttagg agccacctta aagggccaca gcacagggta cgagagcgat     960

aaccacacaa cgcccatcct ctgcggagcc caatacagaa tacacacgca cggtgtcttc    1020

agaggcattc agtga                                                     1035
```

```
<210> SEQ ID NO 389
<211> LENGTH: 1263
<212> TYPE: DNA
<213> ORGANISM: Homo sapiens

<400> SEQUENCE: 389

atgacggccg cgtccgataa cttccagctg tcccagggtg ggcagggatt cgccattccg      60

atcgggcagg cgatggcgat cgcgggccag atcaagcttc ccaccgttca tatcgggcct     120

accgccttcc tcggcttggg tgttgtcgac aacaacggca acggcgcacg agtccaacgc     180

gtggtcggga gcgctccggc ggcaagtctc ggcatctcca ccggcgacgt gatcaccgcg     240

gtcgacggcg ctccgatcaa ctcggccacc gcgatggcgg acgcgcttaa cgggcatcat     300

cccggtgacg tcatctcggt gacctggcaa accaagtcgg gcggcacgcg tacagggaac     360

gtgacattgg ccgagggacc cccggccgaa ttcccgctgg tgccgcgcgg cagcccgatg     420

ggctccgacg ttcgggacct gaacgcactg ctgccggcag ttccgtccct gggtggtggt     480

ggtggttgcg cactgccggt tagcggtgca gcacagtggg ctccggttct ggacttcgca     540

ccgccgggtg catccgcata cggttccctg ggtggtccgg caccgccgcc ggcaccgccg     600

ccgccgccgc cgccgccgcc gcactccttc atcaaacagg aaccgagctg gggtggtgca     660

gaaccgcacg aagaacagtg cctgagcgca ttcaccgttc acttctccgg ccagttcact     720

ggcacagccg gagcctgtcg ctacgggccc ttcggtcctc ctccgcccag ccaggcgtca     780

tccggccagg ccaggatgtt tcctaacgcg ccctacctgc ccagctgcct cgagagccag     840

cccgctattc gcaatcaggg ttacagcacg gtcaccttcg acgggacgcc cagctacggt     900

cacacgccct cgcaccatgc ggcgcagttc cccaaccact cattcaagca tgaggatccc     960

atgggccagc agggctcgct gggtgagcag cagtactcgg tgccgccccc ggtctatggc    1020

tgccacaccc ccaccgacag ctgcaccggc agccaggctt tgctgctgag gacgccctac    1080

agcagtgaca atttatacca aatgacatcc cagcttgaat gcatgacctg gaatcagatg    1140

aacttaggag ccaccttaaa gggccacagc acagggtacg agagcgataa ccacacaacg    1200

cccatcctct gcggagccca atacagaata cacacgcacg gtgtcttcag aggcattcag    1260

tga                                                                  1263
```

```
<210> SEQ ID NO 390
<211> LENGTH: 1707
<212> TYPE: DNA
<213> ORGANISM: Homo sapiens

<400> SEQUENCE: 390

atgacggccg cgtccgataa cttccagctg tcccagggtg ggcagggatt cgccattccg      60

atcgggcagg cgatggcgat cgcgggccag atcaagcttc ccaccgttca tatcgggcct     120
```

```
accgccttcc tcggcttggg tgttgtcgac aacaacggca acggcgcacg agtccaacgc    180
gtggtcggga gcgctccggc ggcaagtctc ggcatctcca ccggcgacgt gatcaccgcg    240
gtcgacggcg ctccgatcaa ctcggccacc gcgatggcgg acgcgcttaa cgggcatcat    300
cccggtgacg tcatctcggt gacctggcaa accaagtcgg gcggcacgcg tacagggaac    360
gtgacattgg ccgagggacc cccggccgaa ttcccgctgg tgccgcgcgg cagcccgatg    420
ggctccgacg ttcgggacct gaacgcactg ctgccggcag ttccgtccct gggtggtggt    480
ggtggttgcg cactgccggt tagcggtgca gcacagtggg ctccggttct ggacttcgca    540
ccgccgggtg catccgcata cggttccctg ggtggtccgg caccgccgcc ggcaccgccg    600
ccgccgccgc cgccgccgcc gcactccttc atcaaacagg aaccgagctg ggtggtgca     660
gaaccgcacg aagaacagtg cctgagcgca ttcaccgttc acttctccgg ccagttcact    720
ggcacagccg gagcctgtcg ctacgggccc ttcggtcctc ctccgcccag ccaggcgtca    780
tccggccagg ccaggatgtt tcctaacgcg ccctacctgc ccagctgcct cgagagccag    840
cccgctattc gcaatcaggg ttacagcacg gtcaccttcg acgggacgcc cagctacggt    900
cacacgccct cgcaccatgc ggcgcagttc cccaaccact cattcaagca tgaggatccc    960
atgggccagc agggctcgct gggtgagcag cagtactcgg tgccgccccc ggtctatggc   1020
tgccacaccc ccaccgacag ctgcaccggc agccaggctt tgctgctgag gacgccctac   1080
agcagtgaca atttatacca aatgacatcc cagcttgaat gcatgacctg gaatcagatg   1140
aacttaggag ccaccttaaa gggccacagc acagggtacg agagcgataa ccacacaacg   1200
cccatcctct gcggagccca atacagaata cacacgcacg gtgtcttcag aggcattcag   1260
gatgtgcgac gtgtgcctgg agtagccccg actcttgtac ggtcggcatc tgagaccagt   1320
gagaaacgcc ccttcatgtg tgcttaccca ggctgcaata agagatattt taagctgtcc   1380
cacttacaga tgcacagcag gaagcacact ggtgagaaac cataccagtg tgacttcaag   1440
gactgtgaac gaaggttttt tcgttcagac cagctcaaaa gacaccaaag gagacataca   1500
ggtgtgaaac cattccagtg taaaacttgt cagcgaaagt tctcccggtc cgaccacctg   1560
aagacccaca ccaggactca tacaggtgaa aagcccttca gctgtcggtg gccaagttgt   1620
cagaaaaagt ttgcccggtc agatgaatta gtccgccatc acaacatgca tcagagaaac   1680
atgaccaaac tccagctggc gctttga                                       1707
```

<210> SEQ ID NO 391
<211> LENGTH: 344
<212> TYPE: PRT
<213> ORGANISM: Homo sapiens

<400> SEQUENCE: 391

```
Met Thr Ala Ala Ser Asp Asn Phe Gln Leu Ser Gln Gly Gly Gln Gly
                5                   10                  15

Phe Ala Ile Pro Ile Gly Gln Ala Met Ala Ile Ala Gly Gln Ile Lys
            20                  25                  30

Leu Pro Thr Val His Ile Gly Pro Thr Ala Phe Leu Gly Leu Gly Val
        35                  40                  45

Val Asp Asn Asn Gly Asn Gly Ala Arg Val Gln Arg Val Val Gly Ser
    50                  55                  60

Ala Pro Ala Ala Ser Leu Gly Ile Ser Thr Gly Asp Val Ile Thr Ala
65                  70                  75                  80

Val Asp Gly Ala Pro Ile Asn Ser Ala Thr Ala Met Ala Asp Ala Leu
                85                  90                  95
```

```
Asn Gly His His Pro Gly Asp Val Ile Ser Val Thr Trp Gln Thr Lys
            100                 105                 110

Ser Gly Gly Thr Arg Thr Gly Asn Val Thr Leu Ala Glu Gly Pro Pro
        115                 120                 125

Ala Glu Phe His Ser Phe Ile Lys Gln Glu Pro Ser Trp Gly Gly Ala
    130                 135                 140

Glu Pro His Glu Glu Gln Cys Leu Ser Ala Phe Thr Val His Phe Ser
145                 150                 155                 160

Gly Gln Phe Thr Gly Thr Ala Gly Ala Cys Arg Tyr Gly Pro Phe Gly
                165                 170                 175

Pro Pro Pro Pro Ser Gln Ala Ser Ser Gly Gln Ala Arg Met Phe Pro
            180                 185                 190

Asn Ala Pro Tyr Leu Pro Ser Cys Leu Glu Ser Gln Pro Ala Ile Arg
        195                 200                 205

Asn Gln Gly Tyr Ser Thr Val Thr Phe Asp Gly Thr Pro Ser Tyr Gly
    210                 215                 220

His Thr Pro Ser His His Ala Ala Gln Phe Pro Asn His Ser Phe Lys
225                 230                 235                 240

His Glu Asp Pro Met Gly Gln Gln Gly Ser Leu Gly Glu Gln Gln Tyr
                245                 250                 255

Ser Val Pro Pro Pro Val Tyr Gly Cys His Thr Pro Thr Asp Ser Cys
            260                 265                 270

Thr Gly Ser Gln Ala Leu Leu Leu Arg Thr Pro Tyr Ser Ser Asp Asn
        275                 280                 285

Leu Tyr Gln Met Thr Ser Gln Leu Glu Cys Met Thr Trp Asn Gln Met
    290                 295                 300

Asn Leu Gly Ala Thr Leu Lys Gly His Ser Thr Gly Tyr Glu Ser Asp
305                 310                 315                 320

Asn His Thr Thr Pro Ile Leu Cys Gly Ala Gln Tyr Arg Ile His Thr
                325                 330                 335

His Gly Val Phe Arg Gly Ile Gln
            340
```

<210> SEQ ID NO 392
<211> LENGTH: 568
<212> TYPE: PRT
<213> ORGANISM: Homo sapiens

<400> SEQUENCE: 392

```
Met Thr Ala Ala Ser Asp Asn Phe Gln Leu Ser Gln Gly Gly Gln Gly
1               5                   10                  15

Phe Ala Ile Pro Ile Gly Gln Ala Met Ala Ile Ala Gly Gln Ile Lys
            20                  25                  30

Leu Pro Thr Val His Ile Gly Pro Thr Ala Phe Leu Gly Leu Gly Val
        35                  40                  45

Val Asp Asn Asn Gly Asn Gly Ala Arg Val Gln Arg Val Val Gly Ser
    50                  55                  60

Ala Pro Ala Ala Ser Leu Gly Ile Ser Thr Gly Asp Val Ile Thr Ala
65                  70                  75                  80

Val Asp Gly Ala Pro Ile Asn Ser Ala Thr Ala Met Ala Asp Ala Leu
                85                  90                  95

Asn Gly His His Pro Gly Asp Val Ile Ser Val Thr Trp Gln Thr Lys
            100                 105                 110

Ser Gly Gly Thr Arg Thr Gly Asn Val Thr Leu Ala Glu Gly Pro Pro
        115                 120                 125
```

```
Ala Glu Phe Pro Leu Val Pro Arg Gly Ser Pro Met Gly Ser Asp Val
    130                 135                 140

Arg Asp Leu Asn Ala Leu Leu Pro Ala Val Pro Ser Leu Gly Gly Gly
145                 150                 155                 160

Gly Gly Cys Ala Leu Pro Val Ser Gly Ala Ala Gln Trp Ala Pro Val
                165                 170                 175

Leu Asp Phe Ala Pro Pro Gly Ala Ser Ala Tyr Gly Ser Leu Gly Gly
            180                 185                 190

Pro Ala Pro Pro Pro Ala Pro Pro Pro Pro Pro Pro Pro Pro Pro His
        195                 200                 205

Ser Phe Ile Lys Gln Glu Pro Ser Trp Gly Gly Ala Glu Pro His Glu
    210                 215                 220

Glu Gln Cys Leu Ser Ala Phe Thr Val His Phe Ser Gly Gln Phe Thr
225                 230                 235                 240

Gly Thr Ala Gly Ala Cys Arg Tyr Gly Pro Phe Gly Pro Pro Pro Pro
                245                 250                 255

Ser Gln Ala Ser Ser Gly Gln Ala Arg Met Phe Pro Asn Ala Pro Tyr
            260                 265                 270

Leu Pro Ser Cys Leu Glu Ser Gln Pro Ala Ile Arg Asn Gln Gly Tyr
        275                 280                 285

Ser Thr Val Thr Phe Asp Gly Thr Pro Ser Tyr Gly His Thr Pro Ser
    290                 295                 300

His His Ala Ala Gln Phe Pro Asn His Ser Phe Lys His Glu Asp Pro
305                 310                 315                 320

Met Gly Gln Gln Gly Ser Leu Gly Glu Gln Gln Tyr Ser Val Pro Pro
                325                 330                 335

Pro Val Tyr Gly Cys His Thr Pro Thr Asp Ser Cys Thr Gly Ser Gln
            340                 345                 350

Ala Leu Leu Leu Arg Thr Pro Tyr Ser Ser Asp Asn Leu Tyr Gln Met
        355                 360                 365

Thr Ser Gln Leu Glu Cys Met Thr Trp Asn Gln Met Asn Leu Gly Ala
    370                 375                 380

Thr Leu Lys Gly His Ser Thr Gly Tyr Glu Ser Asp Asn His Thr Thr
385                 390                 395                 400

Pro Ile Leu Cys Gly Ala Gln Tyr Arg Ile His Thr His Gly Val Phe
                405                 410                 415

Arg Gly Ile Gln Asp Val Arg Arg Val Pro Gly Val Ala Pro Thr Leu
            420                 425                 430

Val Arg Ser Ala Ser Glu Thr Ser Glu Lys Arg Pro Phe Met Cys Ala
        435                 440                 445

Tyr Pro Gly Cys Asn Lys Arg Tyr Phe Lys Leu Ser His Leu Gln Met
    450                 455                 460

His Ser Arg Lys His Thr Gly Glu Lys Pro Tyr Gln Cys Asp Phe Lys
465                 470                 475                 480

Asp Cys Glu Arg Arg Phe Phe Arg Ser Asp Gln Leu Lys Arg His Gln
                485                 490                 495

Arg Arg His Thr Gly Val Lys Pro Phe Gln Cys Lys Thr Cys Gln Arg
            500                 505                 510

Lys Phe Ser Arg Ser Asp His Leu Lys Thr His Thr Arg Thr His Thr
        515                 520                 525

Gly Glu Lys Pro Phe Ser Cys Arg Trp Pro Ser Cys Gln Lys Lys Phe
    530                 535                 540

Ala Arg Ser Asp Glu Leu Val Arg His His Asn Met His Gln Arg Asn
```

545 550 555 560

Met Thr Lys Leu Gln Leu Ala Leu
565

<210> SEQ ID NO 393
<211> LENGTH: 420
<212> TYPE: PRT
<213> ORGANISM: Homo sapiens

<400> SEQUENCE: 393

Met Thr Ala Ala Ser Asp Asn Phe Gln Leu Ser Gln Gly Gly Gln Gly
5 10 15

Phe Ala Ile Pro Ile Gly Gln Ala Met Ala Ile Ala Gly Gln Ile Lys
20 25 30

Leu Pro Thr Val His Ile Gly Pro Thr Ala Phe Leu Gly Leu Gly Val
35 40 45

Val Asp Asn Asn Gly Asn Gly Ala Arg Val Gln Arg Val Val Gly Ser
50 55 60

Ala Pro Ala Ala Ser Leu Gly Ile Ser Thr Gly Asp Val Ile Thr Ala
65 70 75 80

Val Asp Gly Ala Pro Ile Asn Ser Ala Thr Ala Met Ala Asp Ala Leu
85 90 95

Asn Gly His His Pro Gly Asp Val Ile Ser Val Thr Trp Gln Thr Lys
100 105 110

Ser Gly Gly Thr Arg Thr Gly Asn Val Thr Leu Ala Glu Gly Pro Pro
115 120 125

Ala Glu Phe Pro Leu Val Pro Arg Gly Ser Pro Met Gly Ser Asp Val
130 135 140

Arg Asp Leu Asn Ala Leu Leu Pro Ala Val Pro Ser Leu Gly Gly Gly
145 150 155 160

Gly Gly Cys Ala Leu Pro Val Ser Gly Ala Ala Gln Trp Ala Pro Val
165 170 175

Leu Asp Phe Ala Pro Pro Gly Ala Ser Ala Tyr Gly Ser Leu Gly Gly
180 185 190

Pro Ala Pro Pro Pro Ala Pro Pro Pro Pro Pro Pro Pro Pro Pro His
195 200 205

Ser Phe Ile Lys Gln Glu Pro Ser Trp Gly Gly Ala Glu Pro His Glu
210 215 220

Glu Gln Cys Leu Ser Ala Phe Thr Val His Phe Ser Gly Gln Phe Thr
225 230 235 240

Gly Thr Ala Gly Ala Cys Arg Tyr Gly Pro Phe Gly Pro Pro Pro Pro
245 250 255

Ser Gln Ala Ser Ser Gly Gln Ala Arg Met Phe Pro Asn Ala Pro Tyr
260 265 270

Leu Pro Ser Cys Leu Glu Ser Gln Pro Ala Ile Arg Asn Gln Gly Tyr
275 280 285

Ser Thr Val Thr Phe Asp Gly Thr Pro Ser Tyr Gly His Thr Pro Ser
290 295 300

His His Ala Ala Gln Phe Pro Asn His Ser Phe Lys His Glu Asp Pro
305 310 315 320

Met Gly Gln Gln Gly Ser Leu Gly Glu Gln Gln Tyr Ser Val Pro Pro
325 330 335

Pro Val Tyr Gly Cys His Thr Pro Thr Asp Ser Cys Thr Gly Ser Gln
340 345 350

Ala Leu Leu Leu Arg Thr Pro Tyr Ser Ser Asp Asn Leu Tyr Gln Met

```
        355                 360                 365

Thr Ser Gln Leu Glu Cys Met Thr Trp Asn Gln Met Asn Leu Gly Ala
    370                 375                 380

Thr Leu Lys Gly His Ser Thr Gly Tyr Glu Ser Asp Asn His Thr Thr
385                 390                 395                 400

Pro Ile Leu Cys Gly Ala Gln Tyr Arg Ile His Thr His Gly Val Phe
                405                 410                 415

Arg Gly Ile Gln
            420


<210> SEQ ID NO 394
<211> LENGTH: 362
<212> TYPE: PRT
<213> ORGANISM: Homo sapiens

<400> SEQUENCE: 394

Met His Ser Phe Ile Lys Gln Glu Pro Ser Trp Gly Gly Ala Glu Pro
                5                   10                  15

His Glu Glu Gln Cys Leu Ser Ala Phe Thr Val His Phe Ser Gly Gln
            20                  25                  30

Phe Thr Gly Thr Ala Gly Ala Cys Arg Tyr Gly Pro Phe Gly Pro Pro
        35                  40                  45

Pro Pro Ser Gln Ala Ser Ser Gly Gln Ala Arg Met Phe Pro Asn Ala
    50                  55                  60

Pro Tyr Leu Pro Ser Cys Leu Glu Ser Gln Pro Ala Ile Arg Asn Gln
65                  70                  75                  80

Gly Tyr Ser Thr Val Thr Phe Asp Gly Thr Pro Ser Tyr Gly His Thr
                85                  90                  95

Pro Ser His His Ala Ala Gln Phe Pro Asn His Ser Phe Lys His Glu
            100                 105                 110

Asp Pro Met Gly Gln Gln Gly Ser Leu Gly Glu Gln Gln Tyr Ser Val
        115                 120                 125

Pro Pro Pro Val Tyr Gly Cys His Thr Pro Thr Asp Ser Cys Thr Gly
    130                 135                 140

Ser Gln Ala Leu Leu Leu Arg Thr Pro Tyr Ser Ser Asp Asn Leu Tyr
145                 150                 155                 160

Gln Met Thr Ser Gln Leu Glu Cys Met Thr Trp Asn Gln Met Asn Leu
                165                 170                 175

Gly Ala Thr Leu Lys Gly His Ser Thr Gly Tyr Glu Ser Asp Asn His
            180                 185                 190

Thr Thr Pro Ile Leu Cys Gly Ala Gln Tyr Arg Ile His Thr His Gly
        195                 200                 205

Val Phe Arg Gly Ile Gln Asp Val Arg Arg Val Pro Gly Val Ala Pro
    210                 215                 220

Thr Leu Val Arg Ser Ala Ser Glu Thr Ser Glu Lys Arg Pro Phe Met
225                 230                 235                 240

Cys Ala Tyr Pro Gly Cys Asn Lys Arg Tyr Phe Lys Leu Ser His Leu
                245                 250                 255

Gln Met His Ser Arg Lys His Thr Gly Glu Lys Pro Tyr Gln Cys Asp
            260                 265                 270

Phe Lys Asp Cys Glu Arg Arg Phe Phe Arg Ser Asp Gln Leu Lys Arg
        275                 280                 285

His Gln Arg Arg His Thr Gly Val Lys Pro Phe Gln Cys Lys Thr Cys
    290                 295                 300

Gln Arg Lys Phe Ser Arg Ser Asp His Leu Lys Thr His Thr Arg Thr
```

```
305                 310                 315                 320

His Thr Gly Glu Lys Pro Phe Ser Cys Arg Trp Pro Ser Cys Gln Lys
                325                 330                 335

Lys Phe Ala Arg Ser Asp Glu Leu Val Arg His His Asn Met His Gln
            340                 345                 350

Arg Asn Met Thr Lys Leu Gln Leu Ala Leu
        355                 360


<210> SEQ ID NO 395
<211> LENGTH: 214
<212> TYPE: PRT
<213> ORGANISM: Homo sapiens

<400> SEQUENCE: 395

Met His Ser Phe Ile Lys Gln Glu Pro Ser Trp Gly Gly Ala Glu Pro
                5                   10                  15

His Glu Glu Gln Cys Leu Ser Ala Phe Thr Val His Phe Ser Gly Gln
            20                  25                  30

Phe Thr Gly Thr Ala Gly Ala Cys Arg Tyr Gly Pro Phe Gly Pro Pro
        35                  40                  45

Pro Pro Ser Gln Ala Ser Ser Gly Gln Ala Arg Met Phe Pro Asn Ala
    50                  55                  60

Pro Tyr Leu Pro Ser Cys Leu Glu Ser Gln Pro Ala Ile Arg Asn Gln
65                  70                  75                  80

Gly Tyr Ser Thr Val Thr Phe Asp Gly Thr Pro Ser Tyr Gly His Thr
                85                  90                  95

Pro Ser His His Ala Ala Gln Phe Pro Asn His Ser Phe Lys His Glu
            100                 105                 110

Asp Pro Met Gly Gln Gln Gly Ser Leu Gly Glu Gln Gln Tyr Ser Val
        115                 120                 125

Pro Pro Pro Val Tyr Gly Cys His Thr Pro Thr Asp Ser Cys Thr Gly
    130                 135                 140

Ser Gln Ala Leu Leu Leu Arg Thr Pro Tyr Ser Ser Asp Asn Leu Tyr
145                 150                 155                 160

Gln Met Thr Ser Gln Leu Glu Cys Met Thr Trp Asn Gln Met Asn Leu
                165                 170                 175

Gly Ala Thr Leu Lys Gly His Ser Thr Gly Tyr Glu Ser Asp Asn His
            180                 185                 190

Thr Thr Pro Ile Leu Cys Gly Ala Gln Tyr Arg Ile His Thr His Gly
        195                 200                 205

Val Phe Arg Gly Ile Gln
    210


<210> SEQ ID NO 396
<211> LENGTH: 30
<212> TYPE: DNA
<213> ORGANISM: Artificial Sequence
<220> FEATURE:
<223> OTHER INFORMATION: PCR primer

<400> SEQUENCE: 396

gacgaaagca tatgcactcc ttcatcaaac                                       30


<210> SEQ ID NO 397
<211> LENGTH: 31
<212> TYPE: DNA
<213> ORGANISM: Artificial Sequence
<220> FEATURE:
<223> OTHER INFORMATION: PCR primer
```

<400> SEQUENCE: 397
cgcgtgaatt catcactgaa tgcctctgaa g 31

<210> SEQ ID NO 398
<211> LENGTH: 31
<212> TYPE: DNA
<213> ORGANISM: Artificial Sequence
<220> FEATURE:
<223> OTHER INFORMATION: PCR primer

<400> SEQUENCE: 398
cgataagcat atgacggccg cgtccgataa c 31

<210> SEQ ID NO 399
<211> LENGTH: 31
<212> TYPE: DNA
<213> ORGANISM: Artificial Sequence
<220> FEATURE:
<223> OTHER INFORMATION: PCR primer

<400> SEQUENCE: 399
cgcgtgaatt catcactgaa tgcctctgaa g 31

<210> SEQ ID NO 400
<211> LENGTH: 31
<212> TYPE: DNA
<213> ORGANISM: Artificial Sequence
<220> FEATURE:
<223> OTHER INFORMATION: PCR primer

<400> SEQUENCE: 400
cgataagcat atgacggccg cgtccgataa c 31

<210> SEQ ID NO 401
<211> LENGTH: 28
<212> TYPE: DNA
<213> ORGANISM: Artificial Sequence
<220> FEATURE:
<223> OTHER INFORMATION: PCR primer

<400> SEQUENCE: 401
gtctgcagcg gccgctcaaa gcgccagc 28

<210> SEQ ID NO 402
<211> LENGTH: 30
<212> TYPE: DNA
<213> ORGANISM: Artificial Sequence
<220> FEATURE:
<223> OTHER INFORMATION: PCR primer

<400> SEQUENCE: 402
gacgaaagca tatgcactcc ttcatcaaac 30

<210> SEQ ID NO 403
<211> LENGTH: 28
<212> TYPE: DNA
<213> ORGANISM: Artificial Sequence
<220> FEATURE:
<223> OTHER INFORMATION: PCR primer

<400> SEQUENCE: 403
gtctgcagcg gccgctcaaa gcgccagc 28

<210> SEQ ID NO 404
<211> LENGTH: 449

<212> TYPE: PRT
<213> ORGANISM: Homo sapiens

<400> SEQUENCE: 404

```
Met Gly Ser Asp Val Arg Asp Leu Asn Ala Leu Leu Pro Ala Val Pro
 1               5                  10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Pro Ala Pro Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400
```

```
His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
        435                 440                 445

Leu


<210> SEQ ID NO 405
<211> LENGTH: 428
<212> TYPE: PRT
<213> ORGANISM: Homo sapiens

<400> SEQUENCE: 405

Met Gly Ser Asp Val Arg Asp Leu Asn Ala Leu Leu Pro Ala Val Pro
 1               5                  10                  15

Ser Pro Gly Gly Gly Gly Gly Cys Ala Leu Pro Val Ser Gly Ala Thr
            20                  25                  30

Gln Trp Ala Pro Val Leu Asp Phe Val Pro Pro Gly Ala Pro Val Cys
        35                  40                  45

Gly Ser Leu Gly Gly Pro Ala Pro Pro Pro Ala Pro Pro Pro Leu Pro
    50                  55                  60

Pro Pro Pro Ser His Ser Phe Thr Lys Gln Glu Pro Ser Trp Gly Gly
65                  70                  75                  80

Thr Glu Pro His Ala Gly Gln Gly Arg Ser Ala Leu Val Ala His Ser
                85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Ser
                165                 170                 175

Lys His Glu Asp Pro Met Gly Gln Gln Gly Ser Pro Gly Glu Gln Gln
            180                 185                 190

Tyr Ser Ala Pro Pro Pro Val Cys Gly Cys Arg Thr Pro Thr Gly Ser
        195                 200                 205

Cys Thr Gly Ser Gln Ala Leu Leu Leu Arg Ala Pro Tyr Ser Gly Gly
    210                 215                 220

Asp Leu His Gln Thr Thr Ser Gln Leu Gly His Met Ala Trp Asn Gln
225                 230                 235                 240

Thr Asn Leu Gly Ala Thr Leu Lys Gly His Gly Thr Gly Tyr Glu Ser
                245                 250                 255

Asp Asp His Thr Thr Pro Ile Leu Cys Gly Thr Gln Tyr Arg Ile Arg
            260                 265                 270

Ala Arg Gly Val Leu Arg Gly Thr Gln Asp Val Arg Cys Val Pro Gly
        275                 280                 285

Val Ala Pro Thr Leu Val Arg Ser Ala Ser Glu Thr Ser Glu Lys Arg
    290                 295                 300

Pro Leu Met Cys Ala Tyr Pro Gly Cys Asn Lys Arg His Phe Lys Pro
305                 310                 315                 320

Ser Arg Leu Arg Val Arg Gly Arg Glu Arg Thr Gly Glu Lys Pro Tyr
```

```
                325                 330                 335

Gln Arg Asp Phe Lys Asp Arg Gly Arg Gly Leu Leu Arg Pro Asp Gln
            340                 345                 350

Leu Lys Arg His Gln Arg Gly His Thr Gly Val Lys Pro Leu Gln Cys
        355                 360                 365

Glu Ala Arg Arg Arg Pro Pro Arg Pro Gly His Leu Lys Val His Thr
    370                 375                 380

Arg Thr His Thr Gly Gly Glu Pro Phe Ser Cys Arg Trp Pro Ser Cys
385                 390                 395                 400

Gln Glu Lys Ser Ala Arg Pro Asp Glu Ser Ala Arg Arg His Asn Met
                405                 410                 415

His Gln Arg Asn Met Thr Lys Leu Gln Leu Ala Leu
            420                 425


<210> SEQ ID NO 406
<211> LENGTH: 414
<212> TYPE: PRT
<213> ORGANISM: Homo sapiens
<220> FEATURE:
<221> NAME/KEY: VARIANT
<222> LOCATION: 85, 86, 172, 173, 242, 245, 246, 247
<223> OTHER INFORMATION: Xaa = Any Amino Acid

<400> SEQUENCE: 406

Met Gly Ser Asp Val Arg Asp Leu Ser Ala Leu Leu Pro Ala Val Pro
 1               5                  10                  15

Ser Leu Gly Asp Gly Gly Gly Cys Ala Leu Pro Val Ser Gly Ala Ala
            20                  25                  30

Gln Trp Ala Pro Val Leu Asp Phe Ala Pro Pro Gly Ala Ser Ala His
        35                  40                  45

Gly Pro Leu Gly Gly Pro Ala Pro Pro Ser Ala Pro Pro Pro Pro Pro
    50                  55                  60

Pro Pro Pro Pro His Ser Phe Ile Lys Gln Gly Pro Ser Trp Gly Gly
65                  70                  75                  80

Ala Glu Leu His Xaa Xaa Gln Tyr Leu Ser Ala Phe Thr Val His Ser
                85                  90                  95

Ser Gly Gln Val His Trp His Gly Arg Gly Leu Ser Leu Arg Ala Pro
            100                 105                 110

Arg Pro Pro Ser Ala Gln Pro Gly Val Ile Arg Pro Gly Gln Asp Val
        115                 120                 125

Ser Arg Ala Leu Pro Ala Gln Pro Pro Arg Glu Pro Ala Arg Tyr Pro
    130                 135                 140

Gln Ser Gly Leu Gln His Gly His Leu Arg Arg Gly Val Arg Leu Arg
145                 150                 155                 160

Ser His Ala Leu Ala Pro Cys Gly Ala Val Leu Xaa Xaa Thr Arg Ala
                165                 170                 175

Gly Ser His Gly Pro Ala Gly Ser Ala Gly Ala Ala Val Leu Gly Ala
            180                 185                 190

Ala Pro Gly Leu Trp Pro Pro His Pro Arg Arg Gln Leu Arg Arg Gln
        195                 200                 205

Pro Gly Phe Ala Ala Glu Gly Ala Leu Gln Arg Arg Phe Ile Pro Ser
    210                 215                 220

Asp Val Pro Ala Val His Gly Leu Glu Ser Asp Glu Pro Arg Gly Arg
225                 230                 235                 240

Leu Xaa Gly Pro Xaa Xaa Xaa Val Arg Glu Arg Ser His Asn Ala Arg
                245                 250                 255
```

```
Pro Leu Arg Ser Pro Ile Gln Asn Thr His Ala Arg Cys Leu Gln Gly
            260                 265                 270

Arg Ser Gly Cys Ala Pro Cys Ala Trp Ser Ser Pro Asp Ser Cys Thr
        275                 280                 285

Val Gly Ile Gly Gln Gly Thr Pro Pro His Val Cys Leu Pro Arg Leu
    290                 295                 300

Gln Glu Val Ser Glu Ala Ala Pro Leu Thr Asp Ala Arg Glu Ala Arg
305                 310                 315                 320

Trp Glu Thr Ile Pro Val Leu Gln Gly Leu Trp Thr Glu Val Phe Leu
                325                 330                 335

Leu Arg Pro Ala Gln Lys Thr Pro Gly Glu Ala Tyr Arg Cys Glu Ala
            340                 345                 350

Ile Pro Ala Asp Leu Ser Ala Arg Val Leu Pro Ala Gln Pro Pro Glu
        355                 360                 365

Asp Pro Arg Gln Asp Ser Cys Arg Lys Ala Pro Gln Leu Ser Val Val
    370                 375                 380

Arg Leu Ser Glu Lys Ala Cys Pro Val Lys Val Gly Pro Pro Ser Arg
385                 390                 395                 400

His Ala Ser Glu Gly His Asp Arg Thr Pro Ala Gly Ala Leu
                405                 410


<210> SEQ ID NO 407
<211> LENGTH: 417
<212> TYPE: PRT
<213> ORGANISM: Homo sapiens

<400> SEQUENCE: 407

Met Gly Ser Asp Val Arg Asp Leu Ser Ala Leu Leu Pro Thr Ala Pro
 1               5                  10                  15

Ser Leu Gly Gly Gly Gly Asp Cys Thr Leu Pro Val Ser Gly Thr Ala
            20                  25                  30

Gln Trp Ala Pro Val Pro Ala Ser Ala Pro Pro Gly Ala Ser Ala Tyr
        35                  40                  45

Asp Ser Leu Gly Gly Pro Ala Pro Pro Pro Ala Pro Pro Pro Pro Pro
    50                  55                  60

Pro Pro Pro Pro His Ser Cys Gly Glu Gln Gly Pro Ser Trp Gly Gly
65                  70                  75                  80

Ala Glu Pro Arg Glu Gly Gln Cys Leu Ser Ala Pro Ala Val Arg Phe
                85                  90                  95

Ser Gly Arg Phe Thr Gly Thr Val Gly Ala Cys Arg Tyr Gly Pro Leu
            100                 105                 110

Gly Pro Pro Pro Pro Ser Gln Ala Pro Ser Gly Gln Thr Arg Met Leu
        115                 120                 125

Pro Ser Ala Pro Tyr Leu Ser Ser Cys Leu Arg Ser Arg Ser Ala Ile
    130                 135                 140

Arg Ser Gln Gly Arg Ser Thr Ala Pro Ser Ala Gly Arg Pro Ala Met
145                 150                 155                 160

Ala Pro Thr Leu Ala Pro Pro Ala Gln Ser His Tyr Ser Gln His Gly
                165                 170                 175

Val Leu His Gly Pro Ala Gly Leu Ala Gly Ala Ala Val Leu Gly Ala
            180                 185                 190

Ala Pro Gly Leu Trp Leu Pro His Pro His Arg Gln Leu His Arg Gln
        195                 200                 205

Pro Gly Phe Ala Ala Glu Asp Ala Leu Gln Gln Gln Phe Ile Pro Asn
    210                 215                 220
```

```
Asp Ile Pro Ala Met His Asp Leu Glu Ser Asp Glu Leu Arg Ser His
225                 230                 235                 240

Leu Lys Gly Pro Gln His Arg Val Arg Glu Arg Pro His Asn Ala His
                245                 250                 255

Pro Leu Arg Ser Pro Ile Gln Asn Thr His Ala Arg Cys Leu Gln Arg
            260                 265                 270

His Ser Gly Cys Ala Thr Cys Ala Trp Ser Ser Pro Asp Ser Cys Thr
        275                 280                 285

Val Ala Pro Glu Thr Ser Glu Asn Ala Pro Trp Cys Val Leu Pro Gly
    290                 295                 300

Leu Gln Gly Val Phe Ala Val Pro Leu Thr Gly Ala Gln Gln Glu Ala
305                 310                 315                 320

His Trp Asp Ala Thr Pro Val Arg Leu Gln Gly Pro Trp Thr Arg Ala
                325                 330                 335

Ser Pro Phe Gly Thr Ser Pro Arg Asp Thr Lys Gly Asp Ile Gln Val
            340                 345                 350

Arg Asn His Ser Ser Val Arg Leu Val Ser Glu Gly Ser Pro Gly Pro
        355                 360                 365

Thr Thr Gly Pro Thr Pro Gly Pro Thr Arg Val Gly Ser Pro Ser Ala
    370                 375                 380

Ala Gly Gly Gln Ala Ala Arg Glu Gly Ser Pro Ser Gln Thr Asn Ser
385                 390                 395                 400

Val Ile Thr Thr Cys Ile Ser Glu Thr Leu Asn Ser Ser Trp Arg Phe
                405                 410                 415

Glu


<210> SEQ ID NO 408
<211> LENGTH: 429
<212> TYPE: PRT
<213> ORGANISM: Homo sapiens

<400> SEQUENCE: 408

Met Gly Ser Asp Val Arg Asp Leu Asn Ala Leu Leu Pro Ala Val Pro
 1               5                  10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Pro Ala Pro Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
```

```
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly His Ser Thr Gly Tyr Glu Ser
                245                 250                 255

Asp Asn His Thr Thr Pro Ile Leu Cys Gly Ala Gln Tyr Arg Ile His
            260                 265                 270

Thr His Gly Val Phe Arg Gly Ile Gln Asp Val Arg Arg Val Pro Gly
        275                 280                 285

Val Ala Pro Thr Leu Val Arg Ser Ala Ser Glu Thr Ser Glu Lys Arg
    290                 295                 300

Pro Phe Met Cys Ala Tyr Pro Gly Cys Asn Lys Arg Tyr Phe Lys Leu
305                 310                 315                 320

Ser His Leu Gln Met His Ser Arg Lys His Thr Gly Glu Lys Pro Tyr
                325                 330                 335

Gln Cys Asp Phe Lys Asp Cys Glu Arg Arg Phe Phe Arg Ser Asp Gln
            340                 345                 350

Leu Lys Arg His Gln Arg Arg His Thr Gly Val Lys Pro Phe Gln Cys
        355                 360                 365

Lys Thr Cys Gln Arg Lys Phe Ser Arg Ser Asp His Leu Lys Thr His
    370                 375                 380

Thr Arg Thr His Thr Gly Glu Lys Pro Phe Ser Cys Arg Trp Pro Ser
385                 390                 395                 400

Cys Gln Lys Lys Phe Ala Arg Ser Asp Glu Leu Val Arg His His Asn
                405                 410                 415

Met His Gln Arg Asn Met Thr Lys Leu Gln Leu Ala Leu
            420                 425


<210> SEQ ID NO 409
<211> LENGTH: 495
<212> TYPE: PRT
<213> ORGANISM: Homo sapiens

<400> SEQUENCE: 409

Met Ala Ala Pro Gly Ala Arg Arg Ser Leu Leu Leu Leu Leu Leu Ala
 1               5                  10                  15

Gly Leu Ala His Gly Ala Ser Ala Leu Phe Glu Asp Leu Met Gly Ser
            20                  25                  30

Asp Val Arg Asp Leu Asn Ala Leu Leu Pro Ala Val Pro Ser Leu Gly
        35                  40                  45

Gly Gly Gly Gly Cys Ala Leu Pro Val Ser Gly Ala Ala Gln Trp Ala
    50                  55                  60

Pro Val Leu Asp Phe Ala Pro Pro Gly Ala Ser Ala Tyr Gly Ser Leu
65                  70                  75                  80

Gly Gly Pro Ala Pro Pro Pro Ala Pro Pro Pro Pro Pro Pro Pro His
                85                  90                  95

Ser Phe Ile Lys Gln Glu Pro Ser Trp Gly Gly Ala Glu Pro His Glu
            100                 105                 110

Glu Gln Cys Leu Ser Ala Phe Thr Val His Phe Ser Gly Gln Phe Thr
        115                 120                 125

Gly Thr Ala Gly Ala Cys Arg Tyr Gly Pro Phe Gly Pro Pro Pro Pro
```

```
    130                 135                 140

Ser Gln Ala Ser Ser Gly Gln Ala Arg Met Phe Pro Asn Ala Pro Tyr
145                 150                 155                 160

Leu Pro Ser Cys Leu Glu Ser Gln Pro Ala Ile Arg Asn Gln Gly Tyr
                165                 170                 175

Ser Thr Val Thr Phe Asp Gly Thr Pro Ser Tyr Gly His Thr Pro Ser
            180                 185                 190

His His Ala Ala Gln Phe Pro Asn His Ser Phe Lys His Glu Asp Pro
        195                 200                 205

Met Gly Gln Gln Gly Ser Leu Gly Glu Gln Gln Tyr Ser Val Pro Pro
    210                 215                 220

Pro Val Tyr Gly Cys His Thr Pro Thr Asp Ser Cys Thr Gly Ser Gln
225                 230                 235                 240

Ala Leu Leu Leu Arg Thr Pro Tyr Ser Ser Asp Asn Leu Tyr Gln Met
                245                 250                 255

Thr Ser Gln Leu Glu Cys Met Thr Trp Asn Gln Met Asn Leu Gly Ala
            260                 265                 270

Thr Leu Lys Gly His Ser Thr Gly Tyr Glu Ser Asp Asn His Thr Thr
        275                 280                 285

Pro Ile Leu Cys Gly Ala Gln Tyr Arg Ile His Thr His Gly Val Phe
    290                 295                 300

Arg Gly Ile Gln Asp Val Arg Arg Val Pro Gly Val Ala Pro Thr Leu
305                 310                 315                 320

Val Arg Ser Ala Ser Glu Thr Ser Glu Lys Arg Pro Phe Met Cys Ala
                325                 330                 335

Tyr Pro Gly Cys Asn Lys Arg Tyr Phe Lys Leu Ser His Leu Gln Met
            340                 345                 350

His Ser Arg Lys His Thr Gly Glu Lys Pro Tyr Gln Cys Asp Phe Lys
        355                 360                 365

Asp Cys Glu Arg Arg Phe Phe Arg Ser Asp Gln Leu Lys Arg His Gln
    370                 375                 380

Arg Arg His Thr Gly Val Lys Pro Phe Gln Cys Lys Thr Cys Gln Arg
385                 390                 395                 400

Lys Phe Ser Arg Ser Asp His Leu Lys Thr His Thr Arg Thr His Thr
                405                 410                 415

Gly Glu Lys Pro Phe Ser Cys Arg Trp Pro Ser Cys Gln Lys Lys Phe
            420                 425                 430

Ala Arg Ser Asp Glu Leu Val Arg His His Asn Met His Gln Arg Asn
        435                 440                 445

Met Thr Lys Leu Gln Leu Ala Leu Leu Asn Asn Met Leu Ile Pro Ile
    450                 455                 460

Ala Val Gly Gly Ala Leu Ala Gly Leu Val Leu Ile Val Leu Ile Ala
465                 470                 475                 480

Tyr Leu Ile Gly Arg Lys Arg Ser His Ala Gly Tyr Gln Thr Ile
                485                 490                 495


<210> SEQ ID NO 410
<211> LENGTH: 504
<212> TYPE: PRT
<213> ORGANISM: Homo sapiens

<400> SEQUENCE: 410

Met Gln Ile Phe Val Lys Thr Leu Thr Gly Lys Thr Ile Thr Leu Glu
 1               5                  10                  15

Val Glu Pro Ser Asp Thr Ile Glu Asn Val Lys Ala Lys Ile Gln Asp
```

```
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Ala Met Gly Ser Asp
65                  70                  75                  80

Val Arg Asp Leu Asn Ala Leu Leu Pro Ala Val Pro Ser Leu Gly Gly
                85                  90                  95

Gly Gly Gly Cys Ala Leu Pro Val Ser Gly Ala Ala Gln Trp Ala Pro
            100                 105                 110

Val Leu Asp Phe Ala Pro Pro Gly Ala Ser Ala Tyr Gly Ser Leu Gly
        115                 120                 125

Gly Pro Ala Pro Pro Pro Ala Pro Pro Pro Pro Pro Pro Pro Pro His
    130                 135                 140

Ser Phe Ile Lys Gln Glu Pro Ser Trp Gly Gly Ala Glu Pro His Glu
145                 150                 155                 160

Glu Gln Cys Leu Ser Ala Phe Thr Val His Phe Ser Gly Gln Phe Thr
                165                 170                 175

Gly Thr Ala Gly Ala Cys Arg Tyr Gly Pro Phe Gly Pro Pro Pro Pro
            180                 185                 190

Ser Gln Ala Ser Ser Gly Gln Ala Arg Met Phe Pro Asn Ala Pro Tyr
        195                 200                 205

Leu Pro Ser Cys Leu Glu Ser Gln Pro Ala Ile Arg Asn Gln Gly Tyr
    210                 215                 220

Ser Thr Val Thr Phe Asp Gly Thr Pro Ser Tyr Gly His Thr Pro Ser
225                 230                 235                 240

His His Ala Ala Gln Phe Pro Asn His Ser Phe Lys His Glu Asp Pro
                245                 250                 255

Met Gly Gln Gln Gly Ser Leu Gly Glu Gln Gln Tyr Ser Val Pro Pro
            260                 265                 270

Pro Val Tyr Gly Cys His Thr Pro Thr Asp Ser Cys Thr Gly Ser Gln
        275                 280                 285

Ala Leu Leu Leu Arg Thr Pro Tyr Ser Ser Asp Asn Leu Tyr Gln Met
    290                 295                 300

Thr Ser Gln Leu Glu Cys Met Thr Trp Asn Gln Met Asn Leu Gly Ala
305                 310                 315                 320

Thr Leu Lys Gly His Ser Thr Gly Tyr Glu Ser Asp Asn His Thr Thr
                325                 330                 335

Pro Ile Leu Cys Gly Ala Gln Tyr Arg Ile His Thr His Gly Val Phe
            340                 345                 350

Arg Gly Ile Gln Asp Val Arg Arg Val Pro Gly Val Ala Pro Thr Leu
        355                 360                 365

Val Arg Ser Ala Ser Glu Thr Ser Glu Lys Arg Pro Phe Met Cys Ala
    370                 375                 380

Tyr Pro Gly Cys Asn Lys Arg Tyr Phe Lys Leu Ser His Leu Gln Met
385                 390                 395                 400

His Ser Arg Lys His Thr Gly Glu Lys Pro Tyr Gln Cys Asp Phe Lys
                405                 410                 415

Asp Cys Glu Arg Arg Phe Phe Arg Ser Asp Gln Leu Lys Arg His Gln
            420                 425                 430

Arg Arg His Thr Gly Val Lys Pro Phe Gln Cys Lys Thr Cys Gln Arg
        435                 440                 445
```

```
Lys Phe Ser Arg Ser Asp His Leu Lys Thr His Thr Arg Thr His Thr
    450                 455                 460

Gly Glu Lys Pro Phe Ser Cys Arg Trp Pro Ser Cys Gln Lys Lys Phe
465                 470                 475                 480

Ala Arg Ser Asp Glu Leu Val Arg His His Asn Met His Gln Arg Asn
                485                 490                 495

Met Thr Lys Leu Gln Leu Ala Leu
            500


<210> SEQ ID NO 411
<211> LENGTH: 10
<212> TYPE: PRT
<213> ORGANISM: Homo sapiens

<400> SEQUENCE: 411

Val Leu Asp Phe Ala Pro Pro Gly Ala Ser
 1               5                  10


<210> SEQ ID NO 412
<211> LENGTH: 15
<212> TYPE: PRT
<213> ORGANISM: Homo sapiens

<400> SEQUENCE: 412

Gln Trp Ala Pro Val Leu Asp Phe Ala Pro Pro Gly Ala Ser Ala
 1               5                  10                  15


<210> SEQ ID NO 413
<211> LENGTH: 15
<212> TYPE: PRT
<213> ORGANISM: Homo sapiens

<400> SEQUENCE: 413

Val Leu Asp Phe Ala Pro Pro Gly Ala Ser Ala Tyr Gly Ser Leu
 1               5                  10                  15
```